US010206995B2

(12) United States Patent
Whitehead et al.

(10) Patent No.: US 10,206,995 B2
(45) Date of Patent: *Feb. 19, 2019

(54) LIVE ATTENUATED VIRUS VACCINES FOR LA CROSSE VIRUS AND OTHER BUNYAVIRIDAE

(71) Applicant: The United States of America, as represented by the Secretary, Dept. of Health and Human Services, Washington, DC (US)

(72) Inventors: Stephen S. Whitehead, Montgomery Village, MD (US); Richard S. Bennett, North Potomac, MD (US); Brian R. Murphy, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,696

(22) Filed: Dec. 21, 2017

(65) Prior Publication Data

US 2018/0104326 A1 Apr. 19, 2018

Related U.S. Application Data

(62) Division of application No. 15/018,857, filed on Feb. 8, 2016, now Pat. No. 9,884,104, which is a division of application No. 13/633,633, filed on Oct. 2, 2012, now Pat. No. 9,255,252, which is a division of application No. 12/593,818, filed as application No. PCT/US2008/056099 on Mar. 6, 2008, now Pat. No. 8,298,541.

(60) Provisional application No. 60/937,871, filed on Jun. 29, 2007, provisional application No. 60/928,406, filed on May 8, 2007, provisional application No. 60/920,961, filed on Mar. 29, 2007.

(51) Int. Cl.
*A61K 39/12* (2006.01)
*C12Q 1/70* (2006.01)
*C07K 14/005* (2006.01)
*C12N 7/00* (2006.01)
*A61K 39/00* (2006.01)

(52) U.S. Cl.
CPC ............ *A61K 39/12* (2013.01); *C07K 14/005* (2013.01); *C12N 7/00* (2013.01); *C12Q 1/701* (2013.01); *A61K 39/00* (2013.01); *A61K 2039/5252* (2013.01); *A61K 2039/5254* (2013.01); *C12N 2760/12022* (2013.01); *C12N 2760/12034* (2013.01)

(58) Field of Classification Search
None
See application file for complete search history.

(56) References Cited

U.S. PATENT DOCUMENTS

| 8,298,541 B2 | 10/2012 | Whitehead et al. | |
| 9,884,104 B2* | 2/2018 | Whitehead | A61K 39/12 |
| 2005/0019753 A1* | 1/2005 | Kukolj | C12N 9/506 435/5 |
| 2014/0023679 A1 | 1/2014 | Whitehead et al. | |
| 2018/0104326 A1* | 4/2018 | Whitehead | C12Q 1/701 |

FOREIGN PATENT DOCUMENTS

WO  WO 2005/051313  6/2005

OTHER PUBLICATIONS

Putkuri et al, (Infection, Genetics, and Evolution. 2014: 22: 164-173).*
Bennett et al., "A Recombinant Chimeric La Crosse Virus Expressing the Surface Glycoproteins of Jamestown Canyon Virus Is Immunogenic and Protective against Challenge with either Parental Virus in Mice or Monkeys," *Journal of Virology*, vol. 86, No. 1, pp. 420-426, 2012.
Bennett et al., "Genome Sequence Analysis of La Crosse Virus and in Vitro and in Vivo Phenotypes," *Virology Journal*, 4:41, 2007.
Blakqori et al., "Efficient cDNA-Based Rescue of La Crosse Bunyaviruses Expressing or Lacking the Nonstructural Protein NSs," *Journal of Virology*, vol. 79, No. 16, pp. 10420-10428, 2005.
Bridgen et al, "Rescue of a segmented negative-strand RNA virus entirely from cloned complementary DNAs," *PNAS*, vol. 93, pp. 15400-15404, 1996.
Cheng et al, "Potential for evolution of California serogroup bunyaviruses by genome reassortment in Aedes albopictus," *American Journal of Tropical Medicine and Hygiene*, vol. 60, No. 3, pp. 430-438, 1999.
Elliot, "Orthobunyaviruses: recent genetic and structural insights," *Nature Reviews Microbiology*, vol. 12, pp. 673-685, 2014.
Huang et al., "Comparison of the MRNA Genome Segments of Two Human Isolates of La Crosse Virus," *Virus Research*, vol. 36, No. 2-3, pp. 177-185, 1995.
Janssen et al, "Virulence of La Crosse virus is under polygenic control," *Journal of Virology*, vol. 59, No. 1, pp. 1-7, 1986.
Plassmeyer et al., "California serogroup Gc (G1) glycoprotein is the principal determinant of pH-dependent cell fusion and entry," *Virology*, vol. 338, pp. 121-132, 2005.

(Continued)

*Primary Examiner* — Shanon A. Foley
(74) *Attorney, Agent, or Firm* — Klarquist Sparkman, LLP

(57) ABSTRACT

The invention relates to vaccine compositions including CEV serogroup immunogens, attenuated and inactivated viruses of the CEV serogroup and chimeric Bunyaviridae. Also disclosed are methods of treating or preventing CEV serogroup infection in a mammalian host, methods of producing a subunit vaccine composition or an immunogenic composition, isolated polynucleotides comprising a nucleotide sequence encoding a CEV serogroup immunogen, methods for detecting La Crosse virus (LACV) infection in a biological sample and infectious chimeric Bunyaviridae.

7 Claims, 12 Drawing Sheets

Specification includes a Sequence Listing.

(56) References Cited

OTHER PUBLICATIONS

Putkuri et al., "Isolation and characterization of a California encephalitis serogroup orthobunyavirus from Finnish mosquitos," *Infection, Genetics, and Evolution*, vol. 22, pp. 164-173, 2014.

Roberts et al., "Completion of the La Crosse Virus Genome Sequence and Genetic Comparisons of the L Proteins of the Bunyaviridae", *Virology*, vol. 206, No. 1, pp. 742-745, 1995.

Schoen et al. "Orthobunyaviruses and innate immunity induction: alieNSs vs. PredatoRRs," *European Journal of Cell Biology*, vol. 94, pp. 384-390, 2015.

Sidwell et al., "Viruses of the Bunya- and Togaviridae Families: Potential as Bioterrorism Agents and Means of Control," *Antiviral Research*, vol. 57, No. 1-2, pp. 101-111, 2003.

* cited by examiner

```
                           6951                          6980
LACV/human/1960       5'   ..............................   3'
LACV/human/1978       5'   ..............................   3'
LACV/mosquito/1978    5'   ..............................   3'
LACV/mosquito/1977    5'   ..............................   3'
Consensus             5'   GTATAAATTTGTAGATAGGAGCACACTACT   3'
                                    (SEQ ID No.23)
```

Figure 2.2

Figure 4-1 h/1960   GTIYNKSCKKCKLCGLVYHPFTBCGTHCVCCGARYDTSDRMKLHRASGLCPGYKSLRAARV  300
m/1977   GTIYNKSCKKCKLCGLVYHPFTBCGTHCVCCGARYDTSDRMKLHRASGLCPGYKSLRAARV  300
h/1978*  GTIYNKSCKKCKLCGLVYHPFTBCGTHCVCCGARYDTSDRMKLHRASGLCPGYKSLRAARV  300
h/1978   GTIYNKSCKKCKLCGLVYHPFTBCGTHCVCCGARYDTSDRMKLHRASGLCPGYKSLRAARV  300
m/1978   GTIYNKSCKKCKLCGLVYHPFTBCGTHCVCCGARYDTSDRMKLHRASGLCPGYKSLRAARV  300
         ************************************************************ h/1960   MCKSKGPASILSITTAVLIVLIFVTPINSMVLGESKETFELEDLPDMLEMASRINSYYLT   360
m/1977   MCKSKGPASILSITTAVLIVLIFVTPINSMVLGESKETFELEDLPDMLEMASRINGYYLT   360
h/1978*  MCKSKGPASILSITTAVLIVLIFVTPINSMVLGESKETFELEDLPDMLEMASRINSYYLT   360
h/1978   MCKSKGPASILSITTAVLIVLIFVTPINSMVLGESKETFELEDLPDMLEMASRINSYYLT   360
m/1978   MCKRQPASILSITTAVLIVLIFVTPZESMLGESKETFELERLPDMLEMASRINDYYFT;   360
         *  ************  ******* ***** *****  * h/1960   CLMYAVSWGLVTIGLLTGLLFKKYQHRFLNVYAMYCEBCOMTHDKSGLKGHGDFTMKCR   420
m/1977   CLMYAVEWQLVTIGLLIGLLFKKYQHRFLNVYAMYCEBCOMTHDKSGLKAGGFTMKCR    420
h/1978*  CLMYAVSWGLVTIGLLIGLLFKKYQHRFLNYYAMYCEBCOMYHDKSGLKEAGOFTMKCR   420
h/1978   CLMYAVSWGLVTIGLLIGLLFKKYQHRFLNYYAMYCEBCOMYHDKSGLKEAGDFTMKCR   420
m/1978   CLMYAVEWQLVTIGLLIGLLFKKYQHRFLNTYAMYCEBCQMYNDKSGLRAGGFTMKCR    420
         ******* *********** *  *****  ** * * ****** h/1960   QCTCCQYEDAAGLMAHRKTYMCLVQYKAKWMMNFLIYIFLILIKDSAIVVQAAGTDFTT   480
m/1977   QCTCCQYEDAAGLMAHRKTYMCLVQYKAKWMNFLIYIFLILIKDSAIVVQAAGTDFTT    480
h/1978*  QCTCCQYEDAAGLMAHRKTYMCLVQYKAKWMMNFLIYIFLILIKDSAIVVQAAGTDFTT   480
h/1978   QCTCCQYEDAAGLMAHRKTYMCLVQYKAKWMMNFLIYIFLILIKDSAIVVQAAGTDFTT   480
m/1978   QCTCCQYEDAAGLMAHRKTYMCLVQYKAKWMNFLIYIFLILIKDSAIVVQAAGTDFTT    480
         ************************************************************

LIVE ATTENUATED VIRUS VACCINES FOR LA CROSSE VIRUS AND OTHER BUNYAVIRIDAE

CROSS-REFERENCE TO RELATED APPLICATIONS

This Application is a Division of U.S. patent application Ser. No. 15/018,857, filed Feb. 8, 2016, which is a Division of Application U.S. patent application Ser. No. 13/633,633, filed on Oct. 2, 2012, now U.S. Pat. No. 9,255,252, issued Feb. 9, 2016. Application Ser. No. 13/633,633 is a Division of application Ser. No. 12/593,818, filed Apr. 16, 2010, now U.S. Pat. No. 8,298,541, issued Oct. 30, 2012. Application Ser. No. 12/593,818 is the National Stage Entry of International Patent Application No. PCT/US08/056099, filed Mar. 6, 2008, which claims priority to U.S. Provisional Application Nos. 60/937,871, filed Jun. 29, 2007; 60/928,406, filed May 8, 2007; and 60/920,961, filed Mar. 29, 2007. Each of the aforementioned patent applications are hereby incorporated by reference in their entireties.

FIELD OF THE INVENTION

The present invention pertains to immunogenic reagents derived from viruses of the California encephalitis group of Bunyaviruses.

SEQUENCE LISTING

The Sequence Listing is submitted as an ASCII text file in the form of the file named Sequence_Listing.txt, which was created on Dec. 20, 2017, and is 235,503 bytes, which is incorporated by reference herein.

DESCRIPTION OF THE RELATED ART

La Crosse virus (LACV), family Bunyaviridae, is a mosquito-borne pathogen endemic in many regions of the United States. LACV infection results in 70-130 clinical cases a year and is the major cause of pediatric arboviral encephalitis in North America (Rust R S et al. 1999 *J Child Neurol* 14:1-14; McJunkin J E et al. 2001 *N Engl J Med* 344:801-807; Calisher C H 1994 *Clin Microbiol Rev* 7:89-116). LACV was first identified as a human pathogen in 1960 after its isolation from a 4 year-old girl from Minnesota who suffered meningoencephalitis and later died in La Crosse, Wis. (Thompson W H and Gundersen C B 1983 *Prog Clin Biol Res* 123:225-236; Thompson W H et al. 1965 *American Journal of Epidemiology* 81:245-253). The majority of LACV infections are mild and never reported, however serologic studies estimate annual infection rates of 10-30/100,000 in endemic areas (McJunkin J E et al. 2001 *N Engl J Med* 344:801-807; Calisher C H 1994 *Clin Microbiol Rev* 7:89-116; Grimstad P R et al. 1984 *Am J Epidemiol* 119:913-930; McJunkin J E et al. 1998 *Infect Dis Clin North Am* 12:83-93). LACV is a member of the California encephalitis virus (CEV) serogroup of viruses in the genus *Orthobunyavirus*. The serogroup contains members found on five continents that include human pathogens such as La Crosse, Snowshoe hare, and Jamestown Canyon viruses in North America; Guaroa virus in North and South America; Inkoo and Tahyna viruses in Europe; and Lumbo virus in Africa (Nichol S T: "Bunyaviruses" in Fields Virology, Volume 2, Fourth edition, Edited by Knipe D M, Howley P M. Philadelphia, Pa.: Lippincott Williams & Wilkins; 2001: 1603-1633). Children who recover from severe La Crosse encephalitis may have significantly lower IQ scores than expected and a high prevalence (60% of those tested) of attention-deficit-hyperactivity disorder (McJunkin J E et al. 2001 *N Engl J Med* 344:801-807). Seizure disorders are also common in survivors (Balfour H H et al. 1973 Pediatrics 52:680-691). LACV can also cause encephalitis in immunosuppressed adults (Wurtz R and Paleologos N 2000 *Clin Infect Dis* 31:1113-1114). Projected lifelong economic costs associated with neurologic sequelae range from $48,775-3,090,398 per case (Utz J T et al. 2003 *Am J Trop Med Hyg* 69:509-518). At present, a vaccine or FDA approved antiviral therapy is not available.

LACV maintains an enzootic life cycle with the hardwood forest dwelling, tree-hole mosquito, *Aedes triseriatus*, which lives in the eastern half of the United States breeding in tree holes and outdoor containers (Nasci R S et al. 2000 *J Med Entomol* 37:559-570). *Ae. triseriatus* mosquitoes feed on Eastern gray squirrels (*Sciurus carolinensis*) and Eastern chipmunks (*Tamias striatus griseus*) which serve as amplifying hosts for LACV, and undergo sub-clinical infections while maintaining serum viremias high enough to infect feeding mosquitoes (Woodruff B A et al. 1992 *Am J Epidemiol* 136:320-327; Pantuwatana S et al. 1972 *Am J Trop Med Hyg* 21:476-481). Interestingly, the virus can be maintained in the mosquito population in the absence of vertebrate hosts by transovarial (vertical) transmission, thus allowing the virus to over-winter in mosquito eggs. Mosquito infection is lifelong and mosquitoes can become dually infected with other bunyaviruses allowing for the development of intragenus reassortants (Klimas R A et al. 1981 *Am J Epidemiol* 114:112-131; Seymour C et al. 1983 *Am J Trop Med Hyg* 32:1147-1153; Beaty B J et al. 1985 *Science* 230:548-550; Beaty B J et al. 1981 *Virology* 111:662-665).

LACV virions are pleomorphic (90-100 nm in diameter) and have a lipid envelope containing the heteromultimer glycoprotein (Obijeski J F et al. 1976 *J Virol* 19:985-997). The genome consists of three single-stranded, negative-sense RNA genome segments designated small (S), medium (M), and large (L). Each genome segment is complexed with the nucleoprotein (N) to form three separate nucleocapsids. The termini of the 3' and 5' non-coding regions (NCR) of each segment are complementary and highly conserved. The S Segment encodes two proteins in overlapping reading frames: the nucleoprotein (N) and a non-structural protein (NSs). In the related Bunyamwera virus, NSs inhibits transcription via blocking host cell RNA polymerase II, which decreases overall host cell protein synthesis in mammalian cells including a decrease in both the induction of interferon and its signaling in infected cells (Bridgen A et al. 2001 *Proc Natl Acad Sci USA* 98:664-669; Weber F et al. 2002 *J Virol* 76:7949-7955). Recombinant LACV virions lacking the NSs gene are viable, indicating that the NSs is a nonessential accessory protein (Blakqori G and Weber F 2005 *J Virol* 79:10420-10428). The M segment encodes a single polyprotein (M polyprotein) that is post-translationally processed into two glycoproteins ($G_N$ and $G_C$ that form a heteromultimer in the virion and a non-structural protein ($NS_M$) of unknown function (Obijeski J F et al. 1976 *J Virol* 20:664-675). The L segment encodes a single open reading frame for the RNA dependent RNA polymerase (L) (Kohl A et al. 2004 *J Gen Virol* 85:3269-3278; Li M L et al. 1998 *Embo J* 17:5844-5852). The L polymerase uses host-cell 5' mRNA sequences, including the cap structures, to prime its own mRNA synthesis, a process that also contributes to the observed shut-off of host cell protein synthesis following infection.

SUMMARY OF THE INVENTION

The complete genomes of three low-passage LACV isolates, namely, LACV/human/1960, LACV/human/1978, LACV/mosquito/1978, isolated over a 18 year period of time, were screened to identify nucleotide sequences of LACV that are associated with the wild type phenotype, e.g., replication competent in insect and mammalian cells and able to cause encephalitic disease in suckling and weanling mice by a peripheral and intracerebral route of inoculation. Biologically cloned derivatives of each virus were also sequenced. The level of neurovirulence and neuroinvasiveness for each of the three virus isolates and their cloned derivatives was determined in mice by assessing clinical disease following intracerebral or intraperitoneal administration of virus. LACV strains appear highly genetically stable in nature, grow to high titers in monkey and mosquito cell cultures, and are highly neurovirulent and neuroinvasive for mice even at low dosage. Since one of the long-term goals of this project was to develop a live attenuated virus vaccine for LACV, the identification of a nucleotide sequence of LACV that specifies a wild type phenotype was seen as a first step in this process. Several mutations of LACV, which impact the virus were also discovered e.g., a single amino acid substitution in $G_N$ in one of the cloned LACV strains was identified as a mutation that greatly decreases LACV neuroinvasiveness. Such mutations are envisioned as providing the basis for developing live-attenuated virus vaccines and immunogenic compositions.

Aspects of the invention relate to subunit vaccine compositions including California encephalitis virus (CEV) serogroup immunogens, attenuated and inactivated CEV serogroup and chimeric Bunyaviridae. Also disclosed are methods of treating and/or preventing CEV serogroup infection in a mammal, methods of inducing an immune response to an immunogenic composition described herein, methods of producing a subunit vaccine composition or an immunogenic composition, isolated polynucleotides comprising a nucleotide sequence encoding a CEV serogroup immunogen, methods for detecting La Crosse virus (LACV) infection in a biological sample and infectious chimeric Bunyaviridae.

Some embodiments include a live attenuated LACV vaccine or an immunogenic composition that contains a mutation at amino acid 148 of $G_N$ and, optionally, is attenuated for neuroinvasiveness in a mammalian host. Preferred embodiments include a live attenuated LACV vaccine or an immunogenic composition in which the mutated amino acid at position 148 of $G_N$ is Alanine. Some aspects may concern a live attenuated LACV vaccine or immunogenic composition in which amino acid 148 of $G_N$ is deleted and other aspects concern a live attenuated LACV vaccine or an immunogenic composition in which the mutated amino acid at position 148 of $G_N$ is any amino acid other than Threonine.

More embodiments involve a subunit vaccine or immunogenic composition comprising a CEV serogroup immunogen and a pharmaceutically acceptable vehicle, wherein the immunogen is selected from the group consisting of (a) LACV/human/1960 $G_C$; (b) immunogenic fragment thereof; and (c) an immunogenic analog thereof. Some embodiments include an isolated LACV/human/1960 virus or its LACV/human/1960-clone or sequence having at least about 99.9% nucleotide or amino acid identity thereto. Other embodiments include an isolated LACV/mosquito/1978 virus or its LACV/mosquito/1978-clone or sequence having at least about 99.9% nucleotide or amino acid identity thereto. Still more embodiments include an isolated LACV/human/1978 virus or its LACV/human/1978-clone or sequence having at least about 99.99% nucleotide identity thereto.

Some aspects of the invention encompass an immunogenic composition comprising an attenuated LACV/human/1960 virus or its LACV/human/1960-clone or sequence having at least about 99.9% nucleotide or amino acid identity thereto, and a pharmaceutically acceptable vehicle. Other embodiments include an immunogenic composition comprising an attenuated LACV/mosquito/1978 virus or its LACV/mosquito/1978-clone or sequence having at least about 99.9% nucleotide or amino acid identity thereto, and a pharmaceutically acceptable vehicle. Still more embodiments include an immunogenic composition comprising an attenuated LACV/human/1978 virus or its LACV/human/1978-clone or sequence having at least about 99.99% nucleotide identity thereto, and a pharmaceutically acceptable vehicle. In some aspects of the invention, any one or more of the above immunogenic compositions has a mutation, wherein the amino acid at position 148 in $G_N$ is Alanine.

Some embodiments also include an immunogenic composition comprising an attenuated virus of the CEV serogroup and a pharmaceutically acceptable vehicle, wherein the amino acid at position 148 in $G_N$ is Alanine in an exemplary manner or corresponding thereto in other viruses of the CEV serogroup. The CEV virus in the immunogenic composition above can be a La Crosse virus. Some embodiments concern an immunogenic composition comprising an inactivated virus of the CEV serogroup and a pharmaceutically acceptable vehicle, wherein the CEV virus is the La Crosse virus of any of the aforementioned, preferably an LACV/mosquito/1978 immunogen comprising a mutation at amino acid at position 148 of $G_N$, an more preferably the T148A mutation.

More embodiments concern a method of treating or preventing CEV serogroup infection in a mammalian host comprising administering to said subject a therapeutically effective amount of any one or more of the immunogenic compositions described above. Some embodiments encompass a method of producing a subunit vaccine composition comprising the steps of providing a CEV serogroup immunogen wherein the immunogen is selected from the group consisting of (a) LACV/human/1960 $G_C$, (b) immunogenic fragment thereof; and (c) immunogenic analog thereof; and combining said CEV serogroup immunogen with a pharmaceutically acceptable vehicle.

Still more embodiments concern a method of producing an immunogenic composition comprising the steps of providing an attenuated LACV/human/1960 virus or its LACV/human/1960-clone or sequence having at least about 99.9% nucleotide or amino acid identity thereto; or providing an attenuated LACV/mosquito/1978 virus or its LACV/mosquito/1978-clone or sequence having at least about 99.9% nucleotide or amino acid identity thereto; or providing an attenuated LACV/human/1978 virus or its LACV/human/1978-clone or sequence having at least about 99.99% nucleotide identity thereto; and combining said attenuated LACV with a pharmaceutically acceptable vehicle.

Aspects of the invention also include an isolated polynucleotide comprising a nucleotide sequence encoding a CEV serogroup immunogen, wherein the immunogen is selected from the group consisting of (a) LACV/human/1960 $G_C$, (b) immunogenic fragment thereof, and (c) immunogenic analog thereof.

More embodiments concern a method for detecting La Crosse virus (LACV) infection in a biological sample, the method comprising: isolating nucleic acid from a biological sample suspected of containing LACV RNA, wherein if LACV is present, said nucleic acid comprises a target sequence; reacting the LACV nucleic acid with a detectably labeled probe sufficiently complementary to and capable of selectively hybridizing with the target sequence, wherein said reacting is done under conditions that provide for the formation of a probe/target sequence complex; and detecting the presence or absence of label as an indication of the presence or absence of the target sequence, wherein the probe is selected from the group consisting of an oligonucleotide comprising the nucleotide substitution A503G resulting in an amino acid change at position 148 in $G_N$, and reverse complement thereof.

Still more embodiments concern a method for detecting La Crosse virus (LACV) infection in a biological sample, the method comprising: isolating nucleic acid from a biological sample suspected of containing LACV RNA, wherein if LACV is present, said nucleic acid comprises a target sequence; amplifying the nucleic acid using at least two primers wherein each of the primers is not more than about 50 nucleotides in length and each of the primers is sufficiently complementary to a portion of the sense and antisense strands, respectively, of LACV isolated nucleic acid, if present, to hybridize therewith, and further wherein at least one of the primers is capable of selectively hybridizing to the target sequence; and detecting the presence of the amplified nucleic acid as an indication of the presence or absence of LACV in the sample, wherein one of the primers is selected from the group consisting of an oligonucleotide comprising the nucleotide substitution A503G resulting in an amino acid change at position 148 in $G_N$, and reverse complement thereof.

Additional embodiments include a method for detecting La Crosse virus (LACV) infection in a biological sample, the method comprising: isolating nucleic acid from a biological sample suspected of containing LACV RNA, wherein if LACV is present, said nucleic acid comprises a target sequence; amplifying the nucleic acid using at least two primers wherein each of the primers is not more than about 50 nucleotides in length and each of the primers is sufficiently complementary to a portion of the sense and antisense strands, respectively, of LACV isolated nucleic acid, if present, to hybridize therewith; and detecting the presence of the amplified nucleic acid using at least one detectably labeled probe sufficiently complementary to and capable of hybridizing with the LACV nucleic acid, if present, as an indication of the presence or absence of LACV in the sample, wherein at least one of the primers and/or the probe is capable of selectively hybridizing to the target sequence, wherein one of the primers is selected from the group consisting of an oligonucleotide comprising the nucleotide substitution A503G resulting in an amino acid change at position 148 in $G_N$, and reverse complement thereof.

Other embodiments include an infectious chimeric virus which is a member of the Bunyaviridae family comprising a chimeric Bunyaviridae genome which is comprised of a La Crosse virus genome wherein one or both genes $G_C$ and $G_N$ of a different Bunyaviridae subgroup or strain is substituted to replace one or both counterpart $G_C$ and $G_N$ genes in the La Crosse virus genome. In some embodiments, the infectious chimeric virus above is a Jamestown Canyon Virus.

BRIEF DESCRIPTION OF THE DRAWINGS

FIG. 1. Alignment of 3' non-coding region of S, M, and L genome segments (cDNA presented). S segment 3' NCR shows highly conserved sequence with no nucleotide changes from the consensus. For each segment the consensus sequence consists of three or more sequences sharing the same nucleotide at a given position (positions with no clear consensus are indicated with an "N"). A single nucleotide change was reported in the LACV/mosquito/1977 published sequence at position 9 of the M segment. For the 3' NCR of the L segment, 2 changes from the consensus were observed in LACV/mosquito/1978 with position 31 having no clear consensus. Underlined sequence indicates region conserved among all three segments. Putative host-specific nucleotide sequences are indicated with an arrow (↓).

FIG. 2.1. Alignment of 5' non-coding region of S, M, and L genome segments (cDNA presented).

FIG. 2.2. L genome segment with nucleotides sequence 6951-6980.

Among the two human isolates only one nucleotide difference was observed in the NCR of the L segment at position 6888. For each segment, the consensus sequence consists of three or more sequences sharing the same nucleotide at a given position (positions with no clear consensus are indicated with an "N"). Underlined sequence indicates region conserved among all three segments. Putative host-specific nucleotide sequences are indicated with an arrow (↓).

Figure 3A:
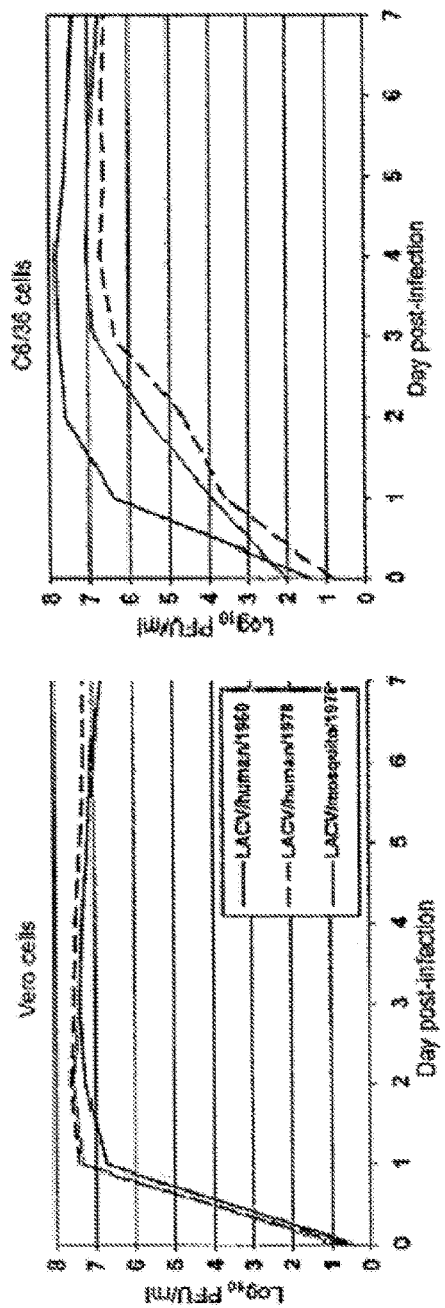

FIG. 3A. Growth kinetics of LACV/human/1960, LACV/human/1978, and LACV/mosquito/1978 in Vero cells or C6/36 cells infected at an MOI of 0.01.

Figure 3B:
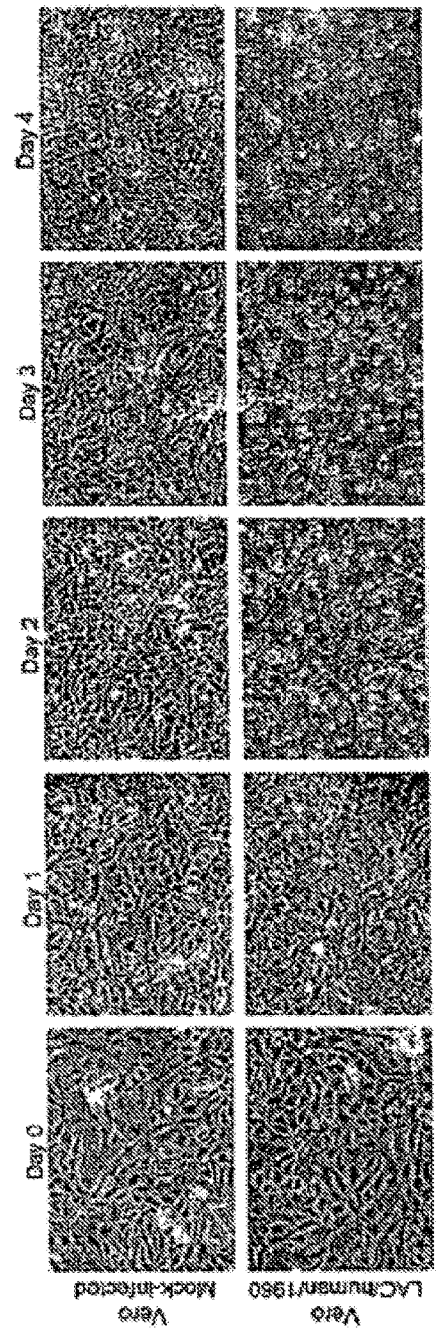

FIG. 3B. Photographs of mock or LACV/human/1960 infected Vero cell monolayers from panel "A". Cell rounding and detachment from the flask can be seen on days 2-4 post-infection in infected monolayers.

Figure 1:
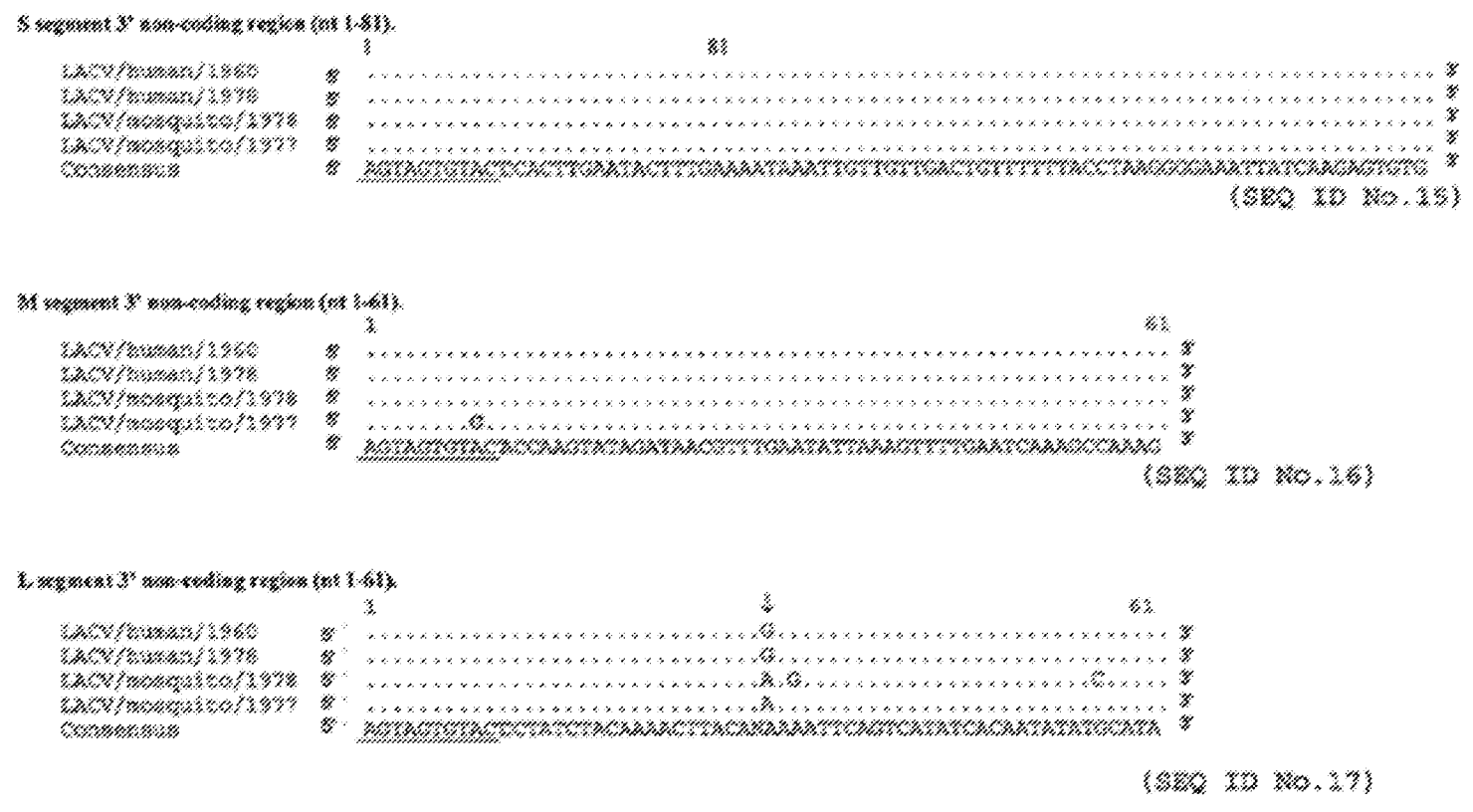

FIG. 4-1. Multiple sequence alignment of the M polyprotein of La Crosse virus isolates showing conserved regions and differences from 1-240 amino acids.

Figure 6:
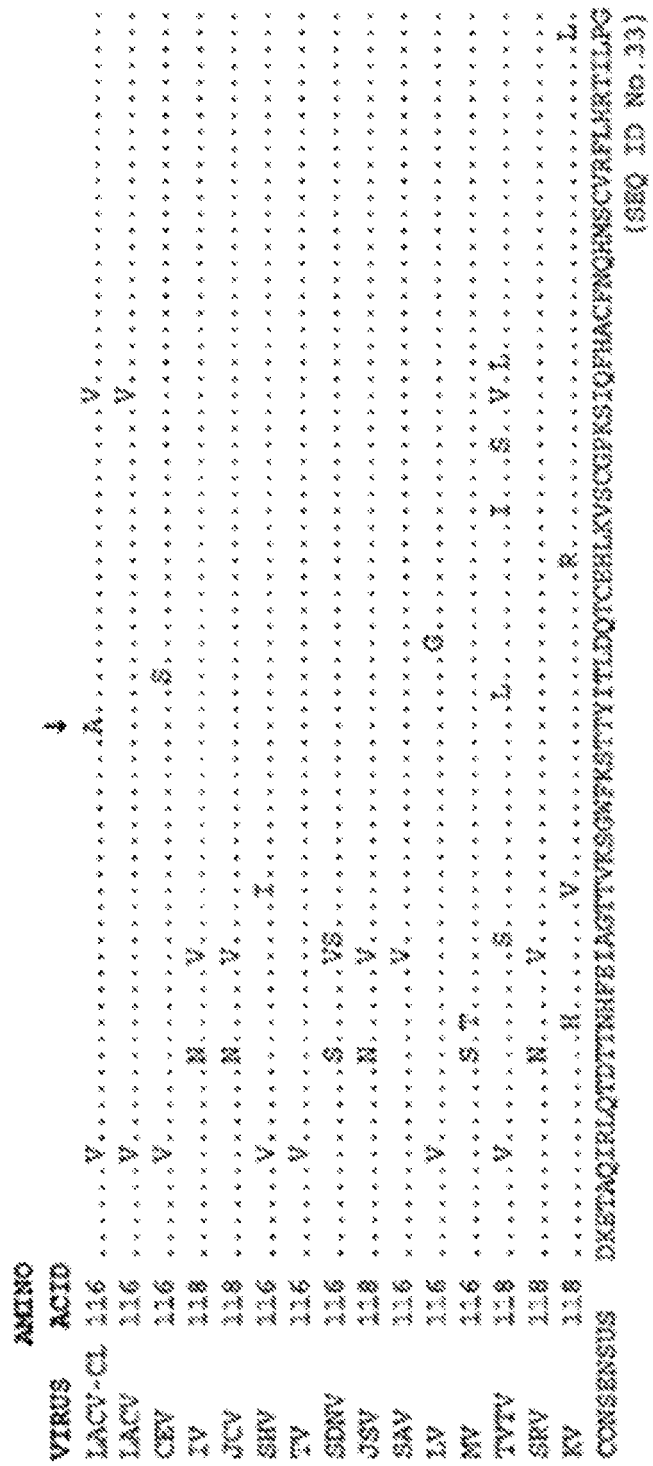

FIG. 4-2. Multiple sequence alignment of the M polyprotein of La Crosse virus isolates showing conserved regions and differences from 241-480 amino acids FIG. 4-3. Multiple sequence alignment of the M polyprotein of La Crosse virus isolates showing conserved regions and differences from 481-720 amino acids FIG. 4-4. Multiple sequence alignment of the M polyprotein of La Crosse virus isolates showing conserved regions and differences from 721-960 amino acids;

Figure 5:
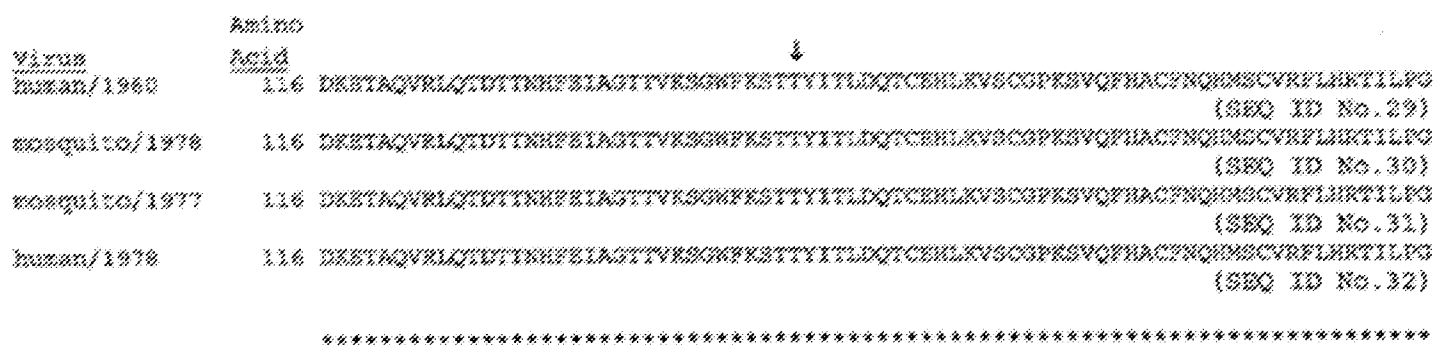

FIG. 4-5. Multiple sequence alignment of the M polyprotein of La Crosse virus isolates showing conserved regions and differences from 961-1200 amino acids;

FIG. 4-6. Multiple sequence alignment of the M polyprotein of La Crosse virus isolates showing conserved regions and differences from 1201-1441 amino acids.

"*" means that the residues or nucleotides in a given column are identical in all sequences in the alignment. Absence of a symbol below a given column means that a non-conservative difference is observed. ":" means that conserved substitutions are observed, and "." means that semi-conserved substitutions are observed.

FIG. 5. Alignment of a portion of the M polyprotein of La Crosse virus isolates showing conservation in the sequence. Amino acid position 148 is indicated by an arrow (↓).

FIG. 6. Alignment of a portion of the M polyprotein of California encephalitis virus serogroup showing conservation in the sequence compared to amino acid 148 of La Crosse virus (indicated by an arrow). LACV-CL is LACV/human/1960 with a mutation at amino acid position 148 of the M polyprotein, LACV is wild-type LACV/human/1960. CEV=California encephalitis virus, IV=Inkoo virus, JCV=Jamestown Canyon virus, SHV=Snowshoe hare virus, TV=Tahyna virus, SDNV=Serra do Navio virus, JSV=Jerry Slough virus, SAV=San Angelo virus, LV=Lumbo virus, MV=Melao virus, TVTV=Trivittatus virus, SRV=South River virus, and KV=Keystone virus.

BRIEF DESCRIPTION OF THE APPENDICES

Appendix 1. Large genomic segment-nucleotide sequence alignment of LACV/human/1978 (Hughes et al. 2002) and LACV/human/1978 (this study).

Appendix 2. Medium genomic segment-nucleotide sequence alignment of LACV/human/1978 (Hughes et al. 2002) and LACV/human/1978 (this study).

Appendix 3. Small genomic segment-nucleotide sequence alignment of LACV/human/1978 (Hughes et al. 2002) and LACV/human/1978 (this study).

Appendix 4. Large genomic segment-amino acid sequence alignment of LACV/human/1978 (Hughes et al. 2002) and LACV/human/1978 (this study).

Appendix 5. Medium genomic segment-amino acid sequence alignment of LACV/human/1978 (Hughes et al. 2002) and LACV/human/1978 (this study).

Appendix 6. Small genomic segment-Nucleoprotein (N) amino acid sequence alignment of LACV/human/1978 (Hughes et al. 2002) and LACV/human/1978 (this study).

Appendix 7. Small genomic segment-Nonstructural protein (NSs) amino acid sequence alignment of LACV/human/1978 (Hughes et al.) and LACV/human/1978 (this study).

DETAILED DESCRIPTION OF THE PREFERRED EMBODIMENT

Definitions

Unless defined otherwise, technical and scientific terms used herein have the same meaning as commonly understood by one of ordinary skill in the art to which this invention belongs. See, e.g., Singleton P and Sainsbury D., Dictionary of Microbiology and Molecular Biology 3rd ed., J. Wiley & Sons, Chichester, N.Y., 2001, and Fields Virology 5th ed., Knipe D. M. and Howley P. M. eds, Lippincott Williams & Wilkins, Philadelphia 2007.

The transitional term "comprising" is synonymous with "including," "containing," or "characterized by," is inclusive or open-ended and does not exclude additional, unrecited elements or method steps.

The transitional phrase "consisting of excludes any element, step, or ingredient not specified in the claim, but does not exclude additional components or steps that are unrelated to the invention such as impurities ordinarily associated therewith.

The transitional phrase "consisting essentially of limits the scope of a claim to the specified materials or steps and those that do not materially affect the basic and novel characteristic(s) of the claimed invention.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

A CEV serogroup polypeptide is a polypeptide, as defined above, derived from a virus of the California encephalitis (CEV) serogroup of the genus *Bunyavirus*, including, without limitation, any of the various isolates of the California encephalitis group of viruses such as California encephalitis, Guaroa, Inkoo, Jamestown Canyon, La Crosse, Snowshoe hare, and Tahyna (Lumbo) virus. The polypeptide need not be physically derived from the particular isolate in question, but may be synthetically or recombinantly produced.

Sequences for polypeptides and the nucleic acid sequences encoding for a number of CEV serogroup are known. Representative sequences are presented herein for LACV polypeptides. Refer to Campbell et al. 1999 *Virus Res* 61:137-144, for a comparison of M RNA among the CEV serogroup of viruses.

The terms "analog" and "mutein" refer to biologically active derivatives of the reference molecule, that retain desired activity, such as immunoreactivity in assays described herein, and/or the capability of eliciting an immune response as defined below, such as the ability to elicit neutralizing antibodies. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity and which are "substantially homologous" to the reference molecule as deemed below. A number of conserved and variable regions are known between the various isolates and, in general, the amino acid sequences of epitopes derived from these regions will have a high degree of sequence homology, e.g., amino acid sequence homology of more than 50%, generally more than 60%-70%, when the two sequences are aligned. The term "mutein" refers to peptides having one or more peptide mimics ("peptoids"). Preferably, the analog or mutein has at least the same immunoreactivity as the native molecule. Methods for making M polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25, 50 or 75 conservative or non-conservative amino acid substitutions, or any integer between 5-75, so long as the desired function of the molecule remains intact. One of skill in the art can readily determine regions of the molecule of interest that can tolerate change by reference to Kyte-Doolittle plots, well known in the art.

By "fragment" is intended a polypeptide consisting of only a part of the intact full-length polypeptide sequence and structure. The fragment can include a C-terminal deletion, an N-terminal deletion, and/or an internal deletion of the native polypeptide.

By a "M polypeptide" is meant a polypeptide, as defined above, encoded by the M region of the CEV serogroup in question. As explained above, the M region encodes the $G_C$ and $G_N$ polypeptides (also referred to formerly as G1 and G2), as well as the $NS_M$ polypeptide. The nucleotide and corresponding amino acid sequences for various CEV serogroup M regions are known. Refer to Campbell et al., supra.

As explained above, $G_C$ and/or $G_N$ polypeptides for use with the present invention include the full-length or substantially full-length proteins, as well as fragments, fusions of $G_C$ and $G_N$ polypeptides, or mutants of the proteins, which include one or more epitopes such that immunological activity is retained.

An "antigen" refers to a molecule, such as a polypeptide as deemed above, containing one or more epitopes (either linear, conformational or both) that will stimulate a host's immune system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated viruses. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide that expresses an antigen or antigenic determinant in vivo, such as in nucleic acid immunization applications, is also included in the definition of antigen herein.

For purposes of the present invention, immunogens can be derived from any of several known viruses of the CEV serogroup, as described above, for example LACV. By "immunogenic fragment" is meant a fragment of a CEV serogroup polypeptide that includes one or more epitopes and thus elicits one or more of the immunological responses described herein. An "immunogenic fragment" of a particular CEV serogroup protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

The term "epitope" as used herein refers to a sequence of at least about 3 to 5, preferably about 5 to 10 or 15, and not more than about 500 amino acids (or any integer therebetween), which define a sequence that by itself or as part of a larger sequence, elicits an immunological response in the subject to which it is administered. Often, an epitope will bind to an antibody generated in response to such sequence. There is no critical upper limit to the length of the epitope, which may comprise nearly the full-length of the protein sequence, or even a fusion protein comprising two or more epitopes from the CEV serogroup molecule in question. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots. One can use computer programs that employ the Kyte-Doolittle technique for hydropathy plots.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effecter cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T lymphocytes can be generated to allow for the future protection of an immunized host.

The ability of a particular immunogen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Methods of measuring cell-mediated immune response include measurement of intracellular cytokines or cytokine secretion by T-cell populations, or by measurement of epitope specific T-cells.

Thus, an immunological response as used herein may be one that stimulates the production of antibodies (e.g., neutralizing antibodies that block viruses of the CEV serogroup from entering cells and/or replicating by binding to the pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or δγ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. Moreover, the immunogenicity of the various polypeptides and polynucleotides described herein can be tested in appropriate animal models. Acceptable animal models for studying viruses of the CEV serogroup are known in the art.

An "immunogenic composition" is a composition that comprises an antigenic molecule where administration of the composition to a subject results in the development in the subject of a humoral and/or a cellular immune response to the antigenic molecule of interest. The immunogenic composition can be introduced directly into a recipient subject, such as by injection, inhalation, oral, intranasal and mucosal (e.g., intra-rectally or intra-vaginally) administration. An "immunogenic composition" also denotes a composition for use in diagnostic assays, described further below.

By "subunit vaccine" is meant a vaccine composition that includes one or more selected antigens but not all antigens, derived from or homologous to, an antigen from the CEV serogroup, such as LACV. Such a composition is substantially free of intact virus or viral particles. Thus, a "subunit vaccine" can be prepared from at least partially purified (preferably substantially purified) immunogenic polypeptides from the pathogen, or analogs thereof. The method of obtaining an antigen included in the subunit vaccine can thus include standard purification techniques, recombinant production, or synthetic production.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different isolates or strains of the CEV serogroup which antigenic determinants are not necessarily identical due to sequence variation, but which occur in equivalent positions in the CEV serogroup sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 99.9%-99.99% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure*, M. O. Dayhoff ed., vol. 5 (Suppl. 3):353-358, National Biomedical Research Foundation, Washington, D.C., which adapts the local homology algorithm of Smith and Waterman 1981 *Advances in Appl Math* 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non-nucleotidic backbones, for example, polyamide (e.g., peptide nucleic acids (PNAs)) and polymorpholino (commercially available from the AVI Biopharma, Corvallis, Oreg., as Neugene) polymers, and other synthetic sequence-specific nucleic acid polymers providing that the polymers contain nucleobases in a configuration, which allows for base pairing and base stacking, such as is found in DNA and RNA.

There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels, which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A "coding sequence" or a sequence which "encodes" a selected polypeptide, is a nucleic acid molecule which is transcribed and translated into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3$^1$-UTRs and when appropriate, leader sequences and enhancers, which collectively provide for the transcription and translation of a coding sequence in a host cell.

A "promoter" as used herein is a regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eukaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation" as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By "nucleic acid immunization" is meant the introduction of a nucleic acid molecule encoding one or more selected immunogens into a host cell, for the in vivo expression of the immunogen. The nucleic acid molecule can be introduced directly into a recipient subject, such as by injection, electroporation, inhalation, oral, intranasal and mucosal administration, or the like, or can be introduced ex vivo, into cells which have been removed from the host. In the latter case, the transformed cells are reintroduced into the subject where an immune response can be mounted against the immunogen encoded by the nucleic acid molecule.

An "antibody" intends a molecule that, through chemical or physical means, specifically binds to a polypeptide of interest. Thus, an anti-LACV $O_N$ antibody is a molecule that specifically binds to an epitope of a LACV $O_N$ protein. The term "antibody" as used herein includes antibodies obtained from both polyclonal and monoclonal preparations, as well as, the following: hybrid (chimeric) antibody molecules; F(ab')2 and F(ab) fragments; Fv molecules (non-covalent heterodimers; single-chain Fv molecules (sFv); dimeric and trimeric antibody fragment constructs; minibodies; humanized antibody molecules; and, any functional fragments obtained from such molecules, wherein such fragments retain immunological binding properties of the parent antibody molecule.

As used herein, a "solid support" refers to a solid surface such as a magnetic bead, latex bead, microtiter plate well, glass plate, nylon, agarose, acrylamide, and the like. "Immunologically reactive" means that the antigen in question will react specifically with anti-CEV serogroup antibodies present in a biological sample from a CEV-infected individual.

"Immune complex" intends the combination formed when an antibody binds to an epitope on an antigen.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands.

The term "primer" or "oligonucleotide primer" as used herein, refers to an oligonucleotide which acts to initiate synthesis of a complementary nucleic acid strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

As used herein, the term "probe" or "oligonucleotide probe" refers to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. Probes may be labeled in order to detect the target sequence. Such a label may be present at the 5' end, at the 3' end, at both the 5' and 3' ends, and/or internally. For example, when an "oligonucleotide probe" is to be used in a 5' nuclease assay, such as the TaqMan™ technique, the probe will contain at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers.

As used herein, the term "capture oligonucleotide" refers to an oligonucleotide; that contains a nucleic acid sequence complementary to a nucleic acid sequence present in the target nucleic acid analyte such that the capture oligonucleotide can "capture" the target nucleic acid. One or more capture oligonucleotides can be used in order to capture the target analyte. The polynucleotide regions of a capture oligonucleotide may be composed of DNA, and/or RNA, and/or synthetic nucleotide analogs. By "capture" is meant that the analyte can be separated from other components of the sample by virtue of the binding of the capture molecule to the analyte. Typically, the capture molecule is associated with a solid support, either directly or indirectly.

It will be appreciated that the hybridizing sequences need not have perfect complementarily to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by; the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences. An oligonucleotide that "specifically binds" to a LACV sequence denotes an oligonucleotide, e.g., a primer, probe or a capture oligonucleotide, that binds to a LACV sequence but does not bind to a sequence from other viruses of the CEV serogroup.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The Tm of a DNA molecule depends on its length and on its base composition. DNA molecules rich in $G_C$ base pairs have a higher Tm than those having an abundance of AT base pairs. Separated complementary strands of DNA spontaneously reassociate or anneal to form duplex DNA when the temperature is lowered below the Tm. The highest rate of nucleic acid hybridization occurs approximately 25° C. below the Tm. The Tm may be estimated using the following relationship: Tm=69.3+0.41(GC) %.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, semiconductor nanoparticles, dyes, metal ions, ligands (e.g., biotin, streptavidin or haptens) and the like. The term "fluoresces" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and β-galactosidase.

The terms "effective amount" or "pharmaceutically effective amount" of an immunogenic composition, as provided herein, refer to a nontoxic but sufficient amount of the composition to provide the desired response, such as an immunological response, and optionally, a corresponding therapeutic effect. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

The term "treatment" as used herein refers to either (1) the prevention of infection or reinfection (prophylaxis), or (2) the reduction or elimination of symptoms of the disease of interest (therapy).

By "mammalian host" is meant any mammal susceptible to infection with the particular member of the CEV serogroup in question. Such mammals include, without limitation, humans and other primates, including non-human primates such as chimpanzees and other apes and monkey species; rodents such as chipmunks, squirrels and laboratory animals including mice, rats and guinea pigs; rabbits, hares (such as the snowshoe hare); and domestic animals such as dogs and cats. The term does not denote a particular age. Thus, both adult and newborn subjects are intended to be covered. The invention described herein is intended for use in any of the above mammalian species, since the immune systems of all of these mammals operate similarly.

Bunyaviridae Viruses

Many viruses in the Bunyaviridae family are significant human, veterinary, and plant pathogens. The family is divided into five genera: *Bunyavirus, Phlebovirus, Nairovirus, Hantavirus*, and *Tospovirus*. All of the viruses, with the exception of the hantaviruses, are vector-borne. All infect vertebrates with the exception of Tospoviruses, which are plant viruses. The genera are further divided into serogroups based on antigenic relationships. La Crosse Virus (LACV) is a member of the genus *Bunyavirus*, California encephalitis virus (CEV) serogroup, and is a major cause of encephalitis and aseptic meningitis in children in the United States. The CEV serogroup includes other viruses that are known to cause human illness, such as Jamestown Canyon, California encephalitis, snowshoe hare (SSH), Tahyna, Inkoo, and Guaroa virus. Notable members of the Bunyaviridae family are listed in Table A.

TABLE A

Notable Bunaviridae family members

| Genus | Main Groups | Notable Virus Members |
|---|---|---|
| Bunyavirus | Anopheles A group | Tacaiuma |
| | | Virgin River |
| | Anopheles B group | Anopheles B |
| | Bakau group | Bakau |
| | Bunyamwera group | Bunyamwera |
| | | Cache Valley |
| | | Fort Sherman |
| | | Germiston |
| | | Ilesha |
| | | Kairi |
| | | Main drain |
| | | Shokwe |
| | | Wyeomyia |
| | | Xingu |
| | Bwamba group | Bwamba |
| | | Pongola |
| | Group C | Apeu |
| | | Carapani |
| | | Itaqui |
| | | Madrid |
| | | Marituba |
| | | Murutucu |
| | | Nepuyo |
| | | Oriboca |
| | | Ossa |
| | | Restan |
| | California encephalitis group | California encephalitis |
| | | Guaroa |
| | | Inkoo |
| | | Jamestown Canyon |
| | | La Crosse |
| | | Snowshoe hare |
| | | Tahyna (Lumbo) |
| | Capim group | Capim |
| | Gamboa group | Gamboa |
| | Guama group | Catu |
| | | Guama |
| | Koongol group | Koongol |
| | Minatitlan group | Minatitlan |
| | Nyando group | Nyando |
| | Olifantsvlei group | Olifantsvlei |
| | Patois group | Patois |
| | | Estero Real |
| | Simbu group | Akabane |
| | | Ingwavuma |
| | | Oropouche |

TABLE A-continued

Notable Bunaviridae family members

| Genus | Main Groups | Notable Virus Members |
|---|---|---|
| | Tete group | Bahig |
| | | Weldona |
| | Turlock | Turlock |
| Phlebo-virus | Sandfly fever group | Candiru |
| | | Punta Toro |
| | | Rift Valley fever |
| | | Sandfly fever Naples |
| | | Toscana |
| | | Sandfly fever |
| | | Sicilian |
| | | Chagres |
| | Uukuniemi group | Uukuniemi |
| Nairo-virus | Crimean-Congo HF group | Crimean-Congo hemorrhagic fever |
| | | Hazara |
| | Nairobi Sheep Disease Group | Nairobi sheep disease |
| | | Dugbe |
| | Dera Ghazi Khan group | Dera Ghazi Khan |
| | Hughes group | Hughes |
| | Qalyub group | Qalyub |
| | Sakhalin group | Sakhalin |
| | Thiafora group | Thiafora |
| Hanta-virus | Hantaan group | Hantaan |
| | | Dobrava |
| | | Seoul |
| | Puumala group | Puumala |
| | Sin Nombre Group | Sin Nombre |
| | | Bayou |
| | | Black Creek Canal |
| | | Andes |
| | | Laguna Negra |
| | | Juquitiba |
| | | Araraquara |
| | | Castelo dos Sonhos |
| | | Choclo |
| | Thottapalayam group | Thottapalayam |
| | Tospovirus | Tomato spotted wilt |
| | | Impatiens necrotic spot |
| | | Groundnut bud necrosis |

The Bunyaviruses have tripartite, negative-sense RNA genomes. Consensus nucleotide sequences are present in the 3' termini of all three RNA segments and cause the segment ends to bind to complementary sequences on 5' ends to form panhandle structures. The consensus sequences may serve as transcriptase recognition structures.

The genomic coding strategies of LAC virus are known: the large (L) RNA segment (6980 nucleotides (nt)) codes for the polymerase; the medium (M) RNA segment (4526 nt) codes for a polyprotein that is post-translationally processed, yielding the $G_C$ and $G_N$ glycoproteins (also referred to formerly as G1 and G2) and a nonstructural protein $NS_M$; and the small (S) RNA segment (984 nt) codes for the nucleocapsid (N) protein and a nonstructural NSs in overlapping reading frames.

The pleomorphic virion is approximately 90-100 nm in diameter. The virion consists of the three genome segments encapsidated with the N protein to form helical structures, a few nucleocapsid-associated polymerase molecules needed to transcribe the negative-sense viral genome, and a surrounding host-derived lipid envelope containing virus-encoded glycoprotein spikes.

Aspects of the present invention are based on the discovery of reagents and methods for preventing, treating and diagnosing infection caused by the CEV serogroup of viruses, such as LACV infection. The methods use attenuated or inactivated viruses, or subunit compositions, to treat or prevent infection. Moreover, polypeptides and polynucleotides derived from the CEV serogroup can be used in diagnostic assays to identify infected subjects.

A more detailed discussion is provided below regarding viruses of the CEV serogroup, various CEV polypeptide and polynucleotide immunogens for use in the subject compositions and methods, as well as, production of the proteins, antibodies thereto and methods of using the proteins and antibodies.

CEV Subgroup Polypeptides and Polynucleotides

As explained above, the CEV serogroup family of viruses belongs to the *Bunyavirus* genus and are enveloped, minus-sense RNA viruses. The RNA of the viral genome is tripartite, consisting of three fragments generally designated as S, M and L for small, medium and large genome fragments, respectively. The M segment encodes two envelope glycoproteins, termed $G_C$ and $G_N$, and a nonstructural protein ($NS_M$), in a single open reading frame. The S segment encodes a nucleocapsid protein, termed N and an additional nonstructural protein termed NSs, in overlapping reading frames. The L segment of the genome encodes an RNA-dependent RNA polymerase.

Several distinct viruses of the CEV serogroup are found in association with specific mammalian hosts worldwide. Polypeptides and polynucleotides derived from any of the various isolates of the CEV serogroup will find use herein, including without limitation, any of the California encephalitis group of viruses such as California encephalitis, Guaroa, Inkoo, Jamestown Canyon, La Crosse, Snowshoe hare, and Tahyna (Lumbo) virus.

Thus, immunogens for use in subunit vaccines and diagnostics include those derived from one or more of the above regions from any CEV serogroup strain or isolate. Either the full-length proteins, fragments thereof containing epitopes of the full-length proteins, as well as fusions of the various regions or fragments thereof, will find use in the subject compositions and methods. Thus, for example, immunogens for use in such compositions can be derived from the $G_C$ and/or $G_N$ envelope regions of any of these CEV serogroup isolates. Immunogenic fragments of the envelope proteins, which comprise epitopes may be used in the subject compositions and methods. For example, fragments of the $G_C$ and/or $G_N$ polypeptide can comprise from about 5 contiguous amino acids to nearly the full-length of the molecule (e.g., at least or equal to 6, 10, 25, 50, 75, 100, 200, 250, 300, 350, 400, 450 or more contiguous amino acids of a $G_C$ and/or $G_N$ polypeptide, or any integer between the stated numbers). Additionally, the entire M region, including $G_C$, $G_N$ and NSm, as well as, complexes of the $G_C$ and $G_N$ polypeptides, with or without NSm, or epitopes from the $G_C$ polypeptide fused to epitopes of the $G_N$ polypeptide with or without NSm, can be used in the subject compositions and methods.

Moreover, the $G_C$ and/or $G_N$ polypeptides for use herein may lack all or a portion of the transmembrane binding domain and/or the cytoplasmic tail found in the C-terminus of the envelope. Thus, aspects of the present invention contemplate the use of envelope polypeptides which retain the transmembrane binding domain and cytoplasmic tail, as well as polypeptides, which lack all or a portion of the transmembrane binding domain and/or the cytoplasmic tail. The location of such domains can be readily determined using computer programs and algorithms well known in the art, such as the Kyte-Doolittle technique.

Polynucleotides and polypeptides for use with the some embodiments can be obtained using standard techniques. For example, polynucleotides encoding the various immunogenic polypeptides can be isolated from a genomic library derived from nucleic acid sequences present in, for example, the plasma, serum, or tissue homogenate of a CEV serogroup-infected individual. Additionally, the nucleic acid can be obtained directly from the virus in question.

Alternatively, viruses of the CEV serogroup can be isolated from infected mosquitos. Once obtained, the virus can be propagated using known techniques, such as described in Pekosz et al. 1995 *J Virol* 69:3475-3481. Generally, viruses of the CEV serogroup are grown in Vero or BHK cell lines. An amplification method such as PCR can be used to amplify polynucleotides from either CEV serogroup genomic RNA or cDNA encoding therefor. Alternatively, polynucleotides can be synthesized in the laboratory, for example, using an automatic synthesizer.

Polynucleotides can comprise coding sequences for the various polypeptides which occur naturally or can include artificial sequences which do not occur in nature. These polynucleotides can be ligated to form a coding sequence for a fusion protein, if desired, using standard molecular biology techniques.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements. The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing.

If present, the signal sequence can be the native leader found in association with the CEV serogroup polypeptide of interest. For example, if the CEV serogroup polypeptide being expressed is the CEV serogroup $G_N$ polypeptide, all or a portion of the native $G_N$ leader sequence can be included. Alternatively, a heterologous signal sequence can be present which can increase the efficiency of secretion. A number of representative leader sequences are known in the art and include, without limitation, the yeast a-factor leader, the TPA signal peptide, the Ig signal peptide, and the like. Sequences for these and other leader sequences are well known in the art.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer, the enhancer/promoter derived from the long terminal repeat (LTR) of the Rous Sarcoma Virus and elements derived from human CMV, such as elements included in the CMV intron A sequence. The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the polypeptide of interest. Mutants or analogs of CEV serogroup polynucleotides and polypeptides for use in the subject compositions may be prepared by the deletion of a portion of the sequence encoding the molecule of interest, by insertion of a sequence, and/or by substitution of one or more nucleotides within the sequence. Techniques for modifying nucleotide sequences, such as site-directed mutagenesis, and the like, are well known to those skilled in the art. It is also to be understood that any of the mutations described herein can be introduced into virus that are related to the LACV viruses described herein at conserved positions (e.g., position 148) so as to create attenuated virus, vaccines, and immunogenic compositions. It is also contemplated that these mutations can be introduced within 1, 2, 3, 4, 5, 6, 7, 8, 9, or 10 amino acid positions before or after the identified sites of mutation described herein (e.g., 148) and obtain an attenuated virus, vaccine, or immunogenic composition. In order to facilitate recombinant expression, the molecule of interest can be expressed as a fusion protein.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook, J., Russell, D. W. (2001) *Molecular Cloning: A Laboratory Manual*, the third edition, Cold Spring Harbor Laboratory Press, Cold Spring Harbor, N.Y. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, Vero cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis,* and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosacchcromyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

Nucleic acid molecules comprising nucleotide sequences of interest can be stably integrated into a host cell genome or maintained on a stable episomal element in a suitable host cell using various gene delivery techniques well known in the art.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

For representative methods for obtaining CEV virus sequences recombinantly, see, e.g., Pekosz et al. 1995 *J Virol* 69:3475-3481. Once produced, the various polypeptides and polynucleotides can be formulated into subunit vaccine compositions for use as prophylactics or therapeutics, or used in diagnostic assays, as described below.

Inactivated CEV Serogroup Vaccines

Aspects of the invention also include compositions comprising inactivated (or killed) viruses of the CEV serogroup, such as inactivated LACV, and methods for the production thereof Inactivated viral compositions can be used as prophylactic or therapeutic vaccines. Preferably the inactivated vaccine compositions comprise an amount of inactivated virus equivalent to a virus titer of from about $10^3$ to $10^{12}$ plaque forming units (PFU) or $10^3$ to $10^{12}$ tissue culture infectious dose 50 ($TCID_{50}$) per milliliter, preferably $10^4$ to $10^{10}$ PFU or $TCID_{50}$ even more preferably from about $10^5$ to $10^9$ PFU or $TCID_{50}$ per milliliter, or any dose within these stated ranges. The vaccine compositions comprise a sufficient amount of the virus antigen to produce an immunological response in a mammal, as defined above. Such compositions are described more fully below.

Virus can be obtained directly from the ATCC as described above. Other sources of virus include plasma, serum, or tissue homogenates from CEV serogroup infected individuals. Alternatively, virus can be isolated from infected mosquitos, or can be genetically modified or chimerized. Once obtained, the virus can be propagated using known techniques, such as described in Pekosz et al. 1995 *J Virol* 69:3475-3481. Viruses of the CEV serogroup are generally cultured in either an adherent or suspension mammalian cell culture.

Methods of inactivating or killing viruses are known in the art. Such methods destroy the ability of the viruses to infect mammalian cells. Inactivation can be achieved using either chemical or physical means. Chemical means for inactivating a virus include treatment of the virus with an effective amount of one or more of the following agents: detergents, formaldehyde, formalin, β-propiolactone, or UV light. Other methods of viral inactivation are known in the art, such as for example binary ethylamine, acetyl ethyleneimine, or gamma irradiation.

Attenuated CEV Serogroup Vaccines

Aspects of the invention also include compositions (e.g., immunogenic compositions) comprising, consisting of, or consisting essentially of attenuated viruses of the CEV serogroup. As used herein, attenuation refers to the decreased virulence of the CEV virus in a mammalian host. The compositions can be used as prophylactics or therapeutics. Methods of attenuating viruses are known in the art. Such methods include serial passage of the virus in cultured cells as described above (e.g., mammalian cell culture, preferably BHK or VERO cells), until the virus demonstrates attenuated function. The temperature at which the virus is grown can be any temperature at which tissue culture passage attenuation occurs. Attenuated function of the virus after one or more passages in cell culture can be measured by one skilled in the art. Evidence of attenuated function may be indicated by decreased levels of viral replication or by decreased virulence in an animal model. Acceptable animal models for studying viruses of the CEV serogroup are known in the art.

Other methods of producing an attenuated viruses from the CEV serogroup include passage of the virus in cell culture at suboptimal or "cold" temperatures and/or introduction of attenuating mutations into the viral genome by random mutagenesis (e.g., chemical mutagenesis) or site-directed mutagenesis.

The attenuated virus derivatives of the CEV serogroup are produced in several ways, such as for example, by introduction of temperature sensitive (ts) mutations either with or without chemical mutagenesis (e.g., 5-fluorouracil), by passage in culture at "cold" temperatures. Such cold adaptation includes passage at temperatures between about 20° C. to about 32° C., and preferably between temperatures of about 22° C. to about 30° C., and most preferably between temperatures of about 24° C. and 28° C. The cold adaptation or attenuation may be performed by passage at increasingly reduced temperatures to introduce additional growth restriction mutations. The number of passages required to obtain safe, immunizing attenuated virus is dependent at least in part on the conditions employed. Periodic testing of the virus culture for virulence and immunizing ability in animals (e.g., mouse, primate) can readily determine the parameters for a particular combination of tissue culture and temperature. The attenuated vaccine and/or immunogenic composition will typically be formulated in a dose of from about $10^2$ to $10^{12}$ PFU or $10^2$ to $10^{12}$ tissue culture infectious dose 50 ($TCID_{50}$) per milliliter, preferably $10^4$ to $10^{10}$ PFU or $TCID_{50}$, even more preferably from about $10^5$ to $10^9$ PFU or $TCID_{50}$ per milliliter, or any dose within these stated ranges.

Viruses of the CEV serogroup can also be attenuated by mutating one or more of the various viral regions to reduce expression of the viral structural or nonstructural proteins. The attenuated CEV may comprise, consist, or consist essentially of one or more additions, deletions or insertions in one or more of the regions of the viral genome. For example, the hydrophobic domains of CEV serogroup proteins are targets for genetic mutation to develop attenuated CEV serogroup vaccines. The hydrophobic domains are also targets for small molecule inhibitors of CEV viruses. The hydrophobic domains may also be used to generate antibodies specific to those regions to treat or prevent CEV serogroup infection.

Transmembrane and hydrophobic regions of the CEV serogroup proteins are readily identified using programs well known in the art, such as the Kyte-Doolittle technique.

In one embodiment, the virus is attenuated by ablation at the translational level without deletion of the gene or of a segment thereof, by, e.g., introducing a translational termination codon into a translational open reading frame (ORF) (e.g., the rLACVdelNSs mutation (Blakqori, G. and Weber F. 2005 *J Virol* 79:10420-10428). Blakqori and Weber generated a mutant virus with an inactivated NSs gene. Because the N and NSs reading frames overlap, complete deletion of the NSs gene is not possible without affecting the N gene. Referring to Blakqori and Weber, two tandem ATG start codons of NSs were changed to ACG and the adjacent, downstream codon was changed to a stop codon. The resulting antigenomic LACV S construct expresses an unaltered N protein but no NSs. Infection with bunyaviruses is known to induce a strong shutoff of host cell protein synthesis. The rLACVdelNS$_S$ virus, by contrast, displayed weaker shutoff. Thus, the rLACVdelNS$_S$ mutation attenuates the virus.

Compositions Comprising CEV Serogroup, Polypeptides, and Polynucleotides

Aspects of the invention provide compositions including the above-described viruses of the CEV serogroup (e.g., inactivated and attenuated), as well as CEV serogroup polypeptides and/or polynucleotides. Some embodiments may comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Some embodiments can also contain liquids or excipients, such as water, saline, glycerol, dextrose, ethanol, or the like, singly or in combination, as well as, substances such as wetting agents, emulsifying agents, or pH buffering agents. Liposomes can also be used as a carrier for a composition of the invention and are described below.

If desired, co-stimulatory molecules which improve immunogen presentation to lymphocytes, such as B7-1 or B7-2, or cytokines such as GM-CSF, IL-2, and IL-12, can be included.

Optionally, adjuvants can also be included in a composition. Adjuvants which can be used include, but are not limited to: (1) aluminum salts (alum), such as aluminum hydroxide, aluminum phosphate, aluminum sulfate, etc.; (2) oil-in-water emulsion formulations (with or without other specific immunostimulating agents; (3) saponin adjuvants, such as QS21 may be used or particles generated therefrom such as ISCOMs (immunostimulating complexes); (4) Complete Freund's Adjuvant (CFA) and Incomplete Freund's Adjuvant (IFA); (5) cytokines, such as interleukins (IL-1, IL-2, IL-4, IL-5, IL-6, IL-7, IL-12, interferons (e.g., gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT); (7) MPL or 3-O-deacylated MPL (3dMPL); (8) combinations of 3dMPL with, for example, QS21 and/or oil-in-water emulsions; (9) oligonucleotides comprising CpG motifs; (10) a polyoxyethylene ether or a polyoxyethylene ester; (11) a polyoxyethylene sorbitan ester surfactant in combination with an octoxynol or a polyoxyethylene alkyl ether or ester surfactant in combination with at least one additional non-ionic surfactant such as an octoxynol; (12) a saponin and an immunostimulatory oligonucleotide such as a CpG oligonucleotide; (13) an immunostimulant and a particle of metal salt; and (14) other substances that act as immunostimulating agents to enhance the effectiveness of the composition.

Some embodiments may comprise, consist of or consist essentially of a therapeutically effective amount of the desired CEV serogroup molecule or inactivated or attenuated viruses of the CEV serogroup and any other of the above-mentioned components, as needed. By "therapeutically effective amount" is meant an amount of a protein or DNA encoding the same which will induce an immunological response, preferably a protective immunological response, in the individual to which it is administered, if the composition is to be used as a vaccine. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

Administration

The immunogenic compositions (both DNA and protein) can be prepared as injectables, either as liquid solutions or suspensions; solid forms suitable for solution in, or suspension in, liquid vehicles prior to injection may also be prepared. Thus, once formulated, the compositions are conventionally administered parenterally, e.g., by injection, either subcutaneously or intramuscularly. For example, the immunogen is preferably administered intramuscularly to a large mammal, such as a primate, for example, a baboon, chimpanzee, or human. Additional formulations suitable for other modes of administration include oral and pulmonary formulations, suppositories, and transdermal formulations, aerosol, intranasal, oral formulations, and sustained release formulations. For example, the immunogenic compositions described herein can be provided as DNA immunogens (e.g., DNA vaccination) intradermally, intramuscularly, or intranasally. (See e.g., *Intervirology* 43: 312321 (2000) and *Human Gene Therapy* 10:1649-1658 (1999), herein expressly incorporated by reference in its entirety).

In one set of experiments, an immunogenic composition prepared as described herein (e.g., LACV/human/1960) was provided to three-week old Swiss Webster weanling mice (n=6/dose) intranasally (IN) in 10 ul volume or intraperitoneally (IP) in 100 ul volume in serial dilutions. The 50% lethal dose (LD50) and 50% infectious dose (ID50) were determined. In both groups, clinical disease was first noted on day 6. Twenty days post-inoculation, the LD50 was determined and the mice were tested for the development of a neutralizing antibody response. The LD50 for both IN and IP groups were similar (2.4 and 2.3 log 10 PFU, respectively). To determine the ID50 titer, mice were considered infected if they either developed clinical disease or a serum neutralizing antibody titer. The ID50 titers (1.5 and 1.6 log 10 PFU for the IN and IP routes, respectively) were slightly lower than the LD50 titers indicating that LACV can cause subclinical infection in weanling mice at low doses.

Controlled or sustained release formulations are made by incorporating the active agent into carriers or vehicles such as liposomes, nonresorbable impermeable polymers such as ethylenevinyl acetate copolymers, swellable polymers such as hydrogels, or resorbable polymers such as collagen and certain polyacids or polyesters such as those used to make resorbable sutures. The immunogens can also be delivered using implanted mini-pumps, well known in the art.

The immunogens described herein can also be provided via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK" recombinant can be selected by culturing the cells in the presence of 5-bromodeoxyuridine and picking viral plaques resistant thereto.

The immunogens can be provided either to a mammal that is not infected with a virus of the CEV serogroup or can be administered to a CEV-infected mammal.

Dosage treatment may be a single dose schedule or a multiple dose schedule. Preferably, the effective amount is sufficient to bring about treatment or prevention of disease symptoms. The exact amount necessary will vary depending on the subject being treated, the age and general condition of the individual to be treated; the capacity of the individual's immune system to synthesize antibodies; the degree of protection desired; the severity of the condition being treated; the particular macromolecule selected and its mode of administration, among other factors. An appropriate effective amount can be readily determined by one of skill in the art. A "therapeutically effective amount" will fall in a relatively broad range that can be determined through routine trials using in vitro and in vivo models known in the art.

Thus, for example, if polypeptide immunogens are delivered, generally the amount administered will be about 0.1 µg to about 750 µg of immunogen per dose, or any amount between the stated ranges, such as 1 µg to about 500 µg, 5 µg to about 250 µg, 10 µg to about 100 µg, 10 µg to about 50 µg, such as 4, 5, 6, 7, 8, 10, 20, 25, 30, 35, 40, 50, 60, 70, 80, 90, 100, etc., µg per dose.

As explained above, expression constructs, such as constructs encoding individual CEV serogroup immunogens or fusions, may be used for nucleic acid immunization to stimulate an immunological response, such as a cellular immune; response and/or humoral immune response, using standard gene delivery protocols. Methods for gene delivery are known in the art. Genes can be delivered either directly to the subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1.

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described in the scientific and patent literature. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV. Such retroviruses may be readily obtained from depositories or collections such as the American Type Culture Collection ("ATCC"; 10801 University Blvd., Manassas, Va. 20110-2209), or isolated from known sources using commonly available techniques.

Additionally, biolistic delivery systems employing particulate carriers such as gold and tungsten, are useful for delivering the expression constructs of the present invention. The particles are coated with the construct to be delivered and accelerated to high velocity, generally under a reduced atmosphere, using a gun powder discharge from a "gene gun".

The amount of CEV serogroup DNA delivered will generally be about 1 µg to 500 mg of DNA (e.g., at least or equal to 5 µg to 100 mg of DNA, e.g., 10 µg to 50 mg, or 100 µg to 5 mg, such as 20, 30, 40, 50, 60, 100, 200 µg and so on, to 500 µg DNA, and any integer between the stated ranges).

Administration of CEV serogroup virions, polypeptide or polynucleotide compositions can elicit a cellular immune response, and/or an anti-CEV serogroup antibody titer in the mammal that lasts for at least 1 week, 2 weeks, 1 month, 2 months, 3 months, 4 months, 6 months, 1 year, or longer. The compositions can also be administered to provide a memory response. If such a response is achieved, antibody titers may decline over time, however exposure to virus or the particular immunogen results in the rapid induction of antibodies, e.g., within only a few days. Optionally, antibody titers can be maintained in a mammal by providing one or more booster injections of the compositions, at e.g., 2 weeks, 1 month, 2 months, 3 months, 4 months, 5 months, 6 months, 1 year, or more after the primary injection.

Preferably, an antibody titer of at least 10, 100, 150, 175, 200, 300, 400, 500, 750, 1,000, 1,500, 2,000, 3,000, 5,000, 10,000, 20,000, 30,000, 40,000, 50,000 (geometric mean titer), or higher, is elicited, air any number between the stated titers, as determined using a standard immunoassay.

CEV Serogroup Antibodies

The CEV serogroup immunogens can be used to produce CEV-specific polyclonal and monoclonal antibodies. CEV-specific polyclonal and monoclonal antibodies specifically bind to CEV serogroup antigens. Polyclonal antibodies can be produced by administering the immunogen to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against CEV serogroup-specific epitopes present in the proteins can also be readily produced. Normal B cells from a mammal, such as a mouse, immunized with a CEV serogroup protein, can be fused with, for example, HAT-sensitive mouse myeloma cells to produce hybridomas. Hybridomas producing CEV serogroup-specific antibodies can be identified using RIA or ELISA and isolated by cloning in semi-solid agar or by limiting dilution. Clones producing CEV serogroup-specific antibodies are isolated by another round of screening.

It may be desirable to provide chimeric antibodies, especially if the antibodies are to be used in preventive or therapeutic pharmaceutical preparations, such as for providing passive protection against CEV serogroup infection, as well as in CEV serogroup diagnostic preparations. Chimeric antibodies composed of human and non-human amino acid sequences may be formed from the mouse monoclonal antibody molecules to reduce their immunogenicity in humans.

Antibody molecule fragments, e.g., F(ab')$_2$, Fv, and sFv molecules, that are capable of exhibiting immunological binding properties of the parent monoclonal antibody molecule can be produced using known techniques. In the alternative, a phage-display system can be used to expand monoclonal antibody molecule populations in vitro.

Once generated, the phage display library can be used to improve the immunological binding affinity of the Fab molecules using known techniques. The coding sequences for the heavy and light chain portions of the Fab molecules selected from the phage display library can be isolated or synthesized, and cloned into any suitable vector or replicon for expression. Any suitable expression system can be used, including those described above.

Antibodies which are directed against CEV serogroup epitopes are particularly useful for detecting the presence of CEV or viral antigens in a sample, such as a serum sample from a CEV serogroup-infected human. An immunoassay for a CEV serogroup antigen may utilize one antibody or several antibodies. An immunoassay for a CEV serogroup antigen may use, for example, a monoclonal antibody directed towards a CEV serogroup epitope, a combination of monoclonal antibodies directed towards epitopes of one CEV serogroup polypeptide, monoclonal antibodies directed towards epitopes of different CEV serogroup polypeptides, polyclonal antibodies directed towards the same CEV serogroup antigen, polyclonal antibodies directed towards different CEV serogroup antigens, or a combination of monoclonal and polyclonal antibodies. Immunoassay protocols may be based, for example, upon competition, direct reaction, or sandwich type assays using, for example, labeled antibody and are described further below. The labels may be, for example, fluorescent, chemiluminescent, or radioactive.

The CEV serogroup antibodies may further be used to isolate CEV serogroup particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind CEV serogroup particles or antigens from a biological sample, such as blood or plasma. The bound CEV serogroup particles or antigens are recovered from the column matrix by, for example, a change in pH.

CEV Serogroup Diagnostic Assays

As explained above, the CEV serogroup immunogens, antibodies and polynucleotides can be used in assays to identify CEV serogroup infection, such as LACV infection. Protein assays include Western blots; agglutination tests; enzyme-labeled and mediated immunoassays, such as ELISAs; biotin/avidin type assays; radioimmunoassays, immunoelectrophoresis; immunoprecipitation, and the like. The reactions generally include revealing labels such as fluorescent, chemiluminescent, radioactive, enzymatic labels or dye molecules, or other methods for detecting the formation of a complex between the mimetic and the antibody or antibodies reacted therewith.

The aforementioned assays generally involve separation of unbound antibody or antigen in a liquid phase from a solid phase support to which antigen-antibody complexes are bound. Solid supports which can be used in the practice of some embodiments include substrates or supports such as nitrocellulose (e.g., in membrane or microtiter well form); polyvinylchloride (e.g., sheets or microtiter wells), polystyrene latex (e.g., beads or microtiter plates), polyvinylidine fluoride; diazotized paper; nylon membranes; activated beads, magnetically responsive beads, and the like.

Typically, a solid support is first reacted with a solid phase component (e.g., one or more CEV serogroup viral antigens or antibodies) under suitable binding conditions such that the component is sufficiently immobilized to the support. Sometimes, immobilization to the support can be enhanced by first coupling to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigen or antibody to the support include polysaccharides, polylactic acids, polyglycolic acids, polymeric amino acids, amino acid copolymers, and the like. Such molecules and methods of coupling these molecules are well known to those of ordinary skill in the art.

After reacting the solid support with the solid phase component, any non-immobilized solid-phase components are removed from the support by washing, and the support-bound component is then contacted with a biological sample suspected of containing the ligand component (i.e., CEV serogroup antigens or antibodies) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with one or more CEV serogroup epitopes or antibodies according to the present invention. A biological sample containing or suspected of containing either anti-CEV virus immunoglobulin molecules or CEV serogroup antigens is then added to the coated wells. After a period of incubation sufficient to allow antigen-antibody binding, the plate(s) can be washed to remove unbound moieties and a detectably labeled secondary binding molecule added. The secondary binding molecule is allowed to react with any captured sample, the plate washed and the presence of the secondary binding molecule detected using methods well known in the art.

Thus, in one particular embodiment, the presence of bound CEV serogroup ligands from a biological sample can be readily detected using a secondary binder comprising an antibody directed against the antibody ligands. A number of anti-human immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the CEV serogroup epitopes or antibodies and ligands specific for these molecules form complexes under precipitating conditions. In one particular embodiment, the molecules can be attached to a solid phase particle (e.g., an agarose bead or the like) using coupling techniques known in the art, such as by direct chemical or indirect coupling. The coated particle is then contacted under suitable binding conditions with a biological sample suspected of containing CEV serogroup antibodies or antigens. Cross-linking between bound antibodies causes the formation of complex aggregates which can be precipitated and separated from the sample using washing and/or centrifugation. The reaction mixture can be analyzed to determine the presence or absence of complexes using any of a number of standard methods, such as those immunodiagnostic methods described above.

In yet a further embodiment, an immunoaffinity matrix can be provided, wherein, for example, a polyclonal population of antibodies from a biological sample suspected of containing CEV serogroup antibodies is immobilized to a substrate. An initial affinity purification of the sample can be carried out using immobilized antigens. The resultant sample preparation will thus only contain anti-CEV serogroup moieties, avoiding potential nonspecific binding properties in the affinity support. A number of methods of immobilizing immunoglobulins (either intact or in specific fragments) at high yield and good retention of antigen binding activity are known in the art. Once the immunoglobulin molecules have been immobilized to provide an immunoaffinity matrix, labeled molecules are contacted with the bound antibodies under suitable binding conditions. After any non-specifically bound CEV serogroup epitope has been washed from the immunoaffinity support, the presence of bound antigen can be determined by assaying for label using methods known in the art.

The above-described assay reagents, including CEV serogroup polypeptides and/or antibodies thereto, the solid supports with bound reagents, as well as other detection reagents, can be provided in kits, with suitable instructions and other necessary reagents, in order to conduct the assays as described above. The kit may also include control formulations (positive and/or negative), labeled reagents when the assay format requires same and signal generating reagents (e.g., enzyme substrate) if the label does not generate a signal directly. Instructions (e.g., written, tape, VCR, CD ROM, etc.) for carrying out the assay usually will be included in the kit. The kit can also contain, depending on the particular assay used, other packaged reagents and materials (i.e., buffers and the like). Standard assays, such as those described above, can be conducted using these kits.

Nucleic acid-based assays can be conducted using CEV serogroup oligonucleotides and polynucleotides described above. For example, probe-based assays, such as hybridization assays, can be conducted that utilize oligonucleotides from the specific virus in question. These assays may also utilize nucleic acid amplification methods such as reverse transcriptase-polymerase chain reaction (RT-PCR), PCR and ligase chain reaction (LCR).

Thus, the various CEV serogroup polynucleotide sequences may be used to produce probes and primers which can be used in assays for the detection of nucleic acids in test samples. The probes and primers may be designed from conserved nucleotide regions of the polynucleotides of interest or from non-conserved nucleotide regions of the polynucleotide of interest. The design of such oligonucleotides is routine in the art. Generally, nucleic acid probes are developed from non-conserved or unique regions when maximum specificity is desired, and nucleic acid probes are developed from conserved regions when assaying for nucleotide regions that are closely related to, for example, different CEV serogroup isolates.

When utilizing a hybridization-based detection system, a nucleic acid probe is chosen that is complementary to a target nucleic acid sequence. By selection of appropriate conditions, the probe and the target sequence "selectively hybridize", or bind to each other to form a hybrid molecule. An oligonucleotide that "selectively hybridizes" to a LACV sequence under hybridization conditions described below, denotes an oligonucleotide, e.g., a primer, probe or a capture oligonucleotide, that binds to a LACV sequence but does not bind to a sequence from other viruses of the CEV serogroup. In one embodiment of the present invention, a nucleic acid molecule is capable of hybridizing selectively to a target sequence under moderately stringent hybridization conditions. In the context of the present invention, moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art. Hybrid molecules can be formed, for example, on a solid support, in solution, and in tissue sections. The formation of hybrids can be monitored by inclusion of a reporter molecule, typically, in the probe. Such reporter molecules, or detectable elements include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well known (see, for example, Sambrook, et al., supra.)

As explained above, the primers and probes may be used in polymerase chain reaction (PCR)-based techniques, such as RT-PCR, to detect CEV serogroup infection in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repented to geometrically increase the number of target sequence molecules. The PCR method for amplifying target nucleic acid sequences in a sample is well known in the art and has been described in, e.g., Innis et al. (eds.) PCR Protocols (Academic Press, NY 1990).

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers that are present in molar excess. Polymerization is catalyzed in the presence of the four deoxyribonucleotide triphosphates (dNTPs dATP, dGTP, dCTP and dTTP) using a primer- and template-dependent polynucleotide polymerizing agent, such as any enzyme capable of producing primer extension products, for example, thermostable DNA polymerases isolated from *Therrmus aquaticus* (Taq), available from a variety of sources (for example, Perkin Elmer). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. Preferably, PCR is carried out with a commercially available thermal cycler, e.g., Perkin Elmer.

RNAs may be amplified by reverse transcribing the RNA into cDNA, and then performing PCR (RT-PCR), as described above. Alternatively, a single enzyme may be used for both steps.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. If the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved.

The fluorogenic 5' nuclease assay, known as the TaqMan™ assay (Perkin-Elmer), is a powerful and versatile PCR-based detection system for nucleic acid targets. Hence, primers and probes derived from conserved and/or non-conserved regions of the CEV serogroup genome in question can be used in TaqMan™ analyses to detect the presence of infection in a biological sample. Analysis is performed in conjunction with thermal cycling by monitoring the generation of fluorescence signals. The assay system dispenses with the need for gel electrophoretic analysis, and is capable of generating quantitative data allowing the determination of target copy numbers. For example, standard curves can be produced using serial dilutions of previously quantified CEV serogroup suspensions. A standard graph can be produced with copy numbers of each of the panel members against which sample unknowns can be compared.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher. Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TaqMan™ probe is designed to hybridize to a target sequence within the desired PCR product. The 5' end of the TaqMan™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence that can be detected.

Accordingly, the present invention relates to methods for amplifying a target CEV serogroup nucleotide sequence using a nucleic acid polymerase having 5' to 3' nuclease activity, one or more primers capable of hybridizing to the CEV serogroup target sequence, and an oligonucleotide probe capable of hybridizing to the CEV serogroup target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

While the length of the primers and probes can vary, the probe sequences are selected such that they have a higher melt temperature than the primer sequences. Preferably, the probe sequences have an estimated melt temperature that is about 10° C. higher than the melt temperature for the amplification primer sequences. Hence, the primer sequences are generally shorter than the probe sequences. Typically, the primer sequences are in the range of between 10-75 nucleotides long, more typically in the range of 20-45. The typical probe is in the range of between 10-50 nucleotides long, more typically 15-40 nucleotides in length. Representative primers and probes useful in TaqMan™ assays are described above.

As is readily apparent, design of the assays described herein are subject to a great deal of variation, and many formats are known in the art. The above descriptions are merely provided as guidance and one of skill in the art can readily modify the described protocols, using techniques well known in the art.

The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly.

Chimeric Attenuated Viruses

Aspects of the present invention provide infectious, chimeric viruses of the Bunyaviridae family that are attenuated and capable of eliciting a prophylactic or therapeutic immune response in mammalian patients susceptible to viral infection. Some embodiments also include methods and compositions for designing and producing attenuated, chimeric viruses of the Bunyaviridae family, as well as methods and compositions for prophylaxis and treatment of infection by viruses of the Bunyaviridae family.

Chimeric Bunyaviridae embodiments are recombinantly engineered to incorporate nucleotide sequences from more than one virus strain or subgroup to produce an infectious, chimeric virus or subviral particle. In this manner, candidate vaccine viruses are recombinantly engineered to elicit an immune response against a virus of the Bunyaviridae family in a mammalian host, including humans, non-human primates, and livestock/food animals. Chimeric Bunyaviridae as described herein may elicit an immune response to a specific Bunyaviridae subgroup or strain, or they may elicit a polyspecific response against multiple Bunyaviridae subgroups or strains.

In exemplary embodiments, heterologous genes, gene segments, or single or multiple nucleotides of one virus of the Bunyaviridae family are added to a partial or complete genome or substituted therein by counterpart sequence(s) from a heterologous virus of the Bunyaviridae family to produce a chimeric genome. The chimeric Bunyaviridae described herein may include a partial or complete "recipient" Bunyaviridae genome from one viral strain or subgroup virus combined with an additional or replacement "donor" gene or gene segment of a different Bunyaviridae strain or subgroup virus.

In preferred embodiments, chimeric Bunyaviridae incorporate a partial or complete LACV genome combined with a heterologous gene or gene segment from a different Bunyaviridae subgroup or strain. For example, one type of chimeric Bunyaviridae incorporates a chimeric genome comprised of a partial or complete genome of a LACV combined with a heterologous gene or gene segment from a hantavirus or Jamestown Canyon virus.

Heterologous donor genes or gene segments from one Bunyaviridae or subgroup are combined with or substituted within a recipient genome that serves as a genetic background for insertion or addition of the donor gene or gene segment. Thus, the recipient genome acts as a vector to import and express heterologous genes or gene segments to yield chimeric Bunyaviridae that exhibit novel structural and/or phenotypic characteristics. Preferably, addition or substitution of a heterologous gene or gene segment within a selected recipient Bunyaviridae strain yields novel phenotypic effects, for example attenuation, growth changes, altered immunogenicity, or other desired phenotypic changes, as compared with corresponding phenotypes of the unmodified recipient and/or donor.

Genes and gene segments that are useful as heterologous inserts or additions within a chimeric Bunyaviridae genome include genes or gene segments encoding a L, $G_N$, $NS_M$, $G_C$, N, or NSs protein, or a portion thereof. The chimeric Bunyaviridae may incorporate a gene segment encoding only a portion of a selected protein, for example a cytoplasmic domain, transmembrane domain, ectodomain or immunogenic epitope.

Thus, the introduction of heterologous immunogenic proteins, domains and epitopes to produce chimeric Bunyaviridae is particularly useful to generate novel immune responses in an immunized host. Addition or substitution of an immunogenic gene or gene segment from a donor Bunyaviridae subgroup or strain within a recipient genome of a different Bunyaviridae subgroup or strain can generate an immune response directed against the donor subgroup or strain, the recipient subgroup or strain, or against both the donor and recipient subgroup or strain. To achieve this purpose, chimeric Bunyaviridae may also be constructed that express a chimeric protein, e.g., an immunogenic protein having a domain specific to a LACV strain or subgroup fused to the domain of a different Bunyaviridae family member. Other exemplary recombinants of this type may express duplicate protein regions, such as duplicate immunogenic regions.

Although it is often useful to add or substitute entire genes (including cis-acting elements and coding regions) within a chimeric genome, it is also useful to transfer only a portion of a donor gene of interest. Quite commonly, non-coding nucleotides such as cis-acting regulatory elements and intergenic sequences need not be transferred with the donor gene coding region. In addition, a variety of gene segments provide useful donor polynucleotides for inclusion within a chimeric genome to express chimeric Bunyaviridae having novel and useful properties. Thus, heterologous gene segments may beneficially encode a cytoplasmic tail, transmembrane domain or ectodomain, an epitopic site or region, a binding site or region, an active site or region containing an active site, etc., of a selected protein from one Bunyaviridae family member. These and other gene segments can be added or substituted for a counterpart gene segment in another member of the Bunyaviridae family of viruses to yield novel chimeric recombinants, for example recombinants expressing a chimeric protein having a cytoplasmic tail and/or transmembrane domain of one member of the Bunyaviridae family fused to an ectodomain of another Bunyaviridae family member. Useful genome segments in this regard range from about 15-35 nucleotides in the case of gene segments encoding small functional domains of proteins, e.g., epitopic sites, to about 50, 75, 100, 200-500, and 500-1,500 or more nucleotides for gene segments encoding larger domains or protein regions.

To construct chimeric Bunyaviridae, heterologous genes may be added or substituted in whole or in part to a background genome to form a chimeric genome. In the case of chimeras generated by substitution, a selected protein or protein region (e.g., a cytoplasmic tail, transmembrane domain or ectodomain, an epitopic site or region, a binding site or region, an active site or region containing an active site, etc.) from one member of the Bunyaviridae family is substituted for a counterpart gene or gene segment in a different Bunyaviridae family member genome to yield novel recombinants having desired phenotypic changes compared to wild-type or parent Bunyaviridae family strains. As used herein, "counterpart" genes, gene segments, proteins or protein regions refers to two counterpart polynucleotides from a heterologous source, including different genes in a single Bunyaviridae strain, or different variants of the same gene, including species and allelic variants among different Bunyaviridae family subgroups or strains.

Counterpart genes and gene segments share at least moderate structural similarity. For example counterpart gene segments may encode a common structural domain of a protein of interest. Typically, they will share a common biological function as well. For example, protein domains encoded by counterpart gene segments may provide a common membrane spanning function, a specific binding activity, an immunological recognition site, etc. Typically, a desired biological activity shared between the products of counterpart genes and gene segments will be substantially similar in quantitative terms, i.e., they will not differ by more than 30%, preferably by no more than 20%, more preferably by no more than 5-10%.

Counterpart genes and gene segments for use within the invention embrace an assemblage of alternate species having a range of size and sequence variation. However, selection of counterpart genes and gene segments relies on substantial sequence identity between the subject counterparts. In this context, a selected polynucleotide "reference sequence" is defined as a sequence or portion thereof present in either the donor or recipient genome. This reference sequence is used as a defined sequence to provide a rational basis for a sequence comparison. For example, the reference sequence may be a defined segment of a cDNA or gene, or a complete cDNA or gene sequence.

Generally, a reference sequence for use in defining counterpart genes and gene segments is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman 1981 *Adv Appl Math* 2:482, by the homology alignment algorithm of Needleman & Wunsch 1970 *J Mol Biol* 48:443, by the search for similarity method of Pearson & Lipman 1988 *Proc Natl Acad Sci USA* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term "sequence identity" as used herein means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by chimeric Bunyaviridae as described herein are also typically selected to have conservative relationships, i.e., to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity.

Preferably, residue positions which are not identical differ by conservative amino acid substitutions. Conservative amino acid substitutions refer to the interchangeability of residues having similar side chains. For example, a conservative group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, ω-phosphoserine, N-acetylserine, N-formylmethionine, 3-methylhistidine, 5-hydroxylysine, ω-N-methylarginine, and other amino and imino acids (e.g., 4-hydroxyproline). Moreover, amino acids may be modified by glycosylation, phosphorylation and the like.

Aspects of the invention disclosed herein also concern cDNA-based methods that are used to construct a large panel of recombinant, chimeric Bunyaviridae viruses and subviral particles. These recombinant constructs offer improved characteristics of attenuation and immunogenicity for use as vaccine agents. Among desired phenotypic changes in this context are resistance to reversion from an attenuated phenotype, improvements in attenuation in culture or in a selected host environment, immunogenic characteristics (e.g., as determined by enhancement, or diminution, of an elicited immune response), upregulation or downregulation of transcription and/or translation of selected viral products, etc.

In preferred embodiments, attenuated, chimeric Bunyaviridae are produced in which the chimeric genome is further modified by introducing one or more attenuating point mutations that specifies an attenuating phenotype. These point mutations may be generated de novo and tested for attenuating effects according to a rational design mutagenesis strategy. Alternatively, the attenuating point mutations are identified in biologically-derived mutant Bunyaviridae family member and thereafter incorporated into a chimeric Bunyaviridae as described herein.

Attenuating point mutations in biologically-derived Bunyaviridae family member for incorporation within a chimeric vaccine strain may occur naturally or may be introduced into wild-type Bunyaviridae family member strains by well-known mutagenesis procedures. For example, incompletely attenuated parental Bunyaviridae family member strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as generally described herein.

By "biologically-derived Bunyaviridae family member" is meant any Bunyaviridae family member not produced by recombinant means. Thus, biologically-derived Bunyaviridae family members include naturally occurring Bunyaviridae family members of all subgroups and strains, including, e.g., a naturally occurring Bunyaviridae family member having a wild-type genomic sequence and a Bunyaviridae family member having genomic variations from a reference wild-type virus sequence, e.g., a Bunyaviridae family member having a mutation specifying an attenuated phenotype. Likewise, biologically-derived Bunyaviridae family members include Bunyaviridae family member mutants derived from a parental Bunyaviridae family member strain by, inter alia, artificial mutagenesis and selection procedures.

To produce a satisfactorily attenuated Bunyaviridae family member from biologically-derived strains, mutations are preferably introduced into a parental strain, which has been incompletely or partially attenuated. Using such partially attenuated strains, additional mutation(s) can be generated that further attenuate the strain, e.g., to a desired level of restricted replication in a mammalian host, while retaining sufficient immunogenicity to confer protection in vaccinees.

As noted above, production of a sufficiently attenuated biologically-derived Bunyaviridae family member mutant can be accomplished by several known methods. One such procedure involves subjecting a partially attenuated virus to passage in cell culture at progressively lower, attenuating temperatures. For example, whereas wild-type virus is typically cultivated at about 34-37° C., the partially attenuated mutants are produced by passage in cell cultures at suboptimal temperatures, e.g., 20-26° C. This selection of mutant virus during cold-passage (cp) substantially eliminates any residual virulence in the derivative strains as compared to the partially attenuated parent.

Alternatively, specific mutations can be introduced into biologically-derived Bunyaviridae family member by subjecting a partially attenuated parent virus to chemical mutagenesis, e.g., to introduce temperature sensitive (ts) mutations or, in the case of viruses which are already ts, additional ts mutations sufficient to confer increased attenuation and/or stability of the ts phenotype on the attenuated derivative. Means for the introduction of ts mutations into a Bunyaviridae family member include replication of the virus in the presence of a mutagen such as 5-fluorouridine or 5-fluorouracil in a concentration of about $10^{-3}$ to $10^{-5}$ M, preferably about $10^{-4}$ M, exposure of virus to nitrosoguanidine at a concentration of about 100 μg/ml, according to the general procedures, or genetic introduction of specific ts mutations. Other chemical mutagens can also be used. Attenuation can result from a ts mutation in almost any Bunyaviridae family member gene.

Mutations thus identified are compiled into a "menu" and are then introduced as desired, singly or in combination, to calibrate a chimeric vaccine virus to an appropriate level of attenuation, immunogenicity, genetic resistance to reversion from an attenuated phenotype, etc., as desired. Preferably, chimeric Bunyaviridae as described herein are attenuated by incorporation of at least one, and more preferably two or more, attenuating point mutations identified from such a menu, which may be defined as a group of known mutations within a panel of biologically-derived mutant Bunyaviridae strains.

Chimeric Bunyaviridae designed and selected for vaccine and immunogenic composition use often have at least two and sometimes three or more attenuating mutations to achieve a satisfactory level of attenuation for broad clinical use. In one embodiment, at least one attenuating mutation occurs in the $G_C$ or $G_N$ gene (either in the donor or recipient gene) and involves a nucleotide substitution specifying an amino acid change in the $G_C$ or $G_N$ protein.

In accordance with the methods described herein, chimeric Bunyaviridae can be readily constructed and characterized that incorporate at least one and up to a full complement of attenuating point mutations present within a panel of biologically-derived mutant Bunyaviridae strains. Thus, mutations can be assembled in any combination from a selected panel of mutants.

In accordance with the foregoing description, the ability to produce infectious Bunyaviridae from cDNA permits introduction of specific engineered changes within chimeric Bunyaviridae. In particular, infectious, recombinant Bunyaviridae are employed for identification of specific mutation(s) in biologically-derived, attenuated Bunyaviridae strains, for example mutations which specify ts and other phenotypes. Desired mutations are thus identified and introduced into recombinant, chimeric Bunyaviridae vaccine strains. The capability of producing virus from cDNA allows for routine incorporation of these mutations, individually or in various selected combinations, into a full-length cDNA clone, whereafter the phenotypes of rescued recombinant viruses containing the introduced mutations can be readily determined.

By identifying and incorporating specific, biologically-derived mutations associated with desired phenotypes into infectious chimeric Bunyaviridae clones, some embodiments provide for other, site-specific modifications at, or within close proximity to, the identified mutation. Whereas most attenuating mutations produced in biologically-derived Bunyaviridae are single nucleotide changes, other "site specific" mutations can also be incorporated by recombinant techniques into biologically-derived or recombinant Bunyaviridae. As used herein, site-specific mutations include insertions, substitutions, deletions or rearrangements of from 1 to 3, up to about 5-15 or more altered nucleotides (e.g., altered from a wild-type Bunyaviridae family member sequence, from a sequence of a selected mutant Bunyaviridae strain, or from a parent recombinant Bunyaviridae clone subjected to mutagenesis). Such site-specific mutations may be incorporated at, or within the region of, a selected, biologically-derived point mutation. Alternatively, the mutations can be introduced in various other contexts within an Bunyaviridae clone, for example at or near a cis-acting regulatory sequence or nucleotide sequence encoding a protein active site, binding site, immunogenic epitope, etc. Site-specific Bunyaviridae mutants typically retain a desired attenuating phenotype, but may exhibit substantially altered phenotypic characteristics unrelated to attenuation, e.g., enhanced or broadened immunogenicity, or improved growth. Further examples of desired, site-specific mutants include recombinant Bunyaviridae designed to incorporate additional, stabilizing nucleotide mutations in a codon specifying an attenuating point mutation. Where possible, two or more nucleotide substitutions are introduced at codons that specify attenuating amino acid changes in a parent mutant or recombinant Bunyaviridae clone, yielding a biologically-derived or recombinant Bunyaviridae having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to chimeric Bunyaviridae disclosed herein include deletions, insertions, substitutions or rearrangements of whole genes or gene segments. These mutations may alter small numbers of bases (e.g., from 15-30 bases, up to 35-50 bases or more), or large blocks of nucleotides (e.g., 50-100, 100-300, 300-500, 500-1,000 bases) in the donor or recipient genome, depending upon the nature of the change (i.e., a small number of bases may be changed to insert or ablate an immunogenic epitope or change a small gene segment, whereas large block(s) of bases are involved when genes or large gene segments are added, substituted, deleted or rearranged.

In additional aspects, some embodiments provide for supplementation of mutations adopted into a chimeric Bunyaviridae clone from biologically-derived Bunyaviridae, e.g., is mutations, with additional types of mutations involving the same or different genes in a further modified chimeric Bunyaviridae clone. Bunyaviridae encode 3 mRNAs and 6 proteins including L, $G_N$, $NS_M$, $G_C$, N, and $NS_S$. These proteins can be selectively altered in terms of expression levels, or can be added, deleted, substituted or rearranged, in whole or in part, alone or in combination, with other desired modifications, to yield a chimeric Bunyaviridae exhibiting novel vaccine characteristics.

Thus, in addition to, or in combination with, attenuating mutations adopted from biologically-derived Bunyaviridae mutants, preferred embodiments also provide a range of additional methods for attenuating chimeric Bunyaviridae based on recombinant engineering of infectious Bunyaviridae clones. In accordance with this aspect, a variety of alterations can be produced in an isolated polynucleotide sequence encoding the chimeric Bunyaviridae genome for incorporation into infectious clones. More specifically, to achieve desired structural and phenotypic changes in chimeric Bunyaviridae, the invention allows for introduction of modifications which delete, substitute, introduce, or rearrange a selected nucleotide or plurality of nucleotides from a parent chimeric genome, as well as mutations which delete, substitute, introduce or rearrange whole gene(s) or gene segment(s), within a chimeric Bunyaviridae clone.

Desired modifications of infectious chimeric Bunyaviridae are typically selected to specify a desired phenotypic change, e.g., a change in viral growth, temperature sensitivity, ability to elicit a host immune response, attenuation, etc. These changes can be brought about either in a donor or recipient genome by, e.g., mutagenesis of a parent LACV clone to ablate, introduce or rearrange a specific gene(s) or gene region(s) (e.g., a gene segment that encodes a protein structural domain, an immunogenic epitope, binding region, active site, etc.). Genes of interest in this regard include all of the genes of the LACV genome: L, $G_N$, $NS_M$, $G_C$, N and NSs, and a variety of genes from other viruses of the Bunyaviridae family.

Also provided are modifications in a chimeric Bunyaviridae which simply alter or ablate expression of a selected gene, e.g., by introducing a termination codon within a selected Bunyaviridae coding sequence, changing the position of an Bunyaviridae gene relative to an operably linked promoter, introducing an upstream start codon to alter rates of expression, modifying (e.g., by changing position, altering an existing sequence, or substituting an existing sequence with a heterologous sequence) transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected protein(s).

The ability to analyze and incorporate other types of attenuating mutations into chimeric Bunyaviridae for vaccine development extends to a broad assemblage of targeted changes in Bunyaviridae clones. In some embodiments, a gene deletion is combined in a chimeric Bunyaviridae with one or more additional mutations specifying an attenuated phenotype, e.g., one or more point mutation(s) adopted from a biologically-derived, attenuated Bunyaviridae family member mutant.

In this regard, any Bunyaviridae gene that is not essential for growth can be ablated or otherwise modified in a chimeric Bunyaviridae to yield desired effects on virulence, pathogenesis, immunogenicity and other phenotypic characteristics.

In addition, a variety of other genetic alterations can be produced in a Bunyaviridae genome for incorporation into infectious chimeric Bunyaviridae, alone or together with one or more attenuating point mutations adopted from a biologically-derived mutant Bunyaviridae. Additional heterologous genes and gene segments (e.g., from different Bunyaviridae genes, different Bunyaviridae strains or types) may be inserted in whole or in part, the order of genes changed, gene overlap removed, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Also provided herein are genetic modifications in a chimeric Bunyaviridae family member which alter or ablate the expression of a selected gene or gene segment without removing the gene or gene segment from the chimeric Bunyaviridae clone. For example, this can be achieved by introducing a termination codon within a selected coding sequence, changing the position of a gene or introducing an upstream start codon to alter its rate of expression. Other mutations within chimeric Bunyaviridae involve replacement of the 5' or 3' ends of the genome.

In another exemplary embodiment, a sequence surrounding a translational start site (preferably including a nucleotide in the −3 position) of a selected Bunyaviridae gene is modified, alone or in combination with introduction of an upstream start codon, to modulate chimeric Bunyaviridae gene expression by specifying up- or down-regulation of translation.

In more embodiments, chimeric Bunyaviridae are provided in which expression of a viral gene, for example the NSs gene, is ablated at the translational level without deletion of the gene or of a segment thereof, by, e.g., introducing two tandem translational termination codons into a translational open reading frame (ORF) (e.g., the rLACVdelNSs mutation (Blakqori, G. and Weber F. 2005 J Virol 79:10420-10428). This yields viable virus in which a selected gene has been silenced at the level of translation, without deleting its gene. These forms of "knock-out" virus will exhibit reduced growth rates and small plaque sizes in tissue culture. Thus, the methods and compositions described herein provide yet additional, novel types of attenuating mutations which ablate expression of a viral gene that is not one of the major viral protective antigens. In this context "knockout" virus phenotypes produced without deletion of a gene or gene segment can be alternatively produced by deletion mutagenesis, as described herein, to effectively preclude correcting mutations that may restore synthesis of a target protein.

Several other gene "knock-outs" for chimeric Bunyaviridae can be made using alternate designs. For example, insertion of translation termination codons into ORFs, or disruption of the RNA editing sites, offer alternatives to silencing or attenuating the expression of selected genes. Methods for producing these and other knock-outs are well known in the art.

Infectious chimeric Bunyaviridae clones can also be engineered according to the methods and compositions disclosed herein to enhance immunogenicity and induce a level of protection greater than that provided by infection with a wild-type Bunyaviridae or a parent chimeric Bunyaviridae. For example, an immunogenic epitope from a heterologous LACV strain or type, or from a non-LACV source such as a hantavirus, can be added to a chimeric clone by appropriate nucleotide changes in the polynucleotide sequence encoding the chimeric genome. Alternatively, chimeric Bunyaviridae can be engineered to add or ablate (e.g., by amino acid insertion, substitution or deletion) immunogenic epitopes associated with desirable or undesirable immunological reactions.

Within the methods described herein, additional genes or gene segments may be inserted into the recipient Bunyaviridae genome. These genes may be under common control with recipient genes, or may be under the control of an independent set of transcription signals. Genes of interest include the Bunyaviridae genes identified above, as well as non-Bunyaviridae genes. Non-Bunyaviridae genes of interest include those encoding cytokines (e.g., IL-2 through IL-15, especially IL-2, IL-6 and IL-12, etc.), gamma-interferon, and proteins rich in T-helper cell epitopes. These additional proteins can be expressed either as a separate protein, or as a chimera engineered from a second copy of one of the Bunyaviridae proteins. This provides the ability to modify and improve the immune responses against Bunyaviridae both quantitatively and qualitatively.

In exemplary embodiments, insertion of foreign genes or gene segments, and in some cases of noncoding nucleotide sequences, within a chimeric Bunyaviridae genome results in a desired increase in genome length causing yet additional, desired phenotypic effects. Increased genome length results in attenuation of the resultant Bunyaviridae, dependent in part upon the length of the insert. In addition, the expression of certain proteins, e.g., a cytokine, from a non-Bunyaviridae gene inserted into chimeric Bunyaviridae as described herein will result in attenuation of the virus due to the action of the protein. This has been described in the scientific literature for IL-2 expressed in vaccinia virus and is also expected for gamma interferon.

Deletions, insertions, substitutions and other mutations involving changes of whole viral genes or gene segments within chimeric Bunyaviridae yield highly stable vaccines, which are particularly important in the case of immunosuppressed individuals. Many of these changes will result in attenuation of resultant vaccine strains, whereas others will specify different types of desired phenotypic changes. For example, certain viral genes are known, which encode proteins that specifically interfere with host immunity. Ablation of such genes in chimeric vaccine viruses is expected to reduce virulence and pathogenesis and/or improve immunogenicity.

In addition to the above described modifications to recombinant Bunyaviridae, different or additional modifications in Bunyaviridae clones can be made to facilitate manipulations, such as the insertion of unique restriction sites in various intergenic regions. Nontranslated gene sequences can be removed to increase capacity for inserting foreign sequences.

In another aspect of the invention, compositions (e.g., isolated polynucleotides and vectors incorporating a chimeric Bunyaviridae-encoding cDNA) are provided for producing an isolated infectious chimeric Bunyaviridae. In some aspects of the invention the DNAs encoding the immunogens described herein are codon-optimized for expression in a particular host (e.g., codon-optimized for expression in humans). These codon optimized DNA immunogens can be introduced into a mammalian subject (e.g., human) by conventional DNA vaccination techniques as described herein including elelctroporation, gene gun, powder injection, aerosol, and inhalation. Using these compositions and methods, infectious chimeric Bunyaviridae are generated from a chimeric Bunyaviridae genome. In related aspects, compositions and methods are provided for introducing the aforementioned structural and phenotypic changes into a recombinant chimeric Bunyaviridae to yield infectious, attenuated vaccine viruses.

Introduction of the foregoing defined mutations into an infectious, chimeric Bunyaviridae clone can be achieved by a variety of well-known methods. By "infectious clone" is meant cDNA or its product, synthetic or otherwise, which can be transcribed into genomic RNA capable of serving as template to produce the genome of an infectious virus or subviral particle. Thus, defined mutations can be introduced by conventional techniques (e.g., site-directed mutagenesis) into a cDNA copy of the genome. The use of genome cDNA subfragments to assemble a complete genome cDNA as described herein has the advantage that each region can be manipulated separately (smaller cDNAs are easier to manipulate than large ones) and then readily assembled into a complete cDNA. Thus, the complete genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete genome cDNA. A variety of other mutagenesis techniques are known and available for use in producing the mutations of interest in the Bunyaviridae genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of a Bunyaviridae genome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome. The plasmid containing the genetically altered genome fragment is then amplified and the mutated piece is then reintroduced into the full-length genome clone.

The ability to introduce defined mutations into infectious Bunyaviridae has many applications, including the analyses of viral molecular biology and pathogenesis. For example, the functions of the Bunyaviridae proteins, including the L, $G_N$, $NS_M$, $G_C$, N and NSs proteins, can be investigated and manipulated by introducing mutations which ablate or reduce their level of expression, or which yield mutant protein.

By "recombinant Bunyaviridae" is meant a Bunyaviridae or Bunyaviridae-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in Bunyaviridae gene expression, for example, a promoter, a structural or coding sequence which is transcribed into Bunyaviridae RNA, and appropriate transcription initiation and termination sequences.

To produce infectious Bunyaviridae from cDNA-expressed genome, the genome is coexpressed with those Bunyaviridae proteins necessary to (i) produce nucleocapsids capable of RNA replication, and (ii) render progeny nucleocapsids competent for both RNA replication and transcription. Transcription by the genome nucleocapsids provide the other Bunyaviridae proteins and initiates a productive infection. Alternatively, additional Bunyaviridae proteins needed for a productive infection can be supplied by coexpression.

In certain embodiments, complementing sequences encoding proteins necessary to generate transcribing, replicating Bunyaviridae nucleocapsids are provided by one or more helper viruses. Such helper viruses can be wild-type or mutant. Preferably, the helper virus can be distinguished phenotypically from the virus encoded by the Bunyaviridae cDNA. For example, it is desirable to provide monoclonal antibodies which react immunologically with the helper virus but not the virus encoded by the Bunyaviridae cDNA. Such antibodies can be neutralizing antibodies. In some embodiments, the antibodies can be used in affinity chromatography to separate the helper virus from the recombinant virus. To aid the procurement of such antibodies, mutations can be introduced into the Bunyaviridae cDNA to provide antigenic diversity from the helper virus.

Alternative means to construct cDNA encoding a Bunyaviridae genome include reverse transcription-PCR using PCR conditions to reduce the number of subunit cDNA components to as few pieces as possible. In other embodiments different promoters can be used (e.g., T7, T3, SP6). Different DNA vectors (e.g., cosmids) can be used for propagation to better accommodate large size genome.

To select candidate chimeric vaccine viruses, the criteria of viability, attenuation and immunogenicity are determined according to well-known methods. Viruses which will be most desired in vaccines and immunogenic compositions as described herein preferably maintain viability, have a stable attenuation phenotype, exhibit replication in an immunized host (albeit at lower levels), and effectively elicit production of an immune response in a vaccine sufficient to confer protection against serious disease caused by subsequent infection from wild-type virus.

Chimeric Bunyaviridae, which have been attenuated as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically-derived or recombinant Bunyaviridae) is tested for temperature sensitivity of virus replication, i.e., is phenotype, and for the small plaque phenotype. Modified viruses are further tested in animal models of Bunyaviridae infection.

In accordance with the foregoing description, some embodiments also concern isolated, infectious chimeric Bunyaviridae compositions for vaccine or immunogenic composition use. The attenuated chimeric virus which is a component of a vaccine is in an isolated and typically purified form. By "isolated" is meant to refer to virus which is in other than a native environment of a wild-type virus. More generally, "isolated" is meant to include the attenuated virus as a component of a cell culture or other artificial medium. For example, attenuated Bunyaviridae of the invention may be produced by an infected cell culture, separated from the cell culture and added to a stabilizer which contains other non-naturally occurring Bunyaviridae family members, such as those that are selected to be attenuated by means of resistance to neutralizing monoclonal antibodies.

Chimeric Bunyaviridae vaccines and immunogenic compositions contain as an active ingredient an immunogenically effective amount of Bunyaviridae produced as described herein. Biologically derived or recombinant Bunyaviridae can be used directly in vaccine formulations, or lyophilized. Lyophilized virus will typically be maintained at about 4° C. When ready for use the lyophilized virus is reconstituted in a stabilizing solution, e.g., saline, with or without adjuvant, as further described below. The biologically-derived or recombinantly modified virus may be introduced into a host with a physiologically acceptable carrier and/or adjuvant. Useful carriers are well known in the art, and include, e.g., water, buffered water, 0.4% saline, 0.3% glycine, sucrose, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Farmingham, Mass.), MPL™ (3-O-deacylated monophosphoryl lipid A; RIBI ImmunoChem Research, Inc., Hamilton, Mont.), and interleukin-12 (Genetics Institute, Cambridge, Mass.).

Upon immunization with a chimeric Bunyaviridae vaccine or immunogenic composition as described herein, via parenteral, oral, topical or other route, the immune system of the host responds to the vaccine by producing antibodies specific for one or more Bunyaviridae proteins. Preferably, in the methods described herein, the host immune response (e.g., T cell recall or antibody titer) is measured. Such measurements can be made by conventional assays. Clinical evaluation and observation of an improvement in condition can also be a measurement of immune response in some contexts. As a result of the vaccination/inoculation the host becomes at least partially or completely immune to Bunyaviridae infection, or resistant to developing moderate or severe Bunyaviridae disease.

Chimeric Bunyaviridae vaccines and/or immunogenic compositions may also comprise attenuated chimeric virus that elicits an immune response against a single Bunyaviridae strain or antigenic subgroup, or against multiple Bunyaviridae strains or subgroups. In this context, the chimeric Bunyaviridae can elicit a monospecific immune response or a polyspecific immune response against multiple Bunyaviridae strains or subgroups. Alternatively, chimeric Bunyaviridae having different immunogenic characteristics can be combined in a vaccine mixture or administered separately in a coordinated treatment protocol to elicit more effective protection against one Bunyaviridae strain, or against multiple Bunyaviridae strains or subgroups.

The host to which the vaccine/immunogenic composition is administered or provided can be any mammal susceptible to infection by a particular virus of the Bunyaviridae family or a closely related virus and capable of generating a protective immune response to antigens of the vaccinizing virus. Thus, suitable hosts include humans, non-human primates, bovine, equine, swine, ovine, rodents, etc. Accordingly, the invention provides methods for creating vaccines for a variety of human and veterinary uses.

The vaccine and immunogenic compositions containing the attenuated chimeric Bunyaviridae as described herein are administered or provided to an individual susceptible to or otherwise at risk of Bunyaviridae infection in an "immunogenically effective dose" which is sufficient to induce or enhance the individual's immune response capabilities against Bunyaviridae. In the case of human subjects, the attenuated virus is administered or provided according to well established human vaccine protocols.

In all subjects, the precise amount of chimeric Bunyaviridae vaccine administered or provided and the timing and repetition of inoculation will be determined based on the patient's state of health and weight, the mode of administration, the nature of the formulation, etc. Dosages will generally range from about $10^2$ to about $10^6$ plaque forming units (PFU) or more of virus per individual, more commonly from about $10^3$ to $10^5$ PFU virus per individual. In any event, the vaccine formulations preferably provide a quantity of attenuated virus as described herein sufficient to effectively stimulate or induce an anti-Bunyaviridae immune response, e.g., as can be determined by complement fixation, plaque neutralization, and/or enzyme-linked immunosorbant assay, among other methods. In this regard, individuals are also monitored for signs and symptoms of illness. As with administration to chimpanzees, the attenuated virus of the vaccine grows in vaccinees at levels approximately 10-fold or more lower than wild-type virus, or approximately 10-fold or more lower when compared to levels of incompletely attenuated virus.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) Bunyaviridae infection. Similarly, adults who are particularly susceptible to repeated or serious Bunyaviridae infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered chimeric Bunyaviridae strain expressing a cytokine or an additional protein rich in T cell epitopes may be particularly advantageous for adults rather than for infants. Bunyaviridae vaccines produced in accordance with the present invention can be combined with viruses expressing antigens of another subgroup or strain of Bunyaviridae to achieve protection against multiple Bunyaviridae subgroups or strains. Alternatively, the vaccine virus may incorporate protective epitopes of multiple Bunyaviridae strains or subgroups engineered into one Bunyaviridae clone as described herein.

Typically when different vaccine viruses are used they will be administered in an admixture simultaneously, but they may also be administered separately. Immunization with one strain may protect against different strains of the same or different subgroup.

The level of attenuation of chimeric vaccine virus may be determined by, for example, quantifying the amount of virus present in an immunized host and comparing the amount to that produced by wild-type Bunyaviridae or other attenuated Bunyaviridae which have been evaluated as candidate vaccine strains. For example, the attenuated chimeric virus of the invention will have a greater degree of restriction of replication in a highly susceptible host, such as a chimpanzee, compared to the levels of replication of wild-type virus, e.g., 10- to 1000-fold less.

Genome Sequence Analysis of La Crosse Virus and In Vitro and In Vivo Phenotypes

LACV genomes were sequenced for two reasons. First, we wanted to determine the genetic diversity of LACV isolated in different regions of the United States at different times, and second, we sought to define a complete genomic sequence that is associated with the wild type phenotype of virulence in mice by both peripheral and intracerebral routes of inoculation. The sequence of only two complete LACV genomes was previously reported, one human isolate (LACV/human/1978, GenBank accession numbers NC_004108-NC_004110) and one mosquito isolate (strain 77, LACV/mosquito/1977, GenBank accession numbers DQ196118-DQ19620) (Table B). We sequenced two additional isolates, including the original La Crosse, Wis. virus (LACV/human/1960) and the LACV/mosquito/1978 virus (GenBank accession numbers EF485036-EF485038) (Table B), and re-sequenced LACV/human/1978 after an additional passage in tissue culture to confirm its identity prior to further biological characterization. See *Virology Journal* 4:41 (2007), herein expressly incorporated by reference in its entirety). In addition, LACV/human/1960, LACV/mosquito/1978, and LACV/human/1978 parental wild-type viruses were biologically cloned to generate a genetically homogeneous viral preparation, and the full sequence of these cloned preparations was also determined. Thus, we have generated full-length sequence for 3 pairs of cloned and uncloned LACV strains. For LACV/human/1978, the newly derived sequence (EF485033-35) was used for all subsequent comparisons since several differences with the former sequence were identified. An examination of the virulence phenotype of these three parental and cloned viruses in mice should define one or more full-length sequences that have a wild type phenotype.

A comparison of the complete genomic nucleotide sequences from low passage LACV isolates of either human or mosquito origin isolated over an 18 year period of time from two geographically different regions of the United States (Table C) indicated little sequence divergence. The S, M, and L genome segments for each virus were 984, 4526, and 6980 nucleotides in length, respectively. The nucleotide length of the segments and the encoded open reading frames for each of the isolates are identical. The S, M, and L segments from each virus isolate share a high nucleotide sequence identity ranging from 97.9-100%, 95.7-99.8%, and 95.7-99.4% respectively (Table C). The N, NSs, M polyprotein, and L protein open reading frames are 235, 92, 1441, and 2263 amino acid codons in length, respectively. The percent identity for encoded proteins is also highly conserved among the isolates with 99.6-100%, 98.9-100%, 97.8-99.6%, and 99.2-99.7% identity for the N, NSs, M polyprotein, and L proteins, respectively (Table C).

TABLE C

Nucleotide and amino acid identity (%) of the LACV genomic segments and their predicted protein products.

| | | Human/ 1960 | Human/ 1978 | Mosquito/ 1978 | Mosquito/ 1977 | |
|---|---|---|---|---|---|---|
| S segment/N protein | | | | | | |
| Human/1960 | Nucle- | — | 99.6 | 100 | 100 | Amino |
| Human/1978 | otide | 99.8 | — | 99.6 | 99.6 | Acid |
| Mosquito/ 1978 | | 98.1 | 97.9 | — | 100 | |
| Mosquito/ 1977 | | 100 | 99.8 | 98.1 | — | |
| S segment/NS$_s$ protein | | | | | | |
| Human/1960 | Nucle- | — | 98.9 | 100 | 100 | Amino |
| Human/1978 | otide | 99.8 | — | 98.9 | 98.9 | Acid |
| Mosquito/ 1978 | | 98.1 | 97.9 | — | 100 | |
| Mosquito/ 1977 | | 100 | 99.8 | 98.1 | — | |
| M segment/M Polyprotein | | | | | | |
| Human/1960 | Nucle- | — | 99.4 | 97.8 | 99.6 | Amino |
| Human/1978 | otide | 99.6 | — | 97.8 | 99.4 | Acid |
| Mosquito/ 1978 | | 95.8 | 95.8 | — | 97.7 | |
| Mosquito/ 1977 | | 99.8 | 99.5 | 98.1 | — | |

TABLE B

Passage history and geographic location of isolation/infection of the LACV isolates for which complete genomic sequences are available.

| Virus | Location | Passage history [a] | GenBank Accession number |
|---|---|---|---|
| LACV/human/1960 | Minnesota | C6/36 2 | EF485030-EF48532 |
| LACV/human/1960-clone | Minnesota | C6/36 2, Vero 4 | NA[b] |
| LACV/mosquito/1978 | North Carolina | Mouse brain 1, Vero 3 | EF485036-EF48538 |
| LACV/mosquito/1978-clone | North Carolina | Mouse brain 1, Vero 7 | NA |
| LACV/human/1978 | Wisconsin | Mouse brain 1, BHK 2, Vero 1 | EF485033-EF48535 |
| LACV/human/1978-clone | Wisconsin | Mouse brain 1, BHK 2, Vero 5 | NA |
| LACV/mosquito/1977 | Wisconsin | Unknown | DQ196118-DQ19620[c] |
| LACV/human/1978 | Wisconsin | Mouse brain 1, BHK 2 | NC 004108-NC 004110[d] |

[a] Cell/tissue type followed by number of passages.
[b] Sequence not submitted. Genetic comparisons with uncloned parental wildtype stocks found in Table 3.
[c] Previous submission by Cheng et al. 2005.
[d] Previous submission by Hughes et al. 2002. Sequence from a derivative of this virus (one additional passage in Vero cells) was generated for this study (EF485033-EF485535) and used for subsequent comparisons since several differences with this sequence were identified.

TABLE C-continued

Nucleotide and amino acid identity (%) of the LACV genomic
segments and their predicted protein products.

|  |  | Human/1960 | Human/1978 | Mosquito/1978 | Mosquito/1977 |  |
| --- | --- | --- | --- | --- | --- | --- |
|  |  | L segment/L Protein |  |  |  |  |
| Human/1960 | Nucleotide | — | 99.7 | 99.2 | 99.5 | Amino |
| Human/1978 |  | 99.4 | — | 99.2 | 99.5 | Acid |
| Mosquito/1978 |  | 95.9 | 95.7 | — | 99.5 |  |
| Mosquito/1977 |  | 97.1 | 96.9 | 96.0 | — |  |

Although the process of biological cloning resulted in an additional four passages in Vero cells, these passages had a minimal effect on genetic stability. A maximum of four nucleotide changes were observed between a wild type parental virus stock and its biologically cloned derivative, and no more than one amino acid change was observed in any cloned virus (Table D). This level of sequence divergence between parental and cloned virus is much less than that between LACV isolates (>500 nucleotides differences for human/1978 compared to mosquito/1978), clearly identifying each isolate as a separate strain.

TABLE D

Nucleotide differences between wild type
parental and biologically cloned virus.

| | Nucleotide Substitution in indicated LACV segment[a] | | |
| --- | --- | --- | --- |
| LACV Virus | S | M | L |
| human/1960-clone | A525T | A503G[b] C2221T | A1837G |
| human/1978-clone | No changes[c] | T391C A1636G A1929G[b] | No changes |
| mosquito/1978-clone | A719G[b] | No changes | A31G G33A |

[a]Parental nucleotide on left, nucleotide substitution in the cloned virus on right.
[b]Indicates a nucleotide substitution resulting in an amino acid substitution.
[c]Parental and cloned virus have identical sequences.

The sequences of two LACV isolates from humans were compared with two isolates from mosquitoes to identify amino acids that are shared by LACVs of human origin but that differ from LACVs of mosquito origin. Such sequence differences are referred to as host-specific sequence substitutions. Five such host-specific amino acid substitutions were identified, and all were located in the L protein (Table E). Four nucleotide substitutions in the non-coding region (NCR) of the L segment at nucleotides 31, 6876, 6877, and 6921 also appear to be host-specific (FIGS. 1 and 2).

TABLE E

Host specific amino acid differences are
located in the RNA polymerase (L).

| Amino acid position | Amino acid residue | |
| --- | --- | --- |
|  | Human | Mosquito |
| 129 | V | I |
| 484 | K | R |
| 1040 | E | G |

TABLE E-continued

Host specific amino acid differences are
located in the RNA polymerase (L).

| Amino acid position | Amino acid residue | |
| --- | --- | --- |
|  | Human | Mosquito |
| 1713 | T | A |
| 1906 | A | S |

Genetic comparisons used all wild-type parental sequences generated for this paper and published sequences of mosquito strain LACV-77 (DQ196118-DQ19620). RNA polymerase amino acid 922 was R or G in the human isolates and K in the two mosquito isolates.

The 3' and 5' genome ends of the LACV genomes were also highly conserved. The first 11 and last 11 nucleotides were identical for each segment end (FIGS. 1 and 2). Each 3' NCR was identical for the S (nt 1-81) and only one nucleotide differed from the consensus in the M (nt 1-61) segments. The 3' NCR of L (nt 1-61) from LACV/mosquito/1978 differed from the consensus by 2 nucleotides (FIG. 1). The 5' NCR of LACV/mosquito/1978 differed from the S, M, and L consensus by 8, 3, and 1 nucleotides, respectively. For the L segment, a clear consensus sequence was not identified at position 31 of the 3' end and at nucleotide positions 6876, 6877, 6888, and 6921 in the 5' NCR. Between the two human isolates, one nucleotide difference in the NCR was identified at position 6888 of the 5' NCR of L (FIG. 2).

In Vitro Growth Kinetics

Comparison of in vitro growth of LACV/human/1960, LACV/mosquito/1978 and LACV/human/1978 viruses was performed in Vero cells and C6/36 cells (FIG. 3). All viruses replicated to high titers in both cell types. LACV/human/1960 replicated more quickly in C6/36 cells, possibly as a result of originally being isolated in these cells. Growth kinetics in Vero cells for all three viruses were nearly identical reaching approximately $10^7$ PFU/ml in 24 hours (FIG. 3A). Each of the three viruses replicated efficiently in C6/36 cells, but, in contrast to the rapid development of cytopathic effects (CPE) in Vero cells, infection of C6/36 cells was not cytopathic over the seven day period. CPE associated with LACV infection of Vero cells consisted of cell rounding and detachment from the flask with 80% of the monolayer destroyed by 3 days post-infection (FIG. 3B).

LACV Clinical Disease in Mice: $LD_{50}$

For LACV, clinical disease in mice is described by two characteristics: neurovirulence and neuroinvasiveness. Neurovirulence, defined as the extent to which a virus can infect tissues of the brain, is determined by direct inoculation of the virus into the brain followed by observation of the clinical outcome, in this case, mortality. Neuroinvasiveness is the ability of a virus introduced outside of the central nervous system (via intraperitoneal inoculation in this case) to gain access and infect the brain, which is also observed as mortality. All six LACV isolates were neurovirulent in Swiss Webster mice regardless of previous passage in mouse brains. Clinical disease in mice included lethargy, tremors, seizures, and limb paralysis, although there was no consistent sequence to the progression of disease. In suckling or weanling mice, the $LD_{50}$ values ranged from −0.50 to 1.50 login PFU (Table F). Thus, each of the three genome sequences of the parental and cloned viruses is a sequence of a fully neurovirulent virus. Of the six LACV isolates tested, five were neuroinvasive for mice of both ages whereas the LACV/human/1960-clone did not induce clinical disease in weanling mice even after inoculation of $10^6$ PFU (Table F). It was determined that this virus has a nucleotide substitution (A503G) resulting in a single amino acid change at position 148 (Threonine→Alanine) in the $G_N$ (formerly G2) attachment glycoprotein and three silent nucleotide substitutions (Table D). This suggests that the alanine residue at position 148 attenuates neuroinvasiveness. As shown in FIGS. 4-6, Threonine is well-conserved at this amino acid position among the other virus members of the CEV serogroup.

TABLE F

La Crosse neurovirulence and neuroinvasiveness after intracerebral (IC) or intraperitoneal (IP) inoculation of Swiss Webster mice.

| Virus | Neurovirulence (IC) ($LD_{50}$ $log_{10}$ PFU) | | Neuroinvasiveness (IP) ($LD_{50}$ $log_{10}$ PFU) | |
|---|---|---|---|---|
| | Suckling mice[a] | Weanling mice[b] | Suckling mice | Weanling mice |
| LACV/human/1960 | 1.35 | 1.30 | 2.17 | 2.56 |
| LACV/human/1960-clone[c] | 1.37 | −0.25 | 1.76 | >6.0 |
| LACV/human/1978 | 0.37 | −0.50 | 0.57 | 1.75 |
| LACV/human1978-clone | 0.42 | −0.15 | 0.83 | 1.25 |
| LACV/mosquito/1978 | 1.19 | 1.13 | 1.08 | 1.84 |
| LACV/mosquito/1978-clone | 1.36 | 1.50 | 1.29 | 2.40 |

[a]Suckling mice are 2-3 days old.
[b]Weanling mice are 21-23 days old.
[c]Biologically cloned viruses were obtained by terminally diluting wild type parental virus three times, then amplified by an additional passage in tissue culture.

As an initial step in vaccine development, we defined a panel of LACV genomic sequences that is associated with wild type in vitro and in vivo phenotypes. This was done by examining the phenotypic properties of parental and biologically cloned derivatives of three LACV viruses. For our purpose, a LACV was defined as exhibiting a wild type phenotype if it was fully replication competent in insect and mammalian cells and was able to cause encephalitic disease in suckling and weanling mice by a peripheral and intracerebral route of inoculation. Although LACV does not appear virulent in either mosquitoes or in its amplifying hosts in nature, it is clearly virulent in humans and mice resulting in severe central nervous system (CNS) infections in both species. Therefore, this virulence for CNS of mice is the phenotype that we envision as being modified as a surrogate phenotype for the development of attenuated vaccines for humans. Five of the six LACV isolates studied, three parental and two cloned viruses, had the wild type virulence phenotype in vivo. These defined wild type sequences can now be used as a baseline for the identification of mutations that attenuate LACV for the CNS. A live, attenuated LACV virus vaccine could reduce the occurrence of LACV encephalitis in the U.S., and could also be useful as a genetic background for the creation of chimeric vaccines against other pathogens in the Bunyaviridae family as has been successfully done for the flaviviruses and paramyxoviruses (Buchholz U J et al. 2000 J Virol 74:1187-1199; Blaney J E, Jr. et al. 2006 Viral Immunol 19:10-32).

In the present study, the complete genomic sequence of two wild type LACV isolates was determined, and one previously determined sequence was confirmed with some minor clarifications of the published sequences. These three LACV sequences, along with a previously determined sequence, were compared to examine the extent of genetic diversity of the LACV genome. Although these four viruses originated in distinct geographic locations and were isolated from either humans or mosquitoes over a period of 18 years, the viruses exhibited a remarkable level of genetic relatedness independent of passage history, location of isolation, or host. The N open reading frame of the S segment was the most conserved protein sequence (>98% identity) among the isolates, followed by that of the RNA polymerase L, NSs, and M polyprotein (>95% identity). It is possible that ecological factors, such as the need to replicate efficiently in both mammalian and insect hosts, have selected for a genotype that has obtained maximum fitness in both hosts. In such a model, variants that arise by genetic drift may be quickly selected against by either host. Although recovery of LACV from humans is unusual and isolates are rare, a greater number of isolates from both hosts might be examined for further sequence analysis.

Since we had complete sequences for two viruses isolated from mosquitoes and two from humans, it was possible to search for host specific sequences that distinguish between LACV isolates obtained from the two species. Five amino acid substitutions were found in the RNA polymerase and may define the host-specific genetic differences. In addition, four nucleotide differences in the NCR of the L segment also appear to be host-specific. Such host-specific differences were not identified in the S or M segments. None of the differences is located in the conserved Bunaviridae L protein motifs A-D (Roberts A et al. 1995 Virology 206:742-745). Since the human isolates would only be obtained from symptomatic cases, it is possible that the L segment of the LACV might be a determinant of virulence in humans and that only those LACVs with a specific L segment sequence are isolated from humans with disease. Since there were nine host-specific differences between the human and mosquito isolates, it is unlikely, although not impossible, that nine shared changes would have co-developed during the replication of a LACV in two different humans following infection with the mosquito genotype. Rather, it is likely that there are subsets of LACV strains in nature, only some of which might be capable of causing severe disease in humans. Since virus with mosquito- or human-specific L segment sequences did not differ in virulence in mice, this suggestion of an association of a sequence with human disease is offered with great caution. As additional virus isolates from humans become available for sequence analysis, it will be important to monitor these specific amino acids and nucleotides for their association with human disease. In addition, it will be interesting to determine if viruses with the human host specific sequences can be directly isolated from mosquitoes.

As a first step towards vaccine development, we sought to establish a reproducible murine model of LACV infection suitable for pathogenesis and vaccine safety/efficacy studies. In humans, disease incidence is age dependent with the majority of cases in children under 15 years old (Woodruff B A et al. 1992 Am J Epidemiol 136:320-327). Previous studies in BALB/C mice using LACV/human/1960, passaged nine times in suckling mouse brain and two times in BHK cells, resulted in an age-specific decrease in neuroinvasiveness most notable at 3 weeks of age (Janssen R et al. 1984 Lab Invest 50:447-455). In our Swiss Webster mouse model, the LD50 values were similar for both age groups, with the exception of the biologically cloned LACV/human/1960. This virus was neuroinvasive in suckling mice but not in weanling mice presumably due to a mutation in the $G_N$ glycoprotein. Although the $G_N$ glycoprotein is believed to play a role in binding of LACV virions to mosquito midgets, it may also have a role in the development of CNS disease (Ludwig G V et al. 1991 Virology 181:564-571). The use of 3-week-old weanling mice was advantageous because they are more mobile than suckling mice allowing for a more detailed observation of clinical disease manifestations. Following inoculation of 5-week-old Swiss Webster mice with $10^5$ PFU of LACV/mosquito/1978 (a dose 100% lethal for 3-week-old mice) only 50% (3 of 6) became ill, suggesting that Swiss Webster mice will also be useful in understanding age-dependent neuroinvasiveness of LACV.

Taken together, these results have implications for our future vaccine development efforts. First, LACV is genetically stable over time and distance, suggesting that a vaccine based on any of these virus isolates should induce a protective immune response against most, if not all, circulating LACV strains. Second, we have identified a mutation in the $G_N$ glycoprotein that appears to be associated with decreased neuroinvasiveness, yet does not affect virus replication in tissue culture. Clearly, our current in vivo testing allows for the identification of mutations effecting neuroinvasiveness. Third, we have identified a convenient mouse model that will allow us to screen numerous mutant viruses for attenuated neuroinvasiveness/neurovirulence and allow us to continue to evaluate the pathogenesis of LACV infection and disease.

Example 1

Several experiments were performed to identify mutations in wild-type La Crosse virus (LACV) that impact various aspects of the virus. These experiments were designed to identify mutations that attenuate the virus in a mammalian subject (e.g., mouse) and, more specifically, to identify mutations that were able to decrease LACV-mediated neurovirulence and/or neuroinvasiveness.

A conventional reverse genetic system for LACV was used to recover virus from cDNA clones, which allowed the introduction of mutations into the LACV genome and the rapid evaluation of the attenuated phenotype of the newly created mutant virus. (See Blakqori et al., *J. Virology* 79:16 (10420-10428) 2005), herein expressly incorporated by reference in its entirety). The reverse genetics system was used to introduce mutations into wild-type LACV (LACV/mosquito/1978, isolated in North Carolina, GenBank accession numbers EF485036-EF485038 and in LACV/human/1960). This analysis revealed one particular mutation (T148A), which attenuates wild-type LACV in mice.

Other approaches to identify additional attenuating mutations were investigated. By one method, a plaque variant technique was employed. Viruses with altered plaque morphologies were isolated from tissue-culture grown wild-type LACV. Several isolates displayed a decreased level of neuroinvasiveness in mice and the genomes of these viruses were sequenced (Table G). Mutation P43L (NSs) from the small plaque isolate and mutation G577E (M) from the large plaque isolate are of particular interest.

TABLE G

Level of neuroinvasiveness and amino acids differences among plaque mutants of LACV/human/1978.

| Virus isolate | Neuroinvasiveness $LD_{50}$ in mice ($log_{10}$pfu/mL) | N 43 | $NS_S$ 148 | M polyprotein 577 623 | | L 751 |
|---|---|---|---|---|---|---|
| "Small" | >4.00 | — | L | T | G E | N — |
| "Turbid" | 1.75 | — | P | T | R E | N — |
| "Large" | >4.00 | — | P | T | E E | N — |
| Human/1978 | $1.75^b$ | — | P | T | G E | X — |

[a]Amino acid number. Unique amino acids shown in bold.
[b]Previously determined $LD_{50}$ value.

By another approach, a technique utilizing 5-fluorouracil (5-FU) mutagenesis was employed. LACV was grown in the presence of the mutagen 5-FU and individual viruses were cloned from the mutagenized stock, and screened for a number of in vitro attenuation phenotypes, including, decreased replication in SH-SY5Y cells (human neuroblastoma), decreased replication in LN-18 cells (human glioblastoma cells), and decreased replication in C6/36 cells (*Aedes* mosquito cells) (Table H). Several virus isolates displayed a decreased level of neuroinvasiveness in mice and the genomes of these viruses (1C9 and 3E7) were sequenced (Table I).

TABLE H

Attenuation phenotypes of selected 5-FU mutant LACV/Human/1960c1

| Virus | Mean virus titer ($log_{10}$pfu/mL on indicated cell type) | | | | Neurovirulence $e^a$ | Neuroinvasiveness $s^b$ |
|---|---|---|---|---|---|---|
| | Vero (35° C.) | SH-Y5Y (35° C.) | LN-18 (35° C.) | C6/36 (32° C.) | $LD_{50}$ in mice ($log_{10}$pfu/mL) | $LD_{50}$ in mice ($log_{10}$pfu/mL) |
| 1C9 | 6.7 | <0.7 | <0.7 | 5.0 | >4.0 | >5.0 |
| 3E7 | 6.5 | 6.2 | <0.7 | <0.7 | >4.0 | >5.0 |
| wt | 7.9 | 6.9 | 7.1 | 7.5 | 1.30 | >6.0 |

[a]Groups of 6 mice each received 10-fold serial dilutions of virus by intracerebral inoculation (0.01 mL)
[b]Groups of 6 mice each received 10-fold serial dilutions of virus by intraperitoneal inoculation (0.1 mL)

TABLE I

Amino acids differences among 5-FU mutants of LACV/human/1960c1
Amino acid residue at the indicated position in each genome segment[a]

| Virus | N | | $M^b$ | | | | | | L | | | |
|---|---|---|---|---|---|---|---|---|---|---|---|---|
| | 11 0 | 85 | 373 | 588 | 611 | 656 | 131 | 213 | 655 | 125 2 | 135 5 | 141 3 | 180 1 |
| 1C9 | N | A | I | R | E | A | M | G | V | Y | H | N | E |
| 3E7 | S | V | T | M | K | V | I | S | M | C | Y | D | K |
| Wt | N | V | I | R | E | A | I | S | M | Y | Y | D | K |

[a]Amino Acid number.
[b]Mutant and wt LACV/human/1960c1 all contain the T148A mutation in M segment.

Accordingly, it is contemplated that an immunogenic composition comprising a peptide that comprises, consists of, or consists essentially of the T148A mutation or a nucleic acid encoding said peptide, which can also be combined with one or more other peptides that comprise, consist of, or consist essentially of any one or more other mutations of LACV as described herein, can be manufactured and used to induce an immune response to LACV (e.g., increase in antibody titer to an LACV antigen) and for the treatment, prevention, or amelioration of LACV infection or a symptom thereof.

Example 2

Cells and Viruses

C6/36 cells (*Aedes albopictus* mosquito larvae) were maintained in Earle's MEM supplemented with 10% fetal bovine serum (HyClone), 2 mM L-glutamine (Invitrogen), and 1 mM non-essential amino acids. Vero cells (African green monkey kidney) were maintained in OptiPRO™ SFM medium (Invitrogen) supplemented with 4 mM L-glutamine (Invitrogen).

LACV/human/1960 was isolated from post-mortem brain tissue collected from a Minnesota patient hospitalized in La Crosse, Wis. and passaged two times in C6/36 cells. LACV/mosquito/1978 was isolated from mosquitoes collected in North Carolina and passaged once in mouse brain and three times in Vero cells. LACV/human/1978 was isolated from post-mortem brain tissue collected in Wisconsin and passaged once in mouse brain, twice in BHK-21 cells, and once in Vero cells (Table B).

Isolation of Biologically Cloned Viruses

Biological clones were generated by terminal dilution in Vero cell cultures. Virus stocks were serially diluted in 2-fold increments and inoculated onto 90% confluent monolayers of Vero cells in 96-well plates using eight wells per dilution. After five days of incubation, cell culture fluid was removed to a holding plate, and the cell monolayers were fixed and stained for 10 minutes with crystal violet solution (1% crystal violet in equal volumes of ethanol and methanol). The virus was selected as a clonal derivative when only 1 or 2 of the 8 wells in a single row was positive for LACV CPE. Each virus was terminally diluted three times (sequentially), amplified in Vero cell culture, and subjected to genome sequence analysis.

Virus Titrations

Vero cells in 24-well plates were infected in duplicate with ten-fold serial dilutions of LACV and overlayed with OptiMEM (Invitrogen) supplemented with 1% methylcellulose, 5% FBS, 2.5 µg/ml amphotericin B, and 20 µg/ml ciprofloxicin. Five days after infection the overlay was removed and cells were washed twice with PBS. The cells were fixed and stained for 10 minutes with crystal violet solution, viral plaques were identified by characteristic CPE, and titers are expressed as login PFU/ml.

Sequence Analysis of Viral Genomes

Viral RNA was isolated using either QIAamp Viral RNA kit (Qiagen) or EZ1 Viral RNA mini kit (Qiagen). Reverse transcription (RT) was performed using random hexamer primers and SuperScript™ First-Strand Synthesis System for RT-PCR (Invitrogen). Overlapping PCR fragments were generated using LACV specific primers and Advantage cDNA polymerase reaction kit (BD Biosciences Clontech). PCR fragments of up to 2000 bp were purified and both strands directly sequenced using viral specific primers in BigDye-terminator cycle sequencing reactions analyzed on an ABI3730 genetic analyzer (Applied Biosystems). Sequence fragments were assembled into a consensus sequence using AutoAssembler 2.1 software (Applied Biosystems).

To sequence the 5' and 3' genome ends, viral RNA was isolated using QIAamp Viral RNA kit (Qiagen) from virus infected cells at 24-48 hours post infection for the 3' non-coding region (NCR) or from cell culture supernatant fluid for the 5' NCR. Viral RNA was reverse transcribed using Reverse Transcriptor (Roche) at 55° C. with random hexamer primers for the 3' NCR or at 60-70° C. with genome specific primers that enhanced reverse transcription though RNA secondary structures. cDNA was purified with High Pure (Roche) and a poly-A tail was added to the 3' end of the cDNA using 5'/3' RACE Kit, Second Generation (Roche). Genome ends were then amplified using virus and poly-A specific primers. Purified PCR fragments were sequenced as described above.

In Vitro Growth Kinetics

LACV/human/1960, LACV/mosquito/1978, and LACV/human/1978 were used to infect 95% confluent monolayers of C6/36 or Vero cells at a multiplicity of infection of 0.01 and incubated for one hour to allow attachment. Infected monolayers were washed twice with sterile PBS and overlaid with medium. Tissue culture fluid (0.5 ml) was collected every 24 hours after infection, mixed 1:10 with 10×SPG buffer (final concentration 218 mM sucrose, 6 mM L-glutamic acid, 3.8 mM dibasic potassium phosphate, pH 7.2), and frozen. Daily samples were titrated as described above. Cell monolayers were photographed on day 0, 1, 2, 3, and 4 for LACV/human/1960 infected, or non-infected Vero cells.

LACV Clinical Disease in Mice

The lethal dose$_{50}$ (LD$_{50}$) of LACV virus was evaluated in Swiss Webster suckling and weanling mice (Taconic Farms, Germantown, N.Y.). All animal experiments were carried out in accordance with the regulations and guidelines of the National Institutes of Health. Litters of 3 day-old suckling mice (n>8/dose) were inoculated with serial dilutions of wild type or biologically-cloned LACV in a volume of 10 µl intracerebrally (IC) or 100 µl intraperitoneally (IP). The experiment was repeated with 3 week-old weanling mice (n=6/dose), however, the older mice were anesthetized with isofluorane prior to IC inoculation. All mice were carefully observed twice daily for clinical disease including tremors and limb paralysis. Because clinically moribund mice were humanely euthanized before succumbing to infection, moribundity served as a surrogate for the determination of lethality.

APPENDIX 1

Large genomic segment-nucleotide sequence alignment of LACV/human/1978
(Hughes et al. 2002) and LACV/human/1978 (this study)

```
NC_004108  AGTAGTGTACCCCTATCTACAAAACTTACAGAAAATTCAGTCATATCACAATATATGCAT  60
EF485035   AGTAGTGTACTCCTATCTACAAAACTTACAGAAAATTCAGTCATATCACAATATATGCAT  60
           ********** *************************************************
```

APPENDIX 1-continued

Large genomic segment-nucleotide sequence alignment of LACV/human/1978
(Hughes et al. 2002) and LACV/human/1978 (this study)

```
NC_004108  AATGGACTATCAAGAGTATCAACAATTCTTGGCTAGGATTAATACTGCAAGGGATGCATG  120
EF485035   AATGGACTATCAAGAGTATCAACAATTCTTGGCTAGGATTAATACTGCAAGGGATGCATG  120
           ************************************************************

NC_004108  TGTAGCCAAGGATATCGATGTTGACCTATTAATGGCCAGACATGATTATTTTGGTAGAGA  180
EF485035   TGTAGCCAAGGATATCGATGTTGACCTATTAATGGCCAGACATGATTATTTTGGTAGAGA  180
           ************************************************************

NC_004108  GCTGTGCAAGTCCTTAAATATAGAATATAGGAATGATGTACCATTTGTAGATATAATTTT  240
EF485035   GCTGTGCAAGTCCTTAAATATAGAATATAGGAATGATGTACCATTTGTAGATATAATTTT  240
           ************************************************************

NC_004108  GGATATAAGGCCCGAAGTAGACCCATTAACCATAGATGCACCACATATTACCCCAGACAA  300
EF485035   GGATATAAGGCCCGAAGTAGACCCATTAACCATAGATGCACCACATATTACCCCAGACAA  300
           ************************************************************

NC_004108  TTATCTATATATAAATAATGTGTTATATATCATAGATTATAAGGTCTCTGTATCGAATGA  360
EF485035   TTATCTATATATAAATAATGTGTTATATATCATAGATTATAAGGTCTCTGTATCGAATGA  360
           ************************************************************

NC_004108  AAGCAGTGTTATAACATATGACAAATATTATGAGTTAACTAGGGACATATCCGATAGATT  420
EF485035   AAGCAGTGTTATAACATATGACAAATATTATGAGTTAACTAGGGACATATCCGATAGATT  420
           ************************************************************

NC_004108  AAGTATTCCAATAGAAATAGTTATCGTCCGTATAGACCCTGTAAGTAAGGATTTGCATAT  480
EF485035   AAGTATTCCAATAGAAATAGTTATCGTCCGTATAGACCCTGTAAGTAAGGATTTGCATAT  480
           ************************************************************

NC_004108  TAACTCTGATAGATTTAAAGAACTTTACCCTACAATAGTGGTGGATATAAACTTCAATCA  540
EF485035   TAACTCTGATAGATTTAAAGAACTTTACCCTACAATAGTGGTGGATATAAACTTCAATCA  540
           ************************************************************

NC_004108  ATTTTTCGACTTAAAACAATTACTCTATGAAAAATTCGGTGATGATGAAGAATTCCTATT  600
EF485035   ATTTTTCGACTTAAAACAATTACTCTATGAAAAATTCGGTGATGATGAAGAATTCCTATT  600
           ************************************************************

NC_004108  GAAAGTTGCACATGGTGACTTCACTCTTACAGCACCCTGGTGCAAGACTGGGTGCCCTGA  660
EF485035   GAAAGTTGCACATGGTGACTTCACTCTTACAGCACCCTGGTGCAAGACTGGGTGCCCTGA  660
           ************************************************************

NC_004108  ATTTTGGAAACACCCCATTTATAAAGAATTTAAAATGAGTATGCCAGTACCTGAGCGGAG  720
EF485035   ATTTTGGAAACACCCCATTTATAAAGAATTTAAAATGAGTATGCCAGTACCTGAGCGGAG  720
           ************************************************************

NC_004108  GCTCTTTGAAGAATCTGTCAAGTTCAATGCTTATGAATCTGAGAGATGGAATACTAACTT  780
EF485035   GCTCTTTGAAGAATCTGTCAAGTTCAATGCTTATGAATCTGAGAGATGGAATACTAACTT  780
           ************************************************************

NC_004108  GGTTAAAATCAGAGAATATACAAAGAAAGACTATTCAGAGCATATTTCAAAATCTGCAAA  840
EF485035   GGTTAAAATCAGAGAATATACAAAGAAAGACTATTCAGAGCATATTTCAAAATCTGCAAA  840
           ************************************************************

NC_004108  AAATATTTTCCTGGCTAGTGGATTTTATAAGCAGCCAAATAAGAATGAGATTAGTGAGGG  900
EF485035   AAATATTTTCCTGGCTAGTGGATTTTATAAGCAGCCAAATAAGAATGAGATTAGTGAGGG  900
           ************************************************************

NC_004108  GTGGACATTAATGGTTGAGAGGGTTCAAGATCAGAGAGAAATCTCAAAATCTCTCCATGA  960
EF485035   GTGGACATTAATGGTTGAGAGGGTTCAAGATCAGAGAGAAATCTCAAAATCTCTCCATGA  960
           ************************************************************

NC_004108  CCAGAAACCTAGCATACATTTTATATGGGGAGCCCATAACCCAGGAAATAGTAATAATGC  1020
EF485035   CCAGAAACCTAGCATACATTTTATATGGGGAGCCCATAACCCAGGAAATAGTAATAATGC  1020
           ************************************************************

NC_004108  AACCTTCAAACTCATATTGCTTTCAAAGTCCTTACAAAGCATAAAAGGTATATCAACTTA  1080
EF485035   AACCTTCAAACTCATATTGCTTTCAAAGTCCTTACAAAGCATAAAAGGTATATCAACTTA  1080
           ************************************************************

NC_004108  CACAGAAGCGTTCAAATCTTTAGGAAAAATGATGGATATTGGAGATAAGGCTATTGAGTA  1140
EF485035   CACAGAAGCGTTCAAATCTTTAGGAAAAATGATGGATATTGGAGATAAGGCTATTGAGTA  1140
           ************************************************************

NC_004108  TGAAGAATTCTGCATGTCCCTAAAAAGCAAAGCAAGATCATCATGGAAGCAAATAATGAA  1200
EF485035   TGAAGAATTCTGCATGTCCCTAAAAAGCAAAGCAAGATCATCATGGAAGCAAATAATGAA  1200
           ************************************************************
```

APPENDIX 1-continued

Large genomic segment-nucleotide sequence alignment of LACV/human/1978
(Hughes et al. 2002) and LACV/human/1978 (this study)

```
NC_004108  CAAAAAATTAGAGCCTAAACAAATAAACAATGCCCTTGTTTTATGGGAACAGCAGTTTAT  1260
EF485035   CAAAAAATTAGAGCCTAAACAAATAAACAATGCCCTTGTTTTATGGGAACAGCAGTTTAT  1260
           ************************************************************

NC_004108  GGTAAATAATGACCTGATAGACAAAAGTGAGAAGTTGAAATTATTCAAAAATTTCTGCGG  1320
EF485035   GGTAAATAATGACCTGATAGACAAAAGTGAGAAGTTGAAATTATTCAAAAATTTCTGCGG  1320
           ************************************************************

NC_004108  TATAGGCAAACACAAGCAATTCAAGAATAAAATGCTAGAGGATCTAGAAGTGTCAAAGCC  1380
EF485035   TATAGGCAAACACAAGCAATTCAAGAATAAAATGCTAGAGGATCTAGAAGTGTCAAAGCC  1380
           ************************************************************

NC_004108  CAAAATATTAGACTTTGATGACGCAAATATGTATCTAGCTAGCCTAACCATGATGGAACA  1440
EF485035   CAAAATATTAGACTTTGATGACGCAAATATGTATCTAGCTAGCCTAACCATGATGGAACA  1440
           ************************************************************

NC_004108  GAGTAAGAAGATATTGTCCAAAAGCAATGGGTTGAAGCCAGATAATTTTATACTGAATGA  1500
EF485035   GAGTAAGAAGATATTGTCCAAAAGCAATGGGTTGAAGCCAGATAATTTTATACTGAATGA  1500
           ************************************************************

NC_004108  ATTTGGATCCAAAATCAAAGATGCTAATAAAGAAACATATGACAATATGCACAAAATATT  1560
EF485035   ATTTGGATCCAAAATCAAAGATGCTAATAAAGAAACATATGACAATATGCACAAAATATT  1560
           ************************************************************

NC_004108  TGAGACAAGATATTGGCAATGTATATCCGACTTCTCTACTCTGATGAAAAATATCTTATC  1620
EF485035   TGAGACAAGATATTGGCAATGTATATCCGACTTCTCTACTCTGATGAAAAATATCTTATC  1620
           ************************************************************

NC_004108  TGTGTCCCAATATAACAGGCACAACACATTTAGGATAGCTATGTGTGCTAATAACAATGT  1680
Ef485035   TGTGTCCCAATATAACAGGCACAACACATTTAGGATAGCTATGTGTGCTAATAACAATGT  1680
           ************************************************************

NC_004108  CTTTGCTATAGTATTTCCTTCGGCTGACATAAAAACTAAGAAAGCAACTGTAGTTTATAG  1740
EF485035   CTTTGCTATAGTATTTCCTTCGGCTGACATAAAAACTAAGAAAGCAACTGTAGTTTATAG  1740
           ************************************************************

NC_004108  CATTATAGTGCTGCATAAAGAGGAAGAAAACATATTCAACCCAGGATGTTTGCACGGCAC  1800
EF485035   CATTATAGTGCTGCATAAAGAGGAAGAAAACATATTCAACCCAGGATGTTTGCACGGCAC  1800
           ************************************************************

NC_004108  ATTTAAGTGTATGAATGGGTATATTTCCATATCTAGAGCTATAAGGCTAGATAAAGAGAG  1860
EF485035   ATTTAAGTGTATGAATGGGTATATTTCCATATCTAGAGCTATAAGGCTAGATAAAGAGAG  1860
           ************************************************************

NC_004108  GTGCCAGAGAATTGTTTCCTCACCTGGACTGTTTTTAACAACTTGCCTACTATTCAAACA  1920
EF485035   GTGCCAGAGAATTGTTTCCTCACCTGGACTGTTTTTAACAACTTGCCTACTATTCAAACA  1920
           ************************************************************

NC_004108  TGATAATCCAACTCTAGTGATGAGCGATATTATGAATTTTTCTATATACACTAGCCTGTC  1980
EF485035   TGATAATCCAACTCTAGTGATGAGCGATATTATGAATTTTTCTATATACACTAGCCTGTC  1980
           ************************************************************

NC_004108  TATCACAAAGAGTGTTCTATCTTTAACAGAGCCAGCACGCTACATGATTATGAACTCATT  2040
EF485035   TATCACAAAGAGTGTTCTATCTTTAACAGAGCCAGCACGCTACATGATTATGAACTCATT  2040
           ************************************************************

NC_004108  AGCTATCTCCAGCAATGTTAAGGACTATATAGCAGAGAAATTTTCCCCTTACACAAAGAC  2100
EF485035   AGCTATCTCCAGCAATGTTAAGGACTATATAGCAGAGAAATTTTCCCCTTACACAAAGAC  2100
           ************************************************************

NC_004108  ACTGTTCAGTGTCTATATGACTAGACTAATTAAAAATGCTTGCTTTGATGCTTATGACCA  2160
EF485035   ACTGTTCAGTGTCTATATGACTAGACTAATTAAAAATGCTTGCTTTGATGCTTATGACCA  2160
           ************************************************************

NC_004100  GAGACAGCGTGTCCAACTTAGAGATATATATTTATCTGATTATGACATAACCCAAAAAGG  2220
EF485035   GAGACAGCGTGTCCAACTTAGAGATATATATTTATCTGATTATGACATAACCCAAAAAGG  2220
           ************************************************************

NC_004108  TATTAAAGACAATAGAGAGCTAACAAGTATATGGTTCCCTGGTAGTGTAACATTAAAGGA  2280
EF485035   TATTAAAGACAATAGAGAGCTAACAAGTATATGGTTCCCTGGTAGTGTAACATTAAAGGA  2280
           ************************************************************

NC_004108  GTATTTAACACAAATATACTTACCATTTTATTTTAATGCTAAAGGACTACATGAGAAGCA  2340
EF485035   GTATTTAACACAAATATACTTACCATTTTATTTTAATGCTAAAGGACTACATGAGAAGCA  2340
           ************************************************************
```

APPENDIX 1-continued

Large genomic segment-nucleotide sequence alignment of LACV/human/1978
(Hughes et al. 2002) and LACV/human/1978 (this study)

```
NC_004108  CCATGTCATGGTGGATCTAGCAAAGACTATATTAGAAATAGAGTGCGAACAGAGGGAAAA  2400
EF485035   CCATGTCATGGTGGATCTAGCAAAGACTATATTAGAAATAGAGTGCGAACAGAGGGAAAA  2400
           ************************************************************

NC_004108  CATAAAGGAGATATGGTCTACAAATTGTACCAAACAGACAGTGAACCTTAAAATTTTGAT  2460
EF485035   CATAAAGGAGATATGGTCTACAAATTGTACCAAACAGACAGTGAACCTTAAAATTTTGAT  2460
           ************************************************************

NC_004108  CCATTCCTTGTGCAAGAATTTACTAGCAGACACTTCAAGACACAACCACTTGCGGAACAG  2520
EF485035   CCATTCCTTGTGCAAGAATTTACTAGCAGACACTTCAAGACACAACCACTTGCGGAACAG  2520
           ************************************************************

NC_004108  AATAGAAAATAGGAACAATTTTAGAAGGTCTATAACAACTATTTCAACATTTACAAGTTC  2580
EF485035   AATAGAAAATAGGAACAATTTTAGAAGGTCTATAACAACTATTTCAACATTTACAAGTTC  2580
           ************************************************************

NC_004108  AAAGTCTTGCCTCAAAATAGGGGACTTTAGAAAAGAGAAAGAGCTGCAGTCAGTTAAACA  2640
EF485035   AAAGTCTTGCCTCAAAATAGGGGACTTTAGAAAAGAGAAAGAGCTGCAGTCAGTTAAACA  2640
           ************************************************************

NC_004108  GAAGAAAATCTTAGAGGTGCAGAGTCGCAAAATGAGATTAGCAAACCCAATGTTCGTGAC  2700
EF485035   GAAGAAAATCTTAGAGGTGCAGAGTCGCAAAATGAGATTAGCAAACCCAATGTTCGTGAC  2700
           ************************************************************

NC_004108  AGATGAACAAGTATGCCTTGAAGTTGGGCACTGCAATTATGAGATGCTGAGGAATGCTAT  2760
EF485035   AGATGAACAAGTATGCCTTGAAGTTGGGCACTGCAATTATGAGATGCTGAGGAATGCTAT  2760
           ************************************************************

NC_004108  GCCGAATTATACAGATTATATATCAACTAAAGTATTTGATAGGTTATATGAGTTATTAGA  2820
EF485035   GCCGAATTATACAGATTATATATCAACTAAAGTATTTGATAGGTTATATGAGTTATTAGA  2820
           ************************************************************

NC_004108  TAAAGGAGTTTTGACAGACAAGCCTGTTATAGAGCAAATAATGGATATGATGGTCGACCA  2880
EF485035   TAAAGGAGTTTTGACAGACAAGCCTGTTATAGAGCAAATAATGGATATGATGGTCGACCA  2880
           ************************************************************

NC_004108  CAAAAAGTTCTATTTCACATTTTTCAATAAAGGCCAGAAAACGTCAAAGGATAGAGAGAT  2940
EF485035   CAAAAAGTTCTATTTCACATTTTTCAATAAAGGCCAGAAAACGTCAAAGGATAGAGAGAT  2940
           ************************************************************

NC_004108  ATTCGTTGGAGAATATGAAGCTAAAATGTGTATGTACGCAGTTGAGAGAATAGCAAAAGA  3000
EF485035   ATTCGTTGGAGAATATGAAGCTAAAATGTGTATGTACGCAGTTGAGAGAATAGCAAAAGA  3000
           ************************************************************

NC_004108  AAGATGTAAATTAAATCCTGATGAAATGATATCTGAGCCGGGTGATGGCAAGTTGAAGGT  3060
EF485035   AAGATGTAAATTAAATCCTGATGAAATGATATCTGAGCCGGGTGATGGCAAGTTGAAGGT  3060
           ************************************************************

NC_004108  GTTGGAGCAAAAATCAGAACAAGAAATTCGATTCTTGGTCGAGACTACAAGGCAAAAGAA  3120
EF485035   GTTGGAGCAAAAATCAGAACAAGAAATTCGATTCTTGGTCGAGACTACAAGGCAAAAGAA  3120
           ************************************************************

NC_004108  TCGTGAAATCGATGAGGCAATTGAAGCATTAGCTGCAGAAGGATATGAGAGTAATCTAGA  3180
EF485035   TCGTGAAATCGATGAGGCAATTGAAGCATTAGCTGCAGAAGGATATGAGAGTAATCTAGA  3180
           ************************************************************

NC_004108  AAAAATTGAAAAGCTTTCACTTGGCAAAGCAAAGGGCCTAAAGATGGAAATAAATGCAGA  3240
EF485035   AAAAATTGAAAAGCTTTCACTTGGCAAAGCAAAGGGCCTAAAGATGGAAATAAATGCAGA  3240
           ************************************************************

NC_004108  TATGTCTAAATGGAGTGCTCAGGATGTTTTTTATAAATATTTCTGGCTCATAGCCTTAGA  3300
EF485035   TATGTCTAAATGGAGTGCTCAGGATGTTTTTTATAAATATTTCTGGCTCATAGCCTTAGA  3300
           ************************************************************

NC_004108  CCCTATCCTCTACCCACAGGAAAAAGAGAGAATATTATACTTTATGTGCAACTACATGGA  3360
EF485035   CCCTATCCTCTACCCACAGGAAAAAGAGAGAATATTATACTTTATGTGCAACTACATGGA  3360
           ************************************************************

NC_004108  TAAAGAATTGATACTGCCAGATGAATTATTATTCAATTTGCTGGACCAAAAAGTTGCATA  3420
EF485035   TAAAGAATTGATACTGCCAGATGAATTATTATTCAATTTGCTGGACCAAAAAGTTGCATA  3420
           ************************************************************

NC_004108  CCAGAATGATATAATAGCTACTATGACTAATCAATTAAATTCAAATACAGTTCTGATAAA  3480
EF485035   CCAGAATGATATAATAGCTACTATGACTAATCAATTAAATTCAAATACAGTTCTGATAAA  3480
           ************************************************************
```

APPENDIX 1-continued

Large genomic segment-nucleotide sequence alignment of LACV/human/1978
(Hughes et al. 2002) and LACV/human/1978 (this study)

```
NC_004108  GAGAAATTGGCTCCAAGGGAATTTCAACTACACCTCAAGTTACGTCCATAGCTGCGCAAT  3540
EF485035   GAGAAATTGGCTCCAAGGGAATTTCAACTACACCTCAAGTTACGTCCATAGCTGCGCAAT  3540
           ************************************************************

NC_004108  GTCTGTGTATAAAGAAATATTAAAAGAGGCCATAACATTACTAGACGGGTCTATATTAGT  3600
EF485035   GTCTGTGTATAAAGAAATATTAAAAGAGGCCATAACATTACTAGACGGGTCTATATTAGT  3600
           ************************************************************

NC_004108  CAACTCATTAGTCCATTCGGATGATAACCAAACATCGATAACAATAGTTCAGGATAAGAT  3660
EF485035   CAACTCATTAGTCCATTCGGATGATAACCAAACATCGATAACAATAGTTCAGGATAAGAT  3660
           ************************************************************

NC_004108  GGAAAATGATAAAATTATAGATTTTGCAATGAAAGAATTTGAGAGAGCCTGTTTGACATT  3720
EF485035   GGAAAATGATAAAATTATAGATTTTGCAATGAAAGAATTTGAGAGAGCCTGTTTGACATT  3720
           ************************************************************

NC_004108  TGGATGCCAAGCAAATATGAAAAAGACATATGTAACAAATTGCATAAAAGAGTTTGTTTC  3780
EF485035   TGGATGCCAAGCAAATATGAAAAAGACATATGTAACAAATTGCATAAAAGAGTTTGTTTC  3780
           ************************************************************

NC_004108  ATTATTTAACTTGTACGGCGAACCCTTTTCAATATATGGCAGATTCCTATTAACATCTGT  3840
EF485035   ATTATTTAACTTGTACGGCGAACCCTTTTCAATATATGGCAGATTCCTATTAACATCTGT  3840
           ************************************************************

NC_004108  GGGTGATTGTGCCTATATAGGGCCTTATGAAGATTTAGCTAGTCGAATATCATCAGCCCA  3900
EF485035   GGGTGATTGTGCCTATATAGGGCCTTATGAAGATTTAGCTAGTCGAATATCATCAGCCCA  3900
           ************************************************************

NC_004108  GACAGCCATAAAGCATGGTTGTCCACCCAGTCTAGCATGGGTGTCCATAGCAATAAGTCA  3960
EF485035   GACAGCCATAAAGCATGGTTGTCCACCCAGTCTAGCATGGGTGTCCATAGCAATAAGTCA  3960
           ************************************************************

NC_004108  TTGGATGACCTCTCTGACATACAACATGCTACCAGGGCAGTCAAATGACCCAATTGATTA  4020
EF485035   TTGGATGACCTCTCTGACATACAACATGCTACCAGGGCAGTCAAATGACCCAATTGATTA  4020
           ************************************************************

NC_004108  TTTCCCTGCAGAAAATAGGAAGGATATCCCTATAGAATTGAATGGTGTATTAGATGCTCC  4080
EF485035   TTTCCCTGCAGAAAATAGGAAGGATATCCCTATAGAATTGAATGGTGTATTAGATGCTCC  4080
           ************************************************************

NC_004108  ATTGTCAATGATTAGTACAGTTGGATTGGAATCTGGGAATTTATACTTCTTGATAAAGTT  4140
EF485035   ATTGTCAATGATTAGTACAGTTGGATTGGAATCTGGGAATTTATACTTCTTGATAAAGTT  4140
           ************************************************************

NC_004108  GTTGAGCAAATATACCCCGGTCATGCAGAAAAGAGAGTCAGTAGTCAACCAAATAGCTGA  4200
EF485035   GTTGAGCAAATATACCCCGGTCATGCAGAAAAGAGAGTCAGTAGTCAACCAAATAGCTGA  4200
           ************************************************************

NC_004108  AGTTAAGAACTGGAAGGTCGAGGATCTAACAGACAATGAAATATTTAGACTTAAAATACT  4260
EF485035   AGTTAAGAACTGGAAGGTCGAGGATCTAACAGACAATGAAATATTTAGACTTAAAATACT  4260
           ************************************************************

NC_004108  CAGATATTTAGTTCTAGATGCAGAGATGGACCCTAGTGATATTATGGGTGAGACAAGCGA  4320
EF485035   CAGATATTTAGTTCTAGATGCAGAGATGGACCCTAGTGATATTATGGGTGAGACAAGCGA  4320
           ************************************************************

NC_004108  CATGAGAGGGAGGTCTATTTTGACACCTAGAAAATTCACAACAGCAGGCAGTTTAAGGAA  4380
EF485035   CATGAGAGGGAGGTCTATTTTGACACCTAGAAAATTCACAACAGCAGGCAGTTTAAGGAA  4380
           ************************************************************

NC_004108  ATTATATTCTTTCAGTAAGTACCAGGATAGACTGTCTTCCCCTGGAGGCATGGTTGAATT  4440
EF485035   ATTATATTCTTTCAGTAAGTACCAGGATAGACTGTCTTCCCCTGGAGGCATGGTTGAATT  4440
           ************************************************************

NC_004108  GTTCACTTATTTGCTTGAGAAACCTGAGTTGTTAGTGACTAAAGGGGAAGATATGAAAGA  4500
EF485035   GTTCACTTATTTGCTTGAGAAACCTGAGTTGTTAGTGACTAAAGGGGAAGATATGAAAGA  4500
           ************************************************************

NC_004108  TTATATGGAATCTGTGATATTCCGATATAATTCCAAAAGGTTCAAAGAAAGTTTGTCAAT  4560
EF485035   TTATATGGAATCTGTGATATTCCGATATAATTCCAAAAGGTTCAAAGAAAGTTTGTCAAT  4560
           ************************************************************

NC_004108  ACAGAACCCAGCACAATTATTTATAGAACAGATATTGTTCTCACATAAGCCCATAATAGA  4620
EF485035   ACAGAACCCAGCACAATTATTTATAGAACAGATATTGTTCTCACATAAGCCCATAATAGA  4620
           ************************************************************
```

APPENDIX 1-continued

Large genomic segment-nucleotide sequence alignment of LACV/human/1978
(Hughes et al. 2002) and LACV/human/1978 (this study)

```
NC_004108  CTTTTCTGGTATCAGGGACAAATATATAAACCTACATGATAGTAGAGCTCTAGAGAAGGA  4680
EF485035   CTTTTCTGGTATCAGGGACAAATATATAAACCTACATGATAGTAGAGCTCTAGAGAAGGA  4680
           ************************************************************

NC_004108  ACCTGACATATTAGGAAAAGTAACATTTACAGAGGCTTATAGATTATTAATGAGGGACCT  4740
EF485035   ACCTGACATATTAGGAAAAGTAACATTTACAGAGGCTTATAGATTATTAATGAGGGACCT  4740
           ************************************************************

NC_004108  GTCTAGCCTAGAACTAACCAATGATGACATTCAAGTAATTTATTCTTACATAATACTTAA  4800
EF485035   GTCTAGCCTAGAACTAACCAATGATGACATTCAAGTAATTTATTCTTACATAATACTTAA  4800
           ************************************************************

NC_004108  TGACCCTATGATGATAACTATTGCAAACACACATATATTGTCAATATACGGGAGTCCTCA  4860
EF485035   TGACCCTATGATGATAACTATTGCAAACACACATATATTGTCAATATACGGGAGTCCTCA  4860
           ************************************************************

NC_004108  ACGGAGGATGGGCATGTCCTGTTCAACGATGCCAGAATTTAGAAATTTAAAATTAATACA  4920
EF485035   ACGGAGGATGGGCATGTCCTGTTCAACGATGCCAGAATTTAGAAATTTAAAATTAATACA  4920
           ************************************************************

NC_004108  TCATTCCCCAGCCTTAGTTTTGAGAGCATATAGTAAAAATAATCCTGACATCCAGGGTGC  4980
EF485035   TCATTCCCCAGCCTTAGTTTTGAGAGCATATAGTAAAAATAATCCTGACATCCAGGGTGC  4980
           ************************************************************

NC_004108  TGATCCCACGGAAATGGCTAGAGATTTAGTTCATCTGAAAGAGTTTGTTGAGAACACAAA  5040
EF485035   TGATCCCACGGAAATGGCTAGAGATTTAGTTCATCTGAAAGAGTTTGTTGAGAACACAAA  5040
           ************************************************************

NC_004108  TTTAGAAGAAAAAATGAAAGTTAGGATTGCTATAAATGAAGCAGAGAAAGGACAACGGGA  5100
EF485035   TTTAGAAGAAAAAATGAAAGTTAGGATTGCTATAAATGAAGCAGAGAAAGGACAACGGGA  5100
           ************************************************************

NC_004108  TATAGTCTTTGAACTAAAAGAGATGACTAGATTTTATCAGGTTTGCTATGAGTATGTCAA  5160
EF485035   TATAGTCTTTGAACTAAAAGAGATGACTAGATTTTATCAGGTTTGCTATGAGTATGTCAA  5160
           ************************************************************

NC_004108  ATCTACAGAACACAAGATAAAAGTCTTCATTCTCCCGACAAAATCATACACAACAACAGA  5220
EF485035   ATCTACAGAACACAAGATAAAAGTCTTCATTCTCCCGACAAAATCATACACAACAACAGA  5220
           ************************************************************

NC_004108  TTTCTGTTCACTCATGCAGGGGAATTTAATAAAAGATAAAGAGTGGTACACAGTTCACTA  5280
EF485035   TTTCTGTTCACTCATGCAGGGGAATTTAATAAAAGATAAAGAGTGGTACACAGTTCACTA  5280
           ************************************************************

NC_004108  CCTAAAACAGATATTGTCTGGTGGCCATAAAGCCATAATGCAGCATAATGCCACTAGTGA  5340
EF485035   CCTAAAACAGATATTGTCTGGTGGCCATAAAGCCATAATGCAGCATAATGCCACTAGTGA  5340
           ************************************************************

NC_004108  GCAAAATATTGCTTTTGAGTGTTTCAAATTAATTACCCATTTTGCAGACTCATTCATAGA  5400
EF485035   GCAAAATATTGCTTTTGAGTGTTTCAAATTAATTACCCATTTTGCAGACTCATTCATAGA  5400
           ************************************************************

NC_004108  TTCATTATCTAGGTCAGCTTTTTTGCAGTTGATAATAGATGAATTCAGTTATAAAGATGT  5460
EF485035   TTCATTATCTAGGTCAGCTTTTTTGCAGTTGATAATAGATGAATTCAGTTATAAAGATGT  5460
           ************************************************************

NC_004108  GAAGGTTAGCAAACTTTATGACATAATAAAGAATGGGTATAATCGAACTGACTTCATACC  5520
EF485035   GAAGGTTAGCAAACTTTATGACATAATAAAGAATGGGTATAATCGAACTGACTTCATACC  5520
           ************************************************************

NC_004108  ATTGCTTTTTAGAACTGGCGATTTAAGACAAGCTGACTTAGACAAGTATGATGCTATGAA  5580
EF485035   ATTGCTTTTTAGAACTGGCGATTTAAGACAAGCTGACTTAGACAAGTATGATGCTATGAA  5580
           ************************************************************

NC_004108  AAGTCATGAGAGGGTTACATGGAATGATTGGCAAACATCTCGTCACTTGGACATGGGCTC  5640
EF485035   AAGTCATGAGAGGGTTACATGGAATGATTGGCAAACATCTCGTCACTTGGACATGGGCTC  5640
           ************************************************************

NC_004108  AATTAATCTAACAATAACCGGTTACAATAGATCAATAACAATAATCGGAGAAGATAACAA  5700
EF485035   AATTAATCTAACAATAACCGGTTACAATAGATCAATAACAATAATCGGAGAAGATAACAA  5700
           ************************************************************

NC_004108  ATTGACATATGCAGAATTATGTCTGACTAGGAAAACTCCTGAGAATATAACTATAAGTGG  5760
EF485035   ATTGACATATGCAGAATTATGTCTGACTAGGAAAACTCCTGAGAATATAACTATAAGTGG  5760
           ************************************************************
```

APPENDIX 1-continued

Large genomic segment-nucleotide sequence alignment of LACV/human/1978
(Hughes et al. 2002) and LACV/human/1978 (this study)

```
NC_004108  CAGAAAATTGCTAGGTGCAAGGCATGGACTTAAATTTGAAAATATGTCCAAAATCCAAAC  5820
EF485035   CAGAAAATTGCTAGGTGCAAGGCATGGACTTAAATTTGAAAATATGTCCAAAATCCAAAC  5820
           ************************************************************

NC_004108  ATACCCAGGCAATTATTATATAACATATAGAAAGAAAGATCGCCACCAGTTTGTATACCA  5880
EF485035   ATACCCAGGCAATTATTATATAACATATAGAAAGAAAGATCGCCACCAGTTTGTATACCA  5880
           ************************************************************

NC_004108  GATACATTCTCATGAATCAATAACAAGGAGGAATGAAGAGCATATGGCTATCAGGACCAG  5940
EF485035   GATACATTCTCATGAATCAATAACAAGGAGGAATGAAGAGCATATGGCTATCAGGACCAG  5940
           ************************************************************

NC_004108  AATATACAATGAAATAACTCCAGTATGTGTAGTTAACGTTGCAGAGGTGGATGGGGACCA  6000
EF485035   AATATACAATGAAATAACTCCAGTATGTGTAGTTAACGTTGCAGAGGTGGATGGGGACCA  6000
           ************************************************************

NC_004108  ACGTATATTGATAAGATCTTTAGACTATCTAAATAATGATATATTTTCTCTTTCAAGGAT  6060
EF485035   ACGTATATTGATAAGATCTTTAGACTATCTAAATAATGATATATTTTCTCTTTCAAGGAT  6060
           ************************************************************

NC_004108  TAAAGTCGGGCTTGACGAATTTGCAACAATAAAAAAAGCACACTTTAGTAAAATGGTCTC  6120
EF485035   TAAAGTCGGGCTTGACGAATTTGCAACAATAAAAAAAGCACACTTTAGTAAAATGGTCTC  6120
           ************************************************************

NC_004108  ATTTGAAGGACCCCCAATTAAGACAGGGCTCCTCGACCTTACTGAATTGATGAAATCTCA  6180
EF485035   ATTTGAAGGACCCCCAATTAAGACAGGGCTCCTCGACCTTACTGAATTGATGAAATCTCA  6180
           ************************************************************

NC_004108  AGATTTGCTTAACCTTAATTATGATAATATAAGGAATAGCAACTTGATATCTTTTTCAAA  6240
EF485035   AGATTTGCTTAACCTTAATTATGATAATATAAGGAATAGCAACTTGATATCTTTTTCAAA  6240
           ************************************************************

NC_004108  ATTGATTTGCTGTGAGGGGTCAGATAATATAAATGATGGGTTAGAGTTTCTGTCCGATGA  6300
EF485035   ATTGATTTGCTGTGAGGGGTCAGATAATATAAATGATGGGTTAGAGTTTCTGTCCGATGA  6300
           ************************************************************

NC_004108  CCCTATGAACTTTACAGAGGGTGAAGCAATACATTCAACACCGATCTTTAATATATATTA  6360
EF485035   CCCTATGAACTTTACAGAGGGTGAAGCAATACATTCAACACCGATCTTTAATATATATTA  6360
           ************************************************************

NC_004108  CTCAAAAAGAGGAGAAAGACATATGACATACAGGAATGCAATTAAATTACTGATAGAAAG  6420
EF485035   CTCAAAAAGAGGAGAAAGACATATGACATACAGGAATGCAATTAAATTACTGATAGAAAG  6420
           ************************************************************

NC_004108  AGAAACTAAGATTTTTGAAGAAGCTTTCACATTCAGTGAGAATGGCTTCATATCGCCAGA  6480
EF485035   AGAAACTAAGATTTTTGAAGAAGCTTTCACATTCAGTGAGAATGGCTTCATATCGCCAGA  6480
           ************************************************************

NC_004108  GAATCTTGGTTGCTTAGAAGCAGTAGTATCATTAATAAAATTGTTGAAAACTAATGAGTG  6540
EF485035   GAATCTTGGTTGCTTAGAAGCAGTAGTATCATTAATAAAATTGTTGAAAACTAATGAGTG  6540
           ************************************************************

NC_004108  GTCCACAGTTATAGATAAATGTATTCATATATGTTTAATAAAGAATGGTATGGATCACAT  6600
EF485035   GTCCACAGTTATAGATAAATGTATTCATATATGTTTAATAAAGAATGGTATGGATCACAT  6600
           ************************************************************

NC_004108  GTACCATTCATTTGATGTCCCTAAATGTTTTATGGGGAATCCTATCACTAGAGACATGAA  6660
EF485035   GTACCATTCATTTGATGTCCCTAAATGTTTTATGGGGAATCCTATCACTAGAGACATGAA  6660
           ************************************************************

NC_004108  TTGGATGATGTTTAGAGAATTCATCAATAGTTTACCAGGGACAGATATACCACCATGGAA  6720
EF485035   TTGGATGATGTTTAGAGAATTCATCAATAGTTTACCAGGGACAGATATACCACCATGGAA  6720
           ************************************************************

NC_004108  TGTCATGACAGAGAACTTCAAAAAGAAATGTATTGCTCTGATAAACTCTAAGTTAGAAAC  6780
EF485035   TGTCATGACAGAGAACTTCAAAAAGAAATGTATTGCTCTGATAAACTCTAAGTTAGAAAC  6780
           ************************************************************

NC_004108  ACAGAGAGATTTCTCAGAATTCACTAAACTGATGAAAAAGGAAGGTGGGAGGAGTAATAT  6840
EF485035   ACAGAGAGATTTCTCAGAATTCACTAAACTGATGAAAAAGGAAGGTGGGAGGAGTAATAT  6840
           ************************************************************

NC_004108  AGAATTTGATTAGTAGTTATGAGTTTACAGAGAACCTACAATTAGGCTATAAATTTGGGA  6900
EF485035   AGAATTTGATTAGTAGTTATGAGTTTACAGAGAACCTACAATTAGGCTATAAATTTGGGA  6900
           ************************************************************
```

APPENDIX 1-continued

Large genomic segment-nucleotide sequence alignment of LACV/human/1978
(Hughes et al. 2002) and LACV/human/1978 (this study)

```
NC_004108  GGGTTTTGGAAATTGGCTAAAATTCAAAAAGAGGGGGATTAACAGCAACTGTATAAATTT  6960
EF485035   GGGTTTTGGAAATTGGCTAAAATTCAAAAAGAGGGGGATTAACAGCAACTGTATAAATTT  6960
           ************************************************************

NC_004108  GTAGATAGGGGCACACTACT  6980 (SEQ. ID. No. 1)
EF485035   GTAGATAGGAGCACACTACT  6980 (SEQ. ID. NO. 2)
           ********* **********
```

APPENDIX 2

Medium genomic segment-nucleotide sequence alignment of
LACV/human/1978 (Hughes et al. 2002) and LACV/human/1978 (this study)

```
NC_004109  AGTAGTGTACTACCAAGTATAGATAACGTTTGAATATTAAAGTTTTGAATCAAAGCCAAA   60
EF485034   AGTAGTGTACTACCAAGTATAGATAACGTTTGAATATTAAAGTTTTGAATCAAAGCCAAA   60
           ************************************************************

NC_004109  GATGATTTGTATATTGGTGCTAATTACAGTTGCAGCTGCAAGCCCAGTGTATCAAAGGTG  120
EF485034   GATGATTTGTATATTGGTGCTAATTACAGTTGCAGCTGCAAGCCCAGTGTATCAAAGGTG  120
           ************************************************************

NC_004109  TTTCCAAGATGGGGCTATAGTGAAGCAAAACCCATCCAAAGAAGCAGTTACAGAGGTGTG  180
EF485034   TTTCCAAGATGGGGCTATAGTGAAGCAAAACCCATCCAAAGAAGCAGTTACAGAGGTGTG  180
           ************************************************************

NC_004109  CCTGAAAGATGATGTTAGCATGATCAAAACAGAGGCCAGGTATGTAAGAAATGCAACAGG  240
EF485034   CCTGAAAGATGATGTTAGCATGATCAAAACAGAGGCCAGGTATGTAAGAAATGCAACAGG  240
           ************************************************************

NC_004109  AGTTTTTTCAAATAATGTCGCAATAAGGAAATGGCTAGTCTCTGATTGGCATGATTGCAG  300
EF485034   AGTTTTTTCAAATAATGTCGCAATAAGGAAATGGCTAGTCTCTGATTGGCATGATTGCAG  300
           ************************************************************

NC_004109  GCCTAAGAAGATCGTTGGGGGACACATCAATGTAATAGAAGTTGGTGATGACCTGTCACT  360
EF485034   GCCTAAGAAGATCGTTGGGGGACACATCAATGTAATAGAAGTTGGTGATGACCTGTCACT  360
           ************************************************************

NC_004109  CCATACTGAATCATATGTTTGCAGCGCAGATTGTACCATAGGTGTAGACAAAGAGACTGC  420
EF485034   CCATACTGAATCATATGTTTGCAGCGCAGATTGTACCATAGGTGTAGACAAAGAGACTGC  420
           ************************************************************

NC_004109  ACAGGTCAGGCTTCAGACAGATACCACAAATCATTTTGAAATTGCAGGCACTACTGTGAA  480
EF485034   ACAGGTCAGGCTTCAGACAGATACCACAAATCATTTTGAAATTGCAGGCACTACTGTGAA  480
           ************************************************************

NC_004109  GTCAGGATGGTTCAAGAGCACGACATATATAACTCTTGATCAAACTTGCGAACACCTTAA  540
EF485034   GTCAGGATGGTTCAAGAGCACGACATATATAACTCTTGATCAAACTTGCGAACACCTTAA  540
           ************************************************************

NC_004109  AGTTTCCTGCGGCCCAAAATCTGTACAGTTCCATGCCTGCTTCAATCAGCATATGTCTTG  600
EF485034   AGTTTCCTGCGGCCCAAAATCTGTACAGTTCCATGCCTGCTTCAATCAGCATATGTCTTG  600
           ************************************************************

NC_004109  CGTCAGATTTTTACACAGGACAATATTGCCTGGCTCTATAGCCAATTCCATATGTCAGAA  660
EF485034   CGTCAGATTTTTACACAGGACAATATTGCCTGGCTCTATAGCCAATTCCATATGTCAGAA  660
           ************************************************************

NC_004109  TATCGAAATCATAATTTTAGTTACACTTACTCTATTAATCTTTATATTGTTAAGCATTTT  720
EF485034   TATCGAAATCATAATTTTAGTTACACTTACTCTATTAATCTTTATATTGTTAAGCATTTT  720
           ************************************************************

NC_004109  AAGTAAGACTTATATATGTTATTTATTAATGCCTATATTCATCCCCATAGCATATATATA  780
EF485034   AAGTAAGACTTATATATGTTATTTATTAATGCCTATATTCATCCCCATAGCATATATATA  780
           ************************************************************

NC_004109  CGGTATAATTTACAATAAGTCGTGCAAAAAATGCAAATTATGTGGCTTAGTGTATCATCC  840
EF485034   CGGTATAATTTACAATAAGTCGTGCAAAAAATGCAAATTATGTGGCTTAGTGTATCATCC  840
           ************************************************************

NC_004109  ATTCACAGAGTGTGGCACACATTGTGTCTGTGGTGCCCGCTATGATACTTCAGATAGAAT  900
EF485034   ATTCACAGAGTGTGGCACACATTGTGTCTGTGGTGCCCGCTATGATACTTCAGATAGAAT  900
           ************************************************************
```

APPENDIX 2-continued

Medium genomic segment-nucleotide sequence alignment of
LACV/human/1978 (Hughes et al. 2002) and LACV/human/1978 (this study)

```
NC_004109  GAAACTGCATAGAGCTTCTGGATTGTGCCCTGGTTATAAAAGCCTAAGAGCTGCCAGAGT  960
EF485034   GAAACTGCATAGAGCTTCTGGATTGTGCCCTGGTTATAAAAGCCTAAGAGCTGCCAGAGT  960
           ************************************************************

NC_004109  CATGTGCAAGTCGAAAGGGCCTGCATCAATATTGTCTATAATTACTGCGGTACTGGTCTT  1020
EF485034   CATGTGCAAGTCGAAAGGGCCTGCATCAATATTGTCTATAATTACTGCGGTACTGGTCTT  1020
           ************************************************************

NC_004109  AACCTTTGTGACACCAATCAACTCCATGGTTTTAGGAGAGAGTAAAGAAACCTTTGAACT  1080
EF485034   AACCTTTGTGACACCAATCAACTCCATGGTTTTAGGAGAGAGTAAAGAAACCTTTGAACT  1080
           ************************************************************

NC_004109  TGAAGATCTTCCAGACGACATGTTGGAAATGGCATCGAGAATAAATTCTTATTATCTCAC  1140
EF485034   TGAAGATCTTCCAGACGACATGTTGGAAATGGCATCGAGAATAAATTCTTATTATCTCAC  1140
           ************************************************************

NC_004109  CTGTATCTTGAATTATGCTGTAAGCTGGGGTCTTGTTATCATTGGATTGTTGATCGGGCT  1200
EF485034   CTGTATCTTGAATTATGCTGTAAGCTGGGGTCTTGTTATCATTGGATTGTTGATCGGGCT  1200
           ************************************************************

NC_004109  GCTTTTTAAGAAATACCAGCACAGATTCTTAAATGTTTACGCAATGTACTGTGAAGAATG  1260
EF485034   GCTTTTTAAGAAATACCAGCACAGATTCTTAAATGTTTACGCAATGTACTGTGAAGAATG  1260
           ************************************************************

NC_004109  TGACATGTATCATGACAAGTCTGGGTTGAAAAGACATGGTGATTTCACCAACAAATGCAG  1320
EF485034   TGACATGTATCATGACAAGTCTGGGTTGAAAAGACATGGTGATTTCACCAACAAATGCAG  1320
           ************************************************************

NC_004109  ACAGTGCACATGTGGTCAATATGAAGATGCTGCAGGTTTGATGGCTCACAGGAAAACCTA  1380
EF485034   ACAGTGCACATGTGGTCAATATGAAGATGCTGCAGGTTTGATGGCTCACAGGAAAACCTA  1380
           ************************************************************

NC_004109  TAACTGCTTAGTGCAGTACAAAGCAAAGTGGATGATGAACTTCCTGATAATTTACATATT  1440
EF485034   TAACTGCTTAGTGCAGTACAAAGCAAAGTGGATGATGAACTTCCTGATAATTTACATATT  1440
           ************************************************************

NC_004109  CTTAATTTTGATCAAAGATTCTGCTATAGTTGTACAAGCTGCTGGAACTGACTTCACCAC  1500
EF485034   CTTAATTTTGATCAAAGATTCTGCTATAGTTGTACAAGCTGCTGGAACTGACTTCACCAC  1500
           ************************************************************

NC_004109  CTGCCTAGAGACTGAGAGTATAAATTGGAACTGCACTGGGCCATTTTTGAACCTCGGGAA  1560
EF485034   CTGCCTAGAGACTGAGAGTATAAATTGGAACTGCACTGGGCCATTTTTGAACCTCGGGAA  1560
           ************************************************************

NC_004109  TTGCCAAAAGCAACAAAAGAAAGAACCTTACACCAACATTGCAACTCAGTTAAAGGGACT  1620
EF485034   TTGCCAAAAGCAACAAAAGAAAGAACCTTACACCAACATTGCAACTCAGTTAAAGGGACT  1620
           ************************************************************

NC_004109  AAAGGCAATTTCCGTACTAGATGTCCCTATAATAACAGGGATACCAGATGATATTGCGGG  1680
EF485034   AAAGGCAATTTCCGTACTAGATGTCCCTATAATAACAGGGATACCAGATGATATTGCGGG  1680
           ************************************************************

NC_004109  TGCTTTAAGATATATAGAAGAGAAGGAAGATTTCCATGTCCAGCTAACTATAGAATATGC  1740
EF485034   TGCTTTAAGATATATAGAAGAGAAGGAAGATTTCCATGTCCAGCTAACTATAGAATATGC  1740
           ************************************************************

NC_004109  GATGTTAAGCAAATACTGTGACTATTATACCCAATTCTCAGATAACTCAGGATACAGTCA  1800
EF485034   GATGTTAAGCAAATACTGTGACTATTATACCCAATTCTCAGATAACTCAGGATACAGTCA  1800
           ************************************************************

NC_004109  GACAACATGGAGAGTGTACTTAAGGTCTCATGATTTTGAAGCCTGTATACTATATCCAAA  1860
EF485034   GACAACATGGAGAGTGTACTTAAGGTCTCATGATTTTGAAGCCTGTATACTATATCCAAA  1860
           ************************************************************

NC_004109  TCAGCACTTTTGCAGATGTGTAAAAAATGGTGAGAAGTGCAGCAGCTCCAATTGGGACTT  1920
EF485034   TCAGCACTTTTGCAGATGTGTAAAAAATGGTGAGAAGTGCAGCAGCTCCAATTGGGACTT  1920
           ************************************************************

NC_004109  TGCCAATGAAATGAAAGATTATTACTCTGGGAAACAAACAAAGTTTGACAAGGACTTAAA  1980
EF485034   TGCCAATGAAATGAAAGATTATTACTCTGGGAAACAAACAAAGTTTGACAAGGACTTAAA  1980
           ************************************************************

NC_004109  TCTAGCCCTAACAGCTTTGCATCATGCCTTCAGGGGACCTCATCTGCATATATAGCAAC  2040
EF485034   TCTAGCCCTAACAGCTTTGCATCATGCCTTCAGGGGACCTCATCTGCATATATAGCAAC  2040
           ************************************************************
```

APPENDIX 2-continued

Medium genomic segment-nucleotide sequence alignment of
LACV/human/1978 (Hughes et al. 2002) and LACV/human/1978 (this study)

```
NC_004109  AATGCTCTCAAAAAAGTCCAATGATGACTTGATTGCATACACAAATAAGATAAAAACAAA 2100
EF485034   AATGCTCTCAAAAAAGTCCAATGATGACTTGATTGCATACACAAATAAGATAAAAACAAA 2100
           ************************************************************

NC_004109  ATTCCCAGGTAATGCATTGTTGAAGGCTATAATAGATTATATAGCATATATGAAAAGTTT 2160
EF485034   ATTCCCAGGTAATGCATTGTTGAAGGCTATAATAGATTATATAGCATATATGAAAAGTTT 2160
           ************************************************************

NC_004109  GCCAGGTATGGCAAATTTCAAATATGATGAATTCTGGGATGAATTACTGTACAAACCCAA 2220
EF485034   GCCAGGTATGGCAAATTTCAAATATGATGAATTCTGGGATGAATTACTGTACAAACCCAA 2220
           ************************************************************

NC_004109  CCCAGCAAAGGCCTCAAACCTTGCTAGAGGAAAGGAGTCATCTTACAACTTCAAACTAGC 2280
EF485034   CCCAGCAAAGGCCTCAAACCTTGCTAGAGGAAAGGAGTCATCTTACAACTTCAAACTAGC 2280
           ************************************************************

NC_004109  AATTTCATCAAAGTCTATAAAAACCTGCAAGAATGTTAAGGATGTTGCCTGCTTATCGCC 2340
EF485034   AATTTCATCAAAGTCTATAAAAACCTGCAAGAATGTTAAGGATGTTGCCTGCTTATCGCC 2340
           ************************************************************

NC_004109  AAGGTCAGGTGCTATATATGCTTCAATAATTGCGTGTGGTGAACCCAATGGGCCAAGTGT 2400
EF485034   AAGGTCAGGTGCTATATATGCTTCAATAATTGCGTGTGGTGAACCCAATGGGCCAAGTGT 2400
           ************************************************************

NC_004109  GTATAGGAAACCATCAGGTGGTGTATTCCAATCTAGCACTGATCGGTCTATATACTGCTT 2460
EF485034   GTATAGGAAACCATCAGGTGGTGTATTCCAATCTAGCACTGATCGGTCTATATACTGCTT 2460
           ************************************************************

NC_004109  GCTGGATAGCCATTGTCTAGAAGAATTTGAGGCCATCGGCCAGGAGGAGCTGGATGCGGT 2520
EF485034   GCTGGATAGCCATTGTCTAGAAGAATTTGAGGCCATCGGCCAGGAGGAGCTGGATGCGGT 2520
           ************************************************************

NC_004109  AAAGAAATCCAAATGTTGGGAAATTGAATATCCTGACGTAAAGCTCATCCAAGAAGGCGA 2580
EF485034   AAAGAAATCCAAATGTTGGGAAATTGAATATCCTGACGTAAAGCTCATCCAAGAAGGCGA 2580
           ************************************************************

NC_004109  TGGGACTAAAAGCTGTAGAATGAAAGATTCTGGGAACTGCAATGTTGCAACTAACAGATG 2640
EF485034   TGGGACTAAAAGCTGTAGAATGAAAGATTCTGGGAACTGCAATGTTGCAACTAACAGATG 2640
           ************************************************************

NC_004109  GCCAGTGATACAATGTGAGAATGACAAATTTTACTACTCAGAGCTTCAAAAAGATTATGA 2700
EF485034   GCCAGTGATACAATGTGAGAATGACAAATTTTACTACTCAGAGCTTCAAAAAGATTATGA 2700
           ************************************************************

NC_004109  CAAAGCTCAAGATATTGGTCACTATTGCTTAAGCCCTGGATGTACTACTGTCCGGTACCC 2760
EF485034   CAAAGCTCAAGATATTGGTCACTATTGCTTAAGCCCTGGATGTACTACTGTCCGGTACCC 2760
           ************************************************************

NC_004109  TATTAATCCAAAGCACATCTCTAACTGTAATTGGCAAGTAAGCAGATCTAGCATAGCGAA 2820
EF485034   TATTAATCCAAAGCACATCTCTAACTGTAATTGGCAAGTAAGCAGATCTAGCATAGCGAA 2820
           ************************************************************

NC_004109  GATAGATGTGCACAATATTGAGGATATTGAGCAATATAAGAAAGCTATAACTCAGAAACT 2880
EF485034   GATAGATGTGCACAATATTGAGGATATTGAGCAATATAAGAAAGCTATAACTCAGAAACT 2880
           ************************************************************

NC_004109  TCAAACGAGCCTATCTCTATTCAAGTATGCAAAAACAAAAAACTTGCCGCACATCAAACC 2940
EF485034   TCAAACGAGCCTATCTCTATTCAAGTATGCAAAAACAAAAAACTTGCCGCACATCAAACC 2940
           ************************************************************

NC_004109  AATTTATAAATATATAACTATAGAAGGAACAGAAACTGCAGAAGGTATAGAGAGTGCATA 3000
EF485034   AATTTATAAATATATAACTATAGAAGGAACAGAAACTGCAGAAGGTATAGAGAGTGCATA 3000
           ************************************************************

NC_004109  CATTGAATCAGAAGTACCTGCATTGGCTGGGACATCTATCGGATTCAAAATCAATTCTAA 3060
EF485034   CATTGAATCAGAAGTACCTGCATTGGCTGGGACATCTATCGGATTCAAAATCAATTCTAA 3060
           ************************************************************

NC_004109  AGAGGGCAAGCACTTGCTAGATGTTATAGCATATGTAAAAAGTGCCTCATACTCTTCAGT 3120
EF485034   AGAGGGCAAGCACTTGCTAGATGTTATAGCATATGTAAAAAGTGCCTCATACTCTTCAGT 3120
           ************************************************************

NC_004109  GTATACAAAATTGTACTCAACTGGCCCAACATCAGGGATAAATACTAAACATGATGAATT 3180
EF485034   GTATACAAAATTGTACTCAACTGGCCCAACATCAGGGATAAATACTAAACATGATGAATT 3180
           ************************************************************
```

APPENDIX 2-continued

Medium genomic segment-nucleotide sequence alignment of
LACV/human/1978 (Hughes et al. 2002) and LACV/human/1978 (this study)

```
NC_004109  GTGTACTGGCCCATGCCCAGCAAATATCAATCATCAGGTTGGGTGGCTGACATTTGCAAG  3240
EF485034   GTGTACTGGCCCATGCCCAGCAAATATCAATCATCAGGTTGGGTGGCTGACATTTGCAAG  3240
           ************************************************************

NC_004109  AGAGAGGACAAGCTCATGGGGATGCGAAGAGTTTGGTTGCCTGGCTGTAAGTGATGGGTG  3300
EF485034   AGAGAGGACAAGCTCATGGGGATGCGAAGAGTTTGGTTGCCTGGCTGTAAGTGATGGGTG  3300
           ************************************************************

NC_004109  TGTATTTGGATCATGCCAAGATATAATAAAAGAAGAACTATCTGTCTATAGGAAGGAGAC  3360
EF485034   TGTATTTGGATCATGCCAAGATATAATAAAAGAAGAACTATCTGTCTATAGGAAGGAGAC  3360
           ************************************************************

NC_004109  CGAGGAAGTGACTGATGTAGAACTGTGTTTGACATTTTCAGACAAAACATACTGTACAAA  3420
EF485034   CGAGGAAGTGACTGATGTAGAACTGTGTTTGACATTTTCAGACAAAACATACTGTACAAA  3420
           ************************************************************

NC_004109  CTTAAACCCTGTTACCCCTATTATAACAGATCTATTTGAGGTACAGTTCAAAACTGTAGA  3480
EF485034   CTTAAACCCTGTTACCCCTATTATAACAGATCTATTTGAGGTACAGTTCAAAACTGTAGA  3480
           ************************************************************

NC_004109  GACCTACAGCTTGCCTAGAATTGTTGCTGTGCAAAACCATGAGATTAAAATTGGGCAAAT  3540
EF485034   GACCTACAGCTTGCCTAGAATTGTTGCTGTGCAAAACCATGAGATTAAAATTGGGCAAAT  3540
           ************************************************************

NC_004109  AAATGATTTAGGAGTTTACTCTAAGGGTTGTGGGAATGTTCAAAAGGTCAATGGAACTAT  3600
EF485034   AAATGATTTAGGAGTTTACTCTAAGGGTTGTGGGAATGTTCAAAAGGTCAATGGAACTAT  3600
           ************************************************************

NC_004109  TTATGGCAATGGAGTTCCCAGATTTGACTACTTATGCCATTTAGCTAGCAGGAAGGAAGT  3660
EF485034   TTATGGCAATGGAGTTCCCAGATTTGACTACTTATGCCATTTAGCTAGCAGGAAGGAAGT  3660
           ************************************************************

NC_004109  CATTGTTAGAAAATGCTTCGACAATGATTACCAAGCATGCAAATTTCTTCAAAGCCCTGC  3720
EF485034   CATTGTTAGAAAATGCTTCGACAATGATTACCAAGCATGCAAATTTCTTCAAAGCCCTGC  3720
           ************************************************************

NC_004109  TAGTTACAGACTTGAAGAAGACAGTGGCACTGTGACCATAATTGACTACAAAAGATTTT  3780
EF485034   TAGTTACAGACTTGAAGAAGACAGTGGCACTGTGACCATAATTGACTACAAAAGATTTT  3780
           ************************************************************

NC_004109  AGGAACAATCAAGATGAAGGCAATTTTAGGAGATGTCAAATATAAAACATTTGCTGATAG  3840
EF485034   AGGAACAATCAAGATGAAGGCAATTTTAGGAGATGTCAAATATAAAACATTTGCTGATAG  3840
           ************************************************************

NC_004109  TGTCGATATAACCGCAGAAGGGTCATGCACCGGCTGTATTAACTGCTTCGAAAATATCCA  3900
EF485034   TGTCGATATAACCGCAGAAGGGTCATGCACCGGCTGTATTAACTGCTTCGAAAATATCCA  3900
           ************************************************************

NC_004109  TTGCGAATTAACGTTGCACACCACAATTGAAGCCAGCTGCCCAATTAAAAGCTCGTGCAC  3960
EF485034   TTGCGAATTAACGTTGCACACCACAATTGAAGCCAGCTGCCCAATTAAAAGCTCGTGCAC  3960
           ************************************************************

NC_004109  AGTATTTCATGACAGGATTCTTGTGACTCCAAATGAACACAAATATGCATTGAAAATGGT  4020
EF485034   AGTATTTCATGACAGGATTCTTGTGACTCCAAATGAACACAAATATGCATTGAAAATGGT  4020
           ************************************************************

NC_004109  GTGCACAGAAAAGCCAGGGAACACACTCACAATTAAAGTCTGCAATACTAAAGTTGAAGC  4080
EF485034   GTGCACAGAAAAGCCAGGGAACACACTCACAATTAAAGTCTGCAATACTAAAGTTGAAGC  4080
           ************************************************************

NC_004109  ATCTATGGCCCTTGTAGACGCAAAGCCTATCATAGAACTAGCACCAGTTGATCAGACAGC  4140
EF485034   ATCTATGGCCCTTGTAGACGCAAAGCCTATCATAGAACTAGCACCAGTTGATCAGACAGC  4140
           ************************************************************

NC_004109  ATATATAAGAGAAAAAGATGAAAGGTGTAAAACTTGGATGTGTAGGGTAAGAGATGAAGG  4200
EF485034   ATATATAAGAGAAAAAGATGAAAGGTGTAAAACTTGGATGTGTAGGGTAAGAGATGAAGG  4200
           ************************************************************

NC_004109  ACTGCAGGTCATCTTGGAGCCATTTAAAAATTTATTTGGATCTTATATTGGGATATTTTA  4260
EF485034   ACTGCAGGTCATCTTGGAGCCATTTAAAAATTTATTTGGATCTTATATTGGGATATTTTA  4260
           ************************************************************

NC_004109  CACATTTATTATATCTATAGTAGTATTATTGGTTATTATCTATGTACTACTACCTATATG  4320
EF485034   CACATTTATTATATCTATAGTAGTATTATTGGTTATTATCTATGTACTACTACCTATATG  4320
           ************************************************************
```

APPENDIX 2-continued

Medium genomic segment-nucleotide sequence alignment of
LACV/human/1978 (Hughes et al. 2002) and LACV/human/1978 (this study)

```
NC_004109  CTTTAAGTTAAGGGATACCCTTAGAAAGCATGAAGATGCATATAAGAGAGAGATGAAAAT 4380
EF485034   CTTTAAGTTAAGGGATACCCTTAGAAAGCATGAAGATGCATATAAGAGAGAGATGAAAAT 4380
           ************************************************************

NC_004109  TAGATAGGGGATCTATGCAGAACAAAATTGAGTCCTGTATTATATACTTCTATTTGTAGT 4440
EF485034   TAGATAGGGGATCTATGCAGAACAAAATTGAGTCCTGTATTATATA-TTCTATTTGTAGT 4439
           ********************************************** *************

NC_004109  ATAGCTGTTGTTAAGTGGGGGGTGGGGAACTAACAACAGCGTAAATTTATTTTGCAAACA 4500
EF485034   ATAGCTGTTGTTAAGTGGGGGGTGGGGAACTAACAACAGCGTAAATTTATTTTGCAAACA 4499
           ************************************************************

NC_004109  TTATTTTATACTTGGTAGCACACTACT 4527 (SEQ. ID. NO. 3)
EF485034   TTATTTTATACTTGGTAGCACACTACT 4526 (SEQ. ID. NO. 4)
           ***************************
```

APPENDIX 3

Small genomic segment-nucleotide sequence alignment of LACV/human/1978
(Hughes et al. 2002) and LACV/human/1978 (this study)

```
NC_004110  AGTAGTGTACCCCACTTGAATACTTTGAAAATAAATTGTTGTTGACTGTTTTTTACCTAA  60
EF485033   AGTAGTGTACTCCACTTGAATACTTTGAAAATAAATTGTTGTTGACTGTTTTTTACCTAA  60
           ********** *************************************************

NC_004110  GGGGAAATTATCAAGAGTGTGATGTCGGATTTGGTGTTTTATGATGTCGCATCAACAGGT 120
EF485033   GGGGAAATTATCAAGAGTGTGATGTCGGATTTGGTGTTTTATGATGTCGCATCAACAGGT 120
           ************************************************************

NC_004110  GCAAATGGATTTGATCCTGATGCAGGGTATATGGACTTCTGTGTTAAAAATGCAGAATTA 180
EF485033   GCAAATGGATTTGATCCTGATGCAGGGTATATGGACTTCTGTGTTAAAAATGCAGAATTA 180
           ************************************************************

NC_004110  CTCAACCTTGCTGCAGTTAGGATCTTCTTCCTCAATGCCGCAAAGGCCAAGGCTGCTCTC 240
EF485033   CTCAACCTTGCTGCAGTTAGGATCTTCTTCCTCAATGCCGCAAAGGCCAAGGCTGCTCTC 240
           ************************************************************

NC_004110  TCGCGTAAGCCAGAGAGGAAGGCTAACCCTAAATTTGGAGAGTGGCAGGTGGAGGTTATC 300
EF485033   TCGCGTAAGCCAGAGAGGAAGGCTAACCCTAAATTTGGAGAGTGGCAGGTGGAGGTTATC 300
           ************************************************************

NC_004110  AATAATCATTTTCCTGGAAACAGGAACAACCCAATTGGTAACAACGATCTTACCATCCAC 360
EF485033   AATAATCATTTTCCTGGAAACAGGAACAACCCAATTGGTAACAACGATCTTACCATCCAC 360
           ************************************************************

NC_004110  AGATTATCTGGGTATTTAGCCAGATGGGTCCTTGATCAGTATAACGAGAATGATGATGAG 420
EF485033   AGATTATCTGGGTATTTAGCCAGATGGGTCCTTGATCAGTATAACGAGAATGATGATGAG 420
           ************************************************************

NC_004110  TCTCAGCACGAGTTGATCAGAACAACTATTATCAACCCAATTGCTGAGTCTAATGGTGTA 480
EF485033   TCTCAGCACGAGTTGATCAGAACAACTATTATCAACCCAATTGCTGAGTCTAATGGTGTA 480
           ************************************************************

NC_004110  GGATGGGACAGTGGGCCAGAGATCTATCTATCATTCTTTCCAGGAACAGAAATGTTTTTG 540
EF485033   GGATGGGACAGTGGGCCAGAGATCTATCTATCATTCTTTCCAGGAACAGAAATGTTTTTG 540
           ************************************************************

NC_004110  GAAACTTTCAAATTCTACCCGCTGACCATTGGAATTCACAGAGTCAAGCAAGGCATGATG 600
EF485033   GAAACTTTCAAATTCTACCCGCTGACCATTGGAATTCACAGAGTCAAGCAAGGCATGATG 600
           ************************************************************

NC_004110  GACCCTCAATACCTGAAGAAGGCCTTAAGGCAACGCTATGGCACTCTCACAGCAGATAAG 660
EF485033   GACCCTCAATACCTGAAGAAGGCCTTAAGGCAACGCTATGGCACTCTCACAGCAGATAAG 660
           ************************************************************

NC_004110  TGGATGTCACAGAAGGTTGCAGCAATTGCTAAGAGCCTGAAGGATGTAGAGCAGCTTAAA 720
EF485033   TGGATGTCACAGAAGGTTGCAGCAATTGCTAAGAGCCTGAAGGATGTAGAGCAGCTTAAA 720
           ************************************************************

NC_004110  TGGGGAAAAGGAGGCCTGAGCGATACTGCTAAAACATTCCTGCAGAAATTTGGCATCAGG 780
EF485033   TGGGGAAAAGGAGGCCTGAGCGATACTGCTAAAACATTCCTGCAGAAATTTGGCATCAGG 780
           ************************************************************
```

APPENDIX 3-continued

Small genomic segment-nucleotide sequence alignment of LACV/human/1978
(Hughes et al. 2002) and LACV/human/1978 (this study)

```
NC_004110  CTTCCATAAATATGGCATGAGGCATTCAAATTAGGTTCTAAATTCTAAATTTATATATGT  840
EF485033   CTTCCATAAATATGGCATGAGGCATTCAAATTAGGTTCTAAATTCTAAATTTATATATGT  840
           ************************************************************

NC_004110  CAATTTGATTAATTGGTTATCCAAAAGGGTTTTCTTAAGGGAACCCACAAAAATAGCAGC  900
EF485033   CAATTTGATTAATTGGTTATCCAAAAGGGTTTTCTTAAGGGAACCCACAAAAATAGCAGC  900
           ************************************************************

NC_004110  TAAATGGGTGGGTGGTAGGGGACAGCAAAAAACTATAAATCAGGTCATAAATAAAATAAA  960
EF485033   TAAATGGGTGGGTGGTAGGGGACAGCAAAAAACTATAAATCAGGTCATAAATAAAATAAA  960
           ************************************************************

NC_004110  ATGTATTCAGTGGGGCACACTACT  984  (SEQ. ID. No. 5)
EF485033   ATGTATTCAGTGGAGCACACTACT  984  (SEQ. ID. No. 6)
           ************* **********
```

APPENDIX 4

Large genomic segment-amino acid sequence alignment of LACV/human/1978
(Hughes et al. 2002) and LACV/human/1978 (this study)

```
NC_004108  MDYQEYQQFLARINTARDACVAKDIDVDLLMARHDYFGRELCKSLNIEYRNDVPFVDIIL   60
EF485035   MDYQEYQQFLARINTARDACVAKDIDVDLLMARHDYFGRELCKSLNIEYRNDVPFVDIIL   60
           ************************************************************

NC_004108  DIRPEVDPLTIDAPHITPDNYLYINNVLYIIDYKVSVSNESSVITYDKYYELTRDISDRL  120
EF485035   DIRPEVDPLTIDAPHITPDNYLYINNVLYIIDYKVSVSNESSVITYDKYYELTRDISDRL  120
           ************************************************************

NC_004108  SIPIEIVIVRIDPVSKDLHINSDRFKELYPTIVVDINFNQFFDLKQLLYEKFGDDEEFLL  180
EF485035   SIPIEIVIVRIDPVSKDLHINSDRFKELYPTIVVDINFNQFFDLKQLLYEKFGDDEEFLL  180
           ************************************************************

NC_004108  KVAHGDFTLTAPWCKTGCPEFWKHPIYKEFKMSMPVPERRLFEESVKFNAYESERWNTNL  240
EF485035   KVAHGDFTLTAPWCKTGCPEFWKHPIYKEFKMSMPVPERRLFEESVKFNAYESERWNTNL  240
           ************************************************************

NC_004108  VKIREYTKKDYSEHISKSAKNIFLASGFYKQPNKNEISEGWTLMVERVQDQREISKSLHD  300
EF485035   VKIREYTKKDYSEHISKSAKNIFLASGFYKQPNKNEISEGWTLMVERVQDQREISKSLHD  300
           ************************************************************

NC_004108  QKPSIHFIWGAHNPGNSNNATFKLILLSKSLQSIKGISTYTEAFKSLGKMMDIGDKAIEY  360
EF485035   QKPSIHFIWGAHNPGNSNNATFKLILLSKSLQSIKGISTYTEAFKSLGKMMDIGDKAIEY  360
           ************************************************************

NC_004108  EEFCMSLKSKARSSWKQIMNKKLEPKQINNALVLWEQQFMVNNDLIDKSEKLKLFKNFCG  420
EF485035   EEFCMSLKSKARSSWKQIMNKKLEPKQINNALVLWEQQFMVNNDLIDKSEKLKLFKNFCG  420
           ************************************************************

NC_004108  IGKHKQFKNKMLEDLEVSKPKILDFDDANMYLASLTMMEQSKKILSKSNGLKPDNFILNE  480
EF485035   IGKHKQFKNKMLEDLEVSKPKILDFDDANMYLASLTMMEQSKKILSKSNGLKPDNFILNE  480
           ************************************************************

NC_004108  FGSKIKDANKRTYDNMHKIFETRYWQCISDFSTLMKNILSVSQYNRHNTFRIAMCANNNV  540
EF485035   FGSKIKDANKRTYDNMHKIFETRYWQCISDFSTLMKNILSVSQYNRHNTFRIAMCANNNV  540
           ************************************************************

NC_004108  FAIVFPSADIKTKKATVVYSIIVLHKEEENIFNPGCLHGTFKCMNGYISISRAIRLDKER  600
EF485035   FAIVFPSADIKTKKATVVYSIIVLHKEEENIFNPGCLHGTFKCMNGYISISRAIRLDKER  600
           ************************************************************

NC_004108  CQRIVSSPGLFLTTCLLFKHDNPTLVMSDIMNFSIYTSLSITKSVLSLTEPARYMIMNSL  660
EF485035   CQRIVSSPGLFLTTCLLFKHDNPTLVMSDIMNFSIYTSLSITKSVLSLTEPARYMIMNSL  660
           ************************************************************

NC_004108  AISSNVKDYIAEKFSPYTKTLFSVYMTRLIKNACFDAYDQRQRVQLRDIYLSDYDITQKG  720
EF485035   AISSNVKDYIAEKFSPYTKTLFSVYMTRLIKNACFDAYDQRQRVQLRDIYLSDYDITQKG  720
           ************************************************************

NC_004108  IKDNRELTSIWFPGSVTLKEYLTQIYLPFYFNAKGLHEKHHVMVDLAKTILEIECEQREN  780
EF485035   IKDNRELTSIWFPGSVTLKEYLTQIYLPFYFNAKGLHEKHHVMVDLAKTILEIECEQREN  780
           ************************************************************
```

APPENDIX 4-continued

Large genomic segment-amino acid sequence alignment of LACV/human/1978
(Hughes et al. 2002) and LACV/human/1978 (this study)

```
NC_004108  IKEIWSTNCTKQTVNLKILIHSLCKNLLADTSRHNHLRNRIENRNNFRRSITTISTFTSS  840
EF485035   IKEIWSTNCTKQTVNLKILIHSLCKNLLADTSRHNHLRNRIENRNNFRRSITTISTFTSS  840
           ************************************************************

NC_004108  KSCLKIGDFRKEKELQSVKQKKILEVQSRKMRLANPMFVTDEQVCLEVGHCNYEMLRNAM  900
EF485035   KSCLKIGDFRKEKELQSVKQKKILEVQSRKMRLANPMFVTDEQVCLEVGHCNYEMLRNAM  900
           ************************************************************

NC_004108  PNYTDYISTKVFDRLYELLDKGVLTDKPVIEQIMDMMVDHKKFYFTFFNKGQKTSKDREI  960
EF485035   PNYTDYISTKVFDRLYELLDKGVLTDKPVIEQIMDMMVDHKKFYFTFFNKGQKTSKDREI  960
           ************************************************************

NC_004108  FVGEYEAKMCMYAVERIAKERCKLNPDEMISEPGDGKLKVLEQKSEQEIRFLVETTRQKN 1020
EF485035   FVGEYEAKMCMYAVERIAKERCKLNPDEMISEPGDGKLKVLEQKSEQEIRFLVETTRQKN 1020
           ************************************************************

NC_004108  REIDEAIEALAAEGYESNLEKIEKLSLGKAKGLKMEINADMSKWSAQDVFYKYFWLIALD 1080
EF485035   REIDEAIEALAAEGYESNLEKIEKLSLGKAKGLKMEINADMSKWSAQDVFYKYFWLIALD 1080
           ************************************************************

NC_004108  PILYPQEKERILYFMCNYMDKELILPDELLFNLLDQKVAYQNDIIATMTNQLNSNTVLIK 1140
EF485035   PILYPQEKERILYFMCNYMDKELILPDELLFNLLDQKVAYQNDIIATMTNQLNSNTVLIK 1140
           ************************************************************

NC_004108  RNWLQGNFNYTSSYVHSCAMSVYKEILKEAITLLDGSILVNSLVHSDDNQTSITIVQDKM 1200
EF485035   RNWLQGNFNYTSSYVHSCAMSVYKEILKEAITLLDGSILVNSLVHSDDNQTSITIVQDKM 1200
           ************************************************************

NC_004108  ENDKIIDFAMKEFERACLTPGCQANMKKTYVTNCIKEFVSLFNLYGEPFSIYGRFLLTSV 1260
EF485035   ENDKIIDFAMKEFERACLTPGCQANMKKTYVTNCIKEFVSLFNLYGEPFSIYGRFLLTSV 1260
           ************************************************************

NC_004108  GDCAYIGPYEDLASRISSAQTAIKHGCPPSLAWVSIAISHWMTSLTYNMLPGQSNDPIDY 1320
EF485035   GDCAYIGPYEDLASRISSAQTAIKHGCPPSLAWVSIAISHWMTSLTYNMLPGQSNDPIDY 1320
           ************************************************************

NC_004108  FPAENRKDIPIELNGVLDAPLSMISTVGLESGNLYFLIKLLSKYTPVMQKRESVVNQIAE 1380
EF485035   FPAENRKDIPIELNGVLDAPLSMISTVGLESGNLYFLIKLLSKYTPVMQKRESVVNQIAE 1380
           ************************************************************

NC_004108  VKNWKVEDLTDNEIFRLKILRYLVLDAEMDPSDIMGETSDMRGRSILTPRKFTTAGSLRK 1440
EF485035   VKNWKVEDLTDNEIFRLKILRYLVLDAEMDPSDIMGETSDMRGRSILTPRKFTTAGSLRK 1440
           ************************************************************

NC_004108  LYSFSKYQDRLSSPGGMVELFTYLLEKPELLVTKGKDMKDYMESVIFRYNSKRFKESLSI 1500
EF485035   LYSFSKYQDRLSSPGGMVELFTYLLEKPELLVTKGKDMKDYMESVIFRYNSKRFKESLSI 1500
           ************************************************************

NC_004108  QNPAQLFIEQILFSHKPIIDFSGIRDKYINLHDSRALEKEPDILGKVTFTEAYRLLMRDL 1560
EF485035   QNPAQLFIEQILFSHKPIIDFSGIRDKYINLHDSRALEKEPDILGKVTFTEAYRLLMRDL 1560
           ************************************************************

NC_004108  SSLELTNDDIQVIYSYIILNDPMMITIANTHILSIYGSPQRRMGMSCSTMPEFRNLKLIH 1620
EF485035   SSLELTNDDIQVIYSYIILNDPMMITIANTHILSIYGSPQRRMGMSCSTMPEFRNLKLIH 1620
           ************************************************************

NC_004108  HSPALVLRAYSKNNPDIQGADPTEMARDLVHLKEFVENTNLEEKMKVRIAINEAEKGQRD 1680
EF485035   HSPALVLRAYSKNNPDIQGADPTEMARDLVHLKEFVENTNLEEKMKVRIAINEAEKGQRD 1680
           ************************************************************

NC_004108  IVFELKEMTRFYQVCYEYVKSTEHKIKVFILPTKSYTTTDFCSLMQGNLIKDKEWYTVHY 1740
EF485035   IVFELKEMTRFYQVCYEYVKSTEHKIKVFILPTKSYTTTDFCSLMQGNLIKDKEWYTVHY 1740
           ************************************************************

NC_004108  LKQILSGGHKAIMQHNATSEQNIAFECFKLITHFADSFIDSLSRSAFLQLIIDEFSYKDV 1800
EF485035   LKQILSGGHKAIMQHNATSEQNIAFECFKLITHFADSFIDSLSRSAFLQLIIDEFSYKDV 1800
           ************************************************************

NC_004108  KVSKLYDIIKNGYNRTDFIPLLFRTGDLRQADLDKYDAMKSHERVTWNDWQTSRHLDMGS 1860
EF485035   KVSKLYDIIKNGYNRTDFIPLLFRTGDLRQADLDKYDAMKSHERVTWNDWQTSRHLDMGS 1860
           ************************************************************

NC_004108  INLTITGYNRSITIIGEDNKLTYAELCLTRKTPENITISGRKLLGARHGLKFENMSKIQT 1920
EF485035   INLTITGYNRSITIIGEDNKLTYAELCLTRKTPENITISGRKLLGARHGLKFENMSKIQT 1920
           ************************************************************
```

APPENDIX 4-continued

Large genomic segment-amino acid sequence alignment of LACV/human/1978
(Hughes et al. 2002) and LACV/human/1978 (this study)

```
NC_004108  YPGNYYITYRKKDRHQFVYQIHSHESITRRNEEHMAIRTRIYNEITPVCVVNVAEVDGDQ  1980
EF485035   YPGNYYITYRKKDRHQFVYQIHSHESITRRNEEHMAIRTRIYNEITPVCVVNVAEVDGDQ  1980
           ************************************************************

NC_004108  RILIRSLDYLNNDIFSLSRIKVGLDEFATIKKAHFSKMVSFEGPPIKTGLLDLTELMKSQ  2040
EF485035   RILIRSLDYLNNDIFSLSRIKVGLDEFATIKKAHFSKMVSFEGPPIKTGLLDLTELMKSQ  2040
           ************************************************************

NC_004108  DLLNLNYDNIRNSNLISFSKLICCEGSDNINDGLEFLSDDPMNFTEGEAIHSTPIFNIYY  2100
EF485035   DLLNLNYDNIRNSNLISFSKLICCEGSDNINDGLEFLSDDPMNFTEGEAIHSTPIFNIYY  2100
           ************************************************************

NC_004108  SKRGERHMTYRNAIKLLIERETKIFEEAFTFSENGFISPENLGCLEAVVSLIKLIKTNEW  2160
EF485035   SKRGERHMTYRNAIKLLIERETKIFEEAFTFSENGFISPENLGCLEAVVSLIKLIKTNEW  2160
           ************************************************************

NC_004108  STVIDKCIHICLIKNGMDHMYHSFDVPKCFMGNPITRDMNWMMFREFINSLPGTDIPPWN  2220
EF485035   STVIDKCIHICLIKNGMDHMYHSFDVPKCFMGNPITRDMNWMMFREFINSLPGTDIPPWN  2220
           ************************************************************

NC_004108  VMTENFKKKCIALINSKLETQRDFSEFTKLMKKEGGRSNIEFD  2263  (SEQ. ID. No. 7)
EF485035   VMTENFKKKCIALINSKLETQRDFSEFTKLMKKEGGRSNIEFD  2263  (SEQ. ID. No. 8)
           *******************************************
```

APPENDIX 5

Medium genomic segment-amino acid sequence alignment of
LACV/human/1978 (Hughes et al. 2002) and LACV/human/1978 (this study)

```
NC_004109  MICILVLITVAAASPVYQRCFQDGAIVKQNPSKEAVTEVCLKDDVSMIKTEARYVRNATG   60
EF485034   MICILVLITVAAASPVYQRCFQDGAIVKQNPSKEAVTEVCLKDDVSMIKTEARYVRNATG   60
           ************************************************************

NC_004109  VFSNNVAIRKWLVSDWHDCRPKKIVGGHINVIEVGDDLSLHTESYVCSADCTIGVDKETA  120
EF485034   VFSNNVAIRKWLVSDWHDCRPKKIVGGHINVIEVGDDLSLHTESYVCSADCTIGVDKETA  120
           ************************************************************

NC_004109  QVRLQTDTTNHFEIAGTTVKSGWFKSTTYITLDQTCEHLKVSCGPKSVQFHACFNQHMSC  180
EF485034   QVRLQTDTTNHFEIAGTTVKSGWFKSTTYITLDQTCEHLKVSCGPKSVQFHACFNQHMSC  180
           ************************************************************

NC_004109  VRFLHRTILPGSIANSICQNIEIIILVTLTLLIFILLSILSKTYICYLLMPIFIPIAYIY  240
EF485034   VRFLHRTILPGSIANSICQNIEIIILVTLTLLIFILLSILSKTYICYLLMPIFIPIAYIY  240
           ************************************************************

NC_004109  GIIYNKSCKKCKLCGLVYHPFTECGTHCVCGARYDTSDRMKLHRASGLCPGYKSLRAARV  300
EF485034   GIIYNKSCKKCKLCGLVYHPFTECGTHCVCGARYDTSDRMKLHRASGLCPGYKSLRAARV  300
           ************************************************************

NC_004109  MCKSKGPASILSIITAVLVLTFVTPINSMVLGESKETFELEDLPDDMLEMASRINSYYLT  360
EF485034   MCKSKGPASILSIITAVLVLTFVTPINSMVLGESKETFELEDLPDDMLEMASRINSYYLT  360
           ************************************************************

NC_004109  CILNYAVSWGLVIIGLLIGLLFKKYQHRFLNVYAMYCEECDMYHDKSGLKRHGDFTNKCR  420
EF485034   CILNYAVSWGLVIIGLLIGLLFKKYQHRFLNVYAMYCEECDMYHDKSGLKRHGDFTNKCR  420
           ************************************************************

NC_004109  QCTCGQYEDAAGLMAHRKTYNCLVQYKAKWMMNFLIIYIFLILIKDSAIVVQAAGTDFTT  480
EF485034   QCTCGQYEDAAGLMAHRKTYNCLVQYKAKWMMNFLIIYIFLILIKDSAIVVQAAGTDFTT  480
           ************************************************************

NC_004109  CLETESINWNCTGPFLNLGNCQKQQKKEPYTNIATQLKGLKAISVLDVPIITGIPDDIAG  540
EF485034   CLETESINWNCTGPFLNLGNCQKQQKKEPYTNIATQLKGLKAISVLDVPIITGIPDDIAG  540
           ************************************************************

NC_004109  ALRYIEEKEDFHVQLTIEYAMLSKYCDYYTQFSDNSGYSQTTWRVYLRSHDFEACILYPN  600
EF485034   ALRYIEEKEDFHVQLTIEYAMLSKYCDYYTQFSDNSGYSQTTWRVYLRSHDFEACILYPN  600
           ************************************************************

NC_004109  QHFCRCVKNGEKCSSSNWDFANEMKDYYSGKQTKFDKDLNLALTALHHAFRGTSSAYIAT  660
EF485034   QHFCRCVKNGEKCSSSNWDFANEMKDYYSGKQTKFDKDLNLALTALHHAFRGTSSAYIAT  660
           ************************************************************
```

APPENDIX 5 -continued

Medium genomic segment-amino acid sequence alignment of
LACV/human/1978 (Hughes et al. 2002) and LACV/human/1978 (this study)

```
NC_004109  MLSKKSNDDLIAYTNKIKTKFPGNALLKAIIDYIAYMKSLPGMANFKYDEFWDELLYKPN  720
EF485034   MLSKKSNDDLIAYTNKIKTKFPGNALLKAIIDYIAYMKSLPGMANFKYDEFWDELLYKPN  720
           ************************************************************

NC_004109  PAKASNLARGKESSYNFKLAISSKSIKTCKNVKDVACLSPRSGAIYASIIACGEPNGPSV  780
EF485034   PAKASNLARGKESSYNFKLAISSKSIKTCKNVKDVACLSPRSGAIYASIIACGEPNGPSV  780
           ************************************************************

NC_004109  YRKPSGGVFQSSTDRSIYCLLDSHCLEEFEAIGQEELDAVKKSKCWEIEYPDVKLIQEGD  840
EF485034   YRKPSGGVFQSSTDRSIYCLLDSHCLEEFEAIGQEELDAVKKSKCWEIEYPDVKLIQEGD  840
           ************************************************************

NC_004109  GTKSCRMKDSGNCNVATNRWPVIQCENDKFYYSELQKDYDKAQDIGHYCLSPGCTTVRYP  900
EF485034   GTKSCRMKDSGNCNVATNRWPVIQCENDKFYYSELQKDYDKAQDIGHYCLSPGCTTVRYP  900
           ************************************************************

NC_004109  INPKHISNCNWQVSRSSIAKIDVHNIEDIEQYKKAITQKLQTSLSLFKYAKTKNLPHIKP  960
EF485034   INPKHISNCNWQVSRSSIAKIDVHNIEDIEQYKKAITQKLQTSLSLFKYAKTKNLPHIKP  960
           ************************************************************

NC_004109  IYKYITIEGTETAEGIESAYIESEVPALAGTSIGFKINSKEGKHLLDVIAYVKSASYSSV 1020
EF485034   IYKYITIEGTETAEGIESAYIESEVPALAGTSIGFKINSKEGKHLLDVIAYVKSASYSSV 1020
           ************************************************************

NC_004109  YTKLYSTGPTSGINTKHDELCTGPCPANINHQVGWLTFARERTSSWGCEEFGCLAVSDGC 1080
EF485034   YTKLYSTGPTSGINTKHDELCTGPCPANINHQVGWLTFARERTSSWGCEEFGCLAVSDGC 1080
           ************************************************************

NC_004109  VFGSCQDIIKEELSVYRKETEEVTDVELCLTFSDKTYCTNLNPVTPIITDLFEVQFKTVE 1140
EF485034   VFGSCQDIIKEELSVYRKETEEVTDVELCLTFSDKTYCTNLNPVTPIITDLFEVQFKTVE 1140
           ************************************************************

NC_004109  TYSLPRIVAVQNHEIKIGQINDLGVYSKGCGNVQKVNGTIYGNGVPRFDYLCHLASRKEV 1200
EF485034   TYSLPRIVAVQNHEIKIGQINDLGVYSKGCGNVQKVNGTIYGNGVPRFDYLCHLASRKEV 1200
           ************************************************************

NC_004109  IVRKCFDNDYQACKFLQSPASYRLEEDSGTVTIIDYKKILGTIKMKAILGDVKYKTFADS 1260
EF485034   IVRKCFDNDYQACKFLQSPASYRLEEDSGTVTIIDYKKILGTIKMKAILGDVKYKTFADS 1260
           ************************************************************

NC_004109  VDITAEGSCTGCINCFENIHCELTLHTTIEASCPIKSSCTVFHDRILVTPNEHKYALKMV 1320
EF485034   VDITAEGSCTGCINCFENIHCELTLHTTIEASCPIKSSCTVFHDRILVTPNEHKYALKMV 1320
           ************************************************************

NC_004109  CTEKPGNTLTIKVCNTKVEASMALVDAKPIIELAPVDQTAYIREKDERCKTWMCRVRDEG 1380
EF485034   CTEKPGNTLTIKVCNTKVEASMALVDAKPIIELAPVDQTAYIREKDERCKTWMCRVRDEG 1380
           ************************************************************

NC_004109  LQVILEPFKNLFGSYIGIFYTFIISIVVLLVIIYVLLPICFKLRDTLRKHEDAYKREMKI 1440
EF485034   LQVILEPFKNLFGSYIGIFYTFIISIVVLLVIIYVLLPICFKLRDTLRKHEDAYKREMKI 1440
           ************************************************************

NC_004109  R 1441 (SEQ. ID. No. 9)
EF485034   R 1441 (Seq. ID. No. 10)
           *
```

APPENDIX 6

Small genomic segment-Nucleoprotein (N) amino acid sequence alignment of
LACV/human/1978 (Hughes et al. 2002) and LACV/human/1978 (this study)

```
NC_004110  MSDLVFYDVASTGANGFDPDAGYMDFCVKNAELLNLAAVRIFFLNAAKAKAALSRKPERK   60
EF485033   MSDLVFYDVASTGANGFDPDAGYMDFCVKNAELLNLAAVRIFFLNAAKAKAALSRKPERK   60
           ************************************************************

NC_004110  ANPKFGEWQVEVINNHFPGNRNNPIGNNDLTIHRLSGYLARWVLDQYNENDDESQHELIR  120
EF485033   ANPKFGEWQVEVINNHFPGNRNNPIGNNDLTIHRLSGYLARWVLDQYNENDDESQHELIR  120
           ************************************************************

NC_004110  TTIINPIAESNGVGWDSGPEIYLSFFPGTEMFLETFKFYPLTIGIHRVKQGMMDPQYLKK  180
EF485033   TTIINPIAESNGVGWDSGPEIYLSFFPGTEMFLETFKFYPLTIGIHRVKQGMMDPQYLKK  180
           ************************************************************
```

APPENDIX 6-continued

Small genomic segment-Nucleoprotein (N) amino acid sequence alignment of
LACV/human/1978 (Hughes et al. 2002) and LACV/human/1978 (this study)

```
NC_004110  ALRQRYGTLTADKWMSQKVAAIAKSLKDVEQLKWGKGGLSDTAKTFLQKFGIRLP 235 (SEQ. ID. No. 11)
EF485033   ALRQRYGTLTADKWMSQKVAAIAKSLKDVEQLKWGKGGLSDTAKTFLQKFGIRLP 235 (SEQ. ID. No. 12)
           ******************************************************
```

APPENDIX 7

Small genomic segment-Nonstructural protein (NSs) amino acid sequence
alignment of LACV/human/1978 (Hughes et al.) and LACV/human/1978 (this study)

```
NC_004110  MMSHQQVQMDLILMQGIWTSVLKMQNYSTLLQLGSSSSMPQRPRLLSRVSQRGRLTLNLE 60
EF485033   MMSHQQVQMDLILMQGIWTSVLKMQNYSTLLQLGSSSSMPQRPRLLSRVSQRGRLTLNLE 60
           ************************************************************

NC_004110  SGRWRLSIIIFLETGTTQLVTTILPSTDYLGI 92 (SEQ. ID. No. 13)
EF485033   SGRWRLSIIIFLETGTTQLVTTILPSTDYLGI 92 (SEQ. ID. No. 14)
           ********************************
```

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

We claim:

1. An isolated polynucleotide comprising a nucleotide sequence encoding a California encephalitis virus (CEV) serogroup immunogen, wherein the immunogen comprises a mutation at amino acid 148 of $G_N$, corresponding to amino acid position 33 of SEQ ID NO: 33.

2. The isolated polynucleotide of claim 1, wherein the mutated amino acid at position 148 of $G_N$ is Alanine.

3. The isolated polynucleotide of claim 1, wherein amino acid 148 of $G_N$ is deleted.

4. The isolated polynucleotide of claim 1, wherein the mutated amino acid at position 148 of $G_N$ is any amino acid other than Threonine.

5. The isolated polynucleotide of claim 1, wherein the polynucleotide is codon-optimized for expression in humans.

6. An immunogenic composition comprising the isolated polynucleotide of claim 1.

7. An immunogenic composition comprising a polypeptide encoded by the isolated polynucleotide of claim 1.

* * * * *

SEQUENCE LISTING

```
<160> NUMBER OF SEQ ID NOS: 79

<210> SEQ ID NO 1
<211> LENGTH: 6980
<212> TYPE: DNA
<213> ORGANISM: La Crosse virus

<400> SEQUENCE: 1
agtagtgtac ccctatctac aaaacttaca gaaaattcag tcatatcaca atatatgcat      60
aatggactat caagagtatc aacaattctt ggctaggatt aatactgcaa gggatgcatg     120
tgtagccaag gatatcgatg ttgacctatt aatggccaga catgattatt ttggtagaga     180
gctgtgcaag tccttaaata tagaatatag gaatgatgta ccatttgtag atataatttt     240
ggatataagg cccgaagtag acccattaac catagatgca ccacatatta ccccagacaa     300
ttatctatat ataaataatg tgttatatat catagattat aaggtctctg tatcgaatga     360
aagcagtgtt ataacatatg acaaatatta tgagttaact agggacatat ccgatagatt     420
aagtattcca atagaaatag ttatcgtccg tatagaccct gtaagtaagg atttgcatat     480
taactctgat agatttaaag aactttaccc tacaatagtg gtggatataa acttcaatca     540
atttttcgac ttaaaacaat tactctatga aaaattcggt gatgatgaag aattcctatt     600
gaaagttgca catggtgact tcactcttac agcaccctgg tgcaagactg ggtgccctga     660
attttggaaa cacccccattt ataaagaatt taaaatgagt atgccagtac ctgagcggag     720
gctctttgaa gaatctgtca agttcaatgc ttatgaatct gagagatgga atactaactt     780
ggttaaaatc agagaatata caagaaaga ctattcagag catatttcaa aatctgcaaa     840
aaatattttc ctggctagtg gattttataa gcagccaaat aagaatgaga ttagtgaggg     900
gtggacatta atggttgaga gggttcaaga tcagagagaa atctcaaaat ctctccatga     960
ccagaaacct agcatacatt ttatatgggg agcccataac ccaggaaata gtaataatgc    1020
aaccttcaaa ctcatattgc tttcaaagtc cttacaaagc ataaaaggta tatcaactta    1080
```

```
cacagaagcg ttcaaatctt taggaaaaat gatggatatt ggagataagg ctattgagta   1140
tgaagaattc tgcatgtccc taaaaagcaa agcaagatca tcatggaagc aaataatgaa   1200
caaaaaatta gagcctaaac aaataaacaa tgcccttgtt ttatgggaac agcagtttat   1260
ggtaaataat gacctgatag acaaaagtga aagttgaaaa ttattcaaaa atttctgcgg   1320
tataggcaaa cacaagcaat tcaagaataa aatgctagag gatctagaag tgtcaaagcc   1380
caaaatatta gactttgatg acgcaaatat gtatctagct agcctaacca tgatggaaca   1440
gagtaagaag atattgtcca aaagcaatgg gttgaagcca gataatttta tactgaatga   1500
atttggatcc aaaatcaaag atgctaataa agaaacatat gacaatatgc acaaaatatt   1560
tgagacaaga tattggcaat gtatatccga cttctctact ctgatgaaaa atatcttatc   1620
tgtgtcccaa tataacaggc acaacacatt taggatagct atgtgtgcta ataacaatgt   1680
ctttgctata gtatttcctt cggctgacat aaaaactaag aaagcaactg tagtttatag   1740
cattatagtg ctgcataaag aggaagaaaa catattcaac ccaggatgtt tgcacggcac   1800
atttaagtgt atgaatgggt atatttccat atctagagct ataaggctag ataaagagag   1860
gtgccagaga attgtttcct cacctggact gttttttaaca acttgcctac tattcaaaca   1920
tgataatcca actctagtga tgagcgatat tatgaatttt tctatataca ctagcctgtc   1980
tatcacaaag agtgttctat ctttaacaga gccagcacgc tacatgatta tgaactcatt   2040
agctatctcc agcaatgtta aggactatat agcagagaaa ttttccccctt acacaaagac   2100 actgttcagt gtctatatga ctagactaat taaaaatgct tgctttgatg cttatgacca   2160
gagacagcgt gtccaactta gagatatata tttatctgat tatgacataa cccaaaaagg   2220
tattaaagac aatagagagc taacaagtat atggttccct ggtagtgtaa cattaaagga   2280
gtatttaaca caaatatact taccatttta tttaatgct aaaggactac atgagaagca   2340
ccatgtcatg gtggatctag caaagactat attagaaata gagtgcgaac agagggaaaa   2400 cataaggag atatggtcta caaattgtac caaacagaca gtgaacctta aaattttgat   2460
ccattccttg tgcaagaatt tactagcaga cacttcaaga cacaaccact tgcggaacag   2520
aatagaaaat aggaacaatt ttagaaggtc tataacaact atttcaacat ttacaagttc   2580
aaagtcttgc ctcaaaatag gggactttag aaaagagaaa gagctgcagt cagttaaaca   2640
gaagaaaatc ttagaggtgc agagtcgcaa aatgagatta gcaaacccaa tgttcgtgac   2700
agatgaacaa gtatgccttg aagttgggca ctgcaattat gagatgctga ggaatgctat   2760
gccgaattat acagattata tatcaactaa agtatttgat aggttatatg agttattaga   2820
taaaggagtt ttgacagaca agcctgttat agagcaaata atggatatga tggtcgacca   2880
caaaaagttc tatttcacat ttttcaataa aggccagaaa acgtcaaagg atagagagat   2940
attcgttgga gaatatgaag ctaaaatgtg tatgtacgca gttgagagaa tagcaaaaga   3000
aagatgtaaa ttaaatcctg atgaaatgat atctgagccg ggtgatggca gttgaaggt   3060 gttggagcaa aaatcagaac aagaaattcg attcttggtc gagactacaa ggcaaaagaa   3120
tcgtgaaatc gatgaggcaa ttgaagcatt agctgcagaa ggatatgaga gtaatctaga   3180
aaaaattgaa aagctttcac ttggcaaagc aaagggccta agatggaaa taaatgcaga   3240 tatgtctaaa tggagtgctc aggatgtttt ttataaatat ttctggctca tagccttaga   3300
ccctatcctc tacccacagg aaaaagagag aatattatac tttatgtgca actacatgga   3360
taaagaattg atactgccag atgaattatt attcaatttg ctggaccaaa aagttgcata   3420
```

```
ccagaatgat ataatagcta ctatgactaa tcaattaaat tcaaatacag ttctgataaa    3480
gagaaattgg ctccaaggga atttcaacta cacctcaagt tacgtccata gctgcgcaat    3540
gtctgtgtat aaagaaatat taaaagaggc cataacatta ctagacgggt ctatattagt    3600
caactcatta gtccattcgg atgataacca aacatcgata acaatagttc aggataagat    3660
ggaaaatgat aaaattatag attttgcaat gaaagaattt gagagagcct gtttgacatt    3720
tggatgccaa gcaaatatga aaaagacata tgtaacaaat tgcataaaag agtttgtttc    3780
attatttaac ttgtacggcg aacccttttc aatatatggc agattcctat taacatctgt    3840
gggtgattgt gcctatatag ggccttatga agatttagct agtcgaatat catcagccca    3900
gacagccata aagcatggtt gtccacccag tctagcatgg gtgtccatag caataagtca    3960
ttggatgacc tctctgacat acaacatgct accagggcag tcaaatgacc caattgatta    4020
tttccctgca gaaaatagga aggatatccc tatagaattg aatggtgtat tagatgctcc    4080
attgtcaatg attagtacag ttggattgga atctgggaat ttatacttct tgataaagtt    4140
gttgagcaaa tataccccgg tcatgcagaa aagagagtca gtagtcaacc aaatagctga    4200
agttaagaac tggaaggtcg aggatctaac agacaatgaa atatttagac ttaaaatact    4260
cagatattta gttctagatg cagagatgga ccctagtgat attatgggtg agacaagcga    4320
catgagaggg aggtctattt tgacacctag aaaattcaca acagcaggca gtttaaggaa    4380
attatattct ttcagtaagt accaggatag actgtcttcc cctggaggca tggttgaatt    4440
gttcacttat ttgcttgaga aacctgagtt gttagtgact aaaggggaag atatgaaaga    4500
ttatatggaa tctgtgatat tccgatataa ttccaaaagg ttcaaagaaa gtttgtcaat    4560
acagaaccca gcacaattat ttatagaaca gatattgttc tcacataagc ccataatagt    4620
cttttctggt atcagggaca atatatataaa cctacatgat agtagagctc tagagaagga    4680
acctgacata ttaggaaaag taacattac agaggcttat agattattaa tgagggacct    4740
gtctagccta gaactaacca atgatgcat tcaagtaatt tattcttaca taatacttaa    4800
tgaccctatg atgataacta ttgcaaacac acatatattg tcaatatacg ggagtcctca    4860
acggaggatg ggcatgtcct gttcaacgat gccagaattt agaaatttaa aattaataca    4920
tcattcccca gccttagttt tgagagcata tagtaaaaat aatcctgaca tccagggtgc    4980
tgatcccacg gaaatggcta gagatttagt tcatctgaaa gagtttgttg agaacacaaa    5040
tttagaagaa aaaatgaaag ttaggattgc tataaatgaa gcagagaaag acaacgggga    5100
tatagtcttt gaactaaaag agatgactag atttttatcag gtttgctatg agtatgtcaa    5160
atctacagaa cacaagataa aagtcttcat tctcccgaca aaatcataca caacaacaga    5220
tttctgttca ctcatgcagg ggaatttaat aaaagataaa gagtggtaca cagttcacta    5280
cctaaaacag atattgtctg gtggccataa agccataatg cagcataatg ccactagtga    5340
gcaaaatatt gcttttgagt gtttcaaatt aattacccat tttgcagact cattcataga    5400
ttcattatct aggtcagctt tttgcagtt gataatagat gaattcagtt ataaagatgt    5460
gaaggttagc aaactttatg acataataaa gaatgggtat aatcgaactg acttcatacc    5520
attgcttttt agaactggcg atttaagaca agctgactta gacaagtatg atgctatgaa    5580
aagtcatgag agggttacat ggaatgattg gcaaacatct cgtcacttgg acatgggctc    5640
aattaatcta acaataaccg ttacaaatag atcaataaca ataatcggag aagataacaa    5700
attgacatat gcagaattat gtctgactag gaaaactcct gagaatataa ctataagtgg    5760
cagaaaattg ctaggtgcaa ggcatggact taaatttgaa aatatgtcca aaatccaaac    5820
```

```
atacccaggc aattattata taacatatag aaagaaagat cgccaccagt ttgtatacca    5880
gatacattct catgaatcaa taacaaggag gaatgaagag catatggcta tcaggaccag    5940
aatatacaat gaaataactc cagtatgtgt agttaacgtt gcagaggtgg atggggacca    6000
acgtatattg ataagatctt tagactatct aaataatgat atattttctc tttcaaggat    6060
taaagtcggg cttgacgaat ttgcaacaat aaaaaaagca cactttagta aaatggtctc    6120
atttgaagga cccccaatta agacagggct cctcgacctt actgaattga tgaaatctca    6180
agatttgctt aaccttaatt atgataatat aaggaatagc aacttgatat cttttttcaaa   6240 attgatttgc tgtgaggggt cagataatat aaatgatggg ttagagtttc tgtccgatga    6300
ccctatgaac tttacagagg gtgaagcaat acattcaaca ccgatcttta atatatatta    6360
ctcaaaaaga ggagaaagac atatgacata caggaatgca attaaattac tgatagaaag    6420
agaaactaag attttttgaag aagctttcac attcagtgag aatggcttca tatcgccaga   6480
gaatcttggt tgcttagaag cagtagtatc attaataaaa ttgttgaaaa ctaatgagtg    6540
gtccacagtt atagataaat gtattcatat atgtttaata aagaatggta tggatcacat    6600
gtaccattca tttgatgtcc ctaaatgttt tatggggaat cctatcacta gagacatgaa    6660
ttggatgatg tttagagaat tcatcaatag tttaccaggg acagatatac caccatggaa    6720
tgtcatgaca gagaacttca aaagaaatg tattgctctg ataaactcta agttagaaac     6780
acagagagat ttctcagaat tcactaaact gatgaaaaag gaaggtggga ggagtaatat    6840
agaatttgat tagtagttat gagtttacag agaacctaca attaggctat aaatttggga    6900
gggttttgga aattggctaa aattcaaaaa gaggggggatt aacagcaact gtataaattt    6960
gtagataggg gcacactact                                                6980
```

<210> SEQ ID NO 2
<211> LENGTH: 6980
<212> TYPE: DNA
<213> ORGANISM: La Crosse virus

<400> SEQUENCE: 2

```
agtagtgtac tcctatctac aaaacttaca gaaaattcag tcatatcaca atatatgcat      60
aatggactat caagagtatc aacaattctt ggctaggatt aatactgcaa gggatgcatg    120
tgtagccaag gatatcgatg ttgacctatt aatggccaga catgattatt ttggtagaga    180
gctgtgcaag tccttaaata tagaatatag gaatgatgta ccatttgtag atataaatttt   240 ggatataagg cccgaagtag acccattaac catagatgca ccacatatta ccccagacaa    300
ttatctatat ataaataatg tgttatatat catagattat aaggtctctg tatcgaatga    360
aagcagtgtt ataacatatg acaaatatta tgagttaact agggacatat ccgatagatt    420
aagtattcca atagaaatag ttatcgtccg tatagaccct gtaagtaagg atttgcatat    480
taactctgat agatttaaag aactttaccc tacaatagtg gtggatataa acttcaatca    540
atttttcgac ttaaaacaat tactctatga aaaattcggt gatgatgaag aattcctatt    600
gaaagttgca catggtgact tcactcttac agcaccctgg tgcaagactg ggtgccctga    660
attttggaaa caccccattt ataaagaatt taaaatgagt atgccagtac ctgagcggag    720 gctcttttgaa gaatctgtca agttcaatgc ttatgaatct gagagatgga atactaactt    780
ggttaaaatc agagaatata caagaaaga ctattcagag catatttcaa aatctgcaaa     840
aaatattttc ctggctagtg gatttttataa gcagccaaat aagaatgaga ttagtgaggg    900
```

```
gtggacatta atggttgaga gggttcaaga tcagagagaa atctcaaaat ctctccatga    960
ccagaaacct agcatacatt ttatatgggg agcccataac ccaggaaata gtaataatgc   1020
aaccttcaaa ctcatattgc tttcaaagtc cttacaaagc ataaaggta tatcaactta    1080
cacagaagcg ttcaaatctt taggaaaaat gatggatatt ggagataagg ctattgagta   1140
tgaagaattc tgcatgtccc taaaaagcaa agcaagatca tcatggaagc aaataatgaa   1200
caaaaaatta gagcctaaac aaataaacaa tgcccttgtt ttatgggaac agcagtttat   1260
ggtaaataat gacctgatag acaaagtga gaagttgaaa ttattcaaaa atttctgcgg    1320
tataggcaaa cacaagcaat tcaagaataa aatgctagag gatctagaag tgtcaaagcc   1380
caaaatatta gactttgatg acgcaaatat gtatctagct agcctaacca tgatggaaca   1440
gagtaagaag atattgtcca aaagcaatgg gttgaagcca gataatttta tactgaatga   1500
atttggatcc aaaatcaaag atgctaataa agaaacatat gacaatatgc acaaaatatt   1560
tgagacaaga tattggcaat gtatatccga cttctctact ctgatgaaaa atatcttatc   1620
tgtgtcccaa tataacaggc acaacacatt taggatagc atgtgtgcta ataacaatgt    1680
ctttgctata gtatttcctt cggctgacat aaaaactaag aaagcaactg tagtttatag   1740
cattatagtg ctgcataaag aggaagaaaa catattcaac ccaggatgtt tgcacggcac   1800
atttaagtgt atgaatgggt atatttccat atctagagct ataaggctag ataagagag    1860
gtgccagaga attgtttcct cacctggact gtttttaaca acttgcctac tattcaaaca   1920
tgataatcca actctagtga tgagcgatat tatgaatttt tctatataca ctagcctgtc   1980
tatcacaaag agtgttctat ctttaacaga gccagcacgc tacatgatta tgaactcatt   2040
agctatctcc agcaatgtta aggactatat agcagagaaa ttttcccctt acacaaagac   2100
actgttcagt gtctatatga ctagactaat taaaaatgct tgctttgatg cttatgacca   2160
gagacagcgt gtccaactta gagatatata tttatctgat tatgacataa cccaaaaagg   2220
tattaaagac aatagagagc taacaagtat atggttccct ggtagtgtaa cattaaagga   2280
gtatttaaca caaatatact taccattta ttttaatgct aaaggactac atgagaagca    2340
ccatgtcatg gtggatctag caagactat attagaaata gagtgcgaac agagggaaa    2400
cataaaggag atatggtcta caaattgtac caaacagaca gtgaacctta aattttgat   2460
ccattccttg tgcaagaatt tactagcaga cacttcaaga cacaaccact gcggaacag    2520
aatagaaaat aggaacaatt ttagaaggtc tataacaact atttcaacat ttacaagttc   2580
gaagtcttgc ctcaaaatag gggactttag aaaagagaaa gagctgcagt cagttaaaca   2640
gaagaaaatc ttagaggtgc agagtcgcaa aatgagatta gcaaacccaa tgttcgtgac   2700
agatgaacaa gtatgccttg aagttgggca ctgcaattat gagatgctga ggaatgctat   2760
gccgaattat acagattata tatcaactaa agtatttgat aggttatatg agttattaga   2820
taaaggagtt ttgacagaca agcctgttat agagcaaata atggatatga tggtcgacca   2880
caaaaagttc tatttcacat ttttcaataa aggccagaaa acgtcaaagg atagagagat   2940
attcgttgga gaatatgaag ctaaaatgtg tatgtacgca gttgagagaa tagcaaaaga   3000
aagatgtaaa ttaaatcctg atgaaatgat atctgagccg ggtgatggca agttgaaggt   3060
gttggagcaa aaatcagaac aagaaattcg attcttggtc gagactacaa ggcaaaagaa   3120
tcgtgaaatc gatgaggcaa ttgaagcatt agctgcagaa ggatatgaga gtaatctaga   3180
aaaaattgaa aagctttcac ttggcaaagc aaagggccta aagatggaaa taaatgcaga   3240
tatgtctaaa tggagtgctc aggatgtttt ttataaatat ttctggctca tagccttaga   3300
```

```
ccctatcctc tacccacagg aaaaagagag aatattatac tttatgtgca actacatgga    3360
taaagaattg atactgccag atgaattatt attcaatttg ctggaccaaa aagttgcata    3420
ccagaatgat ataatagcta ctatgactaa tcaattaaat tcaaatacag ttctgataaa    3480
gagaaattgg ctccaaggga atttcaacta cacctcaagt tacgtccata gctgcgcaat    3540
gtctgtgtat aaagaaatat taaaagaggc cataacatta ctagacgggt ctatattagt    3600
caactcatta gtccattcgg atgataacca aacatcgata acaatagttc aggataagat    3660 ggaaatgat  aaaattatag attttgcaat gaaagaattt gagagagcct gtttgacatt    3720
tggatgccaa gcaaatatga aaagacata  tgtaacaaat tgcataaaag agtttgtttc    3780
attatttaac ttgtacggcg aacccttttc aatatatggc agattcctat aacatctgt     3840 gggtgattgt gcctatatag ggccttatga agatttagct agtcgaatat catcagccca    3900
gacagccata aagcatggtt gtccacccag tctagcatgg gtgtccatag caataagtca    3960
ttggatgacc tctctgacat acaacatgct accagggcag tcaaatgacc caattgatta    4020
tttccctgca gaaaatagga aggatatccc tatagaattg aatggtgtat tagatgctcc    4080
attgtcaatg attagtacag ttggattgga atctgggaat ttatacttct tgataaagtt    4140
gttgagcaaa tataccccgg tcatgcagaa aagagagtca gtagtcaacc aaatagctga    4200
agttaagaac tggaaggtcg aggatctaac agacaatgaa atatttagac ttaaaatact    4260
cagatattta gttctagatg cagagatgga ccctagtgat attatgggtg agacaagcga    4320
catgagaggg aggtctattt tgacacctag aaaattcaca acagcaggca gtttaaggaa    4380
attatattct ttcagtaagt accaggatag actgtcttcc cctggaggca tggttgaatt    4440
gttcacttat ttgcttgaga aacctgagtt gttagtgact aaaggggaag atatgaaaga    4500
ttatatggaa tctgtgatat tccgatataa ttccaaaagg ttcaaagaaa gtttgtcaat    4560
acagaaccca gcacaattat ttatagaaca gatattgttc tcacataagc ccataataga    4620
cttttctggt atcagggaca aatatataaa cctacatgat agtagagctc tagagaagga    4680
acctgacata ttaggaaaag taacatttac agaggcttat agattattaa tgagggacct    4740
gtctagccta gaactaacca atgatgacat tcaagtaatt tattcttaca taatacttaa    4800
tgaccctatg atgataacta ttgcaaacac acatatattg tcaatatacg ggagtcctca    4860
acggaggatg ggcatgtcct gttcaacgat gccagaattt agaaatttaa aattaataca    4920
tcattcccca gccttagttt tgagagcata tagtaaaaat aatcctgaca tccagggtgc    4980
tgatcccacg gaaatggcta gagatttagt tcatctgaaa gagtttgttg agaacacaaa    5040
tttagaagaa aaaatgaaag ttaggattgc tataaatgaa gcagagaaag gacaacggga    5100
tatagtcttt gaactaaaag agatgactag atttttatcag gtttgctatg agtatgtcaa    5160
atctacagaa cacaagataa aagtcttcat tctcccgaca aaatcataca caacaacaga    5220
tttctgttca ctcatgcagg gaatttaat  aaaagataaa gagtggtaca cagttcacta    5280
cctaaaacag atattgtctg gtggccataa agccataatg cagcataatg ccactagtga    5340
gcaaaatatt gcttttgagt gtttcaaatt aattacccat tttgcagact cattcataga    5400
ttcattatct aggtcagctt ttttgcagtt gataatagat gaattcagtt ataaagatgt    5460
gaaggttagc aaactttatg acataataaa gaatgggtat aatcgaactg acttcatacc    5520
attgcttttt agaactggcg atttaagaca agctgactta gacaagtatg atgctatgaa    5580
aagtcatgag agggttacat ggaatgattg gcaaacatct cgtcacttgg acatgggctc    5640
```

| | |
|---|---|
| aattaatcta caataaccg gttacaatag atcaataaca ataatcggag aagataacaa | 5700 |
| attgacatat gcagaattat gtctgactag gaaaactcct gagaatataa ctataagtgg | 5760 |
| cagaaaattg ctaggtgcaa ggcatggact taaattttgaa aatatgtcca aaatccaaac | 5820 |
| atacccaggc aattattata taacatatag aaagaaagat cgccaccagt ttgtatacca | 5880 |
| gatacattct catgaatcaa taacaaggag gaatgaagag catatggcta tcaggaccag | 5940 |
| aatatacaat gaaataactc cagtatgtgt agttaacgtt gcagaggtgg atggggacca | 6000 |
| acgtatattg ataagatctt tagactatct aaataatgat atattttctc tttcaaggat | 6060 |
| taaagtcggg cttgacgaat ttgcaacaat aaaaaaagca cactttagta aaatggtctc | 6120 |
| atttgaagga ccccccaatta agacagggct cctcgacctt actgaattga tgaaatctca | 6180 |
| agatttgctt aaccttaatt atgataatat aaggaatagc aacttgatat cttttttcaaa | 6240 |
| attgatttgc tgtgaggggt cagataatat aaatgatggg ttagagtttc tgtccgatga | 6300 |
| ccctatgaac tttacagagg gtgaagcaat acattcaaca ccgatcttta atatatatta | 6360 |
| ctcaaaaaga ggagaaagac atatgacata caggaatgca attaaattac tgatagaaag | 6420 |
| agaaactaag attttttgaag aagctttcac attcagtgag aatggcttca tatcgccaga | 6480 |
| gaatcttggt tgcttagaag cagtagtatc attaataaaa ttgttgaaaa ctaatgagtg | 6540 |
| gtccacagtt atagataaat gtattcatat atgtttaata aagaatggta tggatcacat | 6600 |
| gtaccattca tttgatgtcc ctaaatgttt tatggggaat cctatcacta gagacatgaa | 6660 |
| ttggatgatg tttagagaat tcatcaatag tttaccaggg acagatatac caccatggaa | 6720 |
| tgtcatgaca gagaacttca aaagaaatg tattgctctg ataaactcta agttagaaac | 6780 |
| acagagagat ttctcagaat tcactaaact gatgaaaaag gaaggtggga ggagtaatat | 6840 |
| agaatttgat tagtagttat gagtttacag agaacctaca attaggctat aaatttggga | 6900 |
| gggttttgga aattggctaa aattcaaaaa gagggggatt aacagcaact gtataaattt | 6960 |
| gtagatagga gcacactact | 6980 |

<210> SEQ ID NO 3
<211> LENGTH: 4527
<212> TYPE: DNA
<213> ORGANISM: La Crosse virus

<400> SEQUENCE: 3

| | |
|---|---|
| agtagtgtac taccaagtat agataacgtt tgaatattaa agttttgaat caaagccaaa | 60 |
| gatgatttgt atattggtgc taattacagt tgcagctgca agcccagtgt atcaaaggtg | 120 |
| tttccaagat ggggctatag tgaagcaaaa cccatccaaa gaagcagtta cagaggtgtg | 180 |
| cctgaaagat gatgttagca tgatcaaaac agaggccagg tatgtaagaa atgcaacagg | 240 |
| agttttttca aataatgtcg caataaggaa atggctagtc tctgattggc atgattgcag | 300 |
| gcctaagaag atcgttgggg gacacatcaa tgtaatagaa gttggtgatg acctgtcact | 360 |
| ccatactgaa tcatatgttt gcagcgcaga ttgtaccata ggtgtagaca aagagactgc | 420 |
| acaggtcagg cttcagacag ataccacaaa tcattttgaa attgcaggca ctactgtgaa | 480 |
| gtcaggatgg ttcaagagca cgacatatat aactcttgat caaacttgcg aacacctaa | 540 |
| agtttcctgc ggcccaaaat ctgtacagtt ccatgcctgc ttcaatcagc atatgtcttg | 600 |
| cgtcagattt ttacacagga caatattgcc tggctctata gccaattcca tgtcagaa | 660 |
| tatcgaaaatc ataattttag ttacacttac tctattaatc tttatattgt taagcatttt | 720 |
| aagtaagact tatatatgtt atttattaat gcctatattc atccccatag catatatata | 780 |

```
cggtataatt tacaataagt cgtgcaaaaa atgcaaatta tgtggcttag tgtatcatcc      840
attcacagag tgtggcacac attgtgtctg tggtgcccgc tatgatactt cagatagaat      900
gaaactgcat agagcttctg gattgtgccc tggttataaa agcctaagag ctgccagagt      960
catgtgcaag tcgaaagggc ctgcatcaat attgtctata attactgcgg tactggtctt     1020
aacctttgtg acaccaatca actccatggt tttaggagag agtaaagaaa cctttgaact     1080
tgaagatctt ccagacgaca tgttggaaat ggcatcgaga ataaattctt attatctcac     1140
ctgtatcttg aattatgctg taagctgggg tcttgttatc attggattgt tgatcgggct     1200
gctttttaag aaataccagc acagattctt aaatgtttac gcaatgtact gtgaagaatg     1260
tgacatgtat catgacaagt ctgggttgaa aagacatggt gatttcacca acaaatgcag     1320
acagtgcaca tgtggtcaat atgaagatgc tgcaggtttg atggctcaca ggaaaaccta     1380
taactgctta gtgcagtaca agcaaagtg gatgatgaac ttcctgataa tttacatatt     1440
cttaattttg atcaaagatt ctgctatagt tgtacaagct gctggaactg acttcaccac     1500
ctgcctagag actgagagta taaattggaa ctgcactggg ccattttga acctcgggaa     1560 ttgccaaaag caacaaaaga agaaccttaa caccaacatt gcaactcagt taaagggact     1620
aaaggcaatt tccgtactag atgtccctat aataacaggg ataccagatg atattgcggg     1680
tgctttaaga tatatagaag agaaggaaga tttccatgtc cagctaacta tagaatatgc     1740
gatgttaagc aaatactgtg actattatac ccaattctca gataactcag gatacagtca     1800
gacaacatgg agagtgtact taaggtctca tgattttgaa gcctgtatac tatatccaaa     1860
tcagcacttt tgcagatgtg taaaaaatgg tgagaagtgc agcagctcca attgggactt     1920
tgccaatgaa atgaaagatt attactctgg gaaacaaaca agtttgaca aggacttaaa     1980 tctagcccta acagctttgc atcatgcctt caggggacc tcatctgcat atatagcaac     2040
aatgctctca aaaagtcca atgatgactt gattgcatac acaaataaga taaaacaaa     2100 attcccaggt aatgcattgt tgaaggctat aatagattat atagcatata tgaaaagttt     2160
gccaggtatg gcaaatttca atatgatga attctgggat gaattactgt acaaacccaa     2220
cccagcaaag gcctcaaacc ttgctagagg aaaggagtca tcttacaact tcaaactagc     2280
aatttcatca aagtctataa aaacctgcaa gaatgttaag gatgttgcct gcttatcgcc     2340
aaggtcaggt gctatatatg cttcaataat tgcgtgtggt gaacccaatg ggccaagtgt     2400
gtataggaaa ccatcaggtg gtgtattcca atctagcact gatcggtcta tatactgctt     2460
gctggatagc cattgtctag aagaatttga ggccatcggc caggaggagc tggatgcggt     2520
aaagaaatcc aaatgttggg aaattgaata tcctgacgta aagctcatcc aagaaggcga     2580
tgggactaaa agctgtagaa tgaaagattc tgggaactgc aatgttgcaa ctaacagatg     2640
gccagtgata caatgtgaga atgacaaatt ttactactca gagcttcaaa aagattatga     2700
caaagctcaa gatattggtc actattgctt aagccctgga tgtactactg tccggtaccc     2760
tattaatcca aagcacatct ctaactgtaa ttggcaagta agcagatcta gcatagcgaa     2820
gatagatgtg cacaatattg aggatattga gcaatataag aaagctataa ctcagaaact     2880
tcaaacgagc ctatctctat tcaagtatgc aaaaacaaaa aacttgccgc acatcaaacc     2940
aatttataaa tatataacta tagaaggaac agaaactgca gaaggtatag agagtgcata     3000
cattgaatca gaagtacctg cattggctgg gacatctatc ggattcaaaa tcaattctaa     3060
agagggcaag cacttgctag atgttatagc atatgtaaaa agtgcctcat actcttcagt     3120
```

| | |
|---|---|
| gtatacaaaa ttgtactcaa ctggcccaac atcagggata aatactaaac atgatgaatt | 3180 |
| gtgtactggc ccatgcccag caaatatcaa tcatcaggtt gggtggctga catttgcaag | 3240 |
| agagaggaca agctcatggg gatgcgaaga gtttggttgc ctggctgtaa gtgatgggtg | 3300 |
| tgtatttgga tcatgccaag atataataaa agaagaacta tctgtctata ggaaggagac | 3360 |
| cgaggaagtg actgatgtag aactgtgttt gacattttca gacaaaacat actgtacaaa | 3420 |
| cttaaacccct gttaccccta ttaacagaa tctatttgag gtacagttca aaactgtaga | 3480 |
| gacctacagc ttgcctagaa ttgttgctgt gcaaaaccat gagattaaaa ttgggcaaat | 3540 |
| aaatgattta ggagtttact ctaagggttg tgggaatgtt caaaaggtca atggaactat | 3600 |
| ttatggcaat ggagttccca gatttgacta cttatgccat ttagctagca ggaaggaagt | 3660 |
| cattgttaga aaatgcttcg acaatgatta ccaagcatgc aaatttcttc aaagccctgc | 3720 |
| tagttacaga cttgaagaag acagtggcac tgtgaccata attgactaca aaaagatttt | 3780 |
| aggaacaatc aagatgaagg caattttagg agatgtcaaa tataaaacat ttgctgatag | 3840 |
| tgtcgatata accgcagaag ggtcatgcac cggctgtatt aactgcttcg aaaatatcca | 3900 |
| ttgcgaatta cgttgcaca ccacaattga agccagctgc ccaattaaaa gctcgtgcac | 3960 |
| agtatttcat gacaggattc ttgtgactcc aaatgaacac aaatatgcat tgaaaatggt | 4020 |
| gtgcacagaa aagccaggga acacactcac aattaaagtc tgcaatacta agttgaagc | 4080 |
| atctatggcc cttgtagacg caaagcctat catgaaacta gcaccagttg atcagacagc | 4140 |
| atatataaga gaaaagatg aaaggtgtaa aacttggatg tgtagggtaa gagatgaagg | 4200 |
| actgcaggtc atcttggagc catttaaaaa tttatttgga tcttatattg ggatatttta | 4260 |
| cacatttatt atatctatag tagtattatt ggttattatc tatgtactac tacctatatg | 4320 |
| ctttaagtta agggataccc ttagaaagca tgaagatgca tataagagag atgaaaat | 4380 |
| tagatagggg atctatgcag aacaaaattg agtcctgtat tatatacttc tatttgtagt | 4440 |
| atagctgttg ttaagtgggg ggtggggaac taacaacagc gtaaatttat tttgcaaaca | 4500 |
| ttattttata cttggtagca cactact | 4527 |

<210> SEQ ID NO 4
<211> LENGTH: 4526
<212> TYPE: DNA
<213> ORGANISM: La Crosse virus

<400> SEQUENCE: 4

| | |
|---|---|
| agtagtgtac taccaagtat agataacgtt tgaatattaa agttttgaat caaagccaaa | 60 |
| gatgatttgt atattggtgc taattacagt tgcagctgca agcccagtgt atcaaaggtg | 120 |
| tttccaagat ggggctatag tgaagcaaaa cccatccaaa gaagcagtta cagaggtgtg | 180 |
| cctgaaagat gatgttagca tgatcaaaac agaggccagg tatgtaagaa atgcaacagg | 240 |
| agttttttca ataatgtcg caataaggaa atggctagtc tctgattggc atgattgcag | 300 |
| gcctaagaag atcgttgggg gacacatcaa tgtaatagaa gttggtgatg acctgtcact | 360 |
| ccatactgaa tcatatgttt gcagcgcaga ttgtaccata ggtgtagaca agagactgc | 420 |
| acaggtcagg cttcagacag ataccacaaa tcattttgaa attgcaggca ctactgtgaa | 480 |
| gtcaggatgg ttcaagagca cgacatatat aactcttgat caaacttgcg aacaccttaa | 540 |
| agtttcctgc ggcccaaaat ctgtacagtt ccatgcctgc ttcaatcagc atatgtcttg | 600 |
| cgtcagattt ttacacagga caatattgcc tggctctata gccaattcca tatgtcagaa | 660 |
| tatcgaaatc ataattttag ttacacttac tctattaatc tttatattgt taagcatttt | 720 |

```
aagtaagact tatatatgtt atttattaat gcctatattc atccccatag catatatata    780
cggtataatt tacaataagt cgtgcaaaaa atgcaaatta tgtggcttag tgtatcatcc    840
attcacagag tgtggcacac attgtgtctg tggtgcccgc tatgatactt cagatagaat    900
gaaactgcat agagcttctg gattgtgccc tggttataaa agcctaagag ctgccagagt    960
catgtgcaag tcgaaagggc ctgcatcaat attgtctata attactgcgg tactggtctt   1020
aacctttgtg acaccaatca actccatggt tttaggagag agtaaagaaa cctttgaact   1080
tgaagatctt ccagacgaca tgttggaaat ggcatcgaga ataaattctt attatctcac   1140
ctgtatcttg aattatgctg taagctgggg tcttgttatc attggattgt tgatcgggct   1200
gcttttaag aaataccagc acagattctt aaatgtttac gcaatgtact gtgaagaatg    1260
tgacatgtat catgacaagt ctgggttgaa aagacatggt gatttcacca acaaatgcag   1320
acagtgcaca tgtggtcaat atgaagatgc tgcaggtttg atggctcaca ggaaaaccta   1380
taactgctta gtgcagtaca aagcaaagtg atgatgaac ttcctgataa tttacatatt     1440
cttaattttg atcaaagatt ctgctatagt tgtacaagct gctggaactg acttcaccac   1500
ctgcctagag actgagagta taaattggaa ctgcactggg ccattttga acctcgggaa    1560
ttgccaaaag caacaaaaga aagaaccta caccaacatt gcaactcagt taagggact     1620
aaaggcaatt tccgtactag atgtccctat aataacaggg ataccagatg atattgcggg   1680
tgctttaaga tatatagaag agaaggaaga tttccatgtc cagctaacta tagaatatgc   1740
gatgttaagc aaatactgtg actattatac ccaattctca gataactcag gatacagtca   1800
gacaacatgg agagtgtact taaggtctca tgattttgaa gcctgtatac tatatccaaa   1860
tcagcacttt tgcagatgtg taaaaaatgg tgagaagtgc agcagctcca attgggactt   1920
tgccaatgaa atgaaagatt attactctgg gaaacaaaca aagtttgaca aggacttaaa   1980
tctagcccta acagctttgc atcatgcctt caggggggacc tcatctgcat atatagcaac   2040
aatgctctca aaaagtccca atgatgactt gattgcatac acaaataaga taaaaacaaa    2100
attcccaggt aatgcattgt tgaaggctat aatagattat atagcatata tgaaaagttt   2160
gccaggtatg gcaaatttca aatatgatga attctgggat gaattactgt acaaacccaa    2220
cccagcaaag gcctcaaacc ttgctagagg aaaggagtca tcttacaact tcaaactagc   2280
aatttcatca aagtctataa aaacctgcaa gaatgttaag gatgttgcct gcttatcgcc   2340
aaggtcaggt gctatatatg cttcaataat tgcgtgtggt gaacccaatg ggccaagtgt   2400
gtataggaaa ccatcaggtg gtgtattcca atctagcact gatcggtcta tatactgctt   2460
gctggatagc cattgtctag aagaatttga ggccatcggc caggaggagc tggatgcggt   2520
aaagaaatcc aaatgttggg aaattgaata tcctgacgta aagctcatcc aagaaggcga   2580
tgggactaaa agctgtagaa tgaaagattc tgggaactgc aatgttgcaa ctaacagatg   2640
gccagtgata caatgtgaga atgacaaatt ttactactca gagcttcaaa agattatga    2700
caaagctcaa gatattggtc actattgctt aagccctgga tgtactactg tccggtaccc   2760
tattaatcca aagcacatct ctaactgtaa ttggcaagta agcagatcta gcatagcgaa   2820
gatagatgtg cacaatattg aggatattga gcaaatataag aaagctataa ctcagaaaact  2880
tcaaacgagc ctatctctat tcaagtatgc aaaaacaaaa aacttgccgc acatcaaacc   2940
aatttataaa tatataacta tagaaggaac agaaactgca gaaggtatag agagtgcata   3000
cattgaatca gaagtacctg cattggctgg gacatctatc ggattcaaaa tcaattctaa   3060
```

| | |
|---|---|
| agagggcaag cacttgctag atgttatagc atatgtaaaa agtgcctcat actcttcagt | 3120 |
| gtatacaaaa ttgtactcaa ctggcccaac atcagggata aatactaaac atgatgaatt | 3180 |
| gtgtactggc ccatgcccag caaatatcaa tcatcaggtt gggtggctga catttgcaag | 3240 |
| agagaggaca agctcatggg gatgcgaaga gtttggttgc ctggctgtaa gtgatgggtg | 3300 |
| tgtatttgga tcatgccaag atataataaa agaagaacta tctgtctata ggaaggagac | 3360 |
| cgaggaagtg actgatgtag aactgtgttt gacattttca gacaaaacat actgtacaaa | 3420 |
| cttaaaccct gttaccccta ttataacaga tctatttgag gtacagttca aaactgtaga | 3480 |
| gacctacagc ttgcctagaa ttgttgctgt gcaaaaccat gagattaaaa ttgggcaaat | 3540 |
| aaatgattta ggagtttact ctaagggttg tgggaatgtt caaaaggtca atggaactat | 3600 |
| ttatggcaat ggagttccca gatttgacta cttatgccat ttagctagca ggaaggaagt | 3660 |
| cattgttaga aaatgcttcg acaatgatta ccaagcatgc aaatttcttc aaagccctgc | 3720 |
| tagttacaga cttgaagaag acagtggcac tgtgaccata attgactaca aaagattttt | 3780 |
| aggaacaatc aagatgaagg caattttagg agatgtcaaa tataaaacat ttgctgatag | 3840 |
| tgtcgatata accgcagaag ggtcatgcac cggctgtatt aactgcttcg aaaatatcca | 3900 |
| ttgcgaatta acgttgcaca ccacaattga agccagctgc ccaattaaaa gctcgtgcac | 3960 |
| agtatttcat gacaggattc ttgtgactcc aaatgaacac aaatatgcat tgaaaatggt | 4020 |
| gtgcacagaa aagccaggga acacactcac aattaaagtc tgcaatacta agttgaagc | 4080 |
| atctatggcc cttgtagacg caaagcctat catagaacta gcaccagttg atcagacagc | 4140 |
| atatataaga gaaaaagatg aaaggtgtaa aacttggatg tgtagggtaa gagatgaagg | 4200 |
| actgcaggtc atcttggagc catttaaaaa tttatttgga tcttatattg ggatatttta | 4260 |
| cacatttatt atatctatag tagtattatt ggttattatc tatgtactac tacctatatg | 4320 |
| ctttaagtta agggataccc ttagaaagca tgaagatgca tataagagag agatgaaaat | 4380 |
| tagatagggg atctatgcag aacaaaattg agtcctgtat tatatattct atttgtagta | 4440 |
| tagctgttgt taagtggggg gtggggaact aacaacagcg taaatttatt ttgcaaacat | 4500 |
| tattttatac ttggtagcac actact | 4526 |

<210> SEQ ID NO 5
<211> LENGTH: 984
<212> TYPE: DNA
<213> ORGANISM: La Crosse virus

<400> SEQUENCE: 5

| | |
|---|---|
| agtagtgtac cccacttgaa tactttgaaa ataaattgtt gttgactgtt ttttacctaa | 60 |
| ggggaaatta tcaagagtgt gatgtcggat ttggtgtttt atgatgtcgc atcaacaggt | 120 |
| gcaaatggat ttgatcctga tgcagggtat atggacttct gtgttaaaaa tgcagaatta | 180 |
| ctcaaccttg ctgcagttag gatcttcttc ctcaatgccg caaaggccaa ggctgctctc | 240 |
| tcgcgtaagc cagagaggaa ggctaaccct aaatttggag agtggcaggt ggaggttatc | 300 |
| aataatcatt ttcctggaaa caggaacaac ccaattggta caacgatctc taccatccac | 360 |
| agattatctg gtatttagc cagatgggtc cttgatcagt ataacgagaa tgatgatgag | 420 |
| tctcagcacg agttgatcag aacaactatt atcaacccaa ttgctgagtc taatggtgta | 480 |
| ggatgggaca gtgggccaga gatctatcta tcattctttc caggaacaga aatgttttg | 540 |
| gaaactttca aattctaccc gctgaccatt ggaattcaca gagtcaagca aggcatgatg | 600 |
| gaccctcaat acctgaagaa ggccttaagg caacgctatg gcactctcac agcagataag | 660 |

```
tggatgtcac agaaggttgc agcaattgct aagagcctga aggatgtaga gcagcttaaa    720
tggggaaaag gaggcctgag cgatactgct aaaacattcc tgcagaaatt tggcatcagg    780
cttccataaa tatggcatga ggcattcaaa ttaggttcta aattctaaat ttatatatgt    840
caatttgatt aattggttat ccaaaagggt tttcttaagg gaacccacaa aaatagcagc    900
taaatgggtg ggtggtaggg gacagcaaaa aactataaat caggtcataa ataaaataaa    960
atgtattcag tggggcacac tact                                           984
```

<210> SEQ ID NO 6
<211> LENGTH: 984
<212> TYPE: DNA
<213> ORGANISM: La Crosse virus

<400> SEQUENCE: 6

```
agtagtgtac tccacttgaa tactttgaaa ataaattgtt gttgactgtt ttttacctaa     60
ggggaaatta tcaagagtgt gatgtcggat ttggtgtttt atgatgtcgc atcaacaggt    120
gcaaatggat ttgatcctga tgcagggtat atggacttct gtgttaaaaa tgcagaatta    180
ctcaaccttg ctgcagttag gatcttcttc ctcaatgccg caaaggccaa ggctgctctc    240
tcgcgtaagc cagagaggaa ggctaaccct aaatttggag agtggcaggt ggaggttatc    300
aataatcatt ttcctggaaa caggaacaac ccaattggta acaacgatct taccatccac    360
agattatctg ggtatttagc cagatgggtc cttgatcagt ataacgagaa tgatgatgag    420
tctcagcacg agttgatcag aacaactatt atcaacccaa ttgctgagtc taatggtgta    480
ggatgggaca gtgggccaga gatctatcta tcattctttc caggaacaga aatgtttttg    540
gaaactttca aattctaccc gctgaccatt ggaattcaca gagtcaagca aggcatgatg    600
gaccctcaat acctgaagaa ggccttaagg caacgctatg gcactctcac agcagataag    660
tggatgtcac agaaggttgc agcaattgct aagagcctga aggatgtaga gcagcttaaa    720
tggggaaaag gaggcctgag cgatactgct aaaacattcc tgcagaaatt tggcatcagg    780
cttccataaa tatggcatga ggcattcaaa ttaggttcta aattctaaat ttatatatgt    840
caatttgatt aattggttat ccaaaagggt tttcttaagg gaacccacaa aaatagcagc    900
taaatgggtg ggtggtaggg gacagcaaaa aactataaat caggtcataa ataaaataaa    960
atgtattcag tggagcacac tact                                           984
```

<210> SEQ ID NO 7
<211> LENGTH: 2263
<212> TYPE: PRT
<213> ORGANISM: La Crosse virus

<400> SEQUENCE: 7

Met Asp Tyr Gln Glu Tyr Gln Gln Phe Leu Ala Arg Ile Asn Thr Ala
1               5                   10                  15

Arg Asp Ala Cys Val Ala Lys Asp Ile Asp Val Asp Leu Leu Met Ala
                20                  25                  30

Arg His Asp Tyr Phe Gly Arg Glu Leu Cys Lys Ser Leu Asn Ile Glu
            35                  40                  45

Tyr Arg Asn Asp Val Pro Phe Val Asp Ile Ile Leu Asp Ile Arg Pro
        50                  55                  60

Glu Val Asp Pro Leu Thr Ile Asp Ala Pro His Ile Thr Pro Asp Asn
65                  70                  75                  80

Tyr Leu Tyr Ile Asn Asn Val Leu Tyr Ile Ile Asp Tyr Lys Val Ser

```
                 85                  90                  95
Val Ser Asn Glu Ser Ser Val Ile Thr Tyr Asp Lys Tyr Tyr Glu Leu
            100                 105                 110

Thr Arg Asp Ile Ser Asp Arg Leu Ser Ile Pro Ile Glu Ile Val Ile
            115                 120                 125

Val Arg Ile Asp Pro Val Ser Lys Asp Leu His Ile Asn Ser Asp Arg
            130                 135                 140

Phe Lys Glu Leu Tyr Pro Thr Ile Val Val Asp Ile Asn Phe Asn Gln
145                 150                 155                 160

Phe Phe Asp Leu Lys Gln Leu Leu Tyr Glu Lys Phe Gly Asp Asp Glu
                165                 170                 175

Glu Phe Leu Leu Lys Val Ala His Gly Asp Phe Thr Leu Thr Ala Pro
                180                 185                 190

Trp Cys Lys Thr Gly Cys Pro Glu Phe Trp Lys His Pro Ile Tyr Lys
                195                 200                 205

Glu Phe Lys Met Ser Met Pro Val Pro Glu Arg Arg Leu Phe Glu Glu
            210                 215                 220

Ser Val Lys Phe Asn Ala Tyr Glu Ser Glu Arg Trp Asn Thr Asn Leu
225                 230                 235                 240

Val Lys Ile Arg Glu Tyr Thr Lys Lys Asp Tyr Ser Glu His Ile Ser
                245                 250                 255

Lys Ser Ala Lys Asn Ile Phe Leu Ala Ser Gly Phe Tyr Lys Gln Pro
            260                 265                 270

Asn Lys Asn Glu Ile Ser Glu Gly Trp Thr Leu Met Val Glu Arg Val
            275                 280                 285

Gln Asp Gln Arg Glu Ile Ser Lys Ser Leu His Asp Gln Lys Pro Ser
            290                 295                 300

Ile His Phe Ile Trp Gly Ala His Asn Pro Gly Asn Ser Asn Asn Ala
305                 310                 315                 320

Thr Phe Lys Leu Ile Leu Leu Ser Lys Ser Leu Gln Ser Ile Lys Gly
                325                 330                 335

Ile Ser Thr Tyr Thr Glu Ala Phe Lys Ser Leu Gly Lys Met Met Asp
                340                 345                 350

Ile Gly Asp Lys Ala Ile Glu Tyr Glu Glu Phe Cys Met Ser Leu Lys
            355                 360                 365

Ser Lys Ala Arg Ser Ser Trp Lys Gln Ile Met Asn Lys Lys Leu Glu
            370                 375                 380

Pro Lys Gln Ile Asn Asn Ala Leu Val Leu Trp Glu Gln Gln Phe Met
385                 390                 395                 400

Val Asn Asn Asp Leu Ile Asp Lys Ser Glu Lys Leu Lys Leu Phe Lys
                405                 410                 415

Asn Phe Cys Gly Ile Gly Lys His Lys Gln Phe Lys Asn Lys Met Leu
                420                 425                 430

Glu Asp Leu Glu Val Ser Lys Pro Lys Ile Leu Asp Phe Asp Asp Ala
            435                 440                 445

Asn Met Tyr Leu Ala Ser Leu Thr Met Met Glu Gln Ser Lys Lys Ile
            450                 455                 460

Leu Ser Lys Ser Asn Gly Leu Lys Pro Asp Asn Phe Ile Leu Asn Glu
465                 470                 475                 480

Phe Gly Ser Lys Ile Lys Asp Ala Asn Lys Glu Thr Tyr Asp Asn Met
                485                 490                 495

His Lys Ile Phe Glu Thr Arg Tyr Trp Gln Cys Ile Ser Asp Phe Ser
            500                 505                 510
```

```
Thr Leu Met Lys Asn Ile Leu Ser Val Ser Gln Tyr Asn Arg His Asn
            515                 520                 525

Thr Phe Arg Ile Ala Met Cys Ala Asn Asn Asn Val Phe Ala Ile Val
        530                 535                 540

Phe Pro Ser Ala Asp Ile Lys Thr Lys Ala Thr Val Val Tyr Ser
545                 550                 555                 560

Ile Ile Val Leu His Lys Glu Glu Asn Ile Phe Asn Pro Gly Cys
                    565                 570                 575

Leu His Gly Thr Phe Lys Cys Met Asn Gly Tyr Ile Ser Ile Ser Arg
            580                 585                 590

Ala Ile Arg Leu Asp Lys Glu Arg Cys Gln Arg Ile Val Ser Ser Pro
        595                 600                 605

Gly Leu Phe Leu Thr Thr Cys Leu Leu Phe Lys His Asp Asn Pro Thr
        610                 615                 620

Leu Val Met Ser Asp Ile Met Asn Phe Ser Ile Tyr Thr Ser Leu Ser
625                 630                 635                 640

Ile Thr Lys Ser Val Leu Ser Leu Thr Glu Pro Ala Arg Tyr Met Ile
                    645                 650                 655

Met Asn Ser Leu Ala Ile Ser Ser Asn Val Lys Asp Tyr Ile Ala Glu
            660                 665                 670

Lys Phe Ser Pro Tyr Thr Lys Thr Leu Phe Ser Val Tyr Met Thr Arg
        675                 680                 685

Leu Ile Lys Asn Ala Cys Phe Asp Ala Tyr Asp Gln Arg Gln Arg Val
        690                 695                 700

Gln Leu Arg Asp Ile Tyr Leu Ser Asp Tyr Asp Ile Thr Gln Lys Gly
705                 710                 715                 720

Ile Lys Asp Asn Arg Glu Leu Thr Ser Ile Trp Phe Pro Gly Ser Val
                    725                 730                 735

Thr Leu Lys Glu Tyr Leu Thr Gln Ile Tyr Leu Pro Phe Tyr Phe Asn
            740                 745                 750

Ala Lys Gly Leu His Glu Lys His His Val Met Val Asp Leu Ala Lys
        755                 760                 765

Thr Ile Leu Glu Ile Glu Cys Glu Gln Arg Gly Asn Ile Lys Glu Ile
770                 775                 780

Trp Ser Thr Asn Cys Thr Lys Gln Thr Val Asn Leu Lys Ile Leu Ile
785                 790                 795                 800

His Ser Leu Cys Lys Asn Leu Leu Ala Asp Thr Ser Arg His Asn His
                    805                 810                 815

Leu Arg Asn Arg Ile Glu Asn Arg Asn Phe Arg Arg Ser Ile Thr
            820                 825                 830

Thr Ile Ser Thr Phe Thr Ser Ser Lys Ser Cys Leu Lys Ile Gly Asp
        835                 840                 845

Phe Arg Lys Glu Lys Glu Leu Gln Ser Val Lys Gln Lys Ile Leu
850                 855                 860

Glu Val Gln Ser Arg Lys Met Arg Leu Ala Asn Pro Met Phe Val Thr
865                 870                 875                 880

Asp Glu Gln Val Cys Leu Glu Val Gly His Cys Asn Tyr Glu Met Leu
                    885                 890                 895

Arg Asn Ala Met Pro Asn Tyr Thr Asp Tyr Ile Ser Thr Lys Val Phe
            900                 905                 910

Asp Arg Leu Tyr Glu Leu Leu Asp Lys Gly Val Leu Thr Asp Lys Pro
        915                 920                 925
```

Val Ile Glu Gln Ile Met Asp Met Met Val Asp His Lys Lys Phe Tyr
930                 935                 940

Phe Thr Phe Phe Asn Lys Gly Gln Lys Thr Ser Lys Asp Arg Glu Ile
945                 950                 955                 960

Phe Val Gly Glu Tyr Glu Ala Lys Met Cys Met Tyr Ala Val Glu Arg
            965                 970                 975

Ile Ala Lys Glu Arg Cys Lys Leu Asn Pro Asp Glu Met Ile Ser Glu
            980                 985                 990

Pro Gly Asp Gly Lys Leu Lys Val Leu Glu Gln Lys Ser Glu Gln Glu
        995                 1000                1005

Ile Arg Phe Leu Val Glu Thr Thr Arg Gln Lys Asn Arg Glu Ile
    1010                1015                1020

Asp Glu Ala Ile Glu Ala Leu Ala Ala Glu Gly Tyr Glu Ser Asn
    1025                1030                1035

Leu Glu Lys Ile Glu Lys Leu Ser Leu Gly Lys Ala Lys Gly Leu
    1040                1045                1050

Lys Met Glu Ile Asn Ala Asp Met Ser Lys Trp Ser Ala Gln Asp
    1055                1060                1065

Val Phe Tyr Lys Tyr Phe Trp Leu Ile Ala Leu Asp Pro Ile Leu
    1070                1075                1080

Tyr Pro Gln Glu Lys Glu Arg Ile Leu Tyr Phe Met Cys Asn Tyr
    1085                1090                1095

Met Asp Lys Glu Leu Ile Leu Pro Asp Glu Leu Leu Phe Asn Leu
    1100                1105                1110

Leu Asp Gln Lys Val Ala Tyr Gln Asn Asp Ile Ile Ala Thr Met
    1115                1120                1125

Thr Asn Gln Leu Asn Ser Asn Thr Val Leu Ile Lys Arg Asn Trp
    1130                1135                1140

Leu Gln Gly Asn Phe Asn Tyr Thr Ser Ser Tyr Val His Ser Cys
    1145                1150                1155

Ala Met Ser Val Tyr Lys Glu Ile Leu Lys Glu Ala Ile Thr Leu
    1160                1165                1170

Leu Asp Gly Ser Ile Leu Val Asn Ser Leu Val His Ser Asp Asp
    1175                1180                1185

Asn Gln Thr Ser Ile Thr Ile Val Gln Asp Lys Met Glu Asn Asp
    1190                1195                1200

Lys Ile Ile Asp Phe Ala Met Lys Glu Phe Glu Arg Ala Cys Leu
    1205                1210                1215

Thr Phe Gly Cys Gln Ala Asn Met Lys Lys Thr Tyr Val Thr Asn
    1220                1225                1230

Cys Ile Lys Glu Phe Val Ser Leu Phe Asn Leu Tyr Gly Glu Pro
    1235                1240                1245

Phe Ser Ile Tyr Gly Arg Phe Leu Leu Thr Ser Val Gly Asp Cys
    1250                1255                1260

Ala Tyr Ile Gly Pro Tyr Glu Asp Leu Ala Ser Arg Ile Ser Ser
    1265                1270                1275

Ala Gln Thr Ala Ile Lys His Gly Cys Pro Pro Ser Leu Ala Trp
    1280                1285                1290

Val Ser Ile Ala Ile Ser His Trp Met Thr Ser Leu Thr Tyr Asn
    1295                1300                1305

Met Leu Pro Gly Gln Ser Asn Asp Pro Ile Asp Tyr Phe Pro Ala
    1310                1315                1320

Glu Asn Arg Lys Asp Ile Pro Ile Glu Leu Asn Gly Val Leu Asp

-continued

```
            1325                1330                1335
Ala Pro Leu Ser Met Ile Ser Thr Val Gly Leu Glu Ser Gly Asn
            1340                1345                1350
Leu Tyr Phe Leu Ile Lys Leu Leu Ser Lys Tyr Thr Pro Val Met
            1355                1360                1365
Gln Lys Arg Glu Ser Val Val Asn Gln Ile Ala Glu Val Lys Asn
            1370                1375                1380
Trp Lys Val Glu Asp Leu Thr Asp Asn Glu Ile Phe Arg Leu Lys
            1385                1390                1395
Ile Leu Arg Tyr Leu Val Leu Asp Ala Glu Met Asp Pro Ser Asp
            1400                1405                1410
Ile Met Gly Glu Thr Ser Asp Met Arg Gly Arg Ser Ile Leu Thr
            1415                1420                1425
Pro Arg Lys Phe Thr Thr Ala Gly Ser Leu Arg Lys Leu Tyr Ser
            1430                1435                1440
Phe Ser Lys Tyr Gln Asp Arg Leu Ser Ser Pro Gly Gly Met Val
            1445                1450                1455
Glu Leu Phe Thr Tyr Leu Leu Glu Lys Pro Glu Leu Leu Val Thr
            1460                1465                1470
Lys Gly Glu Asp Met Lys Asp Tyr Met Glu Ser Val Ile Phe Arg
            1475                1480                1485
Tyr Asn Ser Lys Arg Phe Lys Glu Ser Leu Ser Ile Gln Asn Pro
            1490                1495                1500
Ala Gln Leu Phe Ile Glu Gln Ile Leu Phe Ser His Lys Pro Ile
            1505                1510                1515
Ile Asp Phe Ser Gly Ile Arg Asp Lys Tyr Ile Asn Leu His Asp
            1520                1525                1530
Ser Arg Ala Leu Glu Lys Glu Pro Asp Ile Leu Gly Lys Val Thr
            1535                1540                1545
Phe Thr Glu Ala Tyr Arg Leu Leu Met Arg Asp Leu Ser Ser Leu
            1550                1555                1560
Glu Leu Thr Asn Asp Asp Ile Gln Val Ile Tyr Ser Tyr Ile Ile
            1565                1570                1575
Leu Asn Asp Pro Met Met Ile Thr Ile Ala Asn Thr His Ile Leu
            1580                1585                1590
Ser Ile Tyr Gly Ser Pro Gln Arg Arg Met Gly Met Ser Cys Ser
            1595                1600                1605
Thr Met Pro Glu Phe Arg Asn Leu Lys Leu Ile His His Ser Pro
            1610                1615                1620
Ala Leu Val Leu Arg Ala Tyr Ser Lys Asn Asn Pro Asp Ile Gln
            1625                1630                1635
Gly Ala Asp Pro Thr Glu Met Ala Arg Asp Leu Val His Leu Lys
            1640                1645                1650
Glu Phe Val Glu Asn Thr Asn Leu Glu Glu Lys Met Lys Val Arg
            1655                1660                1665
Ile Ala Ile Asn Glu Ala Glu Lys Gly Gln Arg Asp Ile Val Phe
            1670                1675                1680
Glu Leu Lys Glu Met Thr Arg Phe Tyr Gln Val Cys Tyr Glu Tyr
            1685                1690                1695
Val Lys Ser Thr Glu His Lys Ile Lys Val Phe Ile Leu Pro Thr
            1700                1705                1710
Lys Ser Tyr Thr Thr Thr Asp Phe Cys Ser Leu Met Gln Gly Asn
            1715                1720                1725
```

```
Leu Ile Lys Asp Lys Glu Trp Tyr Thr Val His Tyr Leu Lys Gln
    1730            1735                1740

Ile Leu Ser Gly Gly His Lys Ala Ile Met Gln His Asn Ala Thr
    1745            1750                1755

Ser Glu Gln Asn Ile Ala Phe Glu Cys Phe Lys Leu Ile Thr His
    1760            1765                1770

Phe Ala Asp Ser Phe Ile Asp Ser Leu Ser Arg Ser Ala Phe Leu
    1775            1780                1785

Gln Leu Ile Ile Asp Glu Phe Ser Tyr Lys Asp Val Lys Val Ser
    1790            1795                1800

Lys Leu Tyr Asp Ile Ile Lys Asn Gly Tyr Asn Arg Thr Asp Phe
    1805            1810                1815

Ile Pro Leu Leu Phe Arg Thr Gly Asp Leu Arg Gln Ala Asp Leu
    1820            1825                1830

Asp Lys Tyr Asp Ala Met Lys Ser His Glu Arg Val Thr Trp Asn
    1835            1840                1845

Asp Trp Gln Thr Ser Arg His Leu Asp Met Gly Ser Ile Asn Leu
    1850            1855                1860

Thr Ile Thr Gly Tyr Asn Arg Ser Ile Thr Ile Gly Glu Asp
    1865            1870                1875

Asn Lys Leu Thr Tyr Ala Glu Leu Cys Leu Thr Arg Lys Thr Pro
    1880            1885                1890

Glu Asn Ile Thr Ile Ser Gly Arg Lys Leu Leu Gly Ala Arg His
    1895            1900                1905

Gly Leu Lys Phe Glu Asn Met Ser Lys Ile Gln Thr Tyr Pro Gly
    1910            1915                1920

Asn Tyr Tyr Ile Thr Tyr Arg Lys Lys Asp Arg His Gln Phe Val
    1925            1930                1935

Tyr Gln Ile His Ser His Glu Ser Ile Thr Arg Arg Asn Glu Glu
    1940            1945                1950

His Met Ala Ile Arg Thr Arg Ile Tyr Asn Glu Ile Thr Pro Val
    1955            1960                1965

Cys Val Val Asn Val Ala Glu Val Asp Gly Asp Gln Arg Ile Leu
    1970            1975                1980

Ile Arg Ser Leu Asp Tyr Leu Asn Asn Asp Ile Phe Ser Leu Ser
    1985            1990                1995

Arg Ile Lys Val Gly Leu Asp Glu Phe Ala Thr Ile Lys Lys Ala
    2000            2005                2010

His Phe Ser Lys Met Val Ser Phe Glu Gly Pro Pro Ile Lys Thr
    2015            2020                2025

Gly Leu Leu Asp Leu Thr Glu Leu Met Lys Ser Gln Asp Leu Leu
    2030            2035                2040

Asn Leu Asn Tyr Asp Asn Ile Arg Asn Ser Asn Leu Ile Ser Phe
    2045            2050                2055

Ser Lys Leu Ile Cys Cys Glu Gly Ser Asp Asn Ile Asn Asp Gly
    2060            2065                2070

Leu Glu Phe Leu Ser Asp Asp Pro Met Asn Phe Thr Glu Gly Glu
    2075            2080                2085

Ala Ile His Ser Thr Pro Ile Phe Asn Ile Tyr Tyr Ser Lys Arg
    2090            2095                2100

Gly Glu Arg His Met Thr Tyr Arg Asn Ala Ile Lys Leu Leu Ile
    2105            2110                2115
```

```
Glu Arg Glu Thr Lys Ile Phe Glu Glu Ala Phe Thr Phe Ser Glu
    2120                2125                2130

Asn Gly Phe Ile Ser Pro Glu Asn Leu Gly Cys Leu Glu Ala Val
    2135                2140                2145

Val Ser Leu Ile Lys Leu Leu Lys Thr Asn Glu Trp Ser Thr Val
    2150                2155                2160

Ile Asp Lys Cys Ile His Ile Cys Leu Ile Lys Asn Gly Met Asp
    2165                2170                2175

His Met Tyr His Ser Phe Asp Val Pro Lys Cys Phe Met Gly Asn
    2180                2185                2190

Pro Ile Thr Arg Asp Met Asn Trp Met Met Phe Arg Glu Phe Ile
    2195                2200                2205

Asn Ser Leu Pro Gly Thr Asp Ile Pro Pro Trp Asn Val Met Thr
    2210                2215                2220

Glu Asn Phe Lys Lys Lys Cys Ile Ala Leu Ile Asn Ser Lys Leu
    2225                2230                2235

Glu Thr Gln Arg Asp Phe Ser Glu Phe Thr Lys Leu Met Lys Lys
    2240                2245                2250

Glu Gly Gly Arg Ser Asn Ile Glu Phe Asp
    2255                2260
```

<210> SEQ ID NO 8
<211> LENGTH: 2263
<212> TYPE: PRT
<213> ORGANISM: La Crosse virus

<400> SEQUENCE: 8

```
Met Asp Tyr Gln Glu Tyr Gln Gln Phe Leu Ala Arg Ile Asn Thr Ala
1               5                   10                  15

Arg Asp Ala Cys Val Ala Lys Asp Ile Asp Val Asp Leu Leu Met Ala
            20                  25                  30

Arg His Asp Tyr Phe Gly Arg Glu Leu Cys Lys Ser Leu Asn Ile Glu
        35                  40                  45

Tyr Arg Asn Asp Val Pro Phe Val Asp Ile Ile Leu Asp Ile Arg Pro
    50                  55                  60

Glu Val Asp Pro Leu Thr Ile Asp Ala Pro His Ile Thr Pro Asp Asn
65                  70                  75                  80

Tyr Leu Tyr Ile Asn Asn Val Leu Tyr Ile Ile Asp Tyr Lys Val Ser
                85                  90                  95

Val Ser Asn Glu Ser Ser Val Ile Thr Tyr Asp Lys Tyr Tyr Glu Leu
            100                 105                 110

Thr Arg Asp Ile Ser Asp Arg Leu Ser Ile Pro Ile Glu Ile Val Ile
        115                 120                 125

Val Arg Ile Asp Pro Val Ser Lys Asp Leu His Ile Asn Ser Asp Arg
    130                 135                 140

Phe Lys Glu Leu Tyr Pro Thr Ile Val Val Asp Ile Asn Phe Asn Gln
145                 150                 155                 160

Phe Phe Asp Leu Lys Gln Leu Leu Tyr Glu Lys Phe Gly Asp Asp Glu
                165                 170                 175

Glu Phe Leu Leu Lys Val Ala His Gly Asp Phe Thr Leu Thr Ala Pro
            180                 185                 190

Trp Cys Lys Thr Gly Cys Pro Glu Phe Trp Lys His Pro Ile Tyr Lys
        195                 200                 205

Glu Phe Lys Met Ser Met Pro Val Pro Glu Arg Arg Leu Phe Glu Glu
    210                 215                 220
```

```
Ser Val Lys Phe Asn Ala Tyr Glu Ser Glu Arg Trp Asn Thr Asn Leu
225                 230                 235                 240

Val Lys Ile Arg Glu Tyr Thr Lys Lys Asp Tyr Ser Glu His Ile Ser
            245                 250                 255

Lys Ser Ala Lys Asn Ile Phe Leu Ala Ser Gly Phe Tyr Lys Gln Pro
                260                 265                 270

Asn Lys Asn Glu Ile Ser Glu Gly Trp Thr Leu Met Val Glu Arg Val
            275                 280                 285

Gln Asp Gln Arg Glu Ile Ser Lys Ser Leu His Asp Gln Lys Pro Ser
            290                 295                 300

Ile His Phe Ile Trp Gly Ala His Asn Pro Gly Asn Ser Asn Asn Ala
305                 310                 315                 320

Thr Phe Lys Leu Ile Leu Leu Ser Lys Ser Leu Gln Ser Ile Lys Gly
                325                 330                 335

Ile Ser Thr Tyr Thr Glu Ala Phe Lys Ser Leu Gly Lys Met Met Asp
                340                 345                 350

Ile Gly Asp Lys Ala Ile Glu Tyr Glu Glu Phe Cys Met Ser Leu Lys
            355                 360                 365

Ser Lys Ala Arg Ser Ser Trp Lys Gln Ile Met Asn Lys Lys Leu Glu
370                 375                 380

Pro Lys Gln Ile Asn Asn Ala Leu Val Leu Trp Glu Gln Gln Phe Met
385                 390                 395                 400

Val Asn Asn Asp Leu Ile Asp Lys Ser Glu Lys Leu Lys Leu Phe Lys
                405                 410                 415

Asn Phe Cys Gly Ile Gly Lys His Lys Gln Phe Lys Asn Lys Met Leu
            420                 425                 430

Glu Asp Leu Glu Val Ser Lys Pro Lys Ile Leu Asp Phe Asp Asp Ala
            435                 440                 445

Asn Met Tyr Leu Ala Ser Leu Thr Met Met Glu Gln Ser Lys Lys Ile
            450                 455                 460

Leu Ser Lys Ser Asn Gly Leu Lys Pro Asp Asn Phe Ile Leu Asn Glu
465                 470                 475                 480

Phe Gly Ser Lys Ile Lys Asp Ala Asn Lys Glu Thr Tyr Asp Asn Met
                485                 490                 495

His Lys Ile Phe Glu Thr Arg Tyr Trp Gln Cys Ile Ser Asp Phe Ser
                500                 505                 510

Thr Leu Met Lys Asn Ile Leu Ser Val Ser Gln Tyr Asn Arg His Asn
            515                 520                 525

Thr Phe Arg Ile Ala Met Cys Ala Asn Asn Val Phe Ala Ile Val
            530                 535                 540

Phe Pro Ser Ala Asp Ile Lys Thr Lys Lys Ala Thr Val Val Tyr Ser
545                 550                 555                 560

Ile Ile Val Leu His Lys Glu Glu Asn Ile Phe Asn Pro Gly Cys
                565                 570                 575

Leu His Gly Thr Phe Lys Cys Met Asn Gly Tyr Ile Ser Ile Ser Arg
                580                 585                 590

Ala Ile Arg Leu Asp Lys Glu Arg Cys Gln Arg Ile Val Ser Ser Pro
            595                 600                 605

Gly Leu Phe Leu Thr Thr Cys Leu Leu Phe Lys His Asp Asn Pro Thr
            610                 615                 620

Leu Val Met Ser Asp Ile Met Asn Phe Ser Ile Tyr Thr Ser Leu Ser
625                 630                 635                 640
```

```
Ile Thr Lys Ser Val Leu Ser Leu Thr Glu Pro Ala Arg Tyr Met Ile
            645                 650                 655

Met Asn Ser Leu Ala Ile Ser Ser Asn Val Lys Asp Tyr Ile Ala Glu
            660                 665                 670

Lys Phe Ser Pro Tyr Thr Lys Thr Leu Phe Ser Val Tyr Met Thr Arg
            675                 680                 685

Leu Ile Lys Asn Ala Cys Phe Asp Ala Tyr Asp Gln Arg Gln Arg Val
            690                 695                 700

Gln Leu Arg Asp Ile Tyr Leu Ser Asp Tyr Asp Ile Thr Gln Lys Gly
705                 710                 715                 720

Ile Lys Asp Asn Arg Glu Leu Thr Ser Ile Trp Phe Pro Gly Ser Val
            725                 730                 735

Thr Leu Lys Glu Tyr Leu Thr Gln Ile Tyr Leu Pro Phe Tyr Phe Asn
            740                 745                 750

Ala Lys Gly Leu His Glu Lys His Val Met Val Asp Leu Ala Lys
            755                 760                 765

Thr Ile Leu Glu Ile Glu Cys Glu Gln Arg Glu Asn Ile Lys Glu Ile
            770                 775                 780

Trp Ser Thr Asn Cys Thr Lys Gln Thr Val Asn Leu Lys Ile Leu Ile
785                 790                 795                 800

His Ser Leu Cys Lys Asn Leu Leu Ala Asp Thr Ser Arg His Asn His
            805                 810                 815

Leu Arg Asn Arg Ile Glu Asn Arg Asn Phe Arg Arg Ser Ile Thr
            820                 825                 830

Thr Ile Ser Thr Phe Thr Ser Ser Lys Ser Cys Leu Lys Ile Gly Asp
            835                 840                 845

Phe Arg Lys Glu Lys Glu Leu Gln Ser Val Lys Gln Lys Ile Leu
850                 855                 860

Glu Val Gln Ser Arg Lys Met Arg Leu Ala Asn Pro Met Phe Val Thr
865                 870                 875                 880

Asp Glu Gln Val Cys Leu Glu Val Gly His Cys Asn Tyr Glu Met Leu
            885                 890                 895

Arg Asn Ala Met Pro Asn Tyr Thr Asp Tyr Ile Ser Thr Lys Val Phe
            900                 905                 910

Asp Arg Leu Tyr Glu Leu Leu Asp Lys Gly Val Leu Thr Asp Lys Pro
            915                 920                 925

Val Ile Glu Gln Ile Met Asp Met Val Asp His Lys Lys Phe Tyr
930                 935                 940

Phe Thr Phe Phe Asn Lys Gly Gln Lys Thr Ser Lys Asp Arg Glu Ile
945                 950                 955                 960

Phe Val Gly Glu Tyr Glu Ala Lys Met Cys Met Tyr Ala Val Glu Arg
            965                 970                 975

Ile Ala Lys Glu Arg Cys Lys Leu Asn Pro Asp Glu Met Ile Ser Glu
            980                 985                 990

Pro Gly Asp Gly Lys Leu Lys Val Leu Glu Gln Lys Ser Glu Gln Glu
            995                 1000                1005

Ile Arg Phe Leu Val Glu Thr Arg Gln Lys Asn Arg Glu Ile
            1010                1015                1020

Asp Glu Ala Ile Glu Ala Leu Ala Ala Glu Gly Tyr Glu Ser Asn
            1025                1030                1035

Leu Glu Lys Ile Glu Lys Leu Ser Leu Gly Lys Ala Lys Gly Leu
            1040                1045                1050

Lys Met Glu Ile Asn Ala Asp Met Ser Lys Trp Ser Ala Gln Asp
```

```
                  1055                1060                1065
Val Phe Tyr Lys Tyr Phe Trp Leu Ile Ala Leu Asp Pro Ile Leu
    1070                1075                1080

Tyr Pro Gln Glu Lys Glu Arg Ile Leu Tyr Phe Met Cys Asn Tyr
    1085                1090                1095

Met Asp Lys Glu Leu Ile Leu Pro Asp Glu Leu Leu Phe Asn Leu
    1100                1105                1110

Leu Asp Gln Lys Val Ala Tyr Gln Asn Asp Ile Ile Ala Thr Met
    1115                1120                1125

Thr Asn Gln Leu Asn Ser Asn Thr Val Leu Ile Lys Arg Asn Trp
    1130                1135                1140

Leu Gln Gly Asn Phe Asn Tyr Thr Ser Ser Tyr Val His Ser Cys
    1145                1150                1155

Ala Met Ser Val Tyr Lys Glu Ile Leu Lys Glu Ala Ile Thr Leu
    1160                1165                1170

Leu Asp Gly Ser Ile Leu Val Asn Ser Leu Val His Ser Asp Asp
    1175                1180                1185

Asn Gln Thr Ser Ile Thr Ile Val Gln Asp Lys Met Glu Asn Asp
    1190                1195                1200

Lys Ile Ile Asp Phe Ala Met Lys Glu Phe Glu Arg Ala Cys Leu
    1205                1210                1215

Thr Phe Gly Cys Gln Ala Asn Met Lys Lys Thr Tyr Val Thr Asn
    1220                1225                1230

Cys Ile Lys Glu Phe Val Ser Leu Phe Asn Leu Tyr Gly Glu Pro
    1235                1240                1245

Phe Ser Ile Tyr Gly Arg Phe Leu Leu Thr Ser Val Gly Asp Cys
    1250                1255                1260

Ala Tyr Ile Gly Pro Tyr Glu Asp Leu Ala Ser Arg Ile Ser Ser
    1265                1270                1275

Ala Gln Thr Ala Ile Lys His Gly Cys Pro Pro Ser Leu Ala Trp
    1280                1285                1290

Val Ser Ile Ala Ile Ser His Trp Met Thr Ser Leu Thr Tyr Asn
    1295                1300                1305

Met Leu Pro Gly Gln Ser Asn Asp Pro Ile Asp Tyr Phe Pro Ala
    1310                1315                1320

Glu Asn Arg Lys Asp Ile Pro Ile Glu Leu Asn Gly Val Leu Asp
    1325                1330                1335

Ala Pro Leu Ser Met Ile Ser Thr Val Gly Leu Glu Ser Gly Asn
    1340                1345                1350

Leu Tyr Phe Leu Ile Lys Leu Leu Ser Lys Tyr Thr Pro Val Met
    1355                1360                1365

Gln Lys Arg Glu Ser Val Val Asn Gln Ile Ala Glu Val Lys Asn
    1370                1375                1380

Trp Lys Val Glu Asp Leu Thr Asp Asn Glu Ile Phe Arg Leu Lys
    1385                1390                1395

Ile Leu Arg Tyr Leu Val Leu Asp Ala Glu Met Asp Pro Ser Asp
    1400                1405                1410

Ile Met Gly Glu Thr Ser Asp Met Arg Gly Arg Ser Ile Leu Thr
    1415                1420                1425

Pro Arg Lys Phe Thr Thr Ala Gly Ser Leu Arg Lys Leu Tyr Ser
    1430                1435                1440

Phe Ser Lys Tyr Gln Asp Arg Leu Ser Ser Pro Gly Gly Met Val
    1445                1450                1455
```

```
Glu Leu Phe Thr Tyr Leu Leu Glu Lys Pro Glu Leu Leu Val Thr
    1460                1465                1470

Lys Gly Glu Asp Met Lys Asp Tyr Met Glu Ser Val Ile Phe Arg
    1475                1480                1485

Tyr Asn Ser Lys Arg Phe Lys Glu Ser Leu Ser Ile Gln Asn Pro
    1490                1495                1500

Ala Gln Leu Phe Ile Glu Gln Ile Leu Phe Ser His Lys Pro Ile
    1505                1510                1515

Ile Asp Phe Ser Gly Ile Arg Asp Lys Tyr Ile Asn Leu His Asp
    1520                1525                1530

Ser Arg Ala Leu Glu Lys Glu Pro Asp Ile Leu Gly Lys Val Thr
    1535                1540                1545

Phe Thr Glu Ala Tyr Arg Leu Leu Met Arg Asp Leu Ser Ser Leu
    1550                1555                1560

Glu Leu Thr Asn Asp Asp Ile Gln Val Ile Tyr Ser Tyr Ile Ile
    1565                1570                1575

Leu Asn Asp Pro Met Met Ile Thr Ile Ala Asn Thr His Ile Leu
    1580                1585                1590

Ser Ile Tyr Gly Ser Pro Gln Arg Arg Met Gly Met Ser Cys Ser
    1595                1600                1605

Thr Met Pro Glu Phe Arg Asn Leu Lys Leu Ile His His Ser Pro
    1610                1615                1620

Ala Leu Val Leu Arg Ala Tyr Ser Lys Asn Asn Pro Asp Ile Gln
    1625                1630                1635

Gly Ala Asp Pro Thr Glu Met Ala Arg Asp Leu Val His Leu Lys
    1640                1645                1650

Glu Phe Val Glu Asn Thr Asn Leu Glu Glu Lys Met Lys Val Arg
    1655                1660                1665

Ile Ala Ile Asn Glu Ala Glu Lys Gly Gln Arg Asp Ile Val Phe
    1670                1675                1680

Glu Leu Lys Glu Met Thr Arg Phe Tyr Gln Val Cys Tyr Glu Tyr
    1685                1690                1695

Val Lys Ser Thr Glu His Lys Ile Lys Val Phe Ile Leu Pro Thr
    1700                1705                1710

Lys Ser Tyr Thr Thr Thr Asp Phe Cys Ser Leu Met Gln Gly Asn
    1715                1720                1725

Leu Ile Lys Asp Lys Glu Trp Tyr Thr Val His Tyr Leu Lys Gln
    1730                1735                1740

Ile Leu Ser Gly Gly His Lys Ala Ile Met Gln His Asn Ala Thr
    1745                1750                1755

Ser Glu Gln Asn Ile Ala Phe Glu Cys Phe Lys Leu Ile Thr His
    1760                1765                1770

Phe Ala Asp Ser Phe Ile Asp Ser Leu Ser Arg Ser Ala Phe Leu
    1775                1780                1785

Gln Leu Ile Ile Asp Glu Phe Ser Tyr Lys Asp Val Lys Val Ser
    1790                1795                1800

Lys Leu Tyr Asp Ile Ile Lys Asn Gly Tyr Asn Arg Thr Asp Phe
    1805                1810                1815

Ile Pro Leu Leu Phe Arg Thr Gly Asp Leu Arg Gln Ala Asp Leu
    1820                1825                1830

Asp Lys Tyr Asp Ala Met Lys Ser His Glu Arg Val Thr Trp Asn
    1835                1840                1845
```

```
Asp Trp Gln Thr Ser Arg His Leu Asp Met Gly Ser Ile Asn Leu
    1850                1855                1860

Thr Ile Thr Gly Tyr Asn Arg Ser Ile Thr Ile Ile Gly Glu Asp
    1865                1870                1875

Asn Lys Leu Thr Tyr Ala Glu Leu Cys Leu Thr Arg Lys Thr Pro
    1880                1885                1890

Glu Asn Ile Thr Ile Ser Gly Arg Lys Leu Leu Gly Ala Arg His
    1895                1900                1905

Gly Leu Lys Phe Glu Asn Met Ser Lys Ile Gln Thr Tyr Pro Gly
    1910                1915                1920

Asn Tyr Tyr Ile Thr Tyr Arg Lys Lys Asp Arg His Gln Phe Val
    1925                1930                1935

Tyr Gln Ile His Ser His Glu Ser Ile Thr Arg Arg Asn Glu Glu
    1940                1945                1950

His Met Ala Ile Arg Thr Arg Ile Tyr Asn Glu Ile Thr Pro Val
    1955                1960                1965

Cys Val Val Asn Val Ala Glu Val Asp Gly Asp Gln Arg Ile Leu
    1970                1975                1980

Ile Arg Ser Leu Asp Tyr Leu Asn Asn Asp Ile Phe Ser Leu Ser
    1985                1990                1995

Arg Ile Lys Val Gly Leu Asp Glu Phe Ala Thr Ile Lys Lys Ala
    2000                2005                2010

His Phe Ser Lys Met Val Ser Phe Glu Gly Pro Pro Ile Lys Thr
    2015                2020                2025

Gly Leu Leu Asp Leu Thr Glu Leu Met Lys Ser Gln Asp Leu Leu
    2030                2035                2040

Asn Leu Asn Tyr Asp Asn Ile Arg Asn Ser Asn Leu Ile Ser Phe
    2045                2050                2055

Ser Lys Leu Ile Cys Cys Glu Gly Ser Asp Asn Ile Asn Asp Gly
    2060                2065                2070

Leu Glu Phe Leu Ser Asp Asp Pro Met Asn Phe Thr Glu Gly Glu
    2075                2080                2085

Ala Ile His Ser Thr Pro Ile Phe Asn Ile Tyr Tyr Ser Lys Arg
    2090                2095                2100

Gly Glu Arg His Met Thr Tyr Arg Asn Ala Ile Lys Leu Leu Ile
    2105                2110                2115

Glu Arg Glu Thr Lys Ile Phe Glu Glu Ala Phe Thr Phe Ser Glu
    2120                2125                2130

Asn Gly Phe Ile Ser Pro Glu Asn Leu Gly Cys Leu Glu Ala Val
    2135                2140                2145

Val Ser Leu Ile Lys Leu Leu Lys Thr Asn Glu Trp Ser Thr Val
    2150                2155                2160

Ile Asp Lys Cys Ile His Ile Cys Leu Ile Lys Asn Gly Met Asp
    2165                2170                2175

His Met Tyr His Ser Phe Asp Val Pro Lys Cys Phe Met Gly Asn
    2180                2185                2190

Pro Ile Thr Arg Asp Met Asn Trp Met Met Phe Arg Glu Phe Ile
    2195                2200                2205

Asn Ser Leu Pro Gly Thr Asp Ile Pro Pro Trp Asn Val Met Thr
    2210                2215                2220

Glu Asn Phe Lys Lys Lys Cys Ile Ala Leu Ile Asn Ser Lys Leu
    2225                2230                2235

Glu Thr Gln Arg Asp Phe Ser Glu Phe Thr Lys Leu Met Lys Lys
```

-continued

```
                    2240                2245                2250
        Glu Gly Gly Arg Ser Asn Ile Glu Phe Asp
            2255                2260

<210> SEQ ID NO 9
<211> LENGTH: 1441
<212> TYPE: PRT
<213> ORGANISM: La Crosse virus

<400> SEQUENCE: 9

Met Ile Cys Ile Leu Val Leu Ile Thr Val Ala Ala Ser Pro Val
1               5                   10                  15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
        35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
    130                 135                 140

Lys Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
            180                 185                 190

Ile Ala Asn Ser Ile Cys Gln Asn Ile Glu Ile Ile Leu Val Thr
        195                 200                 205

Leu Thr Leu Leu Ile Phe Ile Leu Leu Ser Ile Leu Ser Lys Thr Tyr
    210                 215                 220

Ile Cys Tyr Leu Leu Met Pro Ile Phe Ile Pro Ile Ala Tyr Ile Tyr
225                 230                 235                 240

Gly Ile Ile Tyr Asn Lys Ser Cys Lys Lys Cys Lys Leu Cys Gly Leu
                245                 250                 255

Val Tyr His Pro Phe Thr Glu Cys Gly Thr His Cys Val Cys Gly Ala
            260                 265                 270

Arg Tyr Asp Thr Ser Asp Arg Met Lys Leu His Arg Ala Ser Gly Leu
        275                 280                 285

Cys Pro Gly Tyr Lys Ser Leu Arg Ala Ala Arg Val Met Cys Lys Ser
    290                 295                 300

Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                325                 330                 335

Thr Phe Glu Leu Glu Asp Leu Pro Asp Asp Met Leu Glu Met Ala Ser
            340                 345                 350
```

Arg Ile Asn Ser Tyr Tyr Leu Thr Cys Ile Leu Asn Tyr Ala Val Ser
            355                 360                 365

Trp Gly Leu Val Ile Ile Gly Leu Leu Ile Gly Leu Leu Phe Lys Lys
    370                 375                 380

Tyr Gln His Arg Phe Leu Asn Val Tyr Ala Met Tyr Cys Glu Glu Cys
385                 390                 395                 400

Asp Met Tyr His Asp Lys Ser Gly Leu Lys Arg His Gly Asp Phe Thr
                405                 410                 415

Asn Lys Cys Arg Gln Cys Thr Cys Gly Gln Tyr Glu Asp Ala Ala Gly
            420                 425                 430

Leu Met Ala His Arg Lys Thr Tyr Asn Cys Leu Val Gln Tyr Lys Ala
        435                 440                 445

Lys Trp Met Met Asn Phe Leu Ile Ile Tyr Ile Phe Leu Ile Leu Ile
    450                 455                 460

Lys Asp Ser Ala Ile Val Val Gln Ala Ala Gly Thr Asp Phe Thr Thr
465                 470                 475                 480

Cys Leu Glu Thr Glu Ser Ile Asn Trp Asn Cys Thr Gly Pro Phe Leu
                485                 490                 495

Asn Leu Gly Asn Cys Gln Lys Gln Gln Lys Lys Glu Pro Tyr Thr Asn
            500                 505                 510

Ile Ala Thr Gln Leu Lys Gly Leu Lys Ala Ile Ser Val Leu Asp Val
        515                 520                 525

Pro Ile Ile Thr Gly Ile Pro Asp Asp Ile Ala Gly Ala Leu Arg Tyr
    530                 535                 540

Ile Glu Glu Lys Glu Asp Phe His Val Gln Leu Thr Ile Glu Tyr Ala
545                 550                 555                 560

Met Leu Ser Lys Tyr Cys Asp Tyr Tyr Thr Gln Phe Ser Asp Asn Ser
                565                 570                 575

Gly Tyr Ser Gln Thr Thr Trp Arg Val Tyr Leu Arg Ser His Asp Phe
            580                 585                 590

Glu Ala Cys Ile Leu Tyr Pro Asn Gln His Phe Cys Arg Cys Val Lys
        595                 600                 605

Asn Gly Glu Lys Cys Ser Ser Ser Asn Trp Asp Phe Ala Asn Glu Met
610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
                645                 650                 655

Tyr Ile Ala Thr Met Leu Ser Lys Lys Ser Asn Asp Asp Leu Ile Ala
            660                 665                 670

Tyr Thr Asn Lys Ile Lys Thr Lys Phe Pro Gly Asn Ala Leu Leu Lys
        675                 680                 685

Ala Ile Ile Asp Tyr Ile Ala Tyr Met Lys Ser Leu Pro Gly Met Ala
    690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
                725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
        755                 760                 765

Ile Ile Ala Cys Gly Glu Pro Asn Gly Pro Ser Val Tyr Arg Lys Pro

```
              770               775               780
Ser Gly Gly Val Phe Gln Ser Ser Thr Asp Arg Ser Ile Tyr Cys Leu
785               790               795               800

Leu Asp Ser His Cys Leu Glu Glu Phe Glu Ala Ile Gly Gln Glu Glu
              805               810               815

Leu Asp Ala Val Lys Lys Ser Lys Cys Trp Glu Ile Glu Tyr Pro Asp
              820               825               830

Val Lys Leu Ile Gln Glu Gly Asp Gly Thr Lys Ser Cys Arg Met Lys
              835               840               845

Asp Ser Gly Asn Cys Asn Val Ala Thr Asn Arg Trp Pro Val Ile Gln
850               855               860

Cys Glu Asn Asp Lys Phe Tyr Tyr Ser Glu Leu Gln Lys Asp Tyr Asp
865               870               875               880

Lys Ala Gln Asp Ile Gly His Tyr Cys Leu Ser Pro Gly Cys Thr Thr
              885               890               895

Val Arg Tyr Pro Ile Asn Pro Lys His Ile Ser Asn Cys Asn Trp Gln
              900               905               910

Val Ser Arg Ser Ser Ile Ala Lys Ile Asp Val His Asn Ile Glu Asp
              915               920               925

Ile Glu Gln Tyr Lys Lys Ala Ile Thr Gln Lys Leu Gln Thr Ser Leu
              930               935               940

Ser Leu Phe Lys Tyr Ala Lys Thr Lys Asn Leu Pro His Ile Lys Pro
945               950               955               960

Ile Tyr Lys Tyr Ile Thr Ile Glu Gly Thr Glu Thr Ala Glu Gly Ile
              965               970               975

Glu Ser Ala Tyr Ile Glu Ser Glu Val Pro Ala Leu Ala Gly Thr Ser
              980               985               990

Ile Gly Phe Lys Ile Asn Ser Lys Glu Gly Lys His Leu Leu Asp Val
              995              1000              1005

Ile Ala Tyr Val Lys Ser Ala Ser Tyr Ser Ser Val Tyr Thr Lys
             1010             1015              1020

Leu Tyr Ser Thr Gly Pro Thr Ser Gly Ile Asn Thr Lys His Asp
             1025             1030              1035

Glu Leu Cys Thr Gly Pro Cys Pro Ala Asn Ile Asn His Gln Val
             1040             1045              1050

Gly Trp Leu Thr Phe Ala Arg Glu Arg Thr Ser Ser Trp Gly Cys
             1055             1060              1065

Glu Glu Phe Gly Cys Leu Ala Val Ser Asp Gly Cys Val Phe Gly
             1070             1075              1080

Ser Cys Gln Asp Ile Ile Lys Glu Glu Leu Ser Val Tyr Arg Lys
             1085             1090              1095

Glu Thr Glu Glu Val Thr Asp Val Glu Leu Cys Leu Thr Phe Ser
             1100             1105              1110

Asp Lys Thr Tyr Cys Thr Asn Leu Asn Pro Val Thr Pro Ile Ile
             1115             1120              1125

Thr Asp Leu Phe Glu Val Gln Phe Lys Thr Val Glu Thr Tyr Ser
             1130             1135              1140

Leu Pro Arg Ile Val Ala Val Gln Asn His Glu Ile Lys Ile Gly
             1145             1150              1155

Gln Ile Asn Asp Leu Gly Val Tyr Ser Lys Gly Cys Gly Asn Val
             1160             1165              1170

Gln Lys Val Asn Gly Thr Ile Tyr Gly Asn Gly Val Pro Arg Phe
             1175             1180              1185
```

-continued

Asp Tyr Leu Cys His Leu Ala Ser Arg Lys Glu Val Ile Val Arg
            1190                1195                1200

Lys Cys Phe Asp Asn Asp Tyr Gln Ala Cys Lys Phe Leu Gln Ser
    1205                1210                1215

Pro Ala Ser Tyr Arg Leu Glu Glu Asp Ser Gly Thr Val Thr Ile
    1220                1225                1230

Ile Asp Tyr Lys Lys Ile Leu Gly Thr Ile Lys Met Lys Ala Ile
    1235                1240                1245

Leu Gly Asp Val Lys Tyr Lys Thr Phe Ala Asp Ser Val Asp Ile
    1250                1255                1260

Thr Ala Glu Gly Ser Cys Thr Gly Cys Ile Asn Cys Phe Glu Asn
    1265                1270                1275

Ile His Cys Glu Leu Thr Leu His Thr Thr Ile Glu Ala Ser Cys
    1280                1285                1290

Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Val
    1325                1330                1335

Glu Ala Ser Met Ala Leu Val Asp Ala Lys Pro Ile Ile Glu Leu
    1340                1345                1350

Ala Pro Val Asp Gln Thr Ala Tyr Ile Arg Glu Lys Asp Glu Arg
    1355                1360                1365

Cys Lys Thr Trp Met Cys Arg Val Arg Asp Glu Gly Leu Gln Val
    1370                1375                1380

Ile Leu Glu Pro Phe Lys Asn Leu Phe Gly Ser Tyr Ile Gly Ile
    1385                1390                1395

Phe Tyr Thr Phe Ile Ile Ser Ile Val Val Leu Val Ile Ile
    1400                1405                1410

Tyr Val Leu Leu Pro Ile Cys Phe Lys Leu Arg Asp Thr Leu Arg
    1415                1420                1425

Lys His Glu Asp Ala Tyr Lys Arg Glu Met Lys Ile Arg
    1430                1435                1440

<210> SEQ ID NO 10
<211> LENGTH: 1441
<212> TYPE: PRT
<213> ORGANISM: La Crosse virus

<400> SEQUENCE: 10

Met Ile Cys Ile Leu Val Leu Ile Thr Val Ala Ala Ala Ser Pro Val
1               5                   10                  15

Tyr Gln Arg Cys Phe Gln Asp Gly Ala Ile Val Lys Gln Asn Pro Ser
                20                  25                  30

Lys Glu Ala Val Thr Glu Val Cys Leu Lys Asp Asp Val Ser Met Ile
            35                  40                  45

Lys Thr Glu Ala Arg Tyr Val Arg Asn Ala Thr Gly Val Phe Ser Asn
        50                  55                  60

Asn Val Ala Ile Arg Lys Trp Leu Val Ser Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr

-continued

```
                100                 105                 110
Ile Gly Val Asp Lys Glu Thr Ala Gln Val Arg Leu Gln Thr Asp Thr
            115                 120                 125
Thr Asn His Phe Glu Ile Ala Gly Thr Thr Val Lys Ser Gly Trp Phe
        130                 135                 140
Lys Ser Thr Thr Tyr Ile Thr Leu Asp Gln Thr Cys Glu His Leu Lys
145                 150                 155                 160
Val Ser Cys Gly Pro Lys Ser Val Gln Phe His Ala Cys Phe Asn Gln
                165                 170                 175
His Met Ser Cys Val Arg Phe Leu His Arg Thr Ile Leu Pro Gly Ser
            180                 185                 190
Ile Ala Asn Ser Ile Cys Gln Asn Ile Glu Ile Ile Leu Val Thr
        195                 200                 205
Leu Thr Leu Leu Ile Phe Ile Leu Leu Ser Ile Leu Ser Lys Thr Tyr
    210                 215                 220
Ile Cys Tyr Leu Leu Met Pro Ile Phe Ile Pro Ile Ala Tyr Ile Tyr
225                 230                 235                 240
Gly Ile Ile Tyr Asn Lys Ser Cys Lys Lys Cys Lys Leu Cys Gly Leu
                245                 250                 255
Val Tyr His Pro Phe Thr Glu Cys Gly Thr His Cys Val Cys Gly Ala
            260                 265                 270
Arg Tyr Asp Thr Ser Asp Arg Met Lys Leu His Arg Ala Ser Gly Leu
        275                 280                 285
Cys Pro Gly Tyr Lys Ser Leu Arg Ala Ala Arg Val Met Cys Lys Ser
    290                 295                 300
Lys Gly Pro Ala Ser Ile Leu Ser Ile Ile Thr Ala Val Leu Val Leu
305                 310                 315                 320
Thr Phe Val Thr Pro Ile Asn Ser Met Val Leu Gly Glu Ser Lys Glu
                325                 330                 335
Thr Phe Glu Leu Glu Asp Leu Pro Asp Asp Met Leu Glu Met Ala Ser
            340                 345                 350
Arg Ile Asn Ser Tyr Tyr Leu Thr Cys Ile Leu Asn Tyr Ala Val Ser
        355                 360                 365
Trp Gly Leu Val Ile Ile Gly Leu Leu Ile Gly Leu Leu Phe Lys Lys
    370                 375                 380
Tyr Gln His Arg Phe Leu Asn Val Tyr Ala Met Tyr Cys Glu Glu Cys
385                 390                 395                 400
Asp Met Tyr His Asp Lys Ser Gly Leu Lys Arg His Gly Asp Phe Thr
                405                 410                 415
Asn Lys Cys Arg Gln Cys Thr Cys Gly Gln Tyr Glu Asp Ala Ala Gly
            420                 425                 430
Leu Met Ala His Arg Lys Thr Tyr Asn Cys Leu Val Gln Tyr Lys Ala
        435                 440                 445
Lys Trp Met Met Asn Phe Leu Ile Ile Tyr Ile Phe Leu Ile Leu Ile
    450                 455                 460
Lys Asp Ser Ala Ile Val Val Gln Ala Ala Gly Thr Asp Phe Thr Thr
465                 470                 475                 480
Cys Leu Glu Thr Glu Ser Ile Asn Trp Asn Cys Thr Gly Pro Phe Leu
                485                 490                 495
Asn Leu Gly Asn Cys Gln Lys Gln Gln Lys Lys Glu Pro Tyr Thr Asn
            500                 505                 510
Ile Ala Thr Gln Leu Lys Gly Leu Lys Ala Ile Ser Val Leu Asp Val
        515                 520                 525
```

```
Pro Ile Ile Thr Gly Ile Pro Asp Asp Ile Ala Gly Ala Leu Arg Tyr
    530                 535                 540

Ile Glu Glu Lys Glu Asp Phe His Val Gln Leu Thr Ile Glu Tyr Ala
545                 550                 555                 560

Met Leu Ser Lys Tyr Cys Asp Tyr Tyr Thr Gln Phe Ser Asp Asn Ser
                565                 570                 575

Gly Tyr Ser Gln Thr Thr Trp Arg Val Tyr Leu Arg Ser His Asp Phe
                580                 585                 590

Glu Ala Cys Ile Leu Tyr Pro Asn Gln His Phe Cys Arg Cys Val Lys
            595                 600                 605

Asn Gly Glu Lys Cys Ser Ser Asn Trp Asp Phe Ala Asn Glu Met
610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
            645                 650                 655

Tyr Ile Ala Thr Met Leu Ser Lys Lys Ser Asn Asp Asp Leu Ile Ala
                660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
                725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
                755                 760                 765

Ile Ile Ala Cys Gly Glu Pro Asn Gly Pro Ser Val Tyr Arg Lys Pro
770                 775                 780

Ser Gly Gly Val Phe Gln Ser Thr Asp Arg Ser Ile Tyr Cys Leu
785                 790                 795                 800

Leu Asp Ser His Cys Leu Glu Glu Phe Glu Ala Ile Gly Gln Glu Glu
                805                 810                 815

Leu Asp Ala Val Lys Lys Ser Lys Cys Trp Glu Ile Glu Tyr Pro Asp
            820                 825                 830

Val Lys Leu Ile Gln Glu Gly Asp Gly Thr Lys Ser Cys Arg Met Lys
                835                 840                 845

Asp Ser Gly Asn Cys Asn Val Ala Thr Asn Arg Trp Pro Val Ile Gln
850                 855                 860

Cys Glu Asn Asp Lys Phe Tyr Tyr Ser Glu Leu Gln Lys Asp Tyr Asp
865                 870                 875                 880

Lys Ala Gln Asp Ile Gly His Tyr Cys Leu Ser Pro Gly Cys Thr Thr
                885                 890                 895

Val Arg Tyr Pro Ile Asn Pro Lys His Ile Ser Asn Cys Asn Trp Gln
                900                 905                 910

Val Ser Arg Ser Ser Ile Ala Lys Ile Asp Val His Asn Ile Glu Asp
            915                 920                 925

Ile Glu Gln Tyr Lys Lys Ala Ile Thr Gln Lys Leu Gln Thr Ser Leu
930                 935                 940
```

-continued

```
Ser Leu Phe Lys Tyr Ala Lys Thr Lys Asn Leu Pro His Ile Lys Pro
945                 950                 955                 960

Ile Tyr Lys Tyr Ile Thr Ile Glu Gly Thr Glu Thr Ala Glu Gly Ile
            965                 970                 975

Glu Ser Ala Tyr Ile Glu Ser Glu Val Pro Ala Leu Ala Gly Thr Ser
        980                 985                 990

Ile Gly Phe Lys Ile Asn Ser Lys Glu Gly Lys His Leu Leu Asp Val
    995                 1000                1005

Ile Ala Tyr Val Lys Ser Ala Ser Tyr Ser Ser Val Tyr Thr Lys
    1010                1015                1020

Leu Tyr Ser Thr Gly Pro Thr Ser Gly Ile Asn Thr Lys His Asp
    1025                1030                1035

Glu Leu Cys Thr Gly Pro Cys Pro Ala Asn Ile Asn His Gln Val
    1040                1045                1050

Gly Trp Leu Thr Phe Ala Arg Glu Arg Thr Ser Ser Trp Gly Cys
    1055                1060                1065

Glu Glu Phe Gly Cys Leu Ala Val Ser Asp Gly Cys Val Phe Gly
    1070                1075                1080

Ser Cys Gln Asp Ile Ile Lys Glu Glu Leu Ser Val Tyr Arg Lys
    1085                1090                1095

Glu Thr Glu Glu Val Thr Asp Val Glu Leu Cys Leu Thr Phe Ser
    1100                1105                1110

Asp Lys Thr Tyr Cys Thr Asn Leu Asn Pro Val Thr Pro Ile Ile
    1115                1120                1125

Thr Asp Leu Phe Glu Val Gln Phe Lys Thr Val Glu Thr Tyr Ser
    1130                1135                1140

Leu Pro Arg Ile Val Ala Val Gln Asn His Glu Ile Lys Ile Gly
    1145                1150                1155

Gln Ile Asn Asp Leu Gly Val Tyr Ser Lys Gly Cys Gly Asn Val
    1160                1165                1170

Gln Lys Val Asn Gly Thr Ile Tyr Gly Asn Gly Val Pro Arg Phe
    1175                1180                1185

Asp Tyr Leu Cys His Leu Ala Ser Arg Lys Glu Val Ile Val Arg
    1190                1195                1200

Lys Cys Phe Asp Asn Asp Tyr Gln Ala Cys Lys Phe Leu Gln Ser
    1205                1210                1215

Pro Ala Ser Tyr Arg Leu Glu Glu Asp Ser Gly Thr Val Thr Ile
    1220                1225                1230

Ile Asp Tyr Lys Lys Ile Leu Gly Thr Ile Lys Met Lys Ala Ile
    1235                1240                1245

Leu Gly Asp Val Lys Tyr Lys Thr Phe Ala Asp Ser Val Asp Ile
    1250                1255                1260

Thr Ala Glu Gly Ser Cys Thr Gly Cys Ile Asn Cys Phe Glu Asn
    1265                1270                1275

Ile His Cys Glu Leu Thr Leu His Thr Thr Ile Glu Ala Ser Cys
    1280                1285                1290

Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Val
    1325                1330                1335

Glu Ala Ser Met Ala Leu Val Asp Ala Lys Pro Ile Ile Glu Leu
```

```
              1340                1345                1350
Ala Pro Val Asp Gln Thr Ala Tyr Ile Arg Glu Lys Asp Glu Arg
          1355                1360                1365
Cys Lys Thr Trp Met Cys Arg Val Arg Asp Glu Gly Leu Gln Val
          1370                1375                1380
Ile Leu Glu Pro Phe Lys Asn Leu Phe Gly Ser Tyr Ile Gly Ile
          1385                1390                1395
Phe Tyr Thr Phe Ile Ile Ser Ile Val Val Leu Val Ile Ile
          1400                1405                1410
Tyr Val Leu Leu Pro Ile Cys Phe Lys Leu Arg Asp Thr Leu Arg
          1415                1420                1425
Lys His Glu Asp Ala Tyr Lys Arg Glu Met Lys Ile Arg
          1430                1435                1440
```

<210> SEQ ID NO 11
<211> LENGTH: 235
<212> TYPE: PRT
<213> ORGANISM: La Crosse virus

<400> SEQUENCE: 11

```
Met Ser Asp Leu Val Phe Tyr Asp Val Ala Ser Thr Gly Ala Asn Gly
1               5                   10                  15
Phe Asp Pro Asp Ala Gly Tyr Met Asp Phe Cys Val Lys Asn Ala Glu
                20                  25                  30
Leu Leu Asn Leu Ala Ala Val Arg Ile Phe Phe Leu Asn Ala Ala Lys
            35                  40                  45
Ala Lys Ala Ala Leu Ser Arg Lys Pro Glu Arg Lys Ala Asn Pro Lys
        50                  55                  60
Phe Gly Glu Trp Gln Val Glu Val Ile Asn Asn His Phe Pro Gly Asn
65                  70                  75                  80
Arg Asn Asn Pro Ile Gly Asn Asn Asp Leu Thr Ile His Arg Leu Ser
                85                  90                  95
Gly Tyr Leu Ala Arg Trp Val Leu Asp Gln Tyr Asn Glu Asn Asp Asp
            100                 105                 110
Glu Ser Gln His Glu Leu Ile Arg Thr Thr Ile Ile Asn Pro Ile Ala
        115                 120                 125
Glu Ser Asn Gly Val Gly Trp Asp Ser Gly Pro Glu Ile Tyr Leu Ser
    130                 135                 140
Phe Phe Pro Gly Thr Glu Met Phe Leu Glu Thr Phe Lys Phe Tyr Pro
145                 150                 155                 160
Leu Thr Ile Gly Ile His Arg Val Lys Gln Gly Met Met Asp Pro Gln
                165                 170                 175
Tyr Leu Lys Lys Ala Leu Arg Gln Arg Tyr Gly Thr Leu Thr Ala Asp
            180                 185                 190
Lys Trp Met Ser Gln Lys Val Ala Ala Ile Ala Lys Ser Leu Lys Asp
        195                 200                 205
Val Glu Gln Leu Lys Trp Gly Lys Gly Leu Ser Asp Thr Ala Lys
    210                 215                 220
Thr Phe Leu Gln Lys Phe Gly Ile Arg Leu Pro
225                 230                 235
```

<210> SEQ ID NO 12
<211> LENGTH: 235
<212> TYPE: PRT
<213> ORGANISM: La Crosse virus -continued

```
<400> SEQUENCE: 12

Met Ser Asp Leu Val Phe Tyr Asp Val Ala Ser Thr Gly Ala Asn Gly
1               5                   10                  15

Phe Asp Pro Asp Ala Gly Tyr Met Asp Phe Cys Val Lys Asn Ala Glu
            20                  25                  30

Leu Leu Asn Leu Ala Ala Val Arg Ile Phe Phe Leu Asn Ala Ala Lys
        35                  40                  45

Ala Lys Ala Ala Leu Ser Arg Lys Pro Glu Arg Lys Ala Asn Pro Lys
50                  55                  60

Phe Gly Glu Trp Gln Val Glu Val Ile Asn Asn His Phe Pro Gly Asn
65                  70                  75                  80

Arg Asn Asn Pro Ile Gly Asn Asn Asp Leu Thr Ile His Arg Leu Ser
                85                  90                  95

Gly Tyr Leu Ala Arg Trp Val Leu Asp Gln Tyr Asn Glu Asn Asp Asp
            100                 105                 110

Glu Ser Gln His Glu Leu Ile Arg Thr Thr Ile Ile Asn Pro Ile Ala
        115                 120                 125

Glu Ser Asn Gly Val Gly Trp Asp Ser Gly Pro Glu Ile Tyr Leu Ser
130                 135                 140

Phe Phe Pro Gly Thr Glu Met Phe Leu Glu Thr Phe Lys Phe Tyr Pro
145                 150                 155                 160

Leu Thr Ile Gly Ile His Arg Val Lys Gln Gly Met Met Asp Pro Gln
                165                 170                 175

Tyr Leu Lys Lys Ala Leu Arg Gln Arg Tyr Gly Thr Leu Thr Ala Asp
            180                 185                 190

Lys Trp Met Ser Gln Lys Val Ala Ala Ile Ala Lys Ser Leu Lys Asp
        195                 200                 205

Val Glu Gln Leu Lys Trp Gly Lys Gly Leu Ser Asp Thr Ala Lys
210                 215                 220

Thr Phe Leu Gln Lys Phe Gly Ile Arg Leu Pro
225                 230                 235

<210> SEQ ID NO 13
<211> LENGTH: 92
<212> TYPE: PRT
<213> ORGANISM: La Crosse virus

<400> SEQUENCE: 13

Met Met Ser His Gln Gln Val Gln Met Asp Leu Ile Leu Met Gln Gly
1               5                   10                  15

Ile Trp Thr Ser Val Leu Lys Met Gln Asn Tyr Ser Thr Leu Leu Gln
            20                  25                  30

Leu Gly Ser Ser Ser Met Pro Gln Arg Pro Arg Leu Leu Ser Arg
        35                  40                  45

Val Ser Gln Arg Gly Arg Leu Thr Leu Asn Leu Glu Ser Gly Arg Trp
50                  55                  60

Arg Leu Ser Ile Ile Ile Phe Leu Glu Thr Gly Thr Thr Gln Leu Val
65                  70                  75                  80

Thr Thr Ile Leu Pro Ser Thr Asp Tyr Leu Gly Ile
                85                  90

<210> SEQ ID NO 14
<211> LENGTH: 92
<212> TYPE: PRT
<213> ORGANISM: La Crosse virus
```

<400> SEQUENCE: 14

Met Met Ser His Gln Val Gln Met Asp Leu Ile Leu Met Gln Gly
1               5                   10                  15

Ile Trp Thr Ser Val Leu Lys Met Gln Asn Tyr Ser Thr Leu Leu Gln
            20                  25                  30

Leu Gly Ser Ser Ser Met Pro Gln Arg Pro Arg Leu Leu Ser Arg
                35                  40                  45

Val Ser Gln Arg Gly Arg Leu Thr Leu Asn Leu Glu Ser Gly Arg Trp
    50                  55                  60

Arg Leu Ser Ile Ile Ile Phe Leu Glu Thr Gly Thr Thr Gln Leu Val
65                  70                  75                  80

Thr Thr Ile Leu Pro Ser Thr Asp Tyr Leu Gly Ile
                85                  90

<210> SEQ ID NO 15
<211> LENGTH: 81
<212> TYPE: DNA
<213> ORGANISM: Artificial Sequence
<220> FEATURE:
<223> OTHER INFORMATION: Synthetic consensus sequence

<400> SEQUENCE: 15
agtagtgtac tccacttgaa tactttgaaa ataaattgtt gttgactgtt ttttacctaa   60
ggggaaatta tcaagagtgt g                                             81

<210> SEQ ID NO 16
<211> LENGTH: 61
<212> TYPE: DNA
<213> ORGANISM: Artificial Sequence
<220> FEATURE:
<223> OTHER INFORMATION: Synthetic consensus sequence

<400> SEQUENCE: 16
agtagtgtac taccaagtat agataacgtt tgaatattaa gttttgaat caaagccaaa   60 g                                                                   61

<210> SEQ ID NO 17
<211> LENGTH: 61
<212> TYPE: DNA
<213> ORGANISM: Artificial Sequence
<220> FEATURE:
<223> OTHER INFORMATION: Synthetic consensus sequence

<400> SEQUENCE: 17
agtagtgtac tcctatctac aaaacttaca raaaattcag tcatatcaca atatatgcat   60
a                                                                   61

<210> SEQ ID NO 18
<211> LENGTH: 100
<212> TYPE: DNA
<213> ORGANISM: Artificial Sequence
<220> FEATURE:
<223> OTHER INFORMATION: Synthetic consensus sequence

<400> SEQUENCE: 18
taaatatggc atgaggcatt caaattaggt tctaaattct aaatttatat atgtcaattt   60
gattaattgg ttatccaaaa gggttttctt aagggaaccc                        100

<210> SEQ ID NO 19
<211> LENGTH: 98

-continued

```
<212> TYPE: DNA
<213> ORGANISM: Artificial Sequence
<220> FEATURE:
<223> OTHER INFORMATION: Synthetic consensus sequence

<400> SEQUENCE: 19
acaaaaatag cagctaaatg ggtgggtggt aggggacagc aaaaaactat aaatcaggtc      60
ataaataaaa taaaatgtat tcagtggagc acactact                             98

<210> SEQ ID NO 20
<211> LENGTH: 100
<212> TYPE: DNA
<213> ORGANISM: Artificial Sequence
<220> FEATURE:
<223> OTHER INFORMATION: Synthetic consensus sequence

<400> SEQUENCE: 20 tagggatct atgcagaaca aaattgagtc ctgtattata tattctattt gtagtatagc       60
tgttgttaag tgggggtgg ggaactaaca acagcgtaaa                            100

<210> SEQ ID NO 21
<211> LENGTH: 42
<212> TYPE: DNA
<213> ORGANISM: Artificial Sequence
<220> FEATURE:
<223> OTHER INFORMATION: Synthetic consensus sequence

<400> SEQUENCE: 21
tttattttgc aaacattatt ttatacttgg tagcacacta ct                        42

<210> SEQ ID NO 22
<211> LENGTH: 100
<212> TYPE: DNA
<213> ORGANISM: Artificial Sequence
<220> FEATURE:
<223> OTHER INFORMATION: Synthetic consensus sequence

<400> SEQUENCE: 22
tagtagttat gagtttacag agaacykaca attaggcyat aaatttggga gggttttgga     60
aattggctaa rattcaaaaa gaggggatt aacagcaact                           100

<210> SEQ ID NO 23
<211> LENGTH: 30
<212> TYPE: DNA
<213> ORGANISM: Artificial Sequence
<220> FEATURE:
<223> OTHER INFORMATION: Synthetic consensus sequence

<400> SEQUENCE: 23
gtataaattt gtagatagga gcacactact                                      30

<210> SEQ ID NO 24
<211> LENGTH: 1441
<212> TYPE: PRT
<213> ORGANISM: La Crosse virus

<400> SEQUENCE: 24

Met Ile Cys Ile Leu Val Leu Ile Thr Val Ala Ala Ala Ser Pro Val
 1               5                  10                  15

Tyr Gln Arg Cys Phe Gln Asp Gly Ala Ile Val Lys Gln Asn Pro Ser
                20                  25                  30

Lys Glu Ala Val Thr Glu Val Cys Leu Lys Asp Asp Val Ser Met Ile
            35                  40                  45
```

```
Lys Thr Glu Ala Arg Tyr Val Arg Asn Ala Thr Gly Val Phe Ser Asn
 50                  55                  60

Asn Val Ala Ile Arg Lys Trp Leu Val Ser Asp Trp His Asp Cys Arg
 65                  70                  75                  80

Pro Lys Lys Ile Val Gly Gly His Ile Asn Val Ile Glu Val Gly Asp
                     85                  90                  95

Asp Leu Ser Leu His Thr Glu Ser Tyr Val Cys Ser Ala Asp Cys Thr
                100                 105                 110

Ile Gly Val Asp Lys Glu Thr Ala Gln Val Arg Leu Gln Thr Asp Thr
                115                 120                 125

Thr Asn His Phe Glu Ile Ala Gly Thr Thr Val Lys Ser Gly Trp Phe
130                 135                 140

Lys Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
                180                 185                 190

Ile Ala Asn Ser Ile Cys Gln Asn Ile Glu Ile Ile Leu Val Thr
                195                 200                 205

Leu Thr Leu Leu Ile Phe Ile Leu Leu Ser Ile Leu Ser Lys Thr Tyr
210                 215                 220

Ile Cys Tyr Leu Leu Met Pro Ile Phe Ile Pro Ile Ala Tyr Ile Tyr
225                 230                 235                 240

Gly Thr Ile Tyr Asn Lys Ser Cys Lys Lys Cys Lys Leu Cys Gly Leu
                245                 250                 255

Val Tyr His Pro Phe Thr Glu Cys Gly Thr His Cys Val Cys Gly Ala
                260                 265                 270

Arg Tyr Asp Thr Ser Asp Arg Met Lys Leu His Arg Ala Ser Gly Leu
                275                 280                 285

Cys Pro Gly Tyr Lys Ser Leu Arg Ala Ala Arg Val Met Cys Lys Ser
290                 295                 300

Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                325                 330                 335

Thr Phe Glu Leu Glu Asp Leu Pro Asp Asp Met Leu Glu Met Ala Ser
                340                 345                 350

Arg Ile Asn Ser Tyr Tyr Leu Thr Cys Ile Leu Asn Tyr Ala Val Ser
                355                 360                 365

Trp Gly Leu Val Ile Ile Gly Leu Leu Ile Gly Leu Leu Phe Lys Lys
                370                 375                 380

Tyr Gln His Arg Phe Leu Asn Val Tyr Ala Met Tyr Cys Glu Glu Cys
385                 390                 395                 400

Asp Met Tyr His Asp Lys Ser Gly Leu Lys Gly His Gly Asp Phe Thr
                405                 410                 415

Asn Lys Cys Arg Gln Cys Thr Cys Gly Gln Tyr Glu Asp Ala Ala Gly
                420                 425                 430

Leu Met Ala His Arg Lys Thr Tyr Asn Cys Leu Val Gln Tyr Lys Ala
                435                 440                 445

Lys Trp Met Met Asn Phe Leu Ile Ile Tyr Ile Phe Leu Ile Leu Ile
                450                 455                 460
```

```
Lys Asp Ser Ala Ile Val Gln Ala Ala Gly Thr Asp Phe Thr Thr
465                 470                 475                 480

Cys Leu Glu Thr Glu Ser Ile Asn Trp Asn Cys Thr Gly Pro Phe Leu
            485                 490                 495

Asn Leu Gly Asn Cys Gln Lys Gln Lys Lys Glu Pro Tyr Thr Asn
        500                 505                 510

Ile Ala Thr Gln Leu Lys Gly Leu Lys Ala Ile Ser Val Leu Asp Val
        515                 520                 525

Pro Ile Ile Thr Gly Ile Pro Asp Asp Ile Ala Gly Ala Leu Arg Tyr
        530                 535                 540

Ile Glu Glu Lys Glu Asp Phe His Val Gln Leu Thr Ile Glu Tyr Ala
545                 550                 555                 560

Met Leu Ser Lys Tyr Cys Asp Tyr Tyr Thr Gln Phe Ser Asp Asn Ser
            565                 570                 575

Gly Tyr Ser Gln Thr Thr Trp Arg Val Tyr Leu Arg Ser His Asp Phe
            580                 585                 590

Glu Ala Cys Ile Leu Tyr Pro Asn Gln His Phe Cys Arg Cys Val Lys
        595                 600                 605

Asn Gly Glu Lys Cys Ser Ser Ser Asn Trp Asp Phe Ala Asn Glu Met
    610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
                645                 650                 655

Tyr Ile Ala Thr Met Leu Ser Lys Lys Ser Asn Asp Asp Leu Ile Ala
            660                 665                 670

Tyr Thr Asn Lys Ile Lys Thr Lys Phe Pro Gly Asp Ala Leu Leu Lys
        675                 680                 685

Ala Ile Ile Asp Tyr Ile Ala Tyr Met Lys Ser Leu Pro Gly Met Ala
        690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
            725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
        755                 760                 765

Ile Ile Ala Cys Gly Glu Pro Asn Gly Pro Ser Val Tyr Arg Lys Pro
        770                 775                 780

Ser Gly Gly Val Phe Gln Ser Ser Thr Asp Gln Ser Ile Tyr Cys Leu
785                 790                 795                 800

Leu Asp Ser His Cys Leu Glu Glu Phe Glu Ala Ile Gly Gln Glu Glu
            805                 810                 815

Leu Asp Ala Val Lys Lys Ser Lys Cys Trp Glu Ile Glu Tyr Pro Asp
            820                 825                 830

Val Lys Leu Ile Gln Glu Gly Asp Gly Thr Lys Ser Cys Arg Met Lys
        835                 840                 845

Asp Ser Gly Asn Cys Asn Val Ala Thr Asn Arg Trp Pro Val Ile Gln
        850                 855                 860

Cys Glu Asn Asp Lys Phe Tyr Tyr Ser Glu Leu Gln Lys Asp Tyr Asp
865                 870                 875                 880

Lys Thr Gln Asp Ile Gly His Tyr Cys Leu Ser Pro Gly Cys Thr Thr
```

-continued

```
                885                 890                 895
Val Arg Tyr Pro Ile Asn Pro Lys His Ile Ser Asn Cys Asn Trp Gln
                900                 905                 910
Val Ser Arg Ser Ser Ile Ala Lys Ile Asp Val His Asn Ile Glu Asp
                915                 920                 925
Ile Glu Gln Tyr Lys Lys Ala Ile Thr Gln Lys Leu Gln Thr Ser Leu
                930                 935                 940
Ser Leu Phe Lys Tyr Ala Lys Thr Lys Asn Leu Pro His Ile Lys Pro
945                 950                 955                 960
Ile Tyr Lys Tyr Ile Thr Ile Glu Gly Thr Glu Thr Ala Glu Gly Ile
                965                 970                 975
Glu Ser Ala Tyr Ile Glu Ser Glu Val Pro Ala Leu Ala Gly Thr Ser
                980                 985                 990
Ile Gly Phe Lys Ile Asn Ser Lys Glu Gly Lys His Leu Leu Asp Val
                995                 1000                1005
Ile Ala Tyr Val Lys Ser Ala Ser Tyr Ser Ser Val Tyr Thr Lys
                1010                1015                1020
Leu Tyr Ser Thr Gly Pro Thr Ser Gly Ile Asn Thr Lys His Asp
                1025                1030                1035
Glu Leu Cys Thr Gly Pro Cys Pro Ala Asn Ile Asn His Gln Val
                1040                1045                1050
Gly Trp Leu Thr Phe Ala Arg Glu Arg Thr Ser Ser Trp Gly Cys
                1055                1060                1065
Glu Glu Phe Gly Cys Leu Ala Val Ser Asp Gly Cys Val Phe Gly
                1070                1075                1080
Ser Cys Gln Asp Ile Ile Lys Glu Glu Leu Ser Val Tyr Arg Lys
                1085                1090                1095
Glu Thr Glu Glu Val Thr Asp Val Glu Leu Cys Leu Thr Phe Ser
                1100                1105                1110
Asp Lys Thr Tyr Cys Thr Asn Leu Asn Pro Val Thr Pro Ile Ile
                1115                1120                1125
Thr Asp Leu Phe Glu Val Gln Phe Lys Thr Val Glu Thr Tyr Ser
                1130                1135                1140
Leu Pro Arg Ile Val Ala Val Gln Asn His Glu Ile Lys Ile Gly
                1145                1150                1155
Gln Ile Asn Asp Leu Gly Val Tyr Ser Lys Gly Cys Gly Asn Val
                1160                1165                1170
Gln Lys Val Asn Gly Thr Ile Tyr Gly Asn Gly Val Pro Arg Phe
                1175                1180                1185
Asp Tyr Leu Cys His Leu Ala Ser Arg Lys Glu Val Ile Val Arg
                1190                1195                1200
Lys Cys Phe Asp Asn Asp Tyr Gln Ala Cys Lys Phe Leu Gln Ser
                1205                1210                1215
Pro Ala Ser Tyr Arg Leu Glu Glu Asp Ser Gly Thr Val Thr Ile
                1220                1225                1230
Ile Asp Tyr Lys Lys Ile Leu Gly Thr Ile Lys Met Lys Ala Ile
                1235                1240                1245
Leu Gly Asp Val Lys Tyr Lys Thr Phe Ala Asp Ser Val Asp Ile
                1250                1255                1260
Thr Ala Glu Gly Ser Cys Thr Gly Cys Ile Asn Cys Phe Glu Asn
                1265                1270                1275
Ile His Cys Glu Leu Thr Leu His Thr Thr Ile Glu Ala Ser Cys
                1280                1285                1290
```

```
Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Ile
    1325                1330                1335

Glu Ala Ser Met Ala Leu Val Asp Ala Lys Pro Ile Ile Glu Leu
    1340                1345                1350

Ala Pro Val Asp Gln Thr Ala Tyr Ile Arg Glu Lys Asp Glu Arg
    1355                1360                1365

Cys Lys Thr Trp Met Cys Arg Val Arg Asp Glu Gly Leu Gln Val
    1370                1375                1380

Ile Leu Glu Pro Phe Lys Asn Leu Phe Gly Ser Tyr Ile Gly Ile
    1385                1390                1395

Phe Tyr Thr Phe Ile Ile Ser Ile Val Ala Leu Leu Val Ile Ile
    1400                1405                1410

Tyr Val Leu Leu Pro Ile Cys Phe Lys Leu Arg Asp Thr Leu Arg
    1415                1420                1425

Lys His Glu Asp Ala Tyr Lys Arg Glu Met Lys Ile Arg
    1430                1435                1440

<210> SEQ ID NO 25
<211> LENGTH: 1441
<212> TYPE: PRT
<213> ORGANISM: La Crosse virus

<400> SEQUENCE: 25

Met Ile Cys Ile Leu Val Leu Ile Thr Val Ala Ala Ala Ser Pro Val
1               5                   10                  15

Tyr Gln Arg Cys Phe Gln Asp Gly Ala Ile Val Lys Gln Asn Pro Ser
                20                  25                  30

Lys Glu Ala Val Thr Glu Val Cys Leu Lys Asp Asp Val Ser Met Ile
            35                  40                  45

Lys Thr Glu Ala Arg Tyr Val Arg Asn Ala Thr Gly Val Phe Ser Asn
        50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
    130                 135                 140

Glu Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
            180                 185                 190

Ile Ala Asn Ser Ile Cys Gln Asn Ile Glu Ile Ile Leu Val Thr
        195                 200                 205

Leu Thr Leu Leu Ile Phe Ile Leu Leu Ser Ile Leu Ser Lys Thr Tyr
```

-continued

```
            210                 215                 220
Ile Cys Tyr Leu Leu Met Pro Ile Phe Ile Pro Ile Ala Tyr Ile Tyr
225                 230                 235                 240
Gly Thr Ile Tyr Asn Lys Ser Cys Lys Lys Cys Lys Leu Cys Gly Leu
                245                 250                 255
Val Tyr His Pro Phe Thr Glu Cys Gly Thr His Cys Ile Cys Gly Ala
            260                 265                 270
Arg Tyr Asp Thr Ser Asp Arg Met Lys Leu His Arg Ala Ser Gly Leu
        275                 280                 285
Cys Pro Gly Tyr Lys Ser Leu Arg Ala Ala Arg Val Met Cys Lys Ser
    290                 295                 300
Lys Gly Pro Ala Ser Ile Leu Ser Ile Ile Thr Ala Val Leu Val Leu
305                 310                 315                 320
Thr Phe Val Thr Pro Ile Asn Ser Met Val Leu Gly Glu Ser Lys Glu
                325                 330                 335
Thr Phe Glu Leu Glu Asp Leu Pro Asp Asp Met Leu Glu Met Ala Ser
            340                 345                 350
Arg Ile Asn Ser Tyr Tyr Leu Thr Cys Ile Leu Asn Tyr Ala Val Ser
        355                 360                 365
Trp Gly Leu Val Ile Ile Gly Leu Leu Ile Gly Leu Leu Phe Lys Lys
    370                 375                 380
Tyr Gln His Arg Phe Leu Asn Val Tyr Ala Met Tyr Cys Glu Glu Cys
385                 390                 395                 400
Asp Met Tyr His Asp Lys Ser Gly Leu Lys Arg His Gly Asp Phe Thr
                405                 410                 415
Asn Lys Cys Arg Gln Cys Thr Cys Gly Gln Tyr Glu Asp Ala Ala Gly
            420                 425                 430
Leu Met Ala His Arg Lys Thr Tyr Asn Cys Leu Val Gln Tyr Lys Ala
        435                 440                 445
Lys Trp Met Met Asn Phe Leu Ile Ile Tyr Ile Phe Leu Ile Leu Ile
    450                 455                 460
Lys Asp Ser Ala Ile Val Val Gln Ala Gly Thr Asp Phe Thr Thr
465                 470                 475                 480
Cys Leu Glu Thr Glu Ser Ile Asn Trp Asn Cys Thr Gly Pro Phe Leu
                485                 490                 495
Asn Leu Gly Asn Cys Gln Lys Gln Gln Lys Lys Glu Pro Tyr Thr Asn
            500                 505                 510
Ile Ala Thr Gln Leu Lys Gly Leu Lys Ala Ile Ser Val Leu Asp Val
        515                 520                 525
Pro Ile Ile Thr Gly Ile Pro Asp Asp Ile Ala Gly Ala Leu Arg Tyr
    530                 535                 540
Ile Glu Glu Lys Glu Asp Phe His Val Gln Leu Thr Ile Glu Tyr Ala
545                 550                 555                 560
Met Leu Ser Lys Tyr Cys Asp Tyr Tyr Thr Gln Phe Ser Asp Asn Ser
                565                 570                 575
Gly Tyr Ser Gln Thr Thr Trp Arg Val Tyr Leu Arg Ser His Asp Phe
            580                 585                 590
Glu Ala Cys Ile Leu Tyr Pro Asn Gln His Phe Cys Arg Cys Val Lys
        595                 600                 605
Asn Gly Glu Lys Cys Ser Ser Ser Asn Arg Asp Phe Ala Asn Glu Met
    610                 615                 620
Lys Asp Tyr Tyr Ser Gly Lys Gln Thr Lys Phe Asp Lys Asp Leu Asn
625                 630                 635                 640
```

-continued

```
Leu Ala Leu Thr Ala Leu His His Ala Phe Arg Gly Thr Ser Ser Ala
            645                 650                 655

Tyr Ile Ala Thr Met Leu Ser Lys Lys Ser Asn Asp Asp Leu Ile Ala
            660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
            690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
            725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
            755                 760                 765

Ile Ile Ala Cys Gly Glu Pro Asn Gly Pro Ser Val Tyr Arg Lys Pro
            770                 775                 780

Ser Gly Gly Val Phe Gln Ser Ser Thr Asp Gln Ser Ile Tyr Cys Leu
785                 790                 795                 800

Leu Asp Ser His Cys Leu Glu Glu Phe Glu Ala Ile Gly Gln Glu Glu
            805                 810                 815

Leu Asp Ala Val Lys Lys Ser Lys Cys Trp Glu Ile Glu Tyr Pro Asp
            820                 825                 830

Val Lys Leu Ile Gln Glu Gly Asp Gly Thr Lys Ser Cys Arg Met Lys
            835                 840                 845

Asp Ser Gly Asn Cys Asn Val Ala Thr Asn Arg Trp Pro Val Ile Gln
850                 855                 860

Cys Glu Asn Asp Lys Phe Tyr Tyr Ser Glu Leu Gln Lys Asp Tyr Asp
865                 870                 875                 880

Lys Thr Gln Asp Ile Gly His Tyr Cys Leu Ser Pro Gly Cys Thr Thr
            885                 890                 895

Val Arg Tyr Pro Ile Asn Pro Lys His Ile Ser Asn Cys Asn Trp Gln
            900                 905                 910

Val Ser Arg Ser Ser Ile Ala Lys Ile Asp Val His Asn Ile Glu Asp
            915                 920                 925

Ile Glu Gln Tyr Lys Lys Ala Ile Thr Gln Lys Leu Gln Thr Ser Leu
            930                 935                 940

Ser Leu Phe Lys Tyr Ala Lys Thr Lys Asn Leu Pro His Ile Lys Pro
945                 950                 955                 960

Ile Tyr Lys Tyr Ile Thr Ile Glu Gly Thr Glu Thr Ala Glu Gly Ile
            965                 970                 975

Glu Ser Ala Tyr Ile Glu Ser Glu Val Pro Ala Leu Ala Gly Thr Ser
            980                 985                 990

Ile Gly Phe Lys Ile Asn Ser Lys Glu Gly Lys His Leu Leu Asp Val
            995                 1000                1005

Ile Ala Tyr Val Lys Ser Ala Ser Tyr Ser Ser Val Tyr Thr Lys
            1010                1015                1020

Leu Tyr Ser Thr Gly Pro Thr Ser Gly Ile Asn Thr Lys His Asp
            1025                1030                1035

Glu Leu Cys Thr Gly Pro Cys Pro Ala Asn Ile Asn His Gln Val
            1040                1045                1050
```

```
Gly Trp Leu Thr Phe Ala Arg Glu Arg Thr Ser Ser Trp Gly Cys
1055                1060                1065

Glu Glu Phe Gly Cys Leu Ala Val Ser Asp Gly Cys Val Phe Gly
1070                1075                1080

Ser Cys Gln Asp Ile Ile Lys Glu Glu Leu Ser Val Tyr Arg Lys
1085                1090                1095

Glu Thr Glu Glu Val Thr Asp Val Glu Leu Cys Leu Thr Phe Ser
1100                1105                1110

Asp Lys Thr Tyr Cys Thr Asn Leu Asn Pro Val Thr Pro Ile Ile
1115                1120                1125

Thr Asp Leu Phe Glu Val Gln Phe Lys Thr Val Glu Ala Tyr Ser
1130                1135                1140

Leu Pro Arg Ile Val Ala Val Gln Asn His Glu Ile Lys Ile Gly
1145                1150                1155

Gln Ile Asn Asp Leu Gly Val Tyr Ser Lys Gly Cys Gly Asn Val
1160                1165                1170

Gln Lys Val Asn Gly Thr Ile Tyr Gly Asn Gly Val Pro Arg Phe
1175                1180                1185

Asp Tyr Leu Cys His Leu Ala Ser Arg Lys Glu Val Ile Val Arg
1190                1195                1200

Lys Cys Phe Asp Asn Asp Tyr Gln Ala Cys Lys Phe Leu Gln Ser
1205                1210                1215

Pro Ala Ser Tyr Arg Leu Glu Glu Asp Ser Gly Thr Val Thr Ile
1220                1225                1230

Ile Asp Tyr Lys Lys Ile Leu Gly Thr Ile Lys Met Lys Ala Ile
1235                1240                1245

Leu Gly Asp Val Lys Tyr Lys Thr Phe Ala Asp Ser Val Asp Ile
1250                1255                1260

Thr Ala Glu Gly Ser Cys Thr Gly Cys Ile Asn Cys Phe Glu Asn
1265                1270                1275

Ile His Cys Glu Leu Thr Leu His Thr Thr Ile Glu Ala Ser Cys
1280                1285                1290

Pro Ile Lys Ser Ser Cys Thr Val Phe His Asp Arg Ile Leu Val
1295                1300                1305

Thr Pro Asn Glu His Lys Tyr Ala Leu Lys Met Val Cys Thr Glu
1310                1315                1320

Lys Pro Gly Asn Thr Leu Thr Ile Lys Val Cys Asn Thr Lys Ile
1325                1330                1335

Glu Ala Ser Met Ala Leu Val Asp Ala Lys Pro Ile Ile Glu Leu
1340                1345                1350

Ala Pro Val Asp Gln Thr Ala Tyr Ile Arg Glu Lys Asp Glu Arg
1355                1360                1365

Cys Lys Thr Trp Met Cys Arg Val Arg Asp Glu Gly Leu Gln Val
1370                1375                1380

Ile Leu Glu Pro Phe Lys Asn Leu Phe Gly Ser Tyr Ile Gly Ile
1385                1390                1395

Phe Tyr Thr Phe Ile Ile Ser Ile Val Ala Leu Val Ile Ile
1400                1405                1410

Tyr Val Leu Leu Pro Ile Cys Phe Lys Leu Arg Asp Thr Leu Arg
1415                1420                1425

Lys His Glu Asp Ala Tyr Lys Arg Glu Met Lys Ile Arg
1430                1435                1440
```

<210> SEQ ID NO 26
<211> LENGTH: 1441
<212> TYPE: PRT
<213> ORGANISM: La Crosse virus

<400> SEQUENCE: 26

```
Met Ile Cys Ile Leu Val Leu Ile Thr Val Ala Ala Ser Pro Val
1               5                   10                  15

Tyr Gln Arg Cys Phe Gln Asp Gly Ala Ile Val Lys Gln Asn Pro Ser
                20                  25                  30

Lys Glu Ala Val Thr Glu Val Cys Leu Lys Asp Asp Val Ser Met Ile
            35                  40                  45

Lys Thr Glu Ala Arg Tyr Val Arg Asn Ala Thr Gly Val Phe Ser Asn
50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
130                 135                 140

Lys Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
            180                 185                 190

Ile Ala Asn Ser Ile Cys Gln Asn Ile Glu Ile Ile Leu Val Thr
        195                 200                 205

Leu Thr Leu Leu Ile Phe Ile Leu Leu Ser Ile Leu Ser Lys Thr Tyr
210                 215                 220

Ile Cys Tyr Leu Leu Met Pro Ile Phe Ile Pro Ile Ala Tyr Ile Tyr
225                 230                 235                 240

Gly Ile Ile Tyr Asn Lys Ser Cys Lys Lys Cys Lys Leu Cys Gly Leu
                245                 250                 255

Val Tyr His Pro Phe Thr Glu Cys Gly Thr His Cys Val Cys Gly Ala
            260                 265                 270

Arg Tyr Asp Thr Ser Asp Arg Met Lys Leu His Arg Ala Ser Gly Leu
        275                 280                 285

Cys Pro Gly Tyr Lys Ser Leu Arg Ala Ala Arg Val Met Cys Lys Ser
290                 295                 300

Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                325                 330                 335

Thr Phe Glu Leu Glu Asp Leu Pro Asp Asp Met Leu Glu Met Ala Ser
            340                 345                 350

Arg Ile Asn Ser Tyr Tyr Leu Thr Cys Ile Leu Asn Tyr Ala Val Ser
        355                 360                 365

Trp Gly Leu Val Ile Ile Gly Leu Leu Ile Gly Leu Leu Phe Lys Lys
370                 375                 380
```

```
Tyr Gln His Arg Phe Leu Asn Val Tyr Ala Met Tyr Cys Glu Glu Cys
385                 390                 395                 400

Asp Met Tyr His Asp Lys Ser Gly Leu Lys Arg His Gly Asp Phe Thr
            405                 410                 415

Asn Lys Cys Arg Gln Cys Thr Cys Gly Gln Tyr Glu Asp Ala Ala Gly
            420                 425                 430

Leu Met Ala His Arg Lys Thr Tyr Asn Cys Leu Val Gln Tyr Lys Ala
            435                 440                 445

Lys Trp Met Met Asn Phe Leu Ile Ile Tyr Ile Phe Leu Ile Leu Ile
450                 455                 460

Lys Asp Ser Ala Ile Val Val Gln Ala Ala Gly Thr Asp Phe Thr Thr
465                 470                 475                 480

Cys Leu Glu Thr Glu Ser Ile Asn Trp Asn Cys Thr Gly Pro Phe Leu
            485                 490                 495

Asn Leu Gly Asn Cys Gln Lys Gln Lys Lys Glu Pro Tyr Thr Asn
            500                 505                 510

Ile Ala Thr Gln Leu Lys Gly Leu Lys Ala Ile Ser Val Leu Asp Val
            515                 520                 525

Pro Ile Ile Thr Gly Ile Pro Asp Asp Ile Ala Gly Ala Leu Arg Tyr
530                 535                 540

Ile Glu Glu Lys Glu Asp Phe His Val Gln Leu Thr Ile Glu Tyr Ala
545                 550                 555                 560

Met Leu Ser Lys Tyr Cys Asp Tyr Tyr Thr Gln Phe Ser Asp Asn Ser
            565                 570                 575

Gly Tyr Ser Gln Thr Thr Trp Arg Val Tyr Leu Arg Ser His Asp Phe
            580                 585                 590

Glu Ala Cys Ile Leu Tyr Pro Asn Gln His Phe Cys Arg Cys Val Lys
            595                 600                 605

Asn Gly Glu Lys Cys Ser Ser Asn Trp Asp Phe Ala Asn Glu Met
610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
            645                 650                 655

Tyr Ile Ala Thr Met Leu Ser Lys Lys Ser Asn Asp Asp Leu Ile Ala
            660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
            690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
            725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
            755                 760                 765

Ile Ile Ala Cys Gly Glu Pro Asn Gly Pro Ser Val Tyr Arg Lys Pro
            770                 775                 780

Ser Gly Gly Val Phe Gln Ser Ser Thr Asp Arg Ser Ile Tyr Cys Leu
785                 790                 795                 800

Leu Asp Ser His Cys Leu Glu Glu Phe Glu Ala Ile Gly Gln Glu Glu
```

```
            805                 810                 815
Leu Asp Ala Val Lys Ser Lys Cys Trp Glu Ile Glu Tyr Pro Asp
            820                 825                 830
Val Lys Leu Ile Gln Glu Gly Asp Gly Thr Lys Ser Cys Arg Met Lys
            835                 840                 845
Asp Ser Gly Asn Cys Asn Val Ala Thr Asn Arg Trp Pro Val Ile Gln
    850                 855                 860
Cys Glu Asn Asp Lys Phe Tyr Tyr Ser Glu Leu Gln Lys Asp Tyr Asp
865                 870                 875                 880
Lys Ala Gln Asp Ile Gly His Tyr Cys Leu Ser Pro Gly Cys Thr Thr
                885                 890                 895
Val Arg Tyr Pro Ile Asn Pro Lys His Ile Ser Asn Cys Asn Trp Gln
            900                 905                 910
Val Ser Arg Ser Ser Ile Ala Lys Ile Asp Val His Asn Ile Glu Asp
            915                 920                 925
Ile Glu Gln Tyr Lys Lys Ala Ile Thr Gln Lys Leu Gln Thr Ser Leu
            930                 935                 940
Ser Leu Phe Lys Tyr Ala Lys Thr Lys Asn Leu Pro His Ile Lys Pro
945                 950                 955                 960
Ile Tyr Lys Tyr Ile Thr Ile Glu Gly Thr Glu Thr Ala Glu Gly Ile
                965                 970                 975
Glu Ser Ala Tyr Ile Glu Ser Glu Val Pro Ala Leu Ala Gly Thr Ser
            980                 985                 990
Ile Gly Phe Lys Ile Asn Ser Lys Glu Gly Lys His Leu Leu Asp Val
            995                 1000                1005
Ile Ala  Tyr Val Lys Ser Ala  Ser Tyr Ser Ser Val  Tyr Thr Lys
    1010                1015                1020
Leu Tyr  Ser Thr Gly Pro Thr  Ser Gly Ile Asn Thr  Lys His Asp
    1025                1030                1035
Glu Leu  Cys Thr Gly Pro Cys  Pro Ala Asn Ile Asn  His Gln Val
    1040                1045                1050
Gly Trp  Leu Thr Phe Ala Arg  Glu Arg Thr Ser Ser  Trp Gly Cys
    1055                1060                1065
Glu Glu  Phe Gly Cys Leu Ala  Val Ser Asp Gly Cys  Val Phe Gly
    1070                1075                1080
Ser Cys  Gln Asp Ile Ile Lys  Glu Glu Leu Ser Val  Tyr Arg Lys
    1085                1090                1095
Glu Thr  Glu Glu Val Thr Asp  Val Glu Leu Cys Leu  Thr Phe Ser
    1100                1105                1110
Asp Lys  Thr Tyr Cys Thr Asn  Leu Asn Pro Val Thr  Pro Ile Ile
    1115                1120                1125
Thr Asp  Leu Phe Glu Val Gln  Phe Lys Thr Val Glu  Thr Tyr Ser
    1130                1135                1140
Leu Pro  Arg Ile Val Ala Val  Gln Asn His Glu Ile  Lys Ile Gly
    1145                1150                1155
Gln Ile  Asn Asp Leu Gly Val  Tyr Ser Lys Gly Cys  Gly Asn Val
    1160                1165                1170
Gln Lys  Val Asn Gly Thr Ile  Tyr Gly Asn Gly Val  Pro Arg Phe
    1175                1180                1185
Asp Tyr  Leu Cys His Leu Ala  Ser Arg Lys Glu Val  Ile Val Arg
    1190                1195                1200
Lys Cys  Phe Asp Asn Asp Tyr  Gln Ala Cys Lys Phe  Leu Gln Ser
    1205                1210                1215
```

```
Pro Ala Ser Tyr Arg Leu Glu Glu Asp Ser Gly Thr Val Thr Ile
    1220                1225                1230

Ile Asp Tyr Lys Lys Ile Leu Gly Thr Ile Lys Met Lys Ala Ile
    1235                1240                1245

Leu Gly Asp Val Lys Tyr Lys Thr Phe Ala Asp Ser Val Asp Ile
    1250                1255                1260

Thr Ala Glu Gly Ser Cys Thr Gly Cys Ile Asn Cys Phe Glu Asn
    1265                1270                1275

Ile His Cys Glu Leu Thr Leu His Thr Thr Ile Glu Ala Ser Cys
    1280                1285                1290

Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Val
    1325                1330                1335

Glu Ala Ser Met Ala Leu Val Asp Ala Lys Pro Ile Ile Glu Leu
    1340                1345                1350

Ala Pro Val Asp Gln Thr Ala Tyr Ile Arg Glu Lys Asp Glu Arg
    1355                1360                1365

Cys Lys Thr Trp Met Cys Arg Val Arg Asp Glu Gly Leu Gln Val
    1370                1375                1380

Ile Leu Glu Pro Phe Lys Asn Leu Phe Gly Ser Tyr Ile Gly Ile
    1385                1390                1395

Phe Tyr Thr Phe Ile Ile Ser Ile Val Val Leu Val Ile Ile
    1400                1405                1410

Tyr Val Leu Leu Pro Ile Cys Phe Lys Leu Arg Asp Thr Leu Arg
    1415                1420                1425

Lys His Glu Asp Ala Tyr Lys Arg Glu Met Lys Ile Arg
    1430                1435                1440

<210> SEQ ID NO 27
<211> LENGTH: 1441
<212> TYPE: PRT
<213> ORGANISM: La Crosse virus

<400> SEQUENCE: 27

Met Ile Cys Ile Leu Val Leu Ile Thr Val Ala Ala Ser Pro Val
1               5                   10                  15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
        35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
```

```
             130              135             140
Lys Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
                180                 185                 190

Ile Ala Asn Ser Ile Cys Gln Asn Ile Glu Ile Ile Leu Val Thr
                195                 200                 205

Leu Thr Leu Leu Ile Phe Ile Leu Leu Ser Ile Leu Ser Lys Thr Tyr
                210                 215                 220

Ile Cys Tyr Leu Leu Met Pro Ile Phe Ile Pro Ile Ala Tyr Ile Tyr
225                 230                 235                 240

Gly Ile Ile Tyr Asn Lys Ser Cys Lys Lys Cys Lys Leu Cys Gly Leu
                245                 250                 255

Val Tyr His Pro Phe Thr Glu Cys Gly Thr His Cys Val Cys Gly Ala
                260                 265                 270

Arg Tyr Asp Thr Ser Asp Arg Met Lys Leu His Arg Ala Ser Gly Leu
                275                 280                 285

Cys Pro Gly Tyr Lys Ser Leu Arg Ala Ala Arg Val Met Cys Lys Ser
                290                 295                 300

Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                325                 330                 335

Thr Phe Glu Leu Glu Asp Leu Pro Asp Asp Met Leu Glu Met Ala Ser
                340                 345                 350

Arg Ile Asn Ser Tyr Tyr Leu Thr Cys Ile Leu Asn Tyr Ala Val Ser
                355                 360                 365

Trp Gly Leu Val Ile Ile Gly Leu Leu Ile Gly Leu Leu Phe Lys Lys
                370                 375                 380

Tyr Gln His Arg Phe Leu Asn Val Tyr Ala Met Tyr Cys Glu Glu Cys
385                 390                 395                 400

Asp Met Tyr His Asp Lys Ser Gly Leu Lys Arg His Gly Asp Phe Thr
                405                 410                 415

Asn Lys Cys Arg Gln Cys Thr Cys Gly Gln Tyr Glu Asp Ala Ala Gly
                420                 425                 430

Leu Met Ala His Arg Lys Thr Tyr Asn Cys Leu Val Gln Tyr Lys Ala
                435                 440                 445

Lys Trp Met Met Asn Phe Leu Ile Ile Tyr Ile Phe Leu Ile Leu Ile
                450                 455                 460

Lys Asp Ser Ala Ile Val Val Gln Ala Ala Gly Thr Asp Phe Thr Thr
465                 470                 475                 480

Cys Leu Glu Thr Glu Ser Ile Asn Trp Asn Cys Thr Gly Pro Phe Leu
                485                 490                 495

Asn Leu Gly Asn Cys Gln Lys Gln Lys Lys Glu Pro Tyr Thr Asn
                500                 505                 510

Ile Ala Thr Gln Leu Lys Gly Leu Lys Ala Ile Ser Val Leu Asp Val
                515                 520                 525

Pro Ile Ile Thr Gly Ile Pro Asp Asp Ile Ala Gly Ala Leu Arg Tyr
                530                 535                 540

Ile Glu Glu Lys Glu Asp Phe His Val Gln Leu Thr Ile Glu Tyr Ala
545                 550                 555                 560
```

```
Met Leu Ser Lys Tyr Cys Asp Tyr Tyr Thr Gln Phe Ser Asp Asn Ser
            565                 570                 575

Gly Tyr Ser Gln Thr Thr Trp Arg Val Tyr Leu Arg Ser His Asp Phe
            580                 585                 590

Glu Ala Cys Ile Leu Tyr Pro Asn Gln His Phe Cys Arg Cys Val Lys
            595                 600                 605

Asn Gly Glu Lys Cys Ser Ser Ser Asn Trp Asp Phe Ala Asn Glu Met
610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
            645                 650                 655

Tyr Ile Ala Thr Met Leu Ser Lys Lys Ser Asn Asp Asp Leu Ile Ala
            660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
            690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
            725                 730                 735

Phe Lys Leu Ala Ile Ser Ser Lys Ser Ile Lys Thr Cys Lys Asn Val
            740                 745                 750

Lys Asp Val Ala Cys Leu Ser Pro Arg Ser Gly Ala Ile Tyr Ala Ser
            755                 760                 765

Ile Ile Ala Cys Gly Glu Pro Asn Gly Pro Ser Val Tyr Arg Lys Pro
            770                 775                 780

Ser Gly Gly Val Phe Gln Ser Ser Thr Asp Arg Ser Ile Tyr Cys Leu
785                 790                 795                 800

Leu Asp Ser His Cys Leu Glu Glu Phe Glu Ala Ile Gly Gln Glu Glu
            805                 810                 815

Leu Asp Ala Val Lys Lys Ser Lys Cys Trp Glu Ile Glu Tyr Pro Asp
            820                 825                 830

Val Lys Leu Ile Gln Glu Gly Asp Gly Thr Lys Ser Cys Arg Met Lys
            835                 840                 845

Asp Ser Gly Asn Cys Asn Val Ala Thr Asn Arg Trp Pro Val Ile Gln
850                 855                 860

Cys Glu Asn Asp Lys Phe Tyr Tyr Ser Glu Leu Gln Lys Asp Tyr Asp
865                 870                 875                 880

Lys Ala Gln Asp Ile Gly His Tyr Cys Leu Ser Pro Gly Cys Thr Thr
            885                 890                 895

Val Arg Tyr Pro Ile Asn Pro Lys His Ile Ser Asn Cys Asn Trp Gln
            900                 905                 910

Val Ser Arg Ser Ser Ile Ala Lys Ile Asp Val His Asn Ile Glu Asp
            915                 920                 925

Ile Glu Gln Tyr Lys Lys Ala Ile Thr Gln Lys Leu Gln Thr Ser Leu
            930                 935                 940

Ser Leu Phe Lys Tyr Ala Lys Thr Lys Asn Leu Pro His Ile Lys Pro
945                 950                 955                 960

Ile Tyr Lys Tyr Ile Thr Ile Glu Gly Thr Glu Thr Ala Glu Gly Ile
            965                 970                 975
```

-continued

Glu Ser Ala Tyr Ile Glu Ser Glu Val Pro Ala Leu Ala Gly Thr Ser
                980                 985                 990

Ile Gly Phe Lys Ile Asn Ser Lys Glu Gly Lys His Leu Leu Asp Val
            995                1000                1005

Ile Ala Tyr Val Lys Ser Ala Ser Tyr Ser Ser Val Tyr Thr Lys
    1010                1015                1020

Leu Tyr Ser Thr Gly Pro Thr Ser Gly Ile Asn Thr Lys His Asp
    1025                1030                1035

Glu Leu Cys Thr Gly Pro Pro Ala Asn Ile Asn His Gln Val
    1040                1045                1050

Gly Trp Leu Thr Phe Ala Arg Glu Arg Thr Ser Ser Trp Gly Cys
    1055                1060                1065

Glu Glu Phe Gly Cys Leu Ala Val Ser Asp Gly Cys Val Phe Gly
    1070                1075                1080

Ser Cys Gln Asp Ile Ile Lys Glu Glu Leu Ser Val Tyr Arg Lys
    1085                1090                1095

Glu Thr Glu Glu Val Thr Asp Val Glu Leu Cys Leu Thr Phe Ser
    1100                1105                1110

Asp Lys Thr Tyr Cys Thr Asn Leu Asn Pro Val Thr Pro Ile Ile
    1115                1120                1125

Thr Asp Leu Phe Glu Val Gln Phe Lys Thr Val Glu Thr Tyr Ser
    1130                1135                1140

Leu Pro Arg Ile Val Ala Val Gln Asn His Glu Ile Lys Ile Gly
    1145                1150                1155

Gln Ile Asn Asp Leu Gly Val Tyr Ser Lys Gly Cys Gly Asn Val
    1160                1165                1170

Gln Lys Val Asn Gly Thr Ile Tyr Gly Asn Gly Val Pro Arg Phe
    1175                1180                1185

Asp Tyr Leu Cys His Leu Ala Ser Arg Lys Glu Val Ile Val Arg
    1190                1195                1200

Lys Cys Phe Asp Asn Asp Tyr Gln Ala Cys Lys Phe Leu Gln Ser
    1205                1210                1215

Pro Ala Ser Tyr Arg Leu Glu Glu Asp Ser Gly Thr Val Thr Ile
    1220                1225                1230

Ile Asp Tyr Lys Lys Ile Leu Gly Thr Ile Lys Met Lys Ala Ile
    1235                1240                1245

Leu Gly Asp Val Lys Tyr Lys Thr Phe Ala Asp Ser Val Asp Ile
    1250                1255                1260

Thr Ala Glu Gly Ser Cys Thr Gly Cys Ile Asn Cys Phe Glu Asn
    1265                1270                1275

Ile His Cys Glu Leu Thr Leu His Thr Thr Ile Glu Ala Ser Cys
    1280                1285                1290

Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Val
    1325                1330                1335

Glu Ala Ser Met Ala Leu Val Asp Ala Lys Pro Ile Ile Glu Leu
    1340                1345                1350

Ala Pro Val Asp Gln Thr Ala Tyr Ile Arg Glu Lys Asp Glu Arg
    1355                1360                1365

Cys Lys Thr Trp Met Cys Arg Val Arg Asp Glu Gly Leu Gln Val

```
             1370               1375              1380

Ile Leu Glu Pro Phe Lys Asn Leu Phe Gly Ser Tyr Ile Gly Ile
         1385              1390             1395

Phe Tyr Thr Phe Ile Ile Ser Ile Val Val Leu Leu Val Ile Ile
         1400              1405             1410

Tyr Val Leu Leu Pro Ile Cys Phe Lys Leu Arg Asp Thr Leu Arg
         1415              1420             1425

Lys His Glu Asp Ala Tyr Lys Arg Glu Met Lys Ile Arg
         1430              1435             1440

<210> SEQ ID NO 28
<211> LENGTH: 1441
<212> TYPE: PRT
<213> ORGANISM: La Crosse virus

<400> SEQUENCE: 28

Met Ile Arg Ile Leu Val Leu Ile Ala Val Thr Ala Ala Ser Pro Val
1               5                   10                  15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
        35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Ile Gly Gly His Ile Asn Val Ile Glu Val Ser Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
    130                 135                 140

Lys Ser Thr Thr Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
            180                 185                 190

Ile Ala Asn Ser Ile Cys Gln Asn Ile Glu Ile Ile Leu Val Thr
        195                 200                 205

Leu Thr Leu Leu Ile Phe Ile Leu Leu Ser Ile Leu Ser Lys Thr Tyr
    210                 215                 220

Ile Cys Tyr Leu Leu Met Pro Ile Phe Ile Pro Ile Ala Tyr Met Tyr
225                 230                 235                 240

Gly Ile Ile Tyr Asn Lys Ser Cys Lys Cys Lys Leu Cys Gly Leu
                245                 250                 255

Val Tyr His Pro Phe Thr Glu Cys Gly Thr His Cys Val Cys Gly Ala
            260                 265                 270

Arg Tyr Asp Thr Ser Asp Arg Met Lys Leu His Arg Ala Ser Gly Leu
        275                 280                 285

Cys Pro Gly Tyr Lys Ser Leu Arg Ala Ala Arg Val Met Cys Lys Ser
    290                 295                 300
```

```
Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                325                 330                 335

Thr Phe Glu Leu Glu Glu Leu Pro Asp Asp Met Leu Glu Met Ala Ser
            340                 345                 350

Arg Ile Asn Ser Tyr Tyr Phe Thr Cys Ile Leu Asn Tyr Ala Val Ser
        355                 360                 365

Trp Gly Leu Val Ile Ile Gly Leu Leu Thr Gly Leu Leu Phe Lys Lys
    370                 375                 380

Tyr Gln His Arg Phe Leu Asn Ile Tyr Ala Met Tyr Cys Glu Glu Cys
385                 390                 395                 400

Asp Met Tyr His Asp Lys Ser Gly Leu Lys Arg His Gly Asp Phe Thr
                405                 410                 415

Asn Lys Cys Arg Gln Cys Thr Cys Gly Gln Tyr Glu Asp Ala Ala Gly
                420                 425                 430

Leu Met Ala His Arg Lys Thr Tyr Asn Cys Leu Val Gln Tyr Lys Ala
            435                 440                 445

Lys Trp Met Met Asn Phe Leu Ile Ile Tyr Ile Phe Leu Ile Leu Ile
450                 455                 460

Lys Asp Ser Ala Ile Val Val Gln Ala Ala Gly Thr Asp Phe Thr Thr
465                 470                 475                 480

Cys Leu Glu Thr Glu Ser Ile Asp Trp Asn Cys Thr Gly Pro Phe Leu
                485                 490                 495

Asn Leu Gly Asn Cys Gln Lys Gln Gln Lys Lys Glu Pro Tyr Thr Asn
                500                 505                 510

Ile Ala Thr Gln Leu Lys Gly Leu Lys Ala Ile Ser Val Leu Asp Ile
            515                 520                 525

Pro Ile Ile Thr Arg Ile Pro Asp Asp Ile Ala Gly Ala Leu Arg Tyr
530                 535                 540

Ile Glu Glu Arg Glu Asp Phe His Val Gln Leu Thr Thr Glu Tyr Ala
545                 550                 555                 560

Met Leu Ser Lys Tyr Cys Asp Tyr Tyr Thr Gln Phe Ser Asp Asn Ser
                565                 570                 575

Gly Tyr Ser Gln Thr Thr Trp Arg Val Tyr Leu Arg Ser His Asp Phe
            580                 585                 590

Glu Ala Cys Ile Leu Tyr Pro Asn Gln Asn Phe Cys Arg Cys Val Lys
        595                 600                 605

Asn Gly Glu Lys Cys Ser Ser Ser Asn Trp Asp Phe Ala Asn Glu Met
    610                 615                 620

Lys Asp Tyr Tyr Pro Gly Lys Gln Ala Lys Phe Asp Lys Asp Leu Asn
625                 630                 635                 640

Leu Ala Leu Thr Ala Leu His His Ala Phe Arg Gly Thr Ser Ser Ala
                645                 650                 655

Tyr Ile Ala Thr Met Leu Ser Lys Lys Ser Asn Asp Asp Leu Ile Ala
                660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
            690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
```

```
                725                 730                 735
Phe Lys Leu Ala Ile Ser Ser Lys Ser Ile Lys Thr Cys Lys Asn Val
                740                 745                 750
Lys Asp Val Ala Cys Leu Ser Pro Arg Ser Gly Ala Ile Tyr Ala Ser
                755                 760                 765
Ile Ile Ala Cys Gly Glu Pro Asn Gly Pro Ser Val Tyr Arg Lys Pro
    770                 775                 780
Ser Gly Gly Val Phe Gln Ser Ser Thr Asp Arg Ser Ile Tyr Cys Leu
785                 790                 795                 800
Leu Asp Ser His Cys Leu Glu Glu Phe Glu Ala Ile Ser Gln Glu Glu
                805                 810                 815
Leu Asp Ala Val Lys Lys Ser Lys Cys Trp Glu Ile Glu Tyr Ser Asp
                820                 825                 830
Val Lys Pro Leu Gln Glu Gly Asn Gly Thr Lys Ser Cys Arg Met Lys
                835                 840                 845
Asp Ser Gly Asn Cys Asn Val Ala Thr Asn Arg Trp Pro Val Ile Gln
850                 855                 860
Cys Glu Asn Asp Lys Phe Tyr Tyr Ser Glu Leu Gln Lys Asp Tyr Asp
865                 870                 875                 880
Lys Thr Gln Asp Ile Gly His Tyr Cys Leu Ser Pro Gly Cys Thr Thr
                885                 890                 895
Val Arg Tyr Pro Ile Asn Pro Lys His Ile Ser Asn Cys Asn Trp Gln
                900                 905                 910
Val Ser Arg Ser Ser Ile Ala Lys Ile Asp Val His Asn Ile Glu Asp
                915                 920                 925
Ile Glu Gln Tyr Lys Lys Ala Ile Thr Gln Lys Leu Gln Thr Ser Leu
    930                 935                 940
Ser Leu Phe Lys Tyr Ala Lys Thr Lys Asn Leu Pro His Ile Lys Pro
945                 950                 955                 960
Ile Tyr Lys Tyr Ile Thr Ile Glu Gly Thr Glu Thr Ala Glu Gly Ile
                965                 970                 975
Glu Ser Ala Tyr Ile Glu Ser Glu Val Pro Ala Leu Ala Gly Thr Ser
                980                 985                 990
Ile Gly Phe Lys Ile Asn Ser Lys  Glu Gly Lys His Leu  Leu Asp Val
    995                 1000                1005
Ile Ala  Tyr Val Lys Ser Ala  Ser Tyr Ser Val  Tyr Ala Lys
    1010                1015                1020
Leu Tyr  Ser Thr Gly Pro Thr  Ser Gly Ile Asn Thr  Lys His Asp
    1025                1030                1035
Glu Leu  Cys Thr Gly Pro Cys  Pro Ala Asn Ile Asn  His Gln Val
    1040                1045                1050
Gly Trp  Leu Thr Phe Ala Lys  Glu Arg Thr Ser Ser  Trp Gly Cys
    1055                1060                1065
Glu Glu  Phe Gly Cys Leu Ala  Val Ser Asp Gly Cys  Val Phe Gly
    1070                1075                1080
Ser Cys  Gln Asp Ile Ile Lys  Glu Glu Leu Ser Val  Tyr Arg Lys
    1085                1090                1095
Glu Thr  Glu Glu Val Thr Asp  Val Glu Leu Cys Leu  Thr Phe Ser
    1100                1105                1110
Asp Lys  Thr Tyr Cys Thr Asn  Leu Asn Pro Val Thr  Pro Ile Ile
    1115                1120                1125
Thr Asp  Leu Phe Glu Val Gln  Phe Lys Thr Val Glu  Thr Tyr Ser
    1130                1135                1140
```

```
Leu Pro Arg Ile Val Ala Val Gln Asn His Glu Ile Lys Ile Gly
    1145                1150                1155

Gln Ile Asn Asp Leu Gly Val Tyr Ser Lys Gly Cys Gly Asn Val
    1160                1165                1170

Gln Lys Val Asn Gly Thr Val Tyr Gly Asn Gly Val Pro Arg Phe
    1175                1180                1185

Asp Tyr Leu Cys His Leu Ala Ser Arg Lys Glu Val Ile Val Arg
    1190                1195                1200

Lys Cys Phe Asp Asn Asp Tyr Gln Ala Cys Lys Phe Leu Gln Ser
    1205                1210                1215

Pro Ala Ser Tyr Arg Leu Glu Glu Asp Ser Gly Thr Val Thr Ile
    1220                1225                1230

Ile Asp Tyr Lys Lys Ile Leu Gly Thr Ile Lys Met Lys Ala Ile
    1235                1240                1245

Leu Gly Asp Val Lys Tyr Lys Thr Phe Ala Asp Ser Val Asp Ile
    1250                1255                1260

Thr Ala Glu Gly Ser Cys Thr Gly Cys Ile Asn Cys Phe Glu Asn
    1265                1270                1275

Ile His Cys Glu Leu Thr Leu His Thr Thr Ile Glu Ala Ser Cys
    1280                1285                1290

Pro Ile Lys Ser Ser Cys Thr Val Phe His Asp Arg Ile Leu Val
    1295                1300                1305

Thr Pro Asn Glu His Lys Tyr Ala Leu Lys Met Val Cys Thr Glu
    1310                1315                1320

Lys Pro Gly Asn Thr Leu Thr Ile Lys Val Cys Asn Thr Lys Ile
    1325                1330                1335

Glu Ala Ser Met Ala Leu Val Asp Ala Lys Pro Ile Ile Glu Leu
    1340                1345                1350

Ala Pro Val Asp Gln Thr Ala Tyr Ile Arg Glu Lys Asp Glu Arg
    1355                1360                1365

Cys Lys Thr Trp Met Cys Arg Val Arg Asp Glu Gly Leu Gln Val
    1370                1375                1380

Ile Leu Glu Pro Phe Lys Asn Leu Phe Gly Ser Tyr Ile Gly Ile
    1385                1390                1395

Phe Tyr Thr Phe Ile Ile Ser Ile Val Ala Leu Leu Ala Ile Ile
    1400                1405                1410

Tyr Val Leu Leu Pro Ile Cys Phe Lys Leu Arg Asp Thr Leu Arg
    1415                1420                1425

Lys His Glu Asp Ala Tyr Lys Arg Glu Met Lys Ile Arg
    1430                1435                1440

<210> SEQ ID NO 29
<211> LENGTH: 76
<212> TYPE: PRT
<213> ORGANISM: La Crosse virus

<400> SEQUENCE: 29

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Val Gln Phe His Ala Cys Phe Asn Gln His Met Ser
```

Cys Val Arg Phe Leu His Arg Thr Ile Leu Pro Gly
65                  70                  75

<210> SEQ ID NO 30
<211> LENGTH: 76
<212> TYPE: PRT
<213> ORGANISM: La Crosse virus

<400> SEQUENCE: 30

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Val Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 31
<211> LENGTH: 76
<212> TYPE: PRT
<213> ORGANISM: La Crosse virus

<400> SEQUENCE: 31

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Val Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 32
<211> LENGTH: 76
<212> TYPE: PRT
<213> ORGANISM: La Crosse virus

<400> SEQUENCE: 32

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Val Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 33
<211> LENGTH: 76
<212> TYPE: PRT
<213> ORGANISM: Artificial Sequence
<220> FEATURE:
<223> OTHER INFORMATION: Synthetic consensus sequence

<400> SEQUENCE: 33

Asp Lys Glu Thr Ala Gln Ile Arg Leu Gln Thr Asp Thr Thr Asn His
1 5 10 15

Phe Glu Ile Ala Gly Thr Thr Val Lys Ser Gly Trp Phe Lys Ser Thr
20 25 30

Thr Tyr Ile Thr Leu Asp Gln Thr Cys Glu His Leu Lys Val Ser Cys
35 40 45

Gly Pro Lys Ser Ile Gln Phe His Ala Cys Phe Asn Gln His Met Ser
50 55 60

Cys Val Arg Phe Leu His Arg Thr Ile Leu Pro Gly
65 70 75

<210> SEQ ID NO 34
<211> LENGTH: 81
<212> TYPE: DNA
<213> ORGANISM: La Crosse virus

<400> SEQUENCE: 34
agtagtgtac tccacttgaa tactttgaaa ataaattgtt gttgactgtt ttttacctaa 60
ggggaaatta tcaagagtgt g 81

<210> SEQ ID NO 35
<211> LENGTH: 81
<212> TYPE: DNA
<213> ORGANISM: La Crosse virus

<400> SEQUENCE: 35
agtagtgtac tccacttgaa tactttgaaa ataaattgtt gttgactgtt ttttacctaa 60
ggggaaatta tcaagagtgt g 81

<210> SEQ ID NO 36
<211> LENGTH: 81
<212> TYPE: DNA
<213> ORGANISM: La Crosse virus

<400> SEQUENCE: 36
agtagtgtac tccacttgaa tactttgaaa ataaattgtt gttgactgtt ttttacctaa 60
ggggaaatta tcaagagtgt g 81

<210> SEQ ID NO 37
<211> LENGTH: 81
<212> TYPE: DNA
<213> ORGANISM: La Crosse virus

<400> SEQUENCE: 37
agtagtgtac tccacttgaa tactttgaaa ataaattgtt gttgactgtt ttttacctaa 60
ggggaaatta tcaagagtgt g 81

<210> SEQ ID NO 38
<211> LENGTH: 61
<212> TYPE: DNA
<213> ORGANISM: La Crosse virus

<400> SEQUENCE: 38
agtagtgtac taccaagtat agataacgtt tgaatattaa agttttgaat caaagccaaa 60
g 61

<210> SEQ ID NO 39
<211> LENGTH: 61
<212> TYPE: DNA
<213> ORGANISM: La Crosse virus

<400> SEQUENCE: 39
agtagtgtac taccaagtat agataacgtt tgaatattaa agttttgaat caaagccaaa    60
g                                                                   61

<210> SEQ ID NO 40
<211> LENGTH: 61
<212> TYPE: DNA
<213> ORGANISM: La Crosse virus

<400> SEQUENCE: 40
agtagtgtac taccaagtat agataacgtt tgaatattaa agttttgaat caaagccaaa    60
g                                                                   61

<210> SEQ ID NO 41
<211> LENGTH: 61
<212> TYPE: DNA
<213> ORGANISM: La Crosse virus

<400> SEQUENCE: 41
agtagtgtgc taccaagtat agataacgtt tgaatattaa agttttgaat caaagccaaa    60
g                                                                   61

<210> SEQ ID NO 42
<211> LENGTH: 61
<212> TYPE: DNA
<213> ORGANISM: La Crosse virus

<400> SEQUENCE: 42
agtagtgtac tcctatctac aaaacttaca gaaaattcag tcatatcaca atatatgcat    60
a                                                                   61

<210> SEQ ID NO 43
<211> LENGTH: 61
<212> TYPE: DNA
<213> ORGANISM: La Crosse virus

<400> SEQUENCE: 43
agtagtgtac tcctatctac aaaacttaca gaaaattcag tcatatcaca atatatgcat    60
a                                                                   61

<210> SEQ ID NO 44
<211> LENGTH: 61
<212> TYPE: DNA
<213> ORGANISM: La Crosse virus

<400> SEQUENCE: 44
agtagtgtac tcctatctac aaaacttaca aagaattcag tcatatcaca atatatccat    60
a                                                                   61

<210> SEQ ID NO 45
<211> LENGTH: 61
<212> TYPE: DNA
<213> ORGANISM: La Crosse virus

```
<400> SEQUENCE: 45
agtagtgtac tcctatctac aaaacttaca aaaaattcag tcatatcaca atatatgcat      60
a                                                                     61

<210> SEQ ID NO 46
<211> LENGTH: 198
<212> TYPE: DNA
<213> ORGANISM: La Crosse virus

<400> SEQUENCE: 46
taaatatggc atgaggcatt caaattaggt tctaaattct aaatttatat atgtcaattt      60
gattaattgg ttatccaaaa gggttttctt aagggaaccc acaaaaatag cagctaaatg     120
ggtgggtggt aggggacagc aaaaaactat aaatcaggtc ataaataaaa taaaatgtat     180
tcagtggagc acactact                                                  198

<210> SEQ ID NO 47
<211> LENGTH: 198
<212> TYPE: DNA
<213> ORGANISM: La Crosse virus

<400> SEQUENCE: 47
taaatatggc atgaggcatt caaattaggt tctaaattct aaatttatat atgtcaattt      60
gattaattgg ttatccaaaa gggttttctt aagggaaccc acaaaaatag cagctaaatg     120
ggtgggtggt aggggacagc aaaaaactat aaatcaggtc ataaataaaa taaaatgtat     180
tcagtggagc acactact                                                  198

<210> SEQ ID NO 48
<211> LENGTH: 198
<212> TYPE: DNA
<213> ORGANISM: La Crosse virus

<400> SEQUENCE: 48
taaatagggc atgaggcatt agaatcaggt tctaaattcc aaatttacat atgttaattt      60
gattaattgg ttatctaaaa gggttttctt aagggaaccc acaaaaatag cagctaaatg     120
ggtgggtggt aggggacagc aaaaaactat aaatcaggtc ataaataaaa taaaatgtat     180
tcagtggagc acactact                                                  198

<210> SEQ ID NO 49
<211> LENGTH: 198
<212> TYPE: DNA
<213> ORGANISM: La Crosse virus

<400> SEQUENCE: 49
taaatatggc atgaggcatt caaattaggt tctaaattct aaatttatat atgtcaattt      60
gattaattgg ttatccaaaa gggttttctt aagggaaccc acaaaaatag cagctaaatg     120
ggtgggtggt aggggacagc aaaaaactat aaatcaggtc ataaataaaa taaaatgtat     180
tcagtggagc acactact                                                  198

<210> SEQ ID NO 50
<211> LENGTH: 198
<212> TYPE: DNA
<213> ORGANISM: Artificial Sequence
<220> FEATURE:
<223> OTHER INFORMATION: Synthetic consensus sequence

<400> SEQUENCE: 50
```

-continued

```
taaatatggc atgaggcatt caaattaggt tctaaattct aaatttatat atgtcaattt      60
gattaattgg ttatccaaaa gggttttctt aagggaaccc acaaaaatag cagctaaatg     120
ggtgggtggt aggggacagc aaaaaactat aaatcaggtc ataaataaaa taaaatgtat     180
tcagtggagc acactact                                                  198

<210> SEQ ID NO 51
<211> LENGTH: 142
<212> TYPE: DNA
<213> ORGANISM: La Crosse virus

<400> SEQUENCE: 51 tagggatct atgcagaaca aaattgagtc ctgtattata tattctattt gtagtatagc       60
tgttgttaag tgggggtgg ggaactaaca acagcgtaaa tttattttgc aaacattatt     120
ttatacttgg tagcacacta ct                                             142

<210> SEQ ID NO 52
<211> LENGTH: 142
<212> TYPE: DNA
<213> ORGANISM: La Crosse virus

<400> SEQUENCE: 52 tagggatct atgcagaaca aaattgagtc ctgtattata tattctattt gtagtatagc       60
tgttgttaag tgggggtgg ggaactaaca acagcgtaaa tttattttgc aaacattatt     120
ttatacttgg tagcacacta ct                                             142

<210> SEQ ID NO 53
<211> LENGTH: 142
<212> TYPE: DNA
<213> ORGANISM: La Crosse virus

<400> SEQUENCE: 53
tagggaatct atgcagaata aaattgagtc ctgtattata tattctattt gtagcatagc      60
tgttgttaag tgggggtgg ggaactaaca acagcgtaaa tttattttgc aaacattatt     120
ttatacttgg tagcacacta ct                                             142

<210> SEQ ID NO 54
<211> LENGTH: 142
<212> TYPE: DNA
<213> ORGANISM: La Crosse virus

<400> SEQUENCE: 54 tagggatct atgcagaaca aaattgagtc ctgtattata tattctattt gtagtatagc       60
tgttgttaag tgggggtgg ggaactaaca acagcgtaaa tttattttgc aaacattatt     120
ttatacttgg tagcacacta ct                                             142

<210> SEQ ID NO 55
<211> LENGTH: 142
<212> TYPE: DNA
<213> ORGANISM: Artificial Sequence
<220> FEATURE:
<223> OTHER INFORMATION: Synthetic consensus sequence

<400> SEQUENCE: 55 tagggatct atgcagaaca aaattgagtc ctgtattata tattctattt gtagtatagc       60
tgttgttaag tgggggtgg ggaactaaca acagcgtaaa tttattttgc aaacattatt     120
```

```
ttatacttgg tagcacacta ct                                              142

<210> SEQ ID NO 56
<211> LENGTH: 130
<212> TYPE: DNA
<213> ORGANISM: La Crosse virus

<400> SEQUENCE: 56
tagtagttat gagtttacag agaacctaca attaggccat aaatttggga gggttttgga     60
aattggctaa aattcaaaaa gaggggatt aacagcaact gtataaattt gtagatagga    120
gcacactact                                                           130

<210> SEQ ID NO 57
<211> LENGTH: 130
<212> TYPE: DNA
<213> ORGANISM: La Crosse virus

<400> SEQUENCE: 57
tagtagttat gagtttacag agaacctaca attaggctat aaatttggga gggttttgga     60
aattggctaa aattcaaaaa gaggggatt aacagcaact gtataaattt gtagatagga    120
gcacactact                                                           130

<210> SEQ ID NO 58
<211> LENGTH: 130
<212> TYPE: DNA
<213> ORGANISM: La Crosse virus

<400> SEQUENCE: 58
tagtagttat gagtttacag agaactgaca attaggctat aaatttggga gggttttgga     60
aattggctaa gattcaaaaa gaggggatt aacagcaact gtataaattt gtagatagga    120
gcacactact                                                           130

<210> SEQ ID NO 59
<211> LENGTH: 130
<212> TYPE: DNA
<213> ORGANISM: La Crosse virus

<400> SEQUENCE: 59
tagtagttat aagtttacag agaactgaca attaggccat aaatttggga gggttttgga     60
aattggctaa gattcaaaaa gaggggatt aacagcaact gtataaattt gtagatagga    120
gcacactact                                                           130

<210> SEQ ID NO 60
<211> LENGTH: 130
<212> TYPE: DNA
<213> ORGANISM: Artificial Sequence
<220> FEATURE:
<223> OTHER INFORMATION: Synthetic consensus sequence

<400> SEQUENCE: 60
tagtagttat gagtttacag agaacykaca attaggcyat aaatttggga gggttttgga     60
aattggctaa rattcaaaaa gaggggatt aacagcaact gtataaattt gtagatagga    120
gcacactact                                                           130

<210> SEQ ID NO 61
<211> LENGTH: 76
<212> TYPE: PRT
<213> ORGANISM: La Crosse virus
```

<400> SEQUENCE: 61

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
            20                  25                  30

Ala Tyr Ile Thr Leu Asp Gln Thr Cys Glu His Leu Lys Val Ser Cys
        35                  40                  45

Gly Pro Lys Ser Val Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 62
<211> LENGTH: 76
<212> TYPE: PRT
<213> ORGANISM: La Crosse virus

<400> SEQUENCE: 62

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
        35                  40                  45

Gly Pro Lys Ser Val Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 63
<211> LENGTH: 76
<212> TYPE: PRT
<213> ORGANISM: California encephalitis virus

<400> SEQUENCE: 63

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
            20                  25                  30

Thr Tyr Ile Ser Leu Asp Gln Thr Cys Glu His Leu Lys Val Ser Cys
        35                  40                  45

Gly Pro Lys Ser Ile Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 64
<211> LENGTH: 76
<212> TYPE: PRT
<213> ORGANISM: Inkoo virus

<400> SEQUENCE: 64

Asp Lys Glu Thr Ala Gln Ile Arg Leu Gln Thr Asp Asn Thr Asn His
1               5                   10                  15

Phe Glu Val Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys 35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 65
<211> LENGTH: 76
<212> TYPE: PRT
<213> ORGANISM: Jamestown Canyon virus

<400> SEQUENCE: 65

Asp Lys Glu Thr Ala Gln Ile Arg Leu Gln Thr Asp Asn Thr Asn His
1               5                   10                  15

Phe Glu Val Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 66
<211> LENGTH: 76
<212> TYPE: PRT
<213> ORGANISM: Snowshoe hare virus

<400> SEQUENCE: 66

Asp Lys Glu Thr Ala Gln Val Arg Leu Gln Thr Asp Thr Thr Asn His
1               5                   10                  15

Phe Glu Ile Ala Gly Thr Ile Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 67
<211> LENGTH: 76
<212> TYPE: PRT
<213> ORGANISM: Tahyna virus

<400> SEQUENCE: 67

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
                20                  25                  30

Thr Tyr Ile Thr Leu Asp Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 68

```
<211> LENGTH: 76
<212> TYPE: PRT
<213> ORGANISM: Serra do Navio virus

<400> SEQUENCE: 68

Asp Lys Glu Thr Ala Gln Ile Arg Leu Gln Thr Asp Ser Thr Asn His
1               5                   10                  15

Phe Glu Val Ser Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
        35                  40                  45

Gly Pro Lys Ser Ile Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 69
<211> LENGTH: 76
<212> TYPE: PRT
<213> ORGANISM: Jerry Slough virus

<400> SEQUENCE: 69

Asp Lys Glu Thr Ala Gln Ile Arg Leu Gln Thr Asp Asn Thr Asn His
1               5                   10                  15

Phe Glu Val Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
        35                  40                  45

Gly Pro Lys Ser Ile Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 70
<211> LENGTH: 76
<212> TYPE: PRT
<213> ORGANISM: San Angelo virus

<400> SEQUENCE: 70

Asp Lys Glu Thr Ala Gln Ile Arg Leu Gln Thr Asp Thr Thr Asn His
1               5                   10                  15

Phe Glu Val Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
        35                  40                  45

Gly Pro Lys Ser Ile Gln Phe His Ala Cys Phe Asn Gln His Met Ser
    50                  55                  60

Cys Val Arg Phe Leu His Arg Thr Ile Leu Pro Gly
65                  70                  75

<210> SEQ ID NO 71
<211> LENGTH: 76
<212> TYPE: PRT
<213> ORGANISM: Lumbo virus

<400> SEQUENCE: 71

Asp Lys Glu Thr Ala Gln Val Arg Leu Gln Thr Asp Thr Thr Asn His
1               5                   10                  15

Phe Glu Ile Ala Gly Thr Thr Val Lys Ser Gly Trp Phe Lys Ser Thr
```

```
            20                  25                  30

Thr Tyr Ile Thr Leu Gly Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 72
<211> LENGTH: 76
<212> TYPE: PRT
<213> ORGANISM: Melao virus

<400> SEQUENCE: 72

Asp Lys Glu Thr Ala Gln Ile Arg Leu Gln Thr Asp Ser Thr Thr His
1               5                   10                  15

Phe Glu Ile Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75

<210> SEQ ID NO 73
<211> LENGTH: 76
<212> TYPE: PRT
<213> ORGANISM: Trivittatus virus

<400> SEQUENCE: 73

Asp Lys Glu Thr Ala Gln Val Arg Leu Gln Thr Asp Thr Thr Asn His
1               5                   10                  15

Phe Glu Ile Ser Gly Thr Thr Val Lys Ser Gly Trp Phe Lys Ser Thr
            20                  25                  30

Thr Tyr Leu Thr Leu Asp Gln Thr Cys Glu His Leu Lys Ile Ser Cys
            35                  40                  45

Gly Ser Lys Ser Val Gln Leu His Ala Cys Phe Asn Gln His Met Ser
        50                  55                  60

Cys Val Arg Phe Leu His Arg Thr Ile Leu Pro Gly
65                  70                  75

<210> SEQ ID NO 74
<211> LENGTH: 76
<212> TYPE: PRT
<213> ORGANISM: South River virus

<400> SEQUENCE: 74

Asp Lys Glu Thr Ala Gln Ile Arg Leu Gln Thr Asp Asn Thr Asn His
1               5                   10                  15

Phe Glu Val Ala Gly Thr Thr Val Lys Ser Gly Trp Phe Lys Ser Thr
            20                  25                  30

Thr Tyr Ile Thr Leu Asp Gln Thr Cys Glu His Leu Lys Val Ser Cys
            35                  40                  45

Gly Pro Lys Ser Ile Gln Phe His Ala Cys Phe Asn Gln His Met Ser
        50                  55                  60

Cys Val Arg Phe Leu His Arg Thr Ile Leu Pro Gly
65                  70                  75
```

<210> SEQ ID NO 75
<211> LENGTH: 76
<212> TYPE: PRT
<213> ORGANISM: Keystone virus

<400> SEQUENCE: 75

```
Asp Lys Glu Thr Ala Gln Ile Arg Leu Gln Thr Asp Thr Thr His His
1               5                   10                  15

Phe Glu Ile Ala Gly Thr Val Val Lys Ser Gly Trp Phe Lys Ser Thr
            20                  25                  30

Thr Tyr Ile Thr Leu Asp Gln Thr Cys Glu Arg Leu Lys Val Ser Cys
        35                  40                  45

Gly Pro Lys Ser Ile Gln Phe His Ala Cys Phe Asn Gln His Met Ser
    50                  55                  60

Cys Val Arg Phe Leu His Arg Thr Ile Leu Leu Gly
65                  70                  75
```

<210> SEQ ID NO 76
<211> LENGTH: 1441
<212> TYPE: PRT
<213> ORGANISM: La Crosse virus

<400> SEQUENCE: 76

```
Met Ile Cys Ile Leu Val Leu Ile Thr Val Ala Ala Ser Pro Val
1               5                   10                  15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
        35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
    130                 135                 140

Lys Ser Thr Ala Tyr Ile Thr Leu Asp Gln Thr Cys Glu His Leu Lys
145                 150                 155                 160

Val Ser Cys Gly Pro Lys Ser Val Gln Phe His Ala Cys Phe Asn Gln
                165                 170                 175

His Met Ser Cys Val Arg Phe Leu His Arg Thr Ile Leu Pro Gly Ser
            180                 185                 190

Ile Ala Asn Ser Ile Cys Gln Asn Ile Glu Ile Ile Leu Val Thr
        195                 200                 205

Leu Thr Leu Leu Ile Phe Ile Leu Leu Ser Ile Leu Ser Lys Thr Tyr
    210                 215                 220

Ile Cys Tyr Leu Leu Met Pro Ile Phe Ile Pro Ile Ala Tyr Ile Tyr
225                 230                 235                 240

Gly Ile Ile Tyr Asn Lys Ser Cys Lys Lys Cys Lys Leu Cys Gly Leu
                245                 250                 255
```

```
Val Tyr His Pro Phe Thr Glu Cys Gly Thr His Cys Val Cys Gly Ala
            260                 265                 270

Arg Tyr Asp Thr Ser Asp Arg Met Lys Leu His Arg Ala Ser Gly Leu
            275                 280                 285

Cys Pro Gly Tyr Lys Ser Leu Arg Ala Arg Val Met Cys Lys Ser
            290                 295                 300

Lys Gly Pro Ala Ser Ile Leu Ser Ile Ile Thr Ala Val Leu Val Leu
305                 310                 315                 320

Thr Phe Val Thr Pro Ile Asn Ser Met Val Leu Gly Glu Ser Lys Glu
                    325                 330                 335

Thr Phe Glu Leu Glu Asp Leu Pro Asp Asp Met Leu Glu Met Ala Ser
                340                 345                 350

Arg Ile Asn Ser Tyr Tyr Leu Thr Cys Ile Leu Asn Tyr Ala Val Ser
                355                 360                 365

Trp Gly Leu Val Ile Ile Gly Leu Leu Ile Gly Leu Leu Phe Lys Lys
            370                 375                 380

Tyr Gln His Arg Phe Leu Asn Val Tyr Ala Met Tyr Cys Glu Glu Cys
385                 390                 395                 400

Asp Met Tyr His Asp Lys Ser Gly Leu Lys Arg His Gly Asp Phe Thr
                405                 410                 415

Asn Lys Cys Arg Gln Cys Thr Cys Gly Gln Tyr Glu Asp Ala Ala Gly
                420                 425                 430

Leu Met Ala His Arg Lys Thr Tyr Asn Cys Leu Val Gln Tyr Lys Ala
                435                 440                 445

Lys Trp Met Met Asn Phe Leu Ile Ile Tyr Ile Phe Leu Ile Leu Ile
450                 455                 460

Lys Asp Ser Ala Ile Val Val Gln Ala Ala Gly Thr Asp Phe Thr Thr
465                 470                 475                 480

Cys Leu Glu Thr Glu Ser Ile Asn Trp Asn Cys Thr Gly Pro Phe Leu
                485                 490                 495

Asn Leu Gly Asn Cys Gln Lys Gln Gln Lys Lys Glu Pro Tyr Thr Asn
                500                 505                 510

Ile Ala Thr Gln Leu Lys Gly Leu Lys Ala Ile Ser Val Leu Asp Val
                515                 520                 525

Pro Ile Ile Thr Gly Ile Pro Asp Asp Ile Ala Gly Ala Leu Arg Tyr
                530                 535                 540

Ile Glu Glu Lys Glu Asp Phe His Val Gln Leu Thr Ile Glu Tyr Ala
545                 550                 555                 560

Met Leu Ser Lys Tyr Cys Asp Tyr Tyr Thr Gln Phe Ser Asp Asn Ser
                565                 570                 575

Gly Tyr Ser Gln Thr Thr Trp Arg Val Tyr Leu Arg Ser His Asp Phe
                580                 585                 590

Glu Ala Cys Ile Leu Tyr Pro Asn Gln His Phe Cys Arg Cys Val Lys
                595                 600                 605

Asn Gly Glu Lys Cys Ser Ser Ser Asn Trp Asp Phe Ala Asn Glu Met
                610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
                645                 650                 655

Tyr Ile Ala Thr Met Leu Ser Lys Lys Ser Asn Asp Asp Leu Ile Ala
                660                 665                 670
```

```
Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
    690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
                725                 730                 735

Phe Lys Leu Ala Ile Ser Ser Lys Ser Ile Lys Thr Cys Lys Asn Val
                740                 745                 750

Lys Asp Val Ala Cys Leu Ser Pro Arg Ser Gly Ala Ile Tyr Ala Ser
            755                 760                 765

Ile Ile Ala Cys Gly Glu Pro Asn Gly Pro Ser Val Tyr Arg Lys Pro
    770                 775                 780

Ser Gly Gly Val Phe Gln Ser Ser Thr Asp Arg Ser Ile Tyr Cys Leu
785                 790                 795                 800

Leu Asp Ser His Cys Leu Glu Glu Phe Glu Ala Ile Gly Gln Glu Glu
                805                 810                 815

Leu Asp Ala Val Lys Lys Ser Lys Cys Trp Glu Ile Glu Tyr Pro Asp
                820                 825                 830

Val Lys Leu Ile Gln Glu Gly Asp Gly Thr Lys Ser Cys Arg Met Lys
            835                 840                 845

Asp Ser Gly Asn Cys Asn Val Ala Thr Asn Arg Trp Pro Val Ile Gln
    850                 855                 860

Cys Glu Asn Asp Lys Phe Tyr Tyr Ser Glu Leu Gln Lys Asp Tyr Asp
865                 870                 875                 880

Lys Ala Gln Asp Ile Gly His Tyr Cys Leu Ser Pro Gly Cys Thr Thr
                885                 890                 895

Val Arg Tyr Pro Ile Asn Pro Lys His Ile Ser Asn Cys Asn Trp Gln
            900                 905                 910

Val Ser Arg Ser Ser Ile Ala Lys Ile Asp Val His Asn Ile Glu Asp
    915                 920                 925

Ile Glu Gln Tyr Lys Lys Ala Ile Thr Gln Lys Leu Gln Thr Ser Leu
930                 935                 940

Ser Leu Phe Lys Tyr Ala Lys Thr Lys Asn Leu Pro His Ile Lys Pro
945                 950                 955                 960

Ile Tyr Lys Tyr Ile Thr Ile Glu Gly Thr Glu Thr Ala Glu Gly Ile
                965                 970                 975

Glu Ser Ala Tyr Ile Glu Ser Val Pro Ala Leu Ala Gly Thr Ser
            980                 985                 990

Ile Gly Phe Lys Ile Asn Ser Lys Glu Gly Lys His Leu Leu Asp Val
    995                 1000                1005

Ile Ala Tyr Val Lys Ser Ala Ser Tyr Ser Ser Val Tyr Thr Lys
    1010                1015                1020

Leu Tyr Ser Thr Gly Pro Thr Ser Gly Ile Asn Thr Lys His Asp
    1025                1030                1035

Glu Leu Cys Thr Gly Pro Cys Pro Ala Asn Ile Asn His Gln Val
    1040                1045                1050

Gly Trp Leu Thr Phe Ala Arg Glu Arg Thr Ser Ser Trp Gly Cys
    1055                1060                1065

Glu Glu Phe Gly Cys Leu Ala Val Ser Asp Gly Cys Val Phe Gly
    1070                1075                1080

Ser Cys Gln Asp Ile Ile Lys Glu Glu Leu Ser Val Tyr Arg Lys
```

```
                    1085                1090                1095
Glu Thr Glu Glu Val Thr Asp Val Glu Leu Cys Leu Thr Phe Ser
            1100                1105                1110
Asp Lys Thr Tyr Cys Thr Asn Leu Asn Pro Val Thr Pro Ile Ile
            1115                1120                1125
Thr Asp Leu Phe Glu Val Gln Phe Lys Thr Val Glu Thr Tyr Ser
            1130                1135                1140
Leu Pro Arg Ile Val Ala Val Gln Asn His Glu Ile Lys Ile Gly
            1145                1150                1155
Gln Ile Asn Asp Leu Gly Val Tyr Ser Lys Gly Cys Gly Asn Val
            1160                1165                1170
Gln Lys Val Asn Gly Thr Ile Tyr Gly Asn Gly Val Pro Arg Phe
            1175                1180                1185
Asp Tyr Leu Cys His Leu Ala Ser Arg Lys Glu Val Ile Val Arg
            1190                1195                1200
Lys Cys Phe Asp Asn Asp Tyr Gln Ala Cys Lys Phe Leu Gln Ser
            1205                1210                1215
Pro Ala Ser Tyr Arg Leu Glu Glu Asp Ser Gly Thr Val Thr Ile
            1220                1225                1230
Ile Asp Tyr Lys Lys Ile Leu Gly Thr Ile Lys Met Lys Ala Ile
            1235                1240                1245
Leu Gly Asp Val Lys Tyr Lys Thr Phe Ala Asp Ser Val Asp Ile
            1250                1255                1260
Thr Ala Glu Gly Ser Cys Thr Gly Cys Ile Asn Cys Phe Glu Asn
            1265                1270                1275
Ile His Cys Glu Leu Thr Leu His Thr Thr Ile Glu Ala Ser Cys
            1280                1285                1290
Pro Ile Lys Ser Ser Cys Thr Val Phe His Asp Arg Ile Leu Val
            1295                1300                1305
Thr Pro Asn Glu His Lys Tyr Ala Leu Lys Met Val Cys Thr Glu
            1310                1315                1320
Lys Pro Gly Asn Thr Leu Thr Ile Lys Val Cys Asn Thr Lys Val
            1325                1330                1335
Glu Ala Ser Met Ala Leu Val Asp Ala Lys Pro Ile Ile Glu Leu
            1340                1345                1350
Ala Pro Val Asp Gln Thr Ala Tyr Ile Arg Glu Lys Asp Glu Arg
            1355                1360                1365
Cys Lys Thr Trp Met Cys Arg Val Arg Asp Glu Gly Leu Gln Val
            1370                1375                1380
Ile Leu Glu Pro Phe Lys Asn Leu Phe Gly Ser Tyr Ile Gly Ile
            1385                1390                1395
Phe Tyr Thr Phe Ile Ile Ser Ile Val Val Leu Leu Val Ile Ile
            1400                1405                1410
Tyr Val Leu Leu Pro Ile Cys Phe Lys Leu Arg Asp Thr Leu Arg
            1415                1420                1425
Lys His Glu Asp Ala Tyr Lys Arg Glu Met Lys Ile Arg
            1430                1435                1440

<210> SEQ ID NO 77
<211> LENGTH: 1440
<212> TYPE: PRT
<213> ORGANISM: La Crosse virus

<400> SEQUENCE: 77
```

```
Met Ile Cys Ile Leu Val Leu Ile Thr Val Ala Ala Ser Pro Val
 1               5                  10                 15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
            35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
            115                 120                 125

Thr Asn His Phe Glu Ile Ala Gly Thr Thr Val Lys Ser Gly Trp Phe
    130                 135                 140

Lys Ser Thr Tyr Ile Thr Leu Asp Gln Thr Cys Glu His Leu Lys Val
145                 150                 155                 160

Ser Cys Gly Pro Lys Ser Val Gln Phe His Ala Cys Phe Asn Gln His
                165                 170                 175

Met Ser Cys Val Arg Phe Leu His Arg Thr Ile Leu Pro Gly Ser Ile
            180                 185                 190

Ala Asn Ser Ile Cys Gln Asn Ile Glu Ile Ile Leu Val Thr Leu
    195                 200                 205

Thr Leu Leu Ile Phe Ile Leu Leu Ser Ile Leu Ser Lys Thr Tyr Ile
    210                 215                 220

Cys Tyr Leu Leu Met Pro Ile Phe Ile Pro Ile Ala Tyr Ile Tyr Gly
225                 230                 235                 240

Ile Ile Tyr Asn Lys Ser Cys Lys Lys Cys Lys Leu Cys Gly Leu Val
                245                 250                 255

Tyr His Pro Phe Thr Glu Cys Gly Thr His Cys Val Cys Gly Ala Arg
            260                 265                 270

Tyr Asp Thr Ser Asp Arg Met Lys Leu His Arg Ala Ser Gly Leu Cys
    275                 280                 285

Pro Gly Tyr Lys Ser Leu Arg Ala Ala Arg Val Met Cys Lys Ser Lys
    290                 295                 300

Gly Pro Ala Ser Ile Leu Ser Ile Ile Thr Ala Val Leu Val Leu Thr
305                 310                 315                 320

Phe Val Thr Pro Ile Asn Ser Met Val Leu Gly Glu Ser Lys Glu Thr
                325                 330                 335

Phe Glu Leu Glu Asp Leu Pro Asp Asp Met Leu Glu Met Ala Ser Arg
            340                 345                 350

Ile Asn Ser Tyr Tyr Leu Thr Cys Ile Leu Asn Tyr Ala Val Ser Trp
    355                 360                 365

Gly Leu Val Ile Ile Gly Leu Leu Ile Gly Leu Leu Phe Lys Lys Tyr
    370                 375                 380

Gln His Arg Phe Leu Asn Val Tyr Ala Met Tyr Cys Glu Glu Cys Asp
385                 390                 395                 400

Met Tyr His Asp Lys Ser Gly Leu Lys Arg His Gly Asp Phe Thr Asn
                405                 410                 415

Lys Cys Arg Gln Cys Thr Cys Gly Gln Tyr Glu Asp Ala Ala Gly Leu
```

```
            420                 425                 430
Met Ala His Arg Lys Thr Tyr Asn Cys Leu Val Gln Tyr Lys Ala Lys
            435                 440                 445

Trp Met Met Asn Phe Leu Ile Ile Tyr Ile Phe Leu Ile Leu Ile Lys
            450                 455                 460

Asp Ser Ala Ile Val Val Gln Ala Ala Gly Thr Asp Phe Thr Thr Cys
465                 470                 475                 480

Leu Glu Thr Glu Ser Ile Asn Trp Asn Cys Thr Gly Pro Phe Leu Asn
                485                 490                 495

Leu Gly Asn Cys Gln Lys Gln Lys Lys Glu Pro Tyr Thr Asn Ile
            500                 505                 510

Ala Thr Gln Leu Lys Gly Leu Lys Ala Ile Ser Val Leu Asp Val Pro
            515                 520                 525

Ile Ile Thr Gly Ile Pro Asp Asp Ile Ala Gly Ala Leu Arg Tyr Ile
            530                 535                 540

Glu Glu Lys Glu Asp Phe His Val Gln Leu Thr Ile Glu Tyr Ala Met
545                 550                 555                 560

Leu Ser Lys Tyr Cys Asp Tyr Tyr Thr Gln Phe Ser Asp Asn Ser Gly
                565                 570                 575

Tyr Ser Gln Thr Thr Trp Arg Val Tyr Leu Arg Ser His Asp Phe Glu
            580                 585                 590

Ala Cys Ile Leu Tyr Pro Asn Gln His Phe Cys Arg Cys Val Lys Asn
            595                 600                 605

Gly Glu Lys Cys Ser Ser Asn Trp Asp Phe Ala Asn Glu Met Lys
            610                 615                 620

Asp Tyr Tyr Ser Gly Lys Gln Thr Lys Phe Asp Lys Asp Leu Asn Leu
625                 630                 635                 640

Ala Leu Thr Ala Leu His His Ala Phe Arg Gly Thr Ser Ser Ala Tyr
                645                 650                 655

Ile Ala Thr Met Leu Ser Lys Lys Ser Asn Asp Asp Leu Ile Ala Tyr
                660                 665                 670

Thr Asn Lys Ile Lys Thr Lys Phe Pro Gly Asn Ala Leu Leu Lys Ala
            675                 680                 685

Ile Ile Asp Tyr Ile Ala Tyr Met Lys Ser Leu Pro Gly Met Ala Asn
            690                 695                 700

Phe Lys Tyr Asp Glu Phe Trp Asp Glu Leu Leu Tyr Lys Pro Asn Pro
705                 710                 715                 720

Ala Lys Ala Ser Asn Leu Ala Arg Gly Lys Glu Ser Ser Tyr Asn Phe
                725                 730                 735

Lys Leu Ala Ile Ser Ser Lys Ser Ile Lys Thr Cys Lys Asn Val Lys
            740                 745                 750

Asp Val Ala Cys Leu Ser Pro Arg Ser Gly Ala Ile Tyr Ala Ser Ile
            755                 760                 765

Ile Ala Cys Gly Glu Pro Asn Gly Pro Ser Val Tyr Arg Lys Pro Ser
            770                 775                 780

Gly Gly Val Phe Gln Ser Ser Thr Asp Arg Ser Ile Tyr Cys Leu Leu
785                 790                 795                 800

Asp Ser His Cys Leu Glu Glu Phe Glu Ala Ile Gly Gln Glu Glu Leu
                805                 810                 815

Asp Ala Val Lys Lys Ser Lys Cys Trp Glu Ile Glu Tyr Pro Asp Val
            820                 825                 830

Lys Leu Ile Gln Glu Gly Asp Gly Thr Lys Ser Cys Arg Met Lys Asp
            835                 840                 845
```

```
Ser Gly Asn Cys Asn Val Ala Thr Asn Arg Trp Pro Val Ile Gln Cys
    850                 855                 860

Glu Asn Asp Lys Phe Tyr Tyr Ser Glu Leu Gln Lys Asp Tyr Asp Lys
865                 870                 875                 880

Ala Gln Asp Ile Gly His Tyr Cys Leu Ser Pro Gly Cys Thr Thr Val
                885                 890                 895

Arg Tyr Pro Ile Asn Pro Lys His Ile Ser Asn Cys Asn Trp Gln Val
            900                 905                 910

Ser Arg Ser Ser Ile Ala Lys Ile Asp Val His Asn Ile Glu Asp Ile
        915                 920                 925

Glu Gln Tyr Lys Lys Ala Ile Thr Gln Lys Leu Gln Thr Ser Leu Ser
930                 935                 940

Leu Phe Lys Tyr Ala Lys Thr Lys Asn Leu Pro His Ile Lys Pro Ile
945                 950                 955                 960

Tyr Lys Tyr Ile Thr Ile Glu Gly Thr Glu Thr Ala Glu Gly Ile Glu
                965                 970                 975

Ser Ala Tyr Ile Glu Ser Glu Val Pro Ala Leu Ala Gly Thr Ser Ile
            980                 985                 990

Gly Phe Lys Ile Asn Ser Lys Glu Gly Lys His Leu Leu Asp Val Ile
        995                 1000                1005

Ala Tyr Val Lys Ser Ala Ser Tyr Ser Ser Val Tyr Thr Lys Leu
    1010                1015                1020

Tyr Ser Thr Gly Pro Thr Ser Gly Ile Asn Thr Lys His Asp Glu
    1025                1030                1035

Leu Cys Thr Gly Pro Cys Pro Ala Asn Ile Asn His Gln Val Gly
    1040                1045                1050

Trp Leu Thr Phe Ala Arg Glu Arg Thr Ser Ser Trp Gly Cys Glu
    1055                1060                1065

Glu Phe Gly Cys Leu Ala Val Ser Asp Gly Cys Val Phe Gly Ser
    1070                1075                1080

Cys Gln Asp Ile Ile Lys Glu Glu Leu Ser Val Tyr Arg Lys Glu
    1085                1090                1095

Thr Glu Glu Val Thr Asp Val Glu Leu Cys Leu Thr Phe Ser Asp
    1100                1105                1110

Lys Thr Tyr Cys Thr Asn Leu Asn Pro Val Thr Pro Ile Ile Thr
    1115                1120                1125

Asp Leu Phe Glu Val Gln Phe Lys Thr Val Glu Thr Tyr Ser Leu
    1130                1135                1140

Pro Arg Ile Val Ala Val Gln Asn His Glu Ile Lys Ile Gly Gln
    1145                1150                1155

Ile Asn Asp Leu Gly Val Tyr Ser Lys Gly Cys Gly Asn Val Gln
    1160                1165                1170

Lys Val Asn Gly Thr Ile Tyr Gly Asn Gly Val Pro Arg Phe Asp
    1175                1180                1185

Tyr Leu Cys His Leu Ala Ser Arg Lys Glu Val Ile Val Arg Lys
    1190                1195                1200

Cys Phe Asp Asn Asp Tyr Gln Ala Cys Lys Phe Leu Gln Ser Pro
    1205                1210                1215

Ala Ser Tyr Arg Leu Glu Glu Asp Ser Gly Thr Val Thr Ile Ile
    1220                1225                1230

Asp Tyr Lys Lys Ile Leu Gly Thr Ile Lys Met Lys Ala Ile Leu
    1235                1240                1245
```

```
Gly Asp Val Lys Tyr Lys Thr Phe Ala Asp Ser Val Asp Ile Thr
    1250                1255                1260

Ala Glu Gly Ser Cys Thr Gly Cys Ile Asn Cys Phe Glu Asn Ile
1265                1270                1275

His Cys Glu Leu Thr Leu His Thr Thr Ile Glu Ala Ser Cys Pro
    1280                1285                1290

Ile Lys Ser Ser Cys Thr Val Phe His Asp Arg Ile Leu Val Thr
    1295                1300                1305

Pro Asn Glu His Lys Tyr Ala Leu Lys Met Val Cys Thr Glu Lys
    1310                1315                1320

Pro Gly Asn Thr Leu Thr Ile Lys Val Cys Asn Thr Lys Val Glu
    1325                1330                1335

Ala Ser Met Ala Leu Val Asp Ala Lys Pro Ile Glu Leu Ala
    1340                1345                1350

Pro Val Asp Gln Thr Ala Tyr Ile Arg Glu Lys Asp Glu Arg Cys
    1355                1360                1365

Lys Thr Trp Met Cys Arg Val Arg Asp Glu Gly Leu Gln Val Ile
    1370                1375                1380

Leu Glu Pro Phe Lys Asn Leu Phe Gly Ser Tyr Ile Gly Ile Phe
    1385                1390                1395

Tyr Thr Phe Ile Ile Ser Ile Val Val Leu Leu Val Ile Ile Tyr
    1400                1405                1410

Val Leu Leu Pro Ile Cys Phe Lys Leu Arg Asp Thr Leu Arg Lys
    1415                1420                1425

His Glu Asp Ala Tyr Lys Arg Glu Met Lys Ile Arg
    1430                1435                1440
```

<210> SEQ ID NO 78
<211> LENGTH: 1441
<212> TYPE: PRT
<213> ORGANISM: La Crosse virus
<220> FEATURE:
<221> NAME/KEY: MOD_RES
<222> LOCATION: (148)..(148)
<223> OTHER INFORMATION: Any amino acid except Thr

<400> SEQUENCE: 78

```
Met Ile Cys Ile Leu Val Leu Ile Thr Val Ala Ala Ala Ser Pro Val
1               5                   10                  15

Tyr Gln Arg Cys Phe Gln Asp Gly Ala Ile Val Lys Gln Asn Pro Ser
            20                  25                  30

Lys Glu Ala Val Thr Glu Val Cys Leu Lys Asp Asp Val Ser Met Ile
        35                  40                  45

Lys Thr Glu Ala Arg Tyr Val Arg Asn Ala Thr Gly Val Phe Ser Asn
    50                  55                  60

Asn Val Ala Ile Arg Lys Trp Leu Val Ser Asp Trp His Asp Cys Arg
65                  70                  75                  80

Pro Lys Lys Ile Val Gly Gly His Ile Asn Val Ile Glu Val Gly Asp
                85                  90                  95

Asp Leu Ser Leu His Thr Glu Ser Tyr Val Cys Ser Ala Asp Cys Thr
            100                 105                 110

Ile Gly Val Asp Lys Glu Thr Ala Gln Val Arg Leu Gln Thr Asp Thr
        115                 120                 125

Thr Asn His Phe Glu Ile Ala Gly Thr Thr Val Lys Ser Gly Trp Phe
    130                 135                 140

Lys Ser Thr Xaa Tyr Ile Thr Leu Asp Gln Thr Cys Glu His Leu Lys
```

```
            145                 150                 155                 160
Val Ser Cys Gly Pro Lys Ser Val Gln Phe His Ala Cys Phe Asn Gln
                165                 170                 175
His Met Ser Cys Val Arg Phe Leu His Arg Thr Ile Leu Pro Gly Ser
                180                 185                 190
Ile Ala Asn Ser Ile Cys Gln Asn Ile Glu Ile Ile Leu Val Thr
                195                 200                 205
Leu Thr Leu Leu Ile Phe Ile Leu Leu Ser Ile Leu Ser Lys Thr Tyr
        210                 215                 220
Ile Cys Tyr Leu Leu Met Pro Ile Phe Ile Pro Ile Ala Tyr Ile Tyr
225                 230                 235                 240
Gly Ile Ile Tyr Asn Lys Ser Cys Lys Lys Cys Lys Leu Cys Gly Leu
                245                 250                 255
Val Tyr His Pro Phe Thr Glu Cys Gly Thr His Cys Val Cys Gly Ala
                260                 265                 270
Arg Tyr Asp Thr Ser Asp Arg Met Lys Leu His Arg Ala Ser Gly Leu
                275                 280                 285
Cys Pro Gly Tyr Lys Ser Leu Arg Ala Ala Arg Val Met Cys Lys Ser
                290                 295                 300
Lys Gly Pro Ala Ser Ile Leu Ser Ile Ile Thr Ala Val Leu Val Leu
305                 310                 315                 320
Thr Phe Val Thr Pro Ile Asn Ser Met Val Leu Gly Glu Ser Lys Glu
                325                 330                 335
Thr Phe Glu Leu Glu Asp Leu Pro Asp Asp Met Leu Glu Met Ala Ser
                340                 345                 350
Arg Ile Asn Ser Tyr Tyr Leu Thr Cys Ile Leu Asn Tyr Ala Val Ser
                355                 360                 365
Trp Gly Leu Val Ile Ile Gly Leu Leu Ile Gly Leu Leu Phe Lys Lys
                370                 375                 380
Tyr Gln His Arg Phe Leu Asn Val Tyr Ala Met Tyr Cys Glu Glu Cys
385                 390                 395                 400
Asp Met Tyr His Asp Lys Ser Gly Leu Lys Arg His Gly Asp Phe Thr
                405                 410                 415
Asn Lys Cys Arg Gln Cys Thr Cys Gly Gln Tyr Glu Asp Ala Ala Gly
                420                 425                 430
Leu Met Ala His Arg Lys Thr Tyr Asn Cys Leu Val Gln Tyr Lys Ala
                435                 440                 445
Lys Trp Met Met Asn Phe Leu Ile Ile Tyr Ile Phe Leu Ile Leu Ile
450                 455                 460
Lys Asp Ser Ala Ile Val Val Gln Ala Ala Gly Thr Asp Phe Thr Thr
465                 470                 475                 480
Cys Leu Glu Thr Glu Ser Ile Asn Trp Asn Cys Thr Gly Pro Phe Leu
                485                 490                 495
Asn Leu Gly Asn Cys Gln Lys Gln Gln Lys Lys Glu Pro Tyr Thr Asn
                500                 505                 510
Ile Ala Thr Gln Leu Lys Gly Leu Lys Ala Ile Ser Val Leu Asp Val
                515                 520                 525
Pro Ile Ile Thr Gly Ile Pro Asp Asp Ile Ala Gly Ala Leu Arg Tyr
                530                 535                 540
Ile Glu Glu Lys Glu Asp Phe His Val Gln Leu Thr Ile Glu Tyr Ala
545                 550                 555                 560
Met Leu Ser Lys Tyr Cys Asp Tyr Tyr Thr Gln Phe Ser Asp Asn Ser
                565                 570                 575
```

```
Gly Tyr Ser Gln Thr Thr Trp Arg Val Tyr Leu Arg Ser His Asp Phe
                580                 585                 590

Glu Ala Cys Ile Leu Tyr Pro Asn Gln His Phe Cys Arg Cys Val Lys
            595                 600                 605

Asn Gly Glu Lys Cys Ser Ser Ser Asn Trp Asp Phe Ala Asn Glu Met
610                 615                 620

Lys Asp Tyr Tyr Ser Gly Lys Gln Thr Lys Phe Asp Lys Asp Leu Asn
625                 630                 635                 640

Leu Ala Leu Thr Ala Leu His His Ala Phe Arg Gly Thr Ser Ser Ala
                645                 650                 655

Tyr Ile Ala Thr Met Leu Ser Lys Lys Ser Asn Asp Asp Leu Ile Ala
                660                 665                 670

Tyr Thr Asn Lys Ile Lys Thr Lys Phe Pro Gly Asn Ala Leu Leu Lys
            675                 680                 685

Ala Ile Ile Asp Tyr Ile Ala Tyr Met Lys Ser Leu Pro Gly Met Ala
        690                 695                 700

Asn Phe Lys Tyr Asp Glu Phe Trp Asp Glu Leu Leu Tyr Lys Pro Asn
705                 710                 715                 720

Pro Ala Lys Ala Ser Asn Leu Ala Arg Gly Lys Glu Ser Ser Tyr Asn
                725                 730                 735

Phe Lys Leu Ala Ile Ser Ser Lys Ser Ile Lys Thr Cys Lys Asn Val
                740                 745                 750

Lys Asp Val Ala Cys Leu Ser Pro Arg Ser Gly Ala Ile Tyr Ala Ser
            755                 760                 765

Ile Ile Ala Cys Gly Glu Pro Asn Gly Pro Ser Val Tyr Arg Lys Pro
        770                 775                 780

Ser Gly Gly Val Phe Gln Ser Ser Thr Asp Arg Ser Ile Tyr Cys Leu
785                 790                 795                 800

Leu Asp Ser His Cys Leu Glu Glu Phe Glu Ala Ile Gly Gln Glu Glu
                805                 810                 815

Leu Asp Ala Val Lys Lys Ser Lys Cys Trp Glu Ile Glu Tyr Pro Asp
                820                 825                 830

Val Lys Leu Ile Gln Glu Gly Asp Gly Thr Lys Ser Cys Arg Met Lys
            835                 840                 845

Asp Ser Gly Asn Cys Asn Val Ala Thr Asn Arg Trp Pro Val Ile Gln
850                 855                 860

Cys Glu Asn Asp Lys Phe Tyr Tyr Ser Glu Leu Gln Lys Asp Tyr Asp
865                 870                 875                 880

Lys Ala Gln Asp Ile Gly His Tyr Cys Leu Ser Pro Gly Cys Thr Thr
                885                 890                 895

Val Arg Tyr Pro Ile Asn Pro Lys His Ile Ser Asn Cys Asn Trp Gln
            900                 905                 910

Val Ser Arg Ser Ser Ile Ala Lys Ile Asp Val His Asn Ile Glu Asp
        915                 920                 925

Ile Glu Gln Tyr Lys Lys Ala Ile Thr Gln Lys Leu Gln Thr Ser Leu
        930                 935                 940

Ser Leu Phe Lys Tyr Ala Lys Thr Lys Asn Leu Pro His Ile Lys Pro
945                 950                 955                 960

Ile Tyr Lys Tyr Ile Thr Ile Glu Gly Thr Glu Thr Ala Glu Gly Ile
                965                 970                 975

Glu Ser Ala Tyr Ile Glu Ser Glu Val Pro Ala Leu Ala Gly Thr Ser
            980                 985                 990
```

```
Ile Gly Phe Lys Ile Asn Ser Lys   Glu Gly Lys His Leu   Leu Asp Val
            995                 1000                1005

Ile Ala Tyr Val Lys Ser Ala   Ser Tyr Ser Ser Val   Tyr Thr Lys
    1010              1015                1020

Leu Tyr Ser Thr Gly Pro Thr   Ser Gly Ile Asn Thr   Lys His Asp
    1025              1030                1035

Glu Leu Cys Thr Gly Pro Cys   Pro Ala Asn Ile Asn   His Gln Val
    1040              1045                1050

Gly Trp Leu Thr Phe Ala Arg   Glu Arg Thr Ser Ser   Trp Gly Cys
    1055              1060                1065

Glu Glu Phe Gly Cys Leu Ala   Val Ser Asp Gly Cys   Val Phe Gly
    1070              1075                1080

Ser Cys Gln Asp Ile Ile Lys   Glu Glu Leu Ser Val   Tyr Arg Lys
    1085              1090                1095

Glu Thr Glu Glu Val Thr Asp   Val Glu Leu Cys Leu   Thr Phe Ser
    1100              1105                1110

Asp Lys Thr Tyr Cys Thr Asn   Leu Asn Pro Val Thr   Pro Ile Ile
    1115              1120                1125

Thr Asp Leu Phe Glu Val Gln   Phe Lys Thr Val Glu   Thr Tyr Ser
    1130              1135                1140

Leu Pro Arg Ile Val Ala Val   Gln Asn His Glu Ile   Lys Ile Gly
    1145              1150                1155

Gln Ile Asn Asp Leu Gly Val   Tyr Ser Lys Gly Cys   Gly Asn Val
    1160              1165                1170

Gln Lys Val Asn Gly Thr Ile   Tyr Gly Asn Gly Val   Pro Arg Phe
    1175              1180                1185

Asp Tyr Leu Cys His Leu Ala   Ser Arg Lys Glu Val   Ile Val Arg
    1190              1195                1200

Lys Cys Phe Asp Asn Asp Tyr   Gln Ala Cys Lys Phe   Leu Gln Ser
    1205              1210                1215

Pro Ala Ser Tyr Arg Leu Glu   Glu Asp Ser Gly Thr   Val Thr Ile
    1220              1225                1230

Ile Asp Tyr Lys Lys Ile Leu   Gly Thr Ile Lys Met   Lys Ala Ile
    1235              1240                1245

Leu Gly Asp Val Lys Tyr Lys   Thr Phe Ala Asp Ser   Val Asp Ile
    1250              1255                1260

Thr Ala Glu Gly Ser Cys Thr   Gly Cys Ile Asn Cys   Phe Glu Asn
    1265              1270                1275

Ile His Cys Glu Leu Thr Leu   His Thr Thr Ile Glu   Ala Ser Cys
    1280              1285                1290

Pro Ile Lys Ser Ser Cys Thr   Val Phe His Asp Arg   Ile Leu Val
    1295              1300                1305

Thr Pro Asn Glu His Lys Tyr   Ala Leu Lys Met Val   Cys Thr Glu
    1310              1315                1320

Lys Pro Gly Asn Thr Leu Thr   Ile Lys Val Cys Asn   Thr Lys Val
    1325              1330                1335

Glu Ala Ser Met Ala Leu Val   Asp Ala Lys Pro Ile   Ile Glu Leu
    1340              1345                1350

Ala Pro Val Asp Gln Thr Ala   Tyr Ile Arg Glu Lys   Asp Glu Arg
    1355              1360                1365

Cys Lys Thr Trp Met Cys Arg   Val Arg Asp Glu Gly   Leu Gln Val
    1370              1375                1380

Ile Leu Glu Pro Phe Lys Asn   Leu Phe Gly Ser Tyr   Ile Gly Ile
```

```
            1385                1390                1395

Phe Tyr Thr Phe Ile Ile Ser  Ile Val Val Leu Leu  Val Ile Ile
            1400                1405                1410

Tyr Val Leu Leu Pro Ile Cys  Phe Lys Leu Arg Asp  Thr Leu Arg
            1415                1420                1425

Lys His Glu Asp Ala Tyr Lys  Arg Glu Met Lys Ile  Arg
            1430                1435                1440

<210> SEQ ID NO 79
<211> LENGTH: 4527
<212> TYPE: DNA
<213> ORGANISM: La Crosse virus

<400> SEQUENCE: 79
```

| | | | | | |
|---|---|---|---|---|---|
| agtagtgtac | taccaagtat | agataacgtt | tgaatattaa | agttttgaat | caaagccaaa | 60 |
| gatgatttgt | atattggtgc | taattacagt | tgcagctgca | agcccagtgt | atcaaaggtg | 120 |
| tttccaagat | ggggctatag | tgaagcaaaa | cccatccaaa | gaagcagtta | cagaggtgtg | 180 |
| cctgaaagat | gatgttagca | tgatcaaaac | agaggccagg | tatgtaagaa | atgcaacagg | 240 |
| agttttttca | ataatgtcg | caataaggaa | atggctagtc | tctgattggc | atgattgcag | 300 |
| gcctaagaag | atcgttgggg | gacacatcaa | tgtaatagaa | gttggtgatg | acctgtcact | 360 |
| ccatactgaa | tcatatgttt | gcagcgcaga | ttgtaccata | ggtgtagaca | agagactgc | 420 |
| acaggtcagg | cttcagacag | ataccacaaa | tcattttgaa | attgcaggca | ctactgtgaa | 480 |
| gtcaggatgg | ttcaagagca | cggcatatat | aactcttgat | caaacttgcg | aacacccttaa | 540 |
| agtttcctgc | ggcccaaaat | ctgtacagtt | ccatgcctgc | ttcaatcagc | atatgtcttg | 600 |
| cgtcagattt | ttacacagga | caatattgcc | tggctctata | gccaattcca | tatgtcagaa | 660 |
| tatcgaaatc | ataattttag | ttacacttac | tctattaatc | tttatattgt | taagcatttt | 720 |
| aagtaagact | tatatatgtt | atttattaat | gcctatattc | atccccatag | catatatata | 780 |
| cggtataatt | tacaataagt | cgtgcaaaaa | atgcaaatta | tgtggcttag | tgtatcatcc | 840 |
| attcacagag | tgtggcacac | attgtgtctg | tggtgcccgc | tatgatactt | cagatagaat | 900 |
| gaaactgcat | agagcttctg | gattgtgccc | tggttataaa | agcctaagag | ctgccagagt | 960 |
| catgtgcaag | tcgaaagggc | ctgcatcaat | attgtctata | attactgcgg | tactggtctt | 1020 |
| aacctttgtg | acaccaatca | actccatggt | tttaggagag | agtaaagaaa | cctttgaact | 1080 |
| tgaagatctt | ccagacgaca | tgttggaaat | ggcatcgaga | ataaattctt | attatctcac | 1140 |
| ctgtatcttg | aattatgctg | taagctgggg | tcttgttatc | attggattgt | tgatcgggct | 1200 |
| gcttttaag | aaataccagc | acagattctt | aaatgtttac | gcaatgtact | gtgaagaatg | 1260 |
| tgacatgtat | catgacaagt | ctgggttgaa | aagacatggt | gatttcacca | acaaatgcag | 1320 |
| acagtgcaca | tgtggtcaat | atgaagatgc | tgcaggtttg | atggctcaca | ggaaaaccta | 1380 |
| taactgctta | gtgcagtaca | agcaaagtg | atgatgaac | ttcctgataa | tttacatatt | 1440 |
| cttaattttg | atcaaagatt | ctgctatagt | tgtacaagct | gctggaactg | acttcaccac | 1500 |
| ctgcctagag | actgagagta | taaattggaa | ctgcactggg | ccattttga | acctcgggaa | 1560 |
| ttgccaaaag | caacaaaaga | aagaacctta | caccaacatt | gcaactcagt | taagggact | 1620 |
| aaaggcaatt | tccgtactag | atgtccctat | aataacaggg | ataccagatg | atattgcggg | 1680 |
| tgctttaaga | tatatagaag | agaaggaaga | tttccatgtc | cagctaacta | tagaatatgc | 1740 |
| gatgttaagc | aaatactgtg | actattatac | ccaattctca | gataactcag | gatacagtca | 1800 |

```
gacaacatgg agagtgtact taaggtctca tgattttgaa gcctgtatac tatatccaaa    1860
tcagcacttt tgcagatgtg taaaaaatgg tgagaagtgc agcagctcca attgggactt    1920
tgccaatgaa atgaaagatt attactctgg gaaacaaaca aagtttgaca aggacttaaa    1980
tctagcccta acagctttgc atcatgcctt caggggacc tcatctgcat atatagcaac    2040
aatgctctca aaaagtccaa atgatgactt gattgcatac acaaataaga taaaaacaaa    2100
attcccaggt aatgcattgt tgaaggctat aatagattat atagcatata tgaaaagttt    2160
gccaggtatg gcaaatttca aatatgatga attctgggat gaattactgt acaaacccaa    2220
cccagcaaag gcctcaaacc ttgctagagg aaaggagtca tcttacaact tcaaactagc    2280
aatttcatca aagtctataa aaacctgcaa gaatgttaag gatgttgcct gcttatcgcc    2340
aaggtcaggt gctatatatg cttcaataat tgcgtgtggt gaacccaatg ggccaagtgt    2400
gtataggaaa ccatcaggtg gtgtattcca atctagcact gatcggtcta tatactgctt    2460
gctggatagc cattgtctag aagaatttga ggccatcggc caggaggagc tggatgcggt    2520
aaagaaatcc aaatgttggg aaattgaata tcctgacgta aagctcatcc aagaaggcga    2580
tgggactaaa agctgtagaa tgaaagattc tgggaactgc aatgttgcaa ctaacagatg    2640
gccagtgata caatgtgaga atgacaaatt ttactactca gagcttcaaa aagattatga    2700
caaagctcaa gatattggtc actattgctt aagccctgga tgtactactg tccggtaccc    2760
tattaatcca aagcacatct ctaactgtaa ttggcaagta agcagatcta gcatagcgaa    2820
gatagatgtg cacaatattg aggatattga gcaatataag aaagctataa ctcagaaact    2880
tcaaacgagc ctatctctat tcaagtatgc aaaaacaaaa aacttgccgc acatcaaacc    2940
aatttataaa tatataacta tagaaggaac agaaactgca gaaggtatag agagtgcata    3000
cattgaatca gaagtacctg cattggctgg gacatctatc ggattcaaaa tcaattctaa    3060
agagggcaag cacttgctag atgttatagc atatgtaaaa agtgcctcat actcttcagt    3120
gtatacaaaa ttgtactcaa ctggcccaac atcaggata aatactaaac atgatgaatt    3180
gtgtactggc ccatgcccag caaatatcaa tcatcaggtt gggtggctga catttgcaag    3240
agagaggaca agctcatggg gatgcgaaga gtttggttgc ctggctgtaa gtgatgggtg    3300
tgtatttgga tcatgccaag atataataaa agaagaacta tctgtctata ggaaggagac    3360
cgaggaagtg actgatgtag aactgtgttt gacattttca gacaaaacat actgtacaaa    3420
cttaaaccct gttacccta ttataacaga tctatttgag gtacagttca aaactgtaga    3480
gacctacagc ttgcctagaa ttgttgctgt gcaaaaccat gagattaaaa ttgggcaaat    3540
aaatgattta ggagtttact ctaagggttg tgggaatgtt caaaaggtca atggaactat    3600
ttatggcaat ggagttccca gatttgacta cttatgccat ttagctagca ggaaggaagt    3660
cattgttaga aaatgcttcg acaatgatta ccaagcatgc aaatttcttc aaagccctgc    3720
tagttacaga cttgaagaag acagtggcac tgtgaccata attgactaca aaagattttt    3780
aggaacaatc aagatgaagg caattttagg agatgtcaaa tataaaacat tgctgatag    3840 tgtcgatata accgcagaag ggtcatgcac cggctgtatt aactgcttcg aaaatatcca    3900
ttgcgaatta acgttgcaca ccacaattga agccagctgc ccaattaaaa gctcgtgcac    3960
agtatttcat gacaggattc ttgtgactcc aaatgaacac aaatatgcat tgaaaatggt    4020
gtgcacagaa aagccaggga acacactcac aattaaagtc tgcaatacta agttgaagc    4080 atctatggcc cttgtagacg caaagcctat catagaacta gcaccagttg atcagacagc    4140
atatataaga gaaaagatg aaaggtgtaa aacttggatg tgtagggtaa gagatgaagg    4200
```

-continued

```
actgcaggtc atcttggagc catttaaaaa tttatttgga tcttatattg ggatatttta    4260
cacatttatt atatctatag tagtattatt ggttattatc tatgtactac tacctatatg    4320
ctttaagtta agggataccc ttagaaagca tgaagatgca tataagagag agatgaaaat    4380
tagatagggg atctatgcag aacaaaattg agtcctgtat tatatacttc tatttgtagt    4440
atagctgttg ttaagtgggg ggtggggaac taacaacagc gtaaatttat tttgcaaaca    4500
ttattttata cttggtagca cactact                                        4527
```